(12) United States Patent
Tan et al.

(10) Patent No.: US 11,840,694 B2
(45) Date of Patent: Dec. 12, 2023

(54) TRUNCATED CRISPR-CAS PROTEINS FOR DNA TARGETING

(71) Applicants: NANYANG TECHNOLOGICAL UNIVERSITY, Singapore (SG); AGENCY FOR SCIENCE, TECHNOLOGY AND RESEARCH, Singapore (SG)

(72) Inventors: Meng How Tan, Singapore (SG); Kean Hean Ooi, Singapore (SG)

(73) Assignees: NANYANG TECHNOLOGICAL UNIVERSITY, Singapore (SG); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 693 days.

(21) Appl. No.: 16/342,319

(22) PCT Filed: Oct. 17, 2017

(86) PCT No.: PCT/SG2017/050523
§ 371 (c)(1),
(2) Date: Apr. 16, 2019

(87) PCT Pub. No.: WO2018/074979
PCT Pub. Date: Apr. 26, 2018

(65) Prior Publication Data
US 2019/0382775 A1    Dec. 19, 2019

(30) Foreign Application Priority Data
Oct. 17, 2016 (SG) .............................. 10201608681P

(51) Int. Cl.
*C12N 9/22* (2006.01)
*C12N 15/74* (2006.01)
*C07K 16/12* (2006.01)

(52) U.S. Cl.
CPC ........ *C12N 15/746* (2013.01); *C07K 16/1275* (2013.01); *C12N 9/22* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 4,873,316 A | 10/1989 | Meade et al. | |
| 6,750,059 B1 | 6/2004 | Blakesley et al. | |
| 7,776,321 B2 | 8/2010 | Cascalho et al. | |
| 10,876,100 B2 * | 12/2020 | Zhang | C12N 9/22 |
| 2004/0171156 A1 | 9/2004 | Hartley et al. | |
| 2011/0027239 A1 | 2/2011 | Paek | |
| 2012/0003201 A1 | 1/2012 | Nicholas et al. | |
| 2018/0163188 A1 * | 6/2018 | Xie | C12N 15/86 |

FOREIGN PATENT DOCUMENTS

| | | | |
|---|---|---|---|
| EP | 0264166 A1 | 4/1988 | |
| WO | 96/39154 A1 | 12/1996 | |
| WO | 97/03211 A1 | 1/1997 | |
| WO | 2011/028929 A2 | 3/2011 | |
| WO | 2014/191521 A2 | 12/2014 | |
| WO | 2015/077318 A1 | 5/2015 | |
| WO | WO-2015103153 A1 * | 7/2015 | ......... C12N 15/1031 |
| WO | 2016/196655 A1 | 12/2016 | |
| WO | WO-2016196655 A1 * | 12/2016 | ........... C12N 15/102 |

OTHER PUBLICATIONS

BLAST alignment #2 (SEQ ID 1 (SpCas9) vs Sternberg SEQ ID 1596 (dHNH-SpCas9)). Using https://blast.ncbi.nlm.nih.gov/Blast.cgi tool. (Year: 2021).*
BLAST alignment #4 (SEQ ID 1 (SpCas9) vs Xie SEQ ID 9 (dRec1-c-Cas9-VPR; miniCas9-1)). Using https://blast.ncbi.nlm.nih.gov/Blast.cgi tool. (Year: 2021).*
Nishimasu et al., Crystal Structure of Cas9 in Complex with Guide RNA and Target DNA. Cell (2014), vol. 156, 935-949 (Year: 2014).*
BLAST alignment #3 (SEQ ID 1 (SpCas9) vs Xie SEQ ID 8 (dCas9-VPR)). Using https://blast.ncbi.nlm.nih.gov/Blast.cgi tool. (Year: 2021).*
BLAST alignment #1 (SEQ ID 1 (SpCas9) vs Sternberg SEQ ID 2 (dHNH-SpCas9)). Using https://blast.ncbi.nlm.nih.gov/Blast.cgi tool (Year: 2021).*
BLAST alignment #4 (SEQ ID 1 (SpCas9) vs Xie SEQ ID 9 (dCas9-VPR-dREC-C)). Using https://blast.ncbi.nlm.nih.gov/Blast.cgi tool (Year: 2021).*

(Continued)

*Primary Examiner* — Samuel C Woolwine
*Assistant Examiner* — Catherine Konopka
(74) *Attorney, Agent, or Firm* — SEED INTELLECTUAL PROPERTY LAW GROUP LLP

(57) ABSTRACT

The present invention relates to a polypeptide comprising at least one at least one deletion selected from the group consisting of $\Delta$HNH ($\Delta$775-909), $\Delta$RuvCIII-b ($\Delta$1002-1074), $\Delta$REC1-a ($\Delta$510-655), $\Delta$REC1-b ($\Delta$525-587), $\Delta$REC1-c ($\Delta$662-710), $\Delta$REC2 ($\Delta$180-308), $\Delta$REC2-a ($\Delta$212-244), $\Delta$REC2-b ($\Delta$244-276), $\Delta$REC2-c ($\Delta$276-308), $\Delta$REC2-d ($\Delta$199-283), $\Delta$REC2-e ($\Delta$198-257), $\Delta$REC2-f ($\Delta$235-286), $\Delta$REC2-g ($\Delta$217-266), $\Delta$REC3 ($\Delta$498-712) and combinations thereof, wherein the position numbering is in accordance with SEQ ID NO: 1 encoding for *S. pyogenes* Cas9, and wherein the polypeptide has CRISPR-Cas DNA-binding activity. The polypeptide may further comprises a missense mutations selected from G12R, T13K, T13R, N14K, N497K, T657K, T657R, N767K, T770K, T770R, Q920K, Q920R, S1109R, D1135K, D1135R, S1338R and combinations thereof. Also claimed are nucleic acid molecules encoding for said polypeptides, compositions and method of site-directed engineering of a target DNA thereof.

10 Claims, 10 Drawing Sheets

Specification includes a Sequence Listing.

(56) References Cited

OTHER PUBLICATIONS

Wright et al., Rational design of a split-Cas9 enzyme complex. PNAS (2105), 112: 2984-2989 and Supplemental material (Year: 2015).*
Amann et al., "Tightly regulated tac promoter vectors useful for the expression of unfused and fused proteins in *Escherichia coli*," *Gene* 69:301-315, 1988.
Baldari et al., "A novel leader peptide which allows efficient secretion of a fragment of human interleukin 1ß in *Saccharomyces cerevisiae*," *The EMBO Journal* 6(1):229-234, 1987.
Banerji et al., "A Lymphocyte-Specific Cellular Enhancer Is Located Downstream of the Joining Region in Immunoglobulin Heavy Chain Genes," *Cell* 33:729-740, 1983.
Boshart et al., "A Very Strong Enhancer Is Located Upstream of an Immediate Early Gene of Human Cytomegalovirus," *Cell* 41:521-530, 1985.
Byrne et al., "Multiplex gene regulation: A two-tiered approach to transgene regulation in transgenic mice," *Proc. Natl. Acad. Sci. USA* 86:5473-5477, 1989.
Calame et al., "Transcriptional Controlling Elements in the Immunoglobulin and T Cell Receptor Loci," *Advances in Immunology* 43:235-275, 1988.
Camper et al., "Postnatal repression of the α-fetoprotein gene is enhancer dependent," *Genes & Development* 3:537-546, 1989. (11 pages).
Chavez et al., "Highly efficient Cas9-mediated transcriptional programming," *Nat Methods* 12(4):326-330, 2015.
Chen et al. "Dynamic Imaging of Genomic Loci in Living Human Cells by an Optimized CRISPR/Cas System," *Cell* 155:1479-1491, 2013.
Edlund et al., "Cell-Specific Expression of the Rat Insulin Gene: Evidence for Role of Two Distinct 5' Flanking Elements" *Science* 230(4728):912-916, 1985. (6 pages).
Fine et al., "Trans-spliced Cas9 allows cleavage of HBB and CCR5 genes in human cells using compact expression cassettes," *Sci Rep* 5:10777, 2015. (10 pages).
Freiburg, "Truncation of the dCas9 protein," The uniCAS Toolkit for Gene Regulation, 2013.
Groenen et al., "Nature of DNA polymorphism in the direct repeat cluster of *Mycobacterium tuberculosis*; application for strain differentiation by a novel typing method," *Molecular Microbiology* 10(5):1057-1065, 1993.
Guilinger et al., "Fusion of catalytically inactive Cas9 to FokI nuclease improves the specificity of genome modification," *Nat Biotechnol* 32(6):577-582, 2014. (8 pages).
Hilton et al., "Epigenome editing by a CRISPR-Cas9-based acetyltransferase activates genes from promoters and enhancers," *Nat Biotechnol* 33(5):510-519, 2015.
Hirano et al., "Structural Basis for the Altered PAM Specificities of Engineered CRISPR-Cas9," *Molecular Cell* 61:886-894, 2016. (10 pages).
Hoe et al., "Rapid Molecular Genetic Subtyping of Serotype M1 Group A *Streptococcus* Strains," *Emerging Infectious Diseases* 5(2):254-263, 1999.
Hsu et al., "Development and Applications of CRISPR-Cas9 for Genome Engineering," *Cell* 157:1262-1278, 2014.
Ishino et al., "Nucleotide Sequence of the iap Gene, Responsible for Alkaline Phosphatase Isozyme Conversion in *Escherichia coli*, and Identification of the Gene Product," *Journal of Bacteriology* 169(12):5429-5433, 1987.
Jansen et al., "Identification of genes that are associated with DNA repeats in prokaryotes," *Molecular Microbiology* 43(6):1565-1575, 2002.
Karginov et al., "The CRISPR system: Small RNA-Guided Defense in Bacteria and Archaea," *Molecular Cell* 37:7-19, 2010.
Kaufman et al., "Translational efficiency of polycistronic mRNA's and their utilization to express heterologous genes in mammalian cells," *The EMBO Journal* 6(1)197-193, 1987.

Kessel et al., "Murine Developmental Control Genes," *Science* 249:374-379, 1990. (7 pages).
Kleinstiver et al., "High-fidelity CRISPR-Cas9 nucleases with no detectable genome-wide off-target effects," *Nature* 529:490-506, 2016.
Komor et al., "Programmable editing of a target base in genomic DNA without double-stranded DNA cleavage," *Nature* 533:420-436, 2016.
Kurjan et al., "Structure of a Yeast Pheromone Gene (MFα): A Putative α-Factor Precursor Contains Four Tandem Copies of Mature α-Factor," *Cell* 30:933-943, 1982.
Luckow et al., "High Level Expression of Nonfused Foreign Genes with *Autographa californica* Nuclear Polyhedrosis Virus Expression Vectors," *Virology* 170:31-39, 1989.
Mandegar et al., "CRISPR Interference Efficiently Induces Specific and Reversible Gene Silencing in Human iPSCs," *Cell Stem Cell* 18:541-553, 2016.
Masepohl et al., "Long tandemly repeated repetitive (LTRR) sequences in the filamentous cyanobacterium *Anabaena* sp. PCC 7120," *Biochimica et Biophysica Acta* 1307:26-30, 1996.
Mojica et al., "Biological significance of a family of regularly spaced repeats in the genomes of Archaea, Bacteria and mitochondria," *Molecular Microbiology* 36(1):244-246, 2000.
Mojica et al., "Long stretches of short tandem repeats are present in the largest replicons of the Archaea Haloferax mediterranei and Haloferax volcanii and could be involved in replicon partition . . ." Molecular Microbiology 17(1):85-93, 1995. (10 pages).
Nakata et al., "Unusual Nucleotide Arrangement with Repeated Sequences in the *Escherichia coli* K-12 Chromosome," *Journal of Bacteriology* 171(6):3553-3556, 1989.
Needleman et al., "A General Method Applicable to the Search for Similarities in the Amino Acid Sequence of Two Proteins," *J. Mol. Biol.* 48:443-453, 1970.
Nilsson et al., "Chemical Synthesis of Proteins," *Annu. Rev. Biophys. Biomol. Struct.* 34:91-118, 2005. (30 pages).
Nishimasu et al., "Crystal Structure of Cas9 in Complex with Guide RNA and Target DNA," *Cell* 156:935-949, 2014.
Nishimasu et al., "Crystal Structure of *Staphylococcus aureus* Cas9," *Cell* 162(5):1113-1126, 2015. (24 pages).
O'Hare et al., "Transformation of mouse fibroblasts to methotrexate resistance by a recombinant plasmid expressing a prokaryotic dihydrofolate reductase," *Proc. Natl. Acad. Sci. USA* 78(3):1527-1532,1981.
Pinkert et al., "An albumin enhancer located 10 kb upstream functions along with its promoter to direct efficient, liver-specific expression in transgenic mice," *Genes & Development* 1:268-276, 1987. (10 pages).
Qi et al., "Repurposing CRISPR as an RNA-Guided Platform for Sequence-Specific Control of Gene Expression," *Cell* 152:1173-1183, 2013.
Queen et al., "Immunoglobulin Gene Transcription Is Activated by Downstream Sequence Elements," *Cell* 33:741-748, 1983.
Ran et al., "In vivo genome editing using *Staphylococcus aureus* Cas9," *Nature* 520:186-191, 2015. (18 pages).
Rice et al., "EMBOSS: The European Molecular Biology Open Software Suite," *TIG* 16(6):276-277, 2000.
Schultz et al., "Expression and secretion in yeast of a 400-kDa envelope glycoprotein derived from Epstein-Barr virus," *Gene* 54:113-123, 1987.
Smith et al., "Production of Human Beta Interferon in Insect Cells Infected with a Baculovirus Expression Vector," *Molecular and Cellular Biology* 3(12):2156-2165, 1983.
Smith et al., "Single-step purification of polypeptides expressed in *Escherichia coli* as fusions with glutathione S-transferase," *Gene* 67:31-40, 1988.
Takebe et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat," *Molecular and Cellular Biology*, 8(1):466-472, 1988.
Van Embden et al., "Genetic Variation and Evolutionary Origin of the Direct Repeat Locus of *Mycobacterium tuberculosis* Complex Bacteria," *Journal of Bacteriology* 182(9):2393-2401, 2000.

(56) References Cited

OTHER PUBLICATIONS

Winoto et al., "A novel, inducible and T cell-specific enhancer located at the 3' end of the T cell receptor α locus," *The EMBO Journal* 8(3):729-733, 1989.

Yamano, "Crystal Structure of Cpf1 in Complex with Guide RNA and Target DNA." *Cell* 165:949-962, 2016.

\* cited by examiner

TRUNCATED CRISPR-CAS PROTEINS FOR DNA TARGETING

CROSS-REFERENCE TO RELATED APPLICATION

This application makes reference to and claims the benefit of priority of the Singapore Patent Application No. 10201608681P filed on 17 Oct. 2016, the content of which is incorporated herein by reference for all purposes, including an incorporation of any element or part of the description, claims or drawings not contained herein and referred to in Rule 20.5(a) of the PCT, pursuant to Rule 4.18 of the PCT.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_554USPC_SEQUENCE_LISTING.txt. The text file is 296 KB, was created on Jul. 6, 2019, and is being submitted electronically via EFS-Web.

FIELD OF THE INVENTION

The present invention generally relates to engineered and optimized CRISPR-Cas proteins and their applications in the site-specific modification of a target DNA.

BACKGROUND OF THE INVENTION

The ability to engineer the genome of any living organism has many biomedical and biotechnological applications, such as the correction of disease-causing mutations, construction of accurate cellular models for disease studies, or generation of agricultural crops with desirable traits. Various technologies have been developed over the past 10-20 years, including meganucleases, zinc finger nucleases, or transcription activator-like effector nucleases (TALENs). However, these technologies are either difficult to program or difficult to assemble, thereby limiting their widespread adoption.

Recently, the CRISPR (clustered regularly interspaced short palindromic repeats)-Cas system has emerged as a powerful new genome engineering technology. Originally an adaptive immune system in bacteria, it has been successfully deployed for genome modification in animals and plants, including human. A key reason why CRISPR-Cas has gained so much popularity in such a short time is that the element that targets the Cas endonuclease to the correct location in the genome is simply a short piece of guide RNA, which is straightforward to design and cheap to synthesize.

The Cas enzyme performs two important and distinct functions. First, it is able to bind to specific loci in the genome with the aid of the guide RNA and a short sequence in the targeted DNA, called the protospacer adjacent motif (PAM). Cas proteins from different bacteria will recognize different PAMs in general. Various protein domains are involved in interacting with the DNA, including the REC1, REC2, and PI domains. Second, the Cas enzyme can cleave both strands of the DNA upon binding, thereby generating a double-stranded break. The Cas protein contains two nuclease domains, the HNH and RuvC domains, each of which cut opposite strands of the DNA. The overall domain architecture of the Cas9 enzyme from *Streptococcus pyogenes* is shown in FIG. 1.

Since the two functions of the Cas enzyme may be separated, it is possible to utilize the CRISPR-Cas system only for the purpose of DNA targeting and not for DNA cleavage. To disable the cleavage function, the common practice is to mutate a catalytic residue in each of the two nuclease domains (D10A and H840A in SpCas9). Various laboratories have successfully fused different effector domains to the catalytically dead Cas enzyme (dCas) for a range of applications, including gene regulation, imaging, and base conversion.

Despite the tremendous potential of CRISPR-Cas for genome engineering, the system suffers from several shortcomings that restricts its use for basic biomedical research and therapeutic applications. In particular, the large size of the Cas protein affects the delivery of the CRISPR-Cas system both in vitro and even more so in vivo. For the purpose of gene therapy in vivo, adeno-associated virus (AAV) vectors are extensively used because the virus can transduce many different cell types, appears to elicit little immune response, and reliably and permanently inserts its gene into a safe genomic locus on human chromosome 19. However, the packaging limit of AAV vectors is around 4.5 kb, excluding the inverted terminal repeats, and this is close to the size of the commonly used SpCas9, which is around 4.2 kb. As a result, there is little room for customization and addition of other genetic elements. Notably, it is currently not possible to package dSpCas9 with a fused effector domain into an AAV. Hence, there is an urgent need to explore alternative strategies to utilize the CRISPR-Cas system for in vivo genome engineering.

SUMMARY OF THE INVENTION

In a first aspect, the invention relates to a polypeptide having at least 50% sequence identity to *Streptococcus pyogenes* Cas9 having the amino acid sequence set forth in SEQ ID NO:1 over its entire length, wherein said polypeptide comprises at least one deletion selected from the group consisting of ΔHNH (Δ775-909), ΔRuvCIII-b (Δ1002-1074), ΔREC1-a (Δ510-655), ΔREC1-b (Δ525-587), ΔREC1-c (Δ662-710), ΔREC2 (Δ180-308), ΔREC2-a (Δ212-244), ΔREC2-b (Δ244-276), ΔREC2-c (Δ276-308), ΔREC2-d (Δ199-283), ΔREC2-e (Δ198-257), ΔREC2-f (Δ235-286), ΔREC2-g (Δ217-266), ΔREC3 (Δ498-712) and combinations thereof, wherein the position numbering is in accordance with SEQ ID NO:1, and wherein the polypeptide has CRISPR-Cas DNA-binding activity.

In various embodiments, the polypeptide comprises at least one combination of deletions selected from the group consisting of ΔREC1-a ΔHNH (Δ510-655 Δ775-909), ΔREC1-c ΔHNH (Δ662-710 Δ775-909), ΔREC2 ΔHNH (Δ180-308 Δ775-909), ΔREC2-d ΔHNH (Δ199-283 Δ775-909), ΔHNH ΔRuvCIII-b (Δ775-909 Δ1002-1074), ΔREC3 ΔHNH (Δ498-712 Δ775-909), ΔREC3 ΔHNH ΔRuvCIII-b (Δ498-712 Δ775-909 Δ1002-1074), ΔREC2 ΔREC3 ΔHNH ΔRuvCIII-b (Δ180-308 Δ498-712 Δ775-909 Δ1002-1074), and ΔREC2 ΔHNH ΔRuvCIII-b (Δ180-308 Δ775-909 Δ1002-1074).

In various embodiments, the polypeptide further comprises at least one missense mutation selected from the group consisting of G12R, T13K, T13R, N14K, N497K, T657K, T657R, N767K, T770K, T770R, Q920K, Q920R, S1109R, D1135K, D1135R, S1338R and combinations thereof.

In various embodiments, the polypeptide comprises at least one combination of modifications selected from the group consisting of ΔREC1-c ΔHNH G12R, ΔREC1-c ΔHNH T13K, ΔREC1-c ΔHNH T13R, ΔREC1-c ΔHNH N14K, ΔREC1-c ΔHNH N497K, ΔREC1-c ΔHNH T657K, ΔREC1-c ΔHNH T657R, ΔREC1-c ΔHNH N767K, ΔREC1-c ΔHNH T770K, ΔREC1-c ΔHNH T770R, ΔREC1-c ΔHNH Q920K, ΔREC1-c ΔHNH Q920R, ΔREC1-c ΔHNH S1109R, ΔREC1-c ΔHNH D1135K, ΔREC1-c ΔHNH D1135R, ΔREC1-c ΔHNH S1338R, ΔREC1-c ΔHNH T657R T13K, ΔREC1-c ΔHNH T657R N497K, ΔREC1-c ΔHNH T657R T770K, ΔREC1-c ΔHNH T657R Q920K, ΔREC1-c ΔHNH T657R S1109R, ΔREC1-c ΔHNH T657R D1135K, ΔREC2 ΔHNH ΔRuvCIII-b T13K, ΔREC2 ΔHNH ΔRuvCIII-b T657K, ΔREC2 ΔHNH ΔRuvCIII-b T657R, ΔREC2 ΔHNH ΔRuvCIII-b 770K, ΔREC2 ΔHNH ΔRuvCIII-b Q920K, ΔREC2 ΔHNH ΔRuvCIII-b S1109R, and ΔREC2 ΔHNH ΔRuvCIII-b D1135K.

In preferred embodiments, the polypeptide has the amino acid sequence set forth in any one of SEQ ID NOs:14-30.

In various embodiments, the polypeptide is further codon optimized for expression in a eukaryotic cell, preferably in a mammalian or human cell.

In a second aspect, the invention relates to a polypeptide having at least 50% sequence identity to *Staphylococcus aureus* Cas9 having the amino acid sequence set forth in SEQ ID NO:2, *Neiserria meningitides* Cas9 having the amino acid sequence set forth in SEQ ID NO:3, *Acidaminococcus* sp. Cpf1 having the amino acid sequence set forth in SEQ ID NO:4, *Streptococcus thermophilus* Cas9 having the amino acid sequence set forth in SEQ ID NO:5, *Sutterella wadsworthensis* Cas9 having the amino acid sequence set forth in SEQ ID NO:6, *Filifactor alocis* Cas9 having the amino acid sequence set forth in SEQ ID NO:7, *Lactobacillus johnsonii* Cas9 having the amino acid sequence set forth in SEQ ID NO:8, *Campylobacter lari* Cas9 having the amino acid sequence set forth in SEQ ID NO:9, *Parvibaculum lavamentivorans* Cas9 having the amino acid sequence set forth in SEQ ID NO:10, *Mycoplasma gallisepticum* Cas9 having the amino acid sequence set forth in SEQ ID NO:11, *Treponema denticola* Cas9 having the amino acid sequence set forth in SEQ ID NO:12, or Lachnospiraceae bacterium ND2006 Cpf1 having the amino acid sequence set forth in SEQ ID NO:13 over its entire length, wherein said polypeptide comprises at least one deletion of said amino acid sequence, wherein said at least one deletion corresponds to at least one deletion of SEQ ID NO:1 selected from the group consisting of ΔHNH (Δ775-909), ΔRuvCIII-b (Δ1002-1074), ΔREC1-a (Δ510-655), ΔREC1-b (Δ525-587), ΔREC1-c (Δ662-710), ΔREC2 (Δ180-308), ΔREC2-a (Δ212-244), ΔREC2-b (Δ244-276), ΔREC2-c (Δ276-308), ΔREC2-d (Δ199-283), ΔREC2-e (Δ198-257), ΔREC2-f (Δ235-286), ΔREC2-g (Δ217-266), ΔREC3 (Δ498-712) and combinations thereof, wherein the position numbering is in accordance with SEQ ID NO:1, wherein the polypeptide has CRISPR-Cas DNA-binding activity.

In various embodiments, the polypeptide comprises at least one combination of deletions selected from the group consisting of ΔREC1-a ΔHNH (Δ510-655 Δ775-909), ΔREC1-c ΔHNH (Δ662-710 Δ775-909), ΔREC2 ΔHNH (Δ180-308 Δ775-909), ΔREC2-d ΔHNH (Δ199-283 Δ775-909), ΔHNH ΔRuvCIII-b (Δ775-909 Δ1002-1074), ΔREC3 ΔHNH (Δ498-712 Δ775-909), ΔREC3 ΔHNH ΔRuvCIII-b (Δ498-712 Δ775-909 Δ1002-1074), ΔREC2 ΔREC3 ΔHNH ΔRuvCIII-b (Δ180-308 Δ498-712 Δ775-909 Δ1002-1074), and ΔREC2 ΔHNH ΔRuvCIII-b (Δ180-308 Δ775-909 Δ1002-1074).

In various embodiments, the polypeptide further comprises at least one missense mutation selected from the group consisting of G12R, T13K, T13R, N14K, N497K, T657K, T657R, N767K, T770K, T770R, Q920K, Q920R, S1109R, D1135K, D1135R, S1338R and combinations thereof, wherein the position numbering is in accordance with SEQ ID NO:1.

In various embodiments, the polypeptide comprises at least one combination of modifications selected from the group consisting of ΔREC1-c ΔHNH G12R, ΔREC1-c ΔHNH T13K, ΔREC1-c ΔHNH T13R, ΔREC1-c ΔHNH N14K, ΔREC1-c ΔHNH N497K, ΔREC1-c ΔHNH T657K, ΔREC1-c ΔHNH T657R, ΔREC1-c ΔHNH N767K, ΔREC1-c ΔHNH T770K, ΔREC1-c ΔHNH T770R, ΔREC1-c ΔHNH Q920K, ΔREC1-c ΔHNH Q920R, ΔREC1-c ΔHNH S1109R, ΔREC1-c ΔHNH D1135K, ΔREC1-c ΔHNH D1135R, ΔREC1-c ΔHNH S1338R, ΔREC1-c ΔHNH T657R T13K, ΔREC1-c ΔHNH T657R N497K, ΔREC1-c ΔHNH T657R T770K, ΔREC1-c ΔHNH T657R Q920K, ΔREC1-c ΔHNH T657R S1109R, ΔREC1-c ΔHNH T657R D1135K, ΔREC2 ΔHNH ΔRuvCIII-b T13K, ΔREC2 ΔHNH ΔRuvCIII-b T657K, ΔREC2 ΔHNH ΔRuvCIII-b T657R, ΔREC2 ΔHNH ΔRuvCIII-b 770K, ΔREC2 ΔHNH ΔRuvCIII-b Q920K, ΔREC2 ΔHNH ΔRuvCIII-b S1109R, and ΔREC2 ΔHNH ΔRuvCIII-b D1135K.

In various embodiments, the polypeptide is further codon optimized for expression in a eukaryotic cell, preferably in a mammalian or human cell, by any techniques known in the art.

In a third aspect, the invention relates to a nucleic acid molecule comprising or consisting of a nucleic acid encoding a polypeptide described herein.

In various embodiments, the nucleic acid molecule is a recombinant expression vector.

In various embodiments, the vector further comprises at least one regulatory element for controlling expression of the polypeptide.

In a fourth aspect, the invention relates to a composition comprising the polypeptide or nucleic acid molecule described herein.

In a fifth aspect, the invention relates to a method of site-specific engineering of a target DNA, the method comprising contacting the target DNA with a CRISPR-Cas system comprising the polypeptide, nucleic acid molecule or composition described herein, wherein the CRISPR-Cas DNA-binding activity of the polypeptide recruits an effector domain to the target DNA. The effector domain includes but is not limited to transcriptional regulatory domains, histone-modifying domains, chromatin remodelers, fluorescent proteins, and deaminases.

In various embodiments, the target DNA is extrachromosomal or is part of a chromosome in vitro, in vivo, or in a cell.

In various embodiments, the CRISPR-Cas nuclease activity of the polypeptide introduces a single-stranded nick or double stranded break in the target DNA.

In a sixth aspect, the invention relates to use of the polypeptide, nucleic acid molecule or composition described herein in site-directed nucleic acid modification, preferably as a component in a CRISPR-Cas system.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
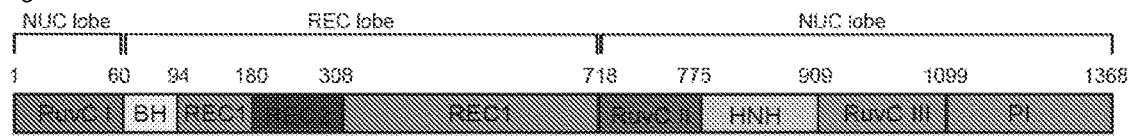
FIG. 1 shows the schematic illustration of the different domains of *Streptococcus pyogenes* Cas9 (SpCas9).
Figure 2:
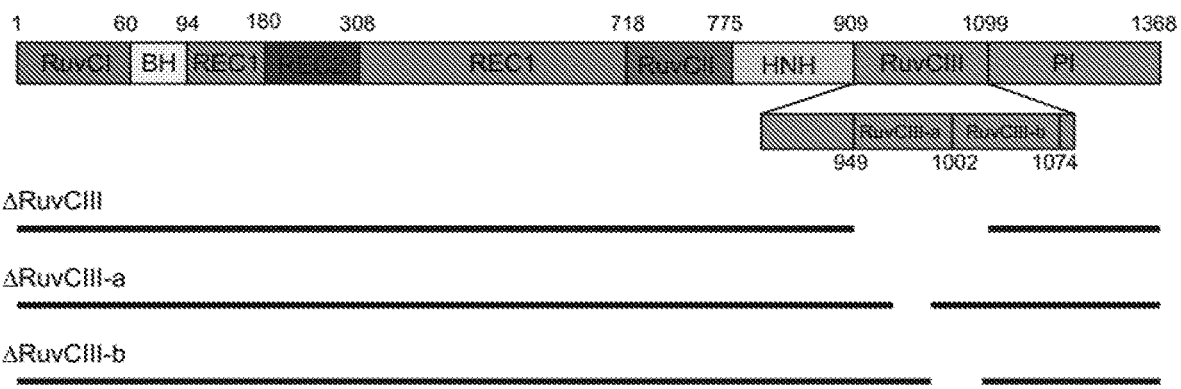
FIG. 2 shows the schematic illustration of ΔRuvCIII, ΔRuvCIII-a, and ΔRuvCIII-b.
Figure 3:
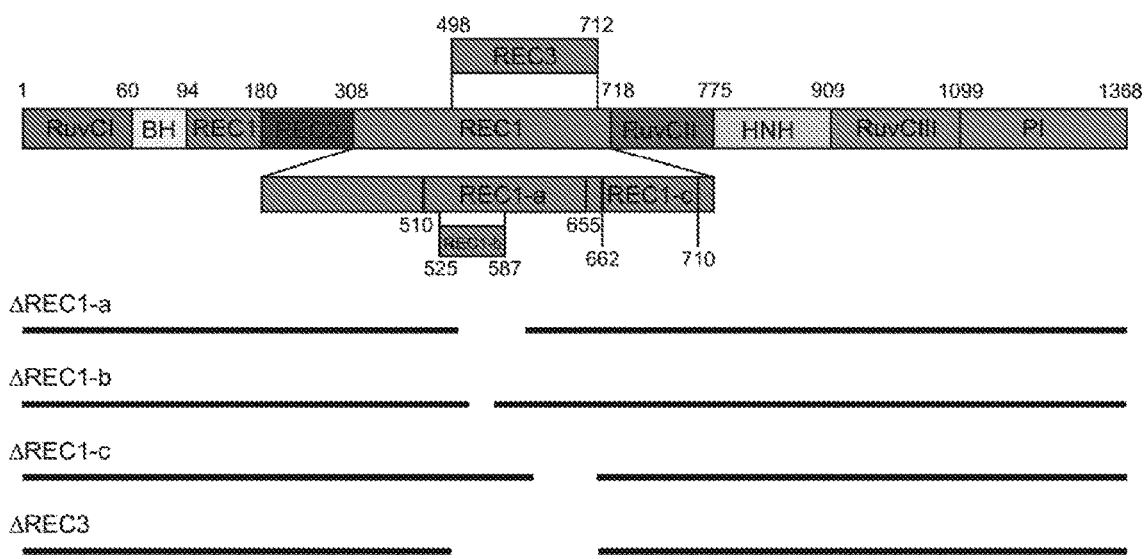
FIG. 3 shows the schematic illustration of ΔREC1-a, ΔREC1-b, ΔREC1-c, and ΔREC3.
Figure 4:
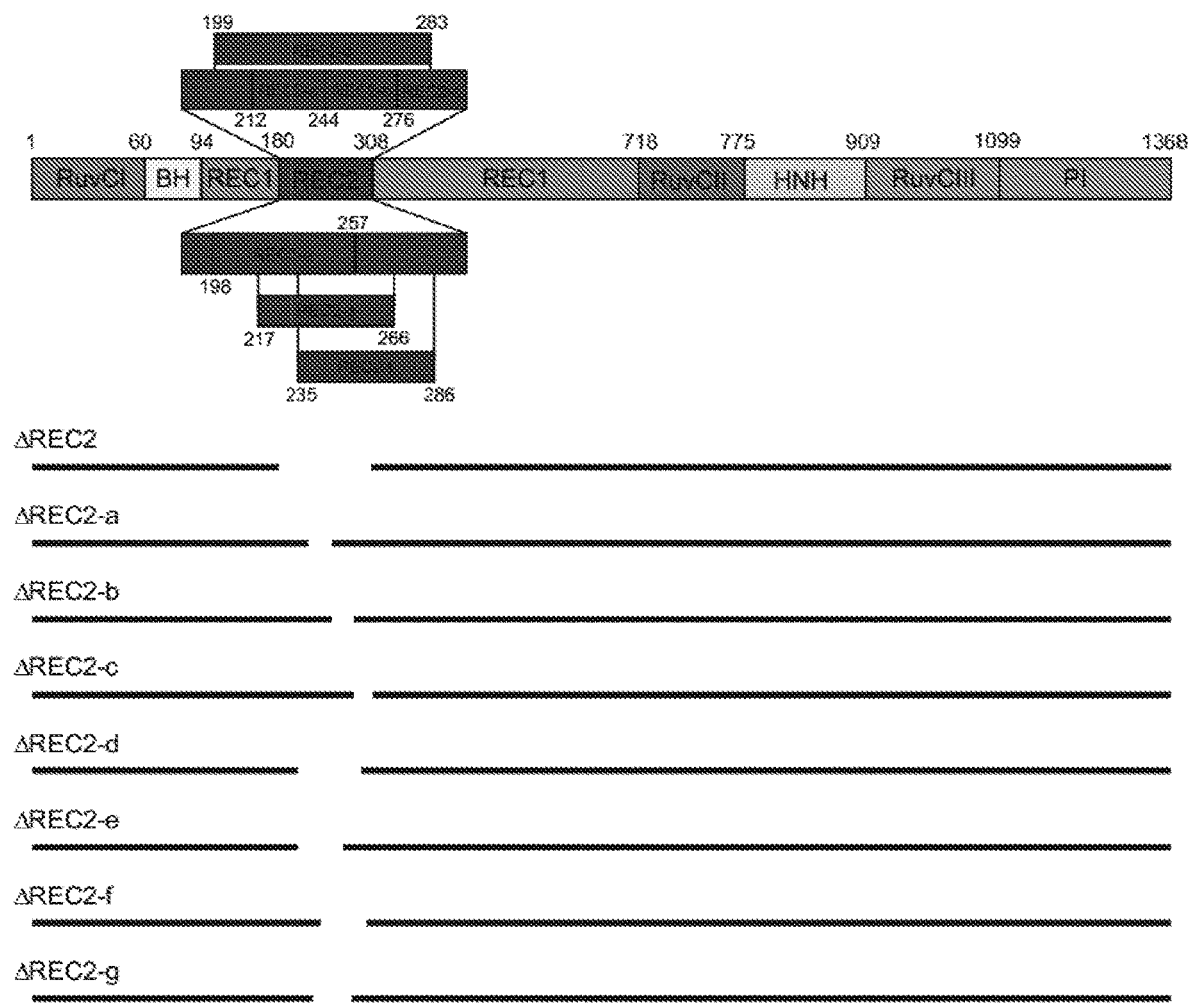
FIG. 4 shows the schematic illustration of ΔREC2, ΔREC2-a, ΔREC2-b, ΔREC2-c, ΔREC2-d, ΔREC2-e, ΔREC-f, and ΔREC2-g.
Figure 5:
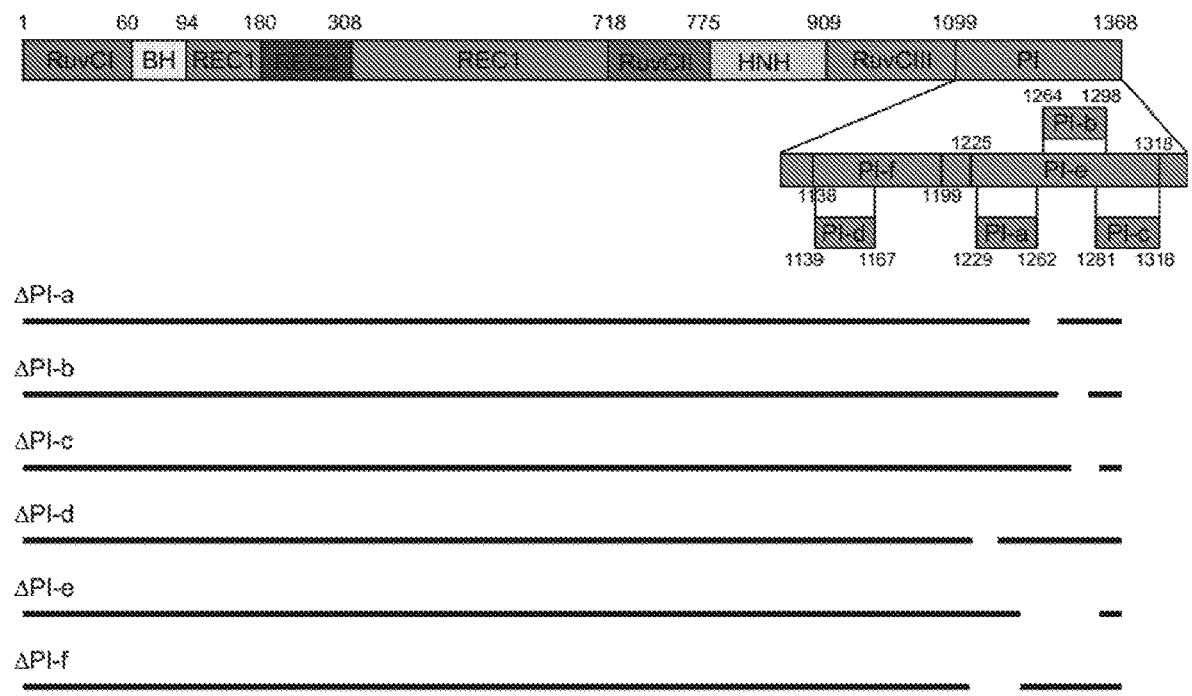
FIG. 5 shows the schematic illustration of API-a, API-b, API-c, API-d, API-e, and API-f.

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

In a first aspect, the invention relates to a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% sequence identity to *Streptococcus pyogenes* Cas9 having the amino acid sequence set forth in SEQ ID NO:1 over its entire length, wherein said polypeptide comprises at least one deletion selected from the group consisting of ΔHNH (Δ775-909), ΔRuvCIII-b (M 002-1074), ΔREC1-a (Δ510-655), ΔREC1-b (Δ525-587), ΔREC1-c (Δ662-710), ΔREC2 (Δ180-308), ΔREC2-a (Δ212-244), ΔREC2-b (Δ244-276), ΔREC2-c (Δ276-308), ΔREC2-d (Δ199-283), ΔREC2-e (Δ198-257), ΔREC2-f (Δ235-286), ΔREC2-g (Δ217-266), ΔREC3 (Δ498-712) and combinations thereof, wherein the position numbering is in accordance with SEQ ID NO:1, and wherein the polypeptide has CRISPR-Cas DNA-binding activity.

The term "polypeptide" is used interchangeably herein with "peptide" and "protein", and refers to polymers of at least two amino acids connected by peptide bonds. The polymer may comprise amino acid analogues or modified amino acids, it may be linear or branched, and it may be interrupted by non-amino acids. The term also encompasses an amino acid polymer that has been modified naturally or artificially; for example, by disulfide bond formation, glycosylation, lipidation, acetylation, phosphorylation, or any other manipulation, such as conjugation to a labeling moiety. However, in preferred embodiments, this term relates to polymers of naturally occurring amino acids, as defined below, which may optionally be modified as defined above, but does not comprise non-amino acid moieties in the polymer backbone.

The term "amino acid" as used herein refers to natural and/or unnatural or synthetic amino acids, including both the D and L optical isomers, amino acid analogs (for example norleucine is an analog of leucine) and derivatives known in the art. The term "naturally occurring amino acid", as used herein, relates to the 20 naturally occurring L-amino acids, namely Gly (G), Ala (A), Val (V), Leu (L), Ile (I), Phe (F), Cys (C), Met (M), Pro (P), Thr (T), Ser (S), Glu (E), Gln (Q), Asp (D), Asn (N), His (H), Lys (K), Arg (R), Tyr (Y), and Trp (W). Generally, in the context of the present application, the peptides and polypeptides are shown in the N- to C-terminal orientation.

The term "sequence identity" as used herein refers to the relatedness between two amino acid sequences or between two nucleotide sequences. For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows: (Identical Residues×100)/(Length of Alignment−Total Number of Gaps in Alignment).

The term "deletion" as used herein refers to a removal of a portion of one or more amino acid residues from the amino acid sequence of the reference polypeptide.

In the context of the present application, the polypeptide is truncated compared to the reference amino acid sequence in that it comprises one or more deletions described herein. A polypeptide having a deletion denoted as Δa-b is one whose amino acid residues of positions a-b inclusive are deleted, while a first fragment of amino acid residues 1 to (a−1) and a second fragment of amino acid residues (b+1) to the C-terminus are joined together by a peptide bond via an optional linker. The polypeptide has a length of at least 500 aa, preferably up to 600, 700, 800, 900, 1000, 1100, 1200, 1300, or 1360 aa.

In the context of the present application, 1, 2, 3, 4, 5, 6, 7, 8, 9, 10, 11, 12, 13, or 14 of the deletions ΔHNH (Δ775-909), ΔRuvCIII-b (Δ1002-1074), ΔREC1-a (Δ510-655), ΔREC1-b (Δ525-587), ΔREC1-c (Δ662-710), ΔREC2 (Δ180-308), ΔREC2-a (Δ212-244), ΔREC2-b (Δ244-276), ΔREC2-c (Δ276-308), ΔREC2-d (Δ199-283), ΔREC2-e (Δ198-257), ΔREC2-f (Δ235-286), ΔREC2-g (Δ217-266), and ΔREC3 (Δ498-712) are present in the polypeptide described herein, meaning that any one or more of the deletions described herein may be present in the polypeptide individually or in different combinations.

In various embodiments, the polypeptide comprises at least one combination of deletions selected from the group consisting of ΔREC1-a ΔHNH (Δ510-655 Δ775-909), ΔREC1-c ΔHNH (Δ662-710 Δ775-909), ΔREC2 ΔHNH (Δ180-308 Δ775-909), ΔREC2-d ΔHNH (Δ199-283 Δ775-909), ΔHNH ΔRuvCIII-b (Δ775-909 Δ1002-1074), ΔREC3 ΔHNH (Δ498-712 Δ775-909), ΔREC3 ΔHNH ΔRuvCIII-b (Δ498-712 Δ775-909 Δ1002-1074), ΔREC2 ΔREC3 ΔHNH ΔRuvCIII-b (Δ180-308 Δ498-712 Δ775-909 Δ1002-1074), and ΔREC2 ΔHNH ΔRuvCIII-b (Δ180-308 Δ775-909 Δ1002-1074).

In various embodiments, the polypeptide further comprises at least one missense mutation selected from the group consisting of G12R, T13K, T13R, N14K, N497K, T657K, T657R, N767K, T770K, T770R, Q920K, Q920R, S1109R, D1135K, D1135R, S1338R and combinations thereof. These mutations are intended to introduce positively charged amino acids (lysine or arginine) to enhance the binding between the polypeptide and the target DNA. They were selected based on their location in poorly conserved regions of *Streptococcus pyogenes* Cas9, which are unlikely to be important residues for the nuclease, as well as their proximity to the target DNA as revealed by computational simulations.

In various embodiments, the polypeptide comprises at least one combination of modifications selected from the group consisting of ΔREC1-c ΔHNH G12R, ΔREC1-c ΔHNH T13K, ΔREC1-c ΔHNH T13R, ΔREC1-c ΔHNH N14K, ΔREC1-c ΔHNH N497K, ΔREC1-c ΔHNH T657K, ΔREC1-c ΔHNH T657R, ΔREC1-c ΔHNH N767K, ΔREC1-c ΔHNH T770K, ΔREC1-c ΔHNH T770R, ΔREC1-c ΔHNH Q920K, ΔREC1-c ΔHNH Q920R, ΔREC1-c ΔHNH S1109R, ΔREC1-c ΔHNH D1135K, ΔREC1-c ΔHNH D1135R, ΔREC1-c ΔHNH S1338R, ΔREC1-c ΔHNH T657R T13K, ΔREC1-c ΔHNH T657R N497K, ΔREC1-c ΔHNH T657R T770K, ΔREC1-c ΔHNH T657R Q920K, ΔREC1-c ΔHNH T657R S1109R, ΔREC1-c ΔHNH T657R D1135K, ΔREC2 ΔHNH ΔRuvCIII-b T13K, ΔREC2 ΔHNH ΔRuvCIII-b T657K, ΔREC2 ΔHNH ΔRuvCIII-b T657R, ΔREC2 ΔHNH ΔRuvCIII-b 770K, ΔREC2 ΔHNH ΔRuvCIII-b Q920K, ΔREC2 ΔHNH ΔRuvCIII-b S1109R, and ΔREC2 ΔHNH ΔRuvCIII-b D1135K.

In preferred embodiments, the polypeptide has the amino acid sequence set forth in any one of SEQ ID NOs:14-30.

TABLE 1

Preferred polypeptides (catalytically dead) in accordance with the first aspect of the invention.

| Name | SEQ ID NO | Amino acid sequence |
|---|---|---|
| ΔHNH | 14 | MDKKYSIGLA IGTNSVGWAV ITDEYKVPSK KFKVLGNTDR HSIKKNLIGA LLFDSGETAE ATRLKRTARR RYTRRKNRIC YLQEIFSNEM AKVDDSFFHR LEESFLVEED KKHERHPIFG NIVDEVAYHE KYPTIYHLRK KLVDSTDKAD LRLIYLALAH MIKFRGHFLI EGDLNPDNSD VDKLFIQLVQ TYNQLFEENP INASGVDAKA ILSARLSKSR RLENLIAQLP GEKKNGLFGN LIALSLGLTP NFKSNFDLAE DAKLQLSKDT YDDDLDNLLA QIGDQYADLF LAAKNLSDAI LLSDILRVNT EITKAPLSAS MIKRYDEHHQ DLTLLKALVR QQLPEKYKEI FFDQSKNGYA GYIDGGASQE EFYKFIKPIL EKMDGTEELL VKLNREDLLR KQRTFDNGSI PHQIHLGELH AILRRQEDFY PFLKDNREKI EKILTFRIPY YVGPLARGNS RFAWMTRKSE ETITPWNFEE VVDKGASAQS FIERMTNFDK NLPNEKVLPK HSLLYEYFTV YNELTKVKYV TEGMRKPAFL SGEQKKAIVD LLFKTNRKVT VKQLKEDYFK KIECFDSVEI SGVEDRFNAS LGTYHDLLKI IKDKDFLDNE ENEDILEDIV LTLTLFEDRE MIEERLKTYA HLFDDKVMKQ LKRRRYTGWG RLSRKLINGI RDKQSGKTIL DFLKSDGFAN RNFMQLIHDD SLTFKEDIQK AQVSGQGDSL HEHIANLAGS PAIKKGILQT VKVVDELVKV MGRHKPENIV IEMARENQTT QKGQKGGGSE LDKAGFIKRQ LVETRQITKH VAQILDSRMN TKYDENDKLI REVKVITLKS KLVSDFRKDF QFYKVREINN YHHAHDAYLN AVVGTALIKK YPKLESEFVY GDYKVYDVRK MIAKSEQEIG KATAKYFFYS NIMNFFKTEI TLANGEIRKR PLIETNGETG EIVWDKGRDF ATVRKVLSMP QVNIVKKTEV QTGGFSKESI LPKRNSDKLI ARKKDWDPKK YGGFDSPTVA YSVLVVAKVE KGKSKKLKSV KELLGITIME RSSFEKNPID FLEAKGYKEV KKDLIIKLPK YSLFELENGR KRMLASAGEL QKGNELALPS KYVNFLYLAS HYEKLKGSPE DNEQKQLFVE QHKHYLDEII EQISEFSKRV ILADANLDKV LSAYNKHRDK PIREQAENII HLFTLTNLGA PAAFKYFDTT IDRKRYTSTK EVLDATLIHQ SITGLYETRI DLSQLGGD |

TABLE 1-continued

Preferred polypeptides (catalytically dead) in accordance with the first aspect of the invention.

| Name | SEQ ID NO | Amino acid sequence |
|---|---|---|
| ΔRuvCIII-b | 15 | MDKKYSIGLA IGTNSVGWAV ITDEYKVPSK KFKVLGNTDR HSIKKNLIGA LLFDSGETAE ATRLKRTARR RYTRRKNRIC YLQEIFSNEM AKVDDSFFHR LEESFLVEED KKHERHPIFG NIVDEVAYHE KYPTIYHLRK KLVDSTDKAD LRLIYLALAH MIKFRGHFLI EGDLNPDNSD VDKLFIQLVQ TYNQLFEENP INASGVDAKA ILSARLSKSR RLENLIAQLP GEKKNGLFGN LIALSLGLTP NFKSNFDLAE DAKLQLSKDT YDDDLDNLLA QIGDQYADLF LAAKNLSDAI LLSDILRVNT EITKAPLSAS MIKRYDEHHQ DLTLLKALVR QQLPEKYKEI FFDQSKNGYA GYIDGGASQE EFYKFIKPIL EKMDGTEELL VKLNREDLLR KQRTFDNGSI PHQIHLGELH AILRRQEDFY PFLKDNREKI EKILTFRIPY YVGPLARGNS RFAWMTRKSE ETITPWNFEE VVDKGASAQS FIERMTNFDK NLPNEKVLPK HSLLYEYFTV YNELTKVKYV TEGMRKPAFL SGEQKKAIVD LLFKTNRKVT VKQLKEDYFK KIECFDSVEI SGVEDRFNAS LGTYHDLLKI IKDKDFLDNE ENEDILEDIV LTLTLFEDRE MIEERLKTYA HLFDDKVMKQ LKRRRYTGWG RLSRKLINGI RDKQSGKTIL DFLKSDGFAN RNFMQLIHDD SLTFKEDIQK AQVSGQGDSL HEHIANLAGS PAIKKGILQT VKVVDELVKV MGRHKPENIV IEMARENQTT QKGQKNSRER MKRIEEGIKE LGSQILKEHP VENTQLQNEK LYLYYLQNGR DMYVDQELDI NRLSDYDVAA IVPQSFLKDD SIDNKVLTRS DKARGKSDNV PSEEVVKKMK NYWRQLLNAK LITQRKFDNL TKAERGGLSE LDKAGFIKRQ LVETRQITKH VAQILDSRMN TKYDENDKLI REVKVITLKS KLVSDFRKDF QFYKVREINN YHHAHDAYLN AVVGTALIKK YPGGGSGGGS DKGRDFATVR KVLSMPQVNI VKKTEVQTGG FSKESILPKR NSDKLIARKK DWDPKKYGGF DSPTVAYSVL VVAKVEKGKS KKLKSVKELL GITIMERSSF EKNPIDFLEA KGYKEVKKDL IIKLPKYSLF ELENGRKRML ASAGELQKGN ELALPSKYVN FLYLASHYEK LKGSPEDNEQ KQLFVEQHKH YLDEIIEQIS EFSKRVILAD ANLDKVLSAY NKHRDKPIRE QAENIIHLFT LTNLGAPAAF KYFDTTIDRK RYTSTKEVLD ATLIHQSITG LYETRIDLSQ LGGD |
| ΔHNH ΔRuvCIII-b | 16 | MDKKYSIGLA IGTNSVGWAV ITDEYKVPSK KFKVLGNTDR HSIKKNLIGA LLFDSGETAE ATRLKRTARR RYTRRKNRIC YLQEIFSNEM AKVDDSFFHR LEESFLVEED KKHERHPIFG NIVDEVAYHE KYPTIYHLRK KLVDSTDKAD LRLIYLALAH MIKFRGHFLI EGDLNPDNSD VDKLFIQLVQ TYNQLFEENP INASGVDAKA ILSARLSKSR RLENLIAQLP GEKKNGLFGN LIALSLGLTP NFKSNFDLAE DAKLQLSKDT YDDDLDNLLA QIGDQYADLF LAAKNLSDAI LLSDILRVNT EITKAPLSAS MIKRYDEHHQ DLTLLKALVR QQLPEKYKEI FFDQSKNGYA GYIDGGASQE EFYKFIKPIL EKMDGTEELL VKLNREDLLR KQRTFDNGSI PHQIHLGELH AILRRQEDFY PFLKDNREKI EKILTFRIPY YVGPLARGNS RFAWMTRKSE ETITPWNFEE VVDKGASAQS FIERMTNFDK NLPNEKVLPK HSLLYEYFTV YNELTKVKYV TEGMRKPAFL SGEQKKAIVD LLFKTNRKVT VKQLKEDYFK KIECFDSVEI SGVEDRFNAS LGTYHDLLKI IKDKDFLDNE ENEDILEDIV LTLTLFEDRE MIEERLKTYA HLFDDKVMKQ LKRRRYTGWG RLSRKLINGI RDKQSGKTIL DFLKSDGFAN RNFMQLIHDD SLTFKEDIQK AQVSGQGDSL HEHIANLAGS PAIKKGILQT VKVVDELVKV MGRHKPENIV IEMARENQTT QKGQKGGGSE LDKAGFIKRQ LVETRQITKH VAQILDSRMN TKYDENDKLI REVKVITLKS KLVSDFRKDF QFYKVREINN YHHAHDAYLN AVVGTALIKK YPGGGSGGGS DKGRDFATVR KVLSMPQVNI VKKTEVQTGG FSKESILPKR NSDKLIARKK DWDPKKYGGF DSPTVAYSVL VVAKVEKGKS KKLKSVKELL GITIMERSSF EKNPIDFLEA KGYKEVKKDL IIKLPKYSLF ELENGRKRML ASAGELQKGN ELALPSKYVN FLYLASHYEK LKGSPEDNEQ KQLFVEQHKH YLDEIIEQIS EFSKRVILAD ANLDKVLSAY NKHRDKPIRE QAENIIHLFT LTNLGAPAAF KYFDTTIDRK RYTSTKEVLD ATLIHQSITG LYETRIDLSQ LGGD |
| ΔREC1-a | 17 | MDKKYSIGLA IGTNSVGWAV ITDEYKVPSK KFKVLGNTDR HSIKKNLIGA LLFDSGETAE ATRLKRTARR RYTRRKNRIC YLQEIFSNEM AKVDDSFFHR LEESFLVEED KKHERHPIFG NIVDEVAYHE KYPTIYHLRK KLVDSTDKAD LRLIYLALAH MIKFRGHFLI EGDLNPDNSD VDKLFIQLVQ TYNQLFEENP INASGVDAKA ILSARLSKSR RLENLIAQLP GEKKNGLFGN LIALSLGLTP NFKSNFDLAE DAKLQLSKDT YDDDLDNLLA QIGDQYADLF LAAKNLSDAI LLSDILRVNT EITKAPLSAS MIKRYDEHHQ DLTLLKALVR QQLPEKYKEI FFDQSKNGYA GYIDGGASQE EFYKFIKPIL EKMDGTEELL VKLNREDLLR KQRTFDNGSI PHQIHLGELH AILRRQEDFY PFLKDNREKI EKILTFRIPY YVGPLARGNS RFAWMTRKSE ETITPWNFEE VVDKGASAQS FIERMTNFDK NLPNEKVLPK GGGSYTGWGR LSRKLINGIR DKQSGKTILD FLKSDGFANR NFMQLIHDDS LTFKEDIQKA QVSGQGDSLH EHIANLAGSP AIKKGILQTV KVVDELVKVM GRHKPENIVI EMARENQTTQ KGQKNSRERM KRIEEGIKEL GSQILKEHPV ENTQLQNEKL YLYYLQNGRD MYVDQELDIN RLSDYDVAAI VPQSFLKDDS IDNKVLTRSD KARGKSDDNVP SEEVVKKMKN YWRQLLNAKL ITQRKFDNLT KAERGGLSEL DKAGFIKRQL VETRQITKHV AQILDSRMNT KYDENDKLIR EVKVITLKSK LVSDFRKDFQ FYKVREINNY HHAHDAYLNA VVGTALIKKY PKLESEFVYG DYKVYDVRKM IAKSEQEIGK ATAKYFFYSN IMNFFKTEIT LANGEIRKRP LIETNGETGE IVWDKGRDFA TVRKVLSMPQ VNIVKKTEVQ TGGFSKESIL PKRNSDKLIA RKKDWDPKKY GGFDSPTVAY |

TABLE 1-continued

Preferred polypeptides (catalytically dead) in accordance with the first aspect of the invention.

| Name | SEQ ID NO | Amino acid sequence |
|---|---|---|
| | | SVLVVAKVEK GKSKKLKSVK ELLGITIMER SSFEKNPIDF LEAKGYKEVK<br>KDLIIKLPKY SLFELENGRK RMLASAGELQ KGNELALPSK YVNFLYLASH<br>YEKLKGSPED NEQKQLFVEQ HKHYLDEIIE QISEFSKRVI LADANLDKVL<br>SAYNKHRDKP IREQAENIIH LFTLTNLGAP AAFKYFDTTI DRKRYTSTKE<br>VLDATLIHQS ITGLYETRID LSQLGGD |
| ΔREC1-c | 18 | MDKKYSIGLA IGTNSVGWAV ITDEYKVPSK KFKVLGNTDR HSIKKNLIGA<br>LLFDSGETAE ATRLKRTARR RYTRRKNRIC YLQEIFSNEM AKVDDSFFHR<br>LEESFLVEED KKHERHPIFG NIVDEVAYHE KYPTIYHLRK KLVDSTDKAD<br>LRLIYLALAH MIKFRGHFLI EGDLNPDNSD VDKLFIQLVQ TYNQLFEENP<br>INASGVDAKA ILSARLSKSR RLENLIAQLP GEKKNGLFGN LIALSLGLTP<br>NFKSNFDLAE DAKLQLSKDT YDDDLDNLLA QIGDQYADLF LAAKNLSDAI<br>LLSDILRVNT EITKAPLSAS MIKRYDEHHQ DLTLLKALVR QQLPEKYKEI<br>FFDQSKNGYA GYIDGGASQE EFYKFIKPIL EKMDGTEELL VKLNREDLLR<br>KQRTFDNGSI PHQIHLGELH AILRRQEDFY PFLKDNREKI EKILTFRIPY<br>YVGPLARGNS RFAWMTRKSE ETITPWNFEE VVDKGASAQS FIERMTNFDK<br>NLPNEKVLPK HSLLYEYFTV YNELTKVKYV TEGMRKPAFL SGEQKKAIVD<br>LLFKTNRKVT VKQLKEDYFK KIECFDSVEI SGVEDRFNAS LGTYHDLLKI<br>IKDKDFLDNE ENEDILEDIV LTLTLFEDRE MIEERLKTYA HLFDDKVMKQ<br>LKRRRYTGWG RLGGGSAQVS GQGDSLHEHI ANLAGSPAIK KGILQTVKVV<br>DELVKVMGRH KPENIVIEMA RENQTTQKGQ KNSRERMKRI EEGIKELGSQ<br>ILKEHPVENT QLQNEKLYLY YLQNGRDMYV DQELDINRLS DYDVAAIVPQ<br>SFLKDDSIDN KVLTRSDKAR GKSDNVPSEE VVKKMKNYWR QLLNAKLITQ<br>RKFDNLTKAE RGGLSELDKA GFIKRQLVET RQITKHVAQI LDSRMNTKYD<br>ENDKLIREVK VITLKSKLVS DFRKDFQFYK VREINNYHHA HDAYLNAVVG<br>TALIKKYPKL ESEFVYGDYK VYDVRKMIAK SEQEIGKATA KYFFYSNIMN<br>FFKTEITLAN GEIRKRPLIE TNGETGEIVW DKGRDFATVR KVLSMPQVNI<br>VKKTEVQTGG FSKESILPKR NSDKLIARKK DWDPKKYGGF DSPTVAYSVL<br>VVAKVEKGKS KKLKSVKELL GITIMERSSF EKNPIDFLEA KGYKEVKKDL<br>IIKLPKYSLF ELENGRKRML ASAGELQKGN ELALPSKYVN FLYLASHYEK<br>LKGSPEDNEQ KQLFVEQHKH YLDEIIEQIS EFSKRVILAD ANLDKVLSAY<br>NKHRDKPIRE QAENIIHLFT LTNLGAPAAF KYFDTTIDRK RYTSTKEVLD<br>ATLIHQSITG LYETRIDLSQ LGGD |
| ΔREC2 | 19 | MDKKYSIGLA IGTNSVGWAV ITDEYKVPSK KFKVLGNTDR HSIKKNLIGA<br>LLFDSGETAE ATRLKRTARR RYTRRKNRIC YLQEIFSNEM AKVDDSFFHR<br>LEESFLVEED KKHERHPIFG NIVDEVAYHE KYPTIYHLRK KLVDSTDKAD<br>LRLIYLALAH MIKFRGHFLI EGDLNPDNSD NTEITKAPLS ASMIKRYDEH<br>HQDLTLLKAL VRQQLPEKYK EIFFDQSKNG YAGYIDGGAS QEEFYKFIKP<br>ILEKMDGTEE LLVKLNREDL LRKQRTFDNG SIPHQIHLGE LHAILRRQED<br>FYPFLKDNRE KIEKILTFRI PYYVGPLARG NSRFAWMTRK SEETITPWNF<br>EEVVDKGASA QSFIERMTNF DKNLPNEKVL PKHSLLYEYF TVYNELTKVK<br>YVTEGMRKPA FLSGEQKKAI VDLLFKTNRK VTVKQLKEDY FKKIECFDSV<br>EISGVEDRFN ASLGTYHDLL KIIKDKDFLD NEENEDILED IVLTLTLFED<br>REMIEERLKT YAHLFDDKVM KQLKRRRYTG WGRLSRKLIN GIRDKQSGKT<br>ILDFLKSDGF ANRNFMQLIH DDSLTFKEDI QKAQVSGQGD SLHEHIANLA<br>GSPAIKKGIL QTVKVVDELV KVMGRHKPEN IVIEMARENQ TTQKGQKNSR<br>ERMKRIEEGI KELGSQILKE HPVENTQLQN EKLYLYLQN GRDMYVDQEL<br>DINRLSDYDV AAIVPQSFLK DDSIDNKVLT RSDKARGKSD NVPSEEVVKK<br>MKNYWRQLLN AKLITQRKFD NLTKAERGGL SELDKAGFIK RQLVETRQIT<br>KHVAQILDSR MNTKYDENDK LIREVKVITL KSKLVSDFRK DFQFYKVREI<br>NNYHHAHDAY LNAVVGTALI KKYPKLESEF VYGDYKVYDV RKMIAKSEQE<br>IGKATAKYFF YSNIMNFFKT EITLANGEIR KRPLIETNGE TGEIVWDKGR<br>DFATVRKVLS MPQVNIVKKT EVQTGGFSKE SILPKRNSDK LIARKKDWDP<br>KKYGGFDSPT VAYSVLVVAK VEKGKSKKLK SVKELLGITI MERSSFEKNP<br>IDFLEAKGYK EVKKDLIIKL PKYSLFELEN GRKRMLASAG ELQKGNELAL<br>PSKYVNFLYL ASHYEKLKGS PEDNEQKQLF VEQHKHYLDE IIEQISEFSK<br>RVILADANLD KVLSAYNKHR DKPIREQAEN IIHLFTLTNL GAPAAFKYFD<br>TTIDRKRYTS TKEVLDATLI HQSITGLYET RIDLSQLGGD |
| ΔHNH ΔREC1-a | 20 | MDKKYSIGLA IGTNSVGWAV ITDEYKVPSK KFKVLGNTDR HSIKKNLIGA<br>LLFDSGETAE ATRLKRTARR RYTRRKNRIC YLQEIFSNEM AKVDDSFFHR<br>LEESFLVEED KKHERHPIFG NIVDEVAYHE KYPTIYHLRK KLVDSTDKAD<br>LRLIYLALAH MIKFRGHFLI EGDLNPDNSD VDKLFIQLVQ TYNQLFEENP<br>INASGVDAKA ILSARLSKSR RLENLIAQLP GEKKNGLFGN LIALSLGLTP<br>NFKSNFDLAE DAKLQLSKDT YDDDLDNLLA QIGDQYADLF LAAKNLSDAI<br>LLSDILRVNT EITKAPLSAS MIKRYDEHHQ DLTLLKALVR QQLPEKYKEI<br>FFDQSKNGYA GYIDGGASQE EFYKFIKPIL EKMDGTEELL VKLNREDLLR<br>KQRTFDNGSI PHQIHLGELH AILRRQEDFY PFLKDNREKI EKILTFRIPY<br>YVGPLARGNS RFAWMTRKSE ETITPWNFEE VVDKGASAQS FIERMTNFDK<br>NLPNEKVLPK GGGSYTGWGR LSRKLINGIR DKQSGKTILD FLKSDGFANR<br>NFMQLIHDDS LTFKEDIQKA QVSGQGDSLH EHIANLAGSP AIKKGILQTV<br>KVVDELVKVM GRHKPENIVI EMARENQTTQ KGQKGGGSEL DKAGFIKRQL<br>VETRQITKHV AQILDSRMNT KYDENDKLIR EVKVITLKSK LVSDFRKDFQ |

TABLE 1-continued

Preferred polypeptides (catalytically dead) in accordance with the first aspect of the invention.

| Name | SEQ ID NO | Amino acid sequence | | | |
|---|---|---|---|---|---|
| | | FYKVREINNY | HHAHDAYLNA | VVGTALIKKY | PKLESEFVYG | DYKVYDVRKM |
| | | IAKSEQEIGK | ATAKYFFYSN | IMNFFKTEIT | LANGEIRKRP | LIETNGETGE |
| | | IVWDKGRDFA | TVRKVLSMPQ | VNIVKKTEVQ | TGGFSKESIL | PKRNSDKLIA |
| | | RKKDWDPKKY | GGFDSPTVAY | SVLVVAKVEK | GKSKKLKSVK | ELLGITIMER |
| | | SSFEKNPIDF | LEAKGYKEVK | KDLIIKLPKY | SLFELENGRK | RMLASAGELQ |
| | | KGNELALPSK | YVNFLYLASH | YEKLKGSPED | NEQKQLFVEQ | HKHYLDEIIE |
| | | QISEFSKRVI | LADANLDKVL | SAYNKHRDKP | IREQAENIIH | LFTLTNLGAP |
| | | AAFKYFDTTI | DRKRYTSTKE | VLDATLIHQS | ITGLYETRID | LSQLGGD |
| ΔHNH ΔREC1-c | 21 | MDKKYSIGLA | IGTNSVGWAV | ITDEYKVPSK | KFKVLGNTDR | HSIKKNLIGA |
| | | LLFDSGETAE | ATRLKRTARR | RYTRRKNRIC | YLQEIFSNEM | AKVDDSFFHR |
| | | LEESFLVEED | KKHERHPIFG | NIVDEVAYHE | KYPTIYHLRK | KLVDSTDKAD |
| | | LRLIYLALAH | MIKFRGHFLI | EGDLNPDNSD | VDKLFIQLVQ | TYNQLFEENP |
| | | INASGVDAKA | ILSARLSKSR | RLENLIAQLP | GEKKNGLFGN | LIALSLGLTP |
| | | NFKSNFDLAE | DAKLQLSKDT | YDDDLDNLLA | QIGDQYADLF | LAAKNLSDAI |
| | | LLSDILRVNT | EITKAPLSAS | MIKRYDEHHQ | DLTLLKALVR | QQLPEKYKEI |
| | | FFDQSKNGYA | GYIDGGASQE | EFYKFIKPIL | EKMDGTEELL | VKLNREDLLR |
| | | KQRTFDNGSI | PHQIHLGELH | AILRRQEDFY | PFLKDNREKI | EKILTFRIPY |
| | | YVGPLARGNS | RFAWMTRKSE | ETITPWNFEE | VVDKGASAQS | FIERMTNFDK |
| | | NLPNEKVLPK | HSLLYEYFTV | YNELTKVKYV | TEGMRKPAFL | SGEQKKAIVD |
| | | LLFKTNRKVT | VKQLKEDYFK | KIECFDSVEI | SGVEDRFNAS | LGTYHDLLKI |
| | | IKDKDFLDNE | ENEDILEDIV | LTLTLFEDRE | MIEERLKTYA | HLFDDKVMKQ |
| | | LKRRRYTGWG | RLGGGSAQVS | GQGDSLHEHI | ANLAGSPAIK | KGILQTVKVV |
| | | DELVKVMGRH | KPENIVIEMA | RENQTTQKGQ | KGGGSELDKA | GFIKRQLVET |
| | | RQITKHVAQI | LDSRMNTKYD | ENDKLIREVK | VITLKSKLVS | DFRKDFQFYK |
| | | VREINNYHHA | HDAYLNAVVG | TALIKKYPKL | ESEFVYGDYK | VYDVRKMIAK |
| | | SEQEIGKATA | KYFFYSNIMN | FFKTEITLAN | GEIRKRPLIE | TNGETGEIVW |
| | | DKGRDFATVR | KVLSMPQVNI | VKKTEVQTGG | FSKESILPKR | NSDKLIARKK |
| | | DWDPKKYGGF | DSPTVAYSVL | VVAKVEKGKS | KKLKSVKELL | GITIMERSSF |
| | | EKNPIDFLEA | KGYKEVKKDL | IIKLPKYSLF | ELENGRKRML | ASAGELQKGN |
| | | ELALPSKYVN | FLYLASHYEK | LKGSPEDNEQ | KQLFVEQHKH | YLDEIIEQIS |
| | | EFSKRVILAD | ANLDKVLSAY | NKHRDKPIRE | QAENIIHLFT | LTNLGAPAAF |
| | | KYFDTTIDRK | RYTSTKEVLD | ATLIHQSITG | LYETRIDLSQ | LGGD |
| ΔHNH ΔREC2 | 22 | MDKKYSIGLA | IGTNSVGWAV | ITDEYKVPSK | KFKVLGNTDR | HSIKKNLIGA |
| | | LLFDSGETAE | ATRLKRTARR | RYTRRKNRIC | YLQEIFSNEM | AKVDDSFFHR |
| | | LEESFLVEED | KKHERHPIFG | NIVDEVAYHE | KYPTIYHLRK | KLVDSTDKAD |
| | | LRLIYLALAH | MIKFRGHFLI | EGDLNPDNSD | NTEITKAPLS | ASMIKRYDEH |
| | | HQDLTLLKAL | VRQQLPEKYK | EIFFDQSKNG | YAGYIDGGAS | QEEFYKFIKP |
| | | ILEKMDGTEE | LLVKLNREDL | LRKQRTFDNG | SIPHQIHLGE | LHAILRRQED |
| | | FYPFLKDNRE | KIEKILTFRI | PYYVGPLARG | NSRFAWMTRK | SEETITPWNF |
| | | EEVVDKGASA | QSFIERMTNF | DKNLPNEKVL | PKHSLLYEYF | TVYNELTKVK |
| | | YVTEGMRKPA | FLSGEQKKAI | VDLLFKTNRK | VTVKQLKEDY | FKKIECFDSV |
| | | EISGVEDRFN | ASLGTYHDLL | KIIKDKDFLD | NEENEDILED | IVLTLTLFED |
| | | REMIEERLKT | YAHLFDDKVM | KQLKRRRYTG | WGRLSRKLIN | GIRDKQSGKT |
| | | ILDFLKSDGF | ANRNFMQLIH | DDSLTFKEDI | QKAQVSGQGD | SLHEHIANLA |
| | | GSPAIKKGIL | QTVKVVDELV | KVMGRHKPEN | IVIEMARENQ | TTQKGQKGGG |
| | | SELDKAGFIK | RQLVETRQIT | KHVAQILDSR | MNTKYDENDK | LIREVKVITL |
| | | KSKLVSDFRK | DFQFYKVREI | NNYHHAHDAY | LNAVVGTALI | KKYPKLESEF |
| | | VYGDYKVYDV | RKMIAKSEQE | IGKATAKYFF | YSNIMNFFKT | EITLANGEIR |
| | | KRPLIETNGE | TGEIVWDKGR | DFATVRKVLS | MPQVNIVKKT | EVQTGGFSKE |
| | | SILPKRNSDK | LIARKKDWDP | KKYGGFDSPT | VAYSVLVVAK | VEKGKSKKLK |
| | | SVKELLGITI | MERSSFEKNP | IDFLEAKGYK | EVKKDLIIKL | PKYSLFELEN |
| | | GRKRMLASAG | ELQKGNELAL | PSKYVNFLYL | ASHYEKLKGS | PEDNEQKQLF |
| | | VEQHKHYLDE | IIEQISEFSK | RVILADANLD | KVLSAYNKHR | DKPIREQAEN |
| | | IIHLFTLTNL | GAPAAFKYFD | TTIDRKRYTS | TKEVLDATLI | HQSITGLYET |
| | | RIDLSQLGGD | | | | |
| ΔHNH ΔRuvCIII-b ΔREC2 | 23 | MDKKYSIGLA | IGTNSVGWAV | ITDEYKVPSK | KFKVLGNTDR | HSIKKNLIGA |
| | | LLFDSGETAE | ATRLKRTARR | RYTRRKNRIC | YLQEIFSNEM | AKVDDSFFHR |
| | | LEESFLVEED | KKHERHPIFG | NIVDEVAYHE | KYPTIYHLRK | KLVDSTDKAD |
| | | LRLIYLALAH | MIKFRGHFLI | EGDLNPDNSD | NTEITKAPLS | ASMIKRYDEH |
| | | HQDLTLLKAL | VRQQLPEKYK | EIFFDQSKNG | YAGYIDGGAS | QEEFYKFIKP |
| | | ILEKMDGTEE | LLVKLNREDL | LRKQRTFDNG | SIPHQIHLGE | LHAILRRQED |
| | | FYPFLKDNRE | KIEKILTFRI | PYYVGPLARG | NSRFAWMTRK | SEETITPWNF |
| | | EEVVDKGASA | QSFIERMTNF | DKNLPNEKVL | PKHSLLYEYF | TVYNELTKVK |
| | | YVTEGMRKPA | FLSGEQKKAI | VDLLFKTNRK | VTVKQLKEDY | FKKIECFDSV |
| | | EISGVEDRFN | ASLGTYHDLL | KIIKDKDFLD | NEENEDILED | IVLTLTLFED |
| | | REMIEERLKT | YAHLFDDKVM | KQLKRRRYTG | WGRLSRKLIN | GIRDKQSGKT |
| | | ILDFLKSDGF | ANRNFMQLIH | DDSLTFKEDI | QKAQVSGQGD | SLHEHIANLA |
| | | GSPAIKKGIL | QTVKVVDELV | KVMGRHKPEN | IVIEMARENQ | TTQKGQKGGG |
| | | SELDKAGFIK | RQLVETRQIT | KHVAQILDSR | MNTKYDENDK | LIREVKVITL |
| | | KSKLVSDFRK | DFQFYKVREI | NNYHHAHDAY | LNAVVGTALI | KKYPGGGSGG |
| | | GSDKGRDFAT | VRKVLSMPQV | NIVKKTEVQT | GGFSKESILP | KRNSDKLIAR |

TABLE 1-continued

Preferred polypeptides (catalytically dead) in accordance with the first aspect of the invention.

| Name | SEQ ID NO | Amino acid sequence |
|---|---|---|
| | | KKDWDPKKYG GFDSPTVAYS VLVVAKVEKG KSKKLKSVKE LLGITIMERS<br>SFEKNPIDFL EAKGYKEVKK DLIIKLPKYS LFELENGRKR MLASAGELQK<br>GNELALPSKY VNFLYLASHY EKLKGSPEDN EQKQLFVEQH KHYLDEIIEQ<br>ISEFSKRVIL ADANLDKVLS AYNKHRDKPI REQAENIIHL FTLTNLGAPA<br>AFKYFDTTID RKRYTSTKEV LDATLIHQSI TGLYETRIDL SQLGGD |
| ΔHNH ΔRuvCIII-b ΔREC2 ΔREC1-a | 24 | MDKKYSIGLA IGTNSVGWAV ITDEYKVPSK KFKVLGNTDR HSIKKNLIGA<br>LLFDSGETAE ATRLKRTARR RYTRRKNRIC YLQEIFSNEM AKVDDSFFHR<br>LEESFLVEED KKHERHPIFG NIVDEVAYHE KYPTIYHLRK KLVDSTDKAD<br>LRLIYLALAH MIKFRGHFLI EGDLNPDNSD NTEITKAPLS ASMIKRYDEH<br>HQDLTLLKAL VRQQLPEKYK EIFFDQSKNG YAGYIDGGAS QEEFYKFIKP<br>ILEKMDGTEE LLVKLNREDL LRKQRTFDNG SIPHQIHLGE LHAILRRQED<br>FYPFLKDNRE KIEKILTFRI PYYVGPLARG NSRFAWMTRK SEETITPWNF<br>EEVVDKGASA QSFIERMTNF DKNLPNEKVL PKGGGSYTGW GRLSRKLING<br>IRDKQSGKTI LDFLKSDGFA NRNFMQLIHD DSLTFKEDIQ KAQVSGQGDS<br>LHEHIANLAG SPAIKKGILQ TVKVVDELVK VMGRHKPENI VIEMARENQT<br>TQKGQKGGGS ELDKAGFIKR QLVETRQITK HVAQILDSRM NTKYDENDKL<br>IREVKVITLK SKLVSDFRKD FQFYKVREIN NYHHAHDAYL NAVVGTALIK<br>KYPGGGSGGG SDKGRDFATV RKVLSMPQVN IVKKTEVQTG GFSKESILPK<br>RNSDKLIARK KDWDPKKYGG FDSPTVAYSV LVVAKVEKGK SKKLKSVKEL<br>LGITIMERSS FEKNPIDFLE AKGYKEVKKD LIIKLPKYSL FELENGRKRM<br>LASAGELQKG NELALPSKYV NFLYLASHYE KLKGSPEDNE QKQLFVEQHK<br>HYLDEIIEQI SEFSKRVILA DANLDKVLSA YNKHRDKPIR EQAENIIHLF<br>TLTNLGAPAA FKYFDTTIDR KRYTSTKEVL DATLIHQSIT GLYETRIDLS<br>QLGGD |
| ΔHNH ΔRuvCIII-b ΔREC2 ΔREC1-c | 25 | MDKKYSIGLA IGTNSVGWAV ITDEYKVPSK KFKVLGNTDR HSIKKNLIGA<br>LLFDSGETAE ATRLKRTARR RYTRRKNRIC YLQEIFSNEM AKVDDSFFHR<br>LEESFLVEED KKHERHPIFG NIVDEVAYHE KYPTIYHLRK KLVDSTDKAD<br>LRLIYLALAH MIKFRGHFLI EGDLNPDNSD NTEITKAPLS ASMIKRYDEH<br>HQDLTLLKAL VRQQLPEKYK EIFFDQSKNG YAGYIDGGAS QEEFYKFIKP<br>ILEKMDGTEE LLVKLNREDL LRKQRTFDNG SIPHQIHLGE LHAILRRQED<br>FYPFLKDNRE KIEKILTFRI PYYVGPLARG NSRFAWMTRK SEETITPWNF<br>EEVVDKGASA QSFIERMTNF DKNLPNEKVL PKHSLLYEYF TVVNELTKVK<br>YVTEGMRKPA FLSGEQKKAI VDLLFKTNRK VTVKQLKEDY FKKIECFDSV<br>EISGVEDRFN ASLGTYHDLL KIIKDKDFLD NEENEDILED IVLTLTLFED<br>REMIEERLKT YAHLFDDKVM KQLKRRRYTG WGRLGGGSAQ VSGQGDSLHE<br>HIANLAGSPA IKKGILQTVK VVDELVKVMG RHKPENIVIE MARENQTTQK<br>GQKGGGSELD KAGFIKRQLV ETRQITKHVA QILDSRMNTK YDENDKLIRE<br>VKVITLKSKL VSDFRKDFQF YKVREINNYH HAHDAYLNAV VGTALIKKYP<br>GGGSGGGSDK GRDFATVRKV LSMPQVNIVK KTEVQTGGFS KESILPKRNS<br>DKLIARKKDW DPKKYGGFDS PTVAYSVLVV AKVEKGKSKK LKSVKELLGI<br>TIMERSSFEK NPIDFLEAKG YKEVKKDLII KLPKYSLFEL ENGRKRMLAS<br>AGELQKGNEL ALPSKYVNFL YLASHYEKLK GSPEDNEQKQ LFVEQHKHYL<br>DEIIEQISEF SKRVILADAN LDKVLSAYNK HRDKPIREQA ENIIHLFTLT<br>NLGAPAAFKY FDTTIDRKRY TSTKEVLDAT LIHQSITGLY ETRIDLSQLG<br>GD |
| ΔHNH ΔRuvCIII-b ΔREC2 ΔREC1-a ΔREC1-c | 26 | MDKKYSIGLA IGTNSVGWAV ITDEYKVPSK KFKVLGNTDR HSIKKNLIGA<br>LLFDSGETAE ATRLKRTARR RYTRRKNRIC YLQEIFSNEM AKVDDSFFHR<br>LEESFLVEED KKHERHPIFG NIVDEVAYHE KYPTIYHLRK KLVDSTDKAD<br>LRLIYLALAH MIKFRGHFLI EGDLNPDNSD NTEITKAPLS ASMIKRYDEH<br>HQDLTLLKAL VRQQLPEKYK EIFFDQSKNG YAGYIDGGAS QEEFYKFIKP<br>ILEKMDGTEE LLVKLNREDL LRKQRTFDNG SIPHQIHLGE LHAILRRQED<br>FYPFLKDNRE KIEKILTFRI PYYVGPLARG NSRFAWMTRK SEETITPWNF<br>EEVVDKGASA QSFIERMTNF DKNLPNEKVL PKGGGSYTGW GRLGGGSAQV<br>SGQGDSLHEH IANLAGSPAI KKGILQTVKV VDELVKVMGR HKPENIVIEM<br>ARENQTTQKG QKGGGSELDK AGFIKRQLVE TRQITKHVAQ ILDSRMNTKY<br>DENDKLIREV KVITLKSKLV SDFRKDFQFY KVREINNYHH AHDAYLNAVV<br>GTALIKKYPG GGSGGGSDKG RDFATVRKVL SMPQVNIVKK TEVQTGGFSK<br>ESILPKRNSD KLIARKKDWD PKKYGGFDSP TVAYSVLVVA KVEKGKSKKL<br>KSVKELLGIT IMERSSFEKN PIDFLEAKGY KEVKKDLIIK LPKYSLFELE<br>NGRKRMLASA GELQKGNELA LPSKYVNFLY LASHYEKLKG SPEDNEQKQL<br>FVEQHKHYLD EIIEQISEFS KRVILADANL DKVLSAYNKH RDKPIREQAE<br>NIIHLFTLTN LGAPAAFKYF DTTIDRKRYT STKEVLDATL IHQSITGLYE<br>TRIDLSQLGG D |
| ΔREC3 | 27 | MDKKYSIGLA IGTNSVGWAV ITDEYKVPSK KFKVLGNTDR HSIKKNLIGA<br>LLFDSGETAE ATRLKRTARR RYTRRKNRIC YLQEIFSNEM AKVDDSFFHR<br>LEESFLVEED KKHERHPIFG NIVDEVAYHE KYPTIYHLRK KLVDSTDKAD<br>LRLIYLALAH MIKFRGHFLI EGDLNPDNSD VDKLFIQLVQ TYNQLFEENP<br>INASGVDAKA ILSARLSKSR RLENLIAQLP GEKKNGLFGN LIALSLGLTP<br>NFKSNFDLAE DAKLQLSKDT YDDDLDNLLA QIGDQYADLF LAAKNLSDAI<br>LLSDILRVNT EITKAPLSAS MIKRYDEHHQ DLTLLKALVR QQLPEKYKEI |

TABLE 1-continued

Preferred polypeptides (catalytically dead) in accordance with the first aspect of the invention.

| Name | SEQ ID NO | Amino acid sequence |
|---|---|---|
| | | FFDQSKNGYA GYIDGGASQE EFYKFIKPIL EKMDGTEELL VKLNREDLLR KQRTFDNGSI PHQIHLGELH AILRRQEDFY PFLKDNREKI EKILTFRIPY YVGPLARGNS RFAWMTRKSE ETITPWNFEE VVDKGASAQS FIERMTNGGS VSGQGDSLHE HIANLAGSPA IKKGILQTVK VVDELVKVMG RHKPENIVIE MARENQTTQK GQKNSRERMK RIEEGIKELG SQILKEHPVE NTQLQNEKLY LYYLQNGRDM YVDQELDINR LSDYDVAAIV PQSFLKDDSI DNKVLTRSDK ARGKSDNVPS EEVVKKMKNY WRQLLNAKLI TQRKFDNLTK AERGGLSELD KAGFIKRQLV ETRQITKHVA QILDSRMNTK YDENDKLIRE VKVITLKSKL VSDFRKDFQF YKVREINNYH HAHDAYLNAV VGTALIKKYP KLESEFVYGD YKVYDVRKMI AKSEQEIGKA TAKYFFYSNI MNFFKTEITL ANGEIRKRPL IETNGETGEI VWDKGRDFAT VRKVLSMPQV NIVKKTEVQT GGFSKESILP KRNSDKLIAR KKDWDPKKYG GFDSPTVAYS VLVVAKVEKG KSKKLKSVKE LLGITIMERS SFEKNPIDFL EAKGYKEVKK DLIIKLPKYS LFELENGRKR MLASAGELQK GNELALPSKY VNFLYLASHY EKLKGSPEDN EQKQLFVEQH KHYLDEIIEQ ISEFSKRVIL ADANLDKVLS AYNKHRDKPI REQAENIIHL FTLTNLGAPA AFKYFDTTID RKRYTSTKEV LDATLIHQSI TGLYETRIDL SQLGGD |
| ΔREC3 ΔHNH | 28 | MDKKYSIGLA IGTNSVGWAV ITDEYKVPSK KFKVLGNTDR HSIKKNLIGA LLFDSGETAE ATRLKRTARR RYTRRKNRIC YLQEIFSNEM AKVDDSFFHR LEESFLVEED KKHERHPIFG NIVDEVAYHE KYPTIYHLRK KLVDSTDKAD LRLIYLALAH MIKFRGHFLI EGDLNPDNSD VDKLFIQLVQ TYNQLFEENP INASGVDAKA ILSARLSKSR RLENLIAQLP GEKKNGLFGN LIALSLGLTP NFKSNFDLAE DAKLQLSKDT YDDDLDNLLA QIGDQYADLF LAAKNLSDAI LLSDILRVNT EITKAPLSAS MIKRYDEHHQ DLTLLKALVR QQLPEKYKEI FFDQSKNGYA GYIDGGASQE EFYKFIKPIL EKMDGTEELL VKLNREDLLR KQRTFDNGSI PHQIHLGELH AILRRQEDFY PFLKDNREKI EKILTFRIPY YVGPLARGNS RFAWMTRKSE ETITPWNFEE VVDKGASAQS FIERMTNGGS VSGQGDSLHE HIANLAGSPA IKKGILQTVK VVDELVKVMG RHKPENIVIE MARENQTTQK GQKGGGSELD KAGFIKRQLV ETRQITKHVA QILDSRMNTK YDENDKLIRE VKVITLKSKL VSDFRKDFQF YKVREINNYH HAHDAYLNAV VGTALIKKYP KLESEFVYGD YKVYDVRKMI AKSEQEIGKA TAKYFFYSNI MNFFKTEITL ANGEIRKRPL IETNGETGEI VWDKGRDFAT VRKVLSMPQV NIVKKTEVQT GGFSKESILP KRNSDKLIAR KKDWDPKKYG GFDSPTVAYS VLVVAKVEKG KSKKLKSVKE LLGITIMERS SFEKNPIDFL EAKGYKEVKK DLIIKLPKYS LFELENGRKR MLASAGELQK GNELALPSKY VNFLYLASHY EKLKGSPEDN EQKQLFVEQH KHYLDEIIEQ ISEFSKRVIL ADANLDKVLS AYNKHRDKPI REQAENIIHL FTLTNLGAPA AFKYFDTTID RKRYTSTKEV LDATLIHQSI TGLYETRIDL SQLGGD |
| ΔREC3 ΔHNH ΔRuvCIII-b | 29 | MDKKYSIGLA IGTNSVGWAV ITDEYKVPSK KFKVLGNTDR HSIKKNLIGA LLFDSGETAE ATRLKRTARR RYTRRKNRIC YLQEIFSNEM AKVDDSFFHR LEESFLVEED KKHERHPIFG NIVDEVAYHE KYPTIYHLRK KLVDSTDKAD LRLIYLALAH MIKFRGHFLI EGDLNPDNSD VDKLFIQLVQ TYNQLFEENP INASGVDAKA ILSARLSKSR RLENLIAQLP GEKKNGLFGN LIALSLGLTP NFKSNFDLAE DAKLQLSKDT YDDDLDNLLA QIGDQYADLF LAAKNLSDAI LLSDILRVNT EITKAPLSAS MIKRYDEHHQ DLTLLKALVR QQLPEKYKEI FFDQSKNGYA GYIDGGASQE EFYKFIKPIL EKMDGTEELL VKLNREDLLR KQRTFDNGSI PHQIHLGELH AILRRQEDFY PFLKDNREKI EKILTFRIPY YVGPLARGNS RFAWMTRKSE ETITPWNFEE VVDKGASAQS FIERMTNGGS VSGQGDSLHE HIANLAGSPA IKKGILQTVK VVDELVKVMG RHKPENIVIE MARENQTTQK GQKGGGSELD KAGFIKRQLV ETRQITKHVA QILDSRMNTK YDENDKLIRE VKVITLKSKL VSDFRKDFQF YKVREINNYH HAHDAYLNAV VGTALIKKYP GGGSGGGSDK GRDFATVRKV LSMPQVNIVK KTEVQTGGFS KESILPKRNS DKLIARKKDW DPKKYGGFDS PTVAYSVLVV AKVEKGKSKK LKSVKELLGI TIMERSSFEK NPIDFLEAKG YKEVKKDLII KLPKYSLFEL ENGRKRMLAS AGELQKGNEL ALPSKYVNFL YLASHYEKLK GSPEDNEQKQ LFVEQHKHYL DEIIEQISEF SKRVILADAN LDKVLSAYNK HRDKPIREQA ENIIHLFTLT NLGAPAAFKY FDTTIDRKRY TSTKEVLDAT LIHQSITGLY ETRIDLSQLG GD |
| ΔREC3 ΔHNH ΔRuvCIII-b ΔREC2 | 30 | MDKKYSIGLA IGTNSVGWAV ITDEYKVPSK KFKVLGNTDR HSIKKNLIGA LLFDSGETAE ATRLKRTARR RYTRRKNRIC YLQEIFSNEM AKVDDSFFHR LEESFLVEED KKHERHPIFG NIVDEVAYHE KYPTIYHLRK KLVDSTDKAD LRLIYLALAH MIKFRGHFLI EGDLNPDNSD NTEITKAPLS ASMIKRYDEH HQDLTLLKAL VRQQLPEKYK EIFFDQSKNG YAGYIDGGAS QEEFYKFIKP ILEKMDGTEE LLVKLNREDL LRKQRTFDNG SIPHQIHLGE LHAILRRQED FYPFLKDNRE KIEKILTFRI PYYVGPLARG NSRFAWMTRK SEETITPWNF EEVVDKGASA QSFIERMTNG GSVSGQGDSL HEHIANLAGS PAIKKGILQT VKVVDELVKV MGRHKPENIV IEMARENQTT QKGQKGGGSE LDKAGFIKRQ LVETRQITKH VAQILDSRMN TKYDENDKLI REVKVITLKS KLVSDFRKDF QFYKVREINN YHHAHDAYLN AVVGTALIKK YPGGGSGGGS DKGRDFATVR KVLSMPQVNI VKKTEVQTGG FSKESILPKR NSDKLIARKK DWDPKKYGGF DSPTVAYSVL VVAKVEKGKS KKLKSVKELL GITIMERSSF EKNPIDFLEA |

TABLE 1-continued

Preferred polypeptides (catalytically dead) in accordance with the first aspect of the invention.

| Name | SEQ ID NO | Amino acid sequence |
|---|---|---|
| | | KGYKEVKKDL IIKLPKYSLF ELENGRKRML ASAGELQKGN ELALPSKYVN FLYLASHYEK LKGSPEDNEQ KQLFVEQHKH YLDEIIEQIS EFSKRVILAD ANLDKVLSAY NKHRDKPIRE QAENIIHLFT LTNLGAPAAF KYFDTTIDRK RYTSTKEVLD ATLIHQSITG LYETRIDLSQ LGGD |

It is to be understood that the various polypeptides having at least one of the aforementioned deletions and/or mutations, even if their amino acid sequences are not explicitly described herein for the sake of conciseness, are contemplated to be within the scope of the present invention.

In a second aspect, the invention relates to a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% sequence identity to *Staphylococcus aureus* Cas9 having the amino acid sequence set forth in SEQ ID NO:2, *Neiserria meningitides* Cas9 having the amino acid sequence set forth in SEQ ID NO:3, *Acidaminococcus* sp. Cpf1 having the amino acid sequence set forth in SEQ ID NO:4, *Streptococcus thermophilus* Cas9 having the amino acid sequence set forth in SEQ ID NO:5, *Sutterella wadsworthensis* Cas9 having the amino acid sequence set forth in SEQ ID NO:6, *Filifactor alocis* Cas9 having the amino acid sequence set forth in SEQ ID NO:7, *Lactobacillus johnsonii* Cas9 having the amino acid sequence set forth in SEQ ID NO:8, *Campylobacter lari* Cas9 having the amino acid sequence set forth in SEQ ID NO:9, *Parvibaculum lavamentivorans* Cas9 having the amino acid sequence set forth in SEQ ID NO:10, *Mycoplasma gallisepticum* Cas9 having the amino acid sequence set forth in SEQ ID NO:11, *Treponema denticola* Cas9 having the amino acid sequence set forth in SEQ ID NO:12, or *Lachnospiraceae bacterium* ND2006 Cpf1 having the amino acid sequence set forth in SEQ ID NO:13 over its entire length, wherein said polypeptide comprises at least one truncation of said amino acid sequence, wherein said at least one truncation corresponds to at least one truncation of SEQ ID NO:1 selected from the group consisting of ΔHNH (Δ775-909), ΔRuvCIII-b (Δ1002-1074), ΔREC1-a (Δ510-655), ΔREC1-b (Δ525-587), ΔREC1-c (Δ662-710), ΔREC2 (Δ180-308), ΔREC2-a (Δ212-244), ΔREC2-b (Δ244-276), ΔREC2-c (Δ276-308), ΔREC2-d (Δ199-283), ΔREC2-e (Δ198-257), ΔREC2-f (Δ235-286), ΔREC2-g (Δ217-266), ΔREC3 (Δ498-712) and combinations thereof, wherein the position numbering is in accordance with SEQ ID NO:1, wherein the polypeptide has CRISPR-Cas DNA-binding activity.

TABLE 2

Cas proteins of different organisms

| Name | UniProt Entry number | SEQ ID NO | Amino acid sequence |
|---|---|---|---|
| Streptococcus pyogenes Cas9 | Q99ZW2 | 1 | MDKKYSIGLDIGTNSVGWAVITDEYKVPSKKFKVLGNTDRHSIKKNLIGALLFDSGETAE ATRLKRTARRRYTRRKNRICYLQEIFSNEMAKVDDSFFHRLEESFLVEEDKKHERHPIFG NIVDEVAYHEKYPTIYHLRKKLVDSTDKADLRLIYLALAHMIKFRGHFLIEGDLNPDNSD VDKLFIQLVQTYNQLFEENPINASGVDAKAILSARLSKSRRLENLIAQLPGEKKNGLFGN LIALSLGLTPNFKSNFDLAEDAKLQLSKDTYDDDLDNLLAQIGDQYADLFLAAKNLSDAI LLSDILRVNTEITKAPLSASMIKRYDEHHQDLTLLKALVRQQLPEKYKEIFFDQSKNGYA GYIDGGASQEEFYKFIKPILEKMDGTEELLVKLNREDLLRKQRTFDNGSIPHQIHLGELH AILRRQEDFYPFLKDNREKIEKILTFRIPYYVGPLARGNSRFAWMTRKSEETITPWNFEE VVDKGASAQSFIERMTNFDKNLPNEKVLPKHSLLYEYFTVYNELTKVKYVTEGMRKPAFL SGEQKKAIVDLLFKTNRKVTVKQLKEDYFKKIECFDSVEISGVEDRFNASLGTYHDLLKI IKDKDFLDNEENEDILEDIVLTLTLFEDREMIEERLKTYAHLFDDKVMKQLKRRRYTGWG RLSRKLINGIRDKQSGKTILDFLKSDGFANRNFMQLIHDDSLTFKEDIQKAQVSGQGDSL HEHIANLAGSPAIKKGILQTVKVVDELVKVMGRHKPENIVIEMARENQTTQKGQKNSRER MKRIEEGIKELGSQILKEHPVENTQLQNEKLYLYYLQNGRDMYVDQELDINRLSDYDVDH IVPQSFLKDDSIDNKVLTRSDKNRCKSDNVPSEEVVKKMKNYWRQLLNAKLITQRKFDNL TKAERGGLSELDKAGFIKRQLVETRQITKHVAQILDSRMNTKYDENDKLIREVKVITLKS KLVSDFRKDFQFYKVREINNYHHAHDAYLNAVVGTALIKKYPKLESEFVYGDYKVYDVRK MIAKSEQEIGKATAKYFFYSNIMNFFKTEITLANGEIRKRPLIETNGETGEIVWDKGRDF ATVRKVLSMPQVNIVKKTEVQTGGFSKESILPKRNSDKLIARKKDWDPKKYGGFDSPTVA YSVLVVAKVEKGKSKKLKSVKELLGITIMERSSFEKNPIDFLEAKGYKEVKKDLIIKLPK YSLFELENGRKRMLASAGELQKGNELALPSKYVNFLYLASHYEKLKGSPEDNEQKQLFVE QHKHYLDEIIEQISEFSKRVILADANLDKVLSAYNKHRDKPIREQAENIIHLFTLTNLGA PAAFKYFDTTIDRKRYTSTKEVLDATLIHQSITGLYETRIDLSQLGGD |
| Staphylococcus aureus Cas9 | J7RUA5 | 2 | MKRNYILGLDIGITSVGYGIIDYETRDVIDAGVRLFKEANVENNEGRRSKRGARRLKRRR RHRIQRVKKLLFDYNLLTDHSELSGINPYEARVKGLSQKLSEEEFSAALLHLAKRRGVHN VNEVEEDTGNELSTKEQISRNSKALEEKYVAELQLERLKKDGEVRGSINRFKTSDYVKEA KQLLKVQKAYHQLDQSFIDTYIDLLETRRTYYEGPGEGSPFGWKDIKEWYEMLMGHCTYF PEELRSVKYAYNADLYNALNDLNNLVITRDENEKLEYYEKFQIIENVFKQKKKPTLKQIA KEILVNEEDIKGYRVTSTGKPEFTNLKVYHDIKDITARKEIIENAELLDQIAKILTIYQS SEDIQEELTNLNSELTQEEIEQISNLKGYTGTHNLSLKAINLILDELWHTNDNQIAIFNR |

TABLE 2-continued

Cas proteins of different organisms

| Name | UniProt Entry number | SEQ ID NO | Amino acid sequence |
|---|---|---|---|
| | | | LKLVPKKVDLSQQKEIPTTLVDDFILSPVVKRSFIQSIKVINAIIKKYGLPNDIIIELAR EKNSKDAQKMINEMQKRNRQTNERIEEIIRTTGKENAKYLIEKIKLHDMQEGKCLYSLEA IPLEDLLNNPFNYEVDHIIPRSVSFDNSFNNKVLVKQEENSKKGNRTPFQYLSSSDSKIS YETFKKHILNLAKGKGRISKTKKEYLLEERDINRFSVQKDFINRNLVDTRYATRGLMNLL RSYFRVNNLDVKVKSINGGFTSFLRRKWKFKKERNKGYKHHAEDALIIANADFIFKEWKK LDKAKKVMENQMFEEKQAESMPEIETEQEYKEIFITPHQIKHIKDFKDYKYSHRVDKKPN RELINDTLYSTRKDDKGNTLIVNNLNGLYDKDNDKLKKLINKSPEKLLMYHHDPQTYQKL KLIMEQYGDEKNPLYKYYEETGNYLTKYSKKDNGPVIKKIKYYGNKLNAHLDITDDYPNS RNKVVKLSLKPYRFDVYLDNGVYKFVTVKNLDVIKKENYYEVNSKCYEEAKKLKKISNQA EFIASFYNNDLIKINGELYRVIGVNNDLLNRIEVNMIDITYREYLENMNDKRPPRIIKTI ASKTQSIKKYSTDILGNLYEVKSKKHPQIIKKG |
| Neiserria meningitides Cas9 | C9X1G5 | 3 | MAAFKPNSINYILGLDIGIASVGWAMVEIDEEENPIRLIDLGVRVFERAEVPKTGDSLAM ARRLARSVRRLTRRRAHRLLRTRRLLKREGVLQAANFDENGLIKSLPNTPWQLRAAALDR KLTPLEWSAVLLHLIKHRGYLSQRKNEGETADKELGALLKGVAGNAHALQTGDFRTPAEL ALNKFEKESGHIRNQRSDYSHTFSRKDLQAELILLFEKQKEFGNPHVSGGLKEGIETLLM TQRPALSGDAVQKMLGHCTFEPAEPKAAKNTYTAERFIWLTKLNNLRILEQGSERPLTDT ERATLMDEPYRKSKLTYAQARKLLGLEDTAFFKGLRYGKDNAEASTLMEMKAYHAISRAL EKEGLKDKKSPLNLSPELQDEIGTAFSLFKTDEDITGRLKDRIQPEILEALLKHISFDKF VQISLKALRRIVPLMEQGKRYDEACAEIYGDHYGKKNTEEKIYLPPIPADEIRNPVVLRA LSQARKVINGVVRRYGSPARIHIETAREVGKSFKDRKEIEKRQEENRDREKAAAKFREY FPNFVGEPKSKDILKLRLYEQQHGKCLYSGKEINLGRLNEKGYVEIDHALPFSRTWDDSF NNKVLVLGSENQNKGNQTPYEYFNGKDNSREWQEFKARVETSRFPRSKKQRILLQKFDED GFKERNLNDTRYVNRFLCQFVADRMRLTGKGKKRVFASNGQITNLLRGFWGLRKVRAEND RHHALDAVVVACSTVAMQQKITRFVRYKEMNAFDGKTIDKETGEVLHQKTHPQWEFFA QEVMIRVFGKPDGKPEFEEADTLEKLRTLLAEKLSSRPEAVHEYVTPLFVSRAPNRKMSG QGHMETVKSAKRLDEGVSVLRVPLTQLKLKDLEKMVNREREPKLYEALKARLEAHKDDPA KAFAEPFYKYDKAGNRTQQVKAVRVEQVQKTGVWVRNHNGIADNATMVRVDVFEKGDKYY LVPIYSWQVAKGILPDRAVVQGKDEEDWQLIDDSFNFKFSLHPNDLVEVITKKARMFGYF ASCHROTGNINIRIHDLDHKIGKNGILEGIGVKTALSFQKYQIDELGKEIRPCRLKKRPP VR |
| Acidaminococcus sp. Cpf1 | U2UMQ6 | 4 | MTQFEGFTNLYQVSKTLRFELIPQGKTLKHIQEQGFIEEDKARNDHYKELKPIIDRIYKT YADQCLQLVQLDWENLSAAIDSYRKEKTEETRNALIEEQATYRNAIHDYFIGRTDNLTDA INKRHAEIYKGLFKAELFNGKVLKQLGTVTTTEHENALLRSFDKFTTYFSGFYENRKNVF SAEDISTAIPHRIVQDNFPKFKENCHIFTRLITAVPSLREHFENVKKAIGIFVSTSIEEV FSFPFYNQLLTQTQIDLYNQLLGGISREAGTEKIKGLNEVLNLAIQKNDETAHIIASLPH RFIPLFKQILSDRNTLSFILEEFKSDEEVIQSFCKYKTLLRNENVLETAEALFNELNSID LTHIFISHKKLETISSALCDHWDTLRNALYERRISELTGKITKSAKEKVQRSLKHEDINL QEIISAAGKELSEAFKQKTSEILSHAHAALDQPLPTTLKKQEEKEILKSQLDSLLGLYHL LDWFAVDESNEVDPEFSARLTGIKLEMEPSLSFYNKARNYATKKPYSVEKFKLNFQMPTL ASGWDVNKEKNNGAILFVKNGLYYLGIMPKQKGRYKALSFEPTEKTSEGFDKMYYDYFPD AAKMIPKCSTQLKAVTAHFQTHTTPILLSNNFIEPLEITKEIYDLNNPEKEPKKFQTAYA KKTGDQKGYREALCKWIDFTRDFLSKYYTKTTSIDLSSLRPSSQYKDLGEYYAELNPLLYH ISFQRIAEKEIMDAVETGKLYLFQIYNKDFAKGHHGKPNLHTLYWTGLFSPENLAKTSIK LNGQAELFYRPKSRMKRMAHRLGEKMLNKKLKDQKTPIPDTLYQELYDYVNHRLSHDLSD EARALLPNVITKEVSHEIIKDRRFTSDKFFFHVPITLNYQAANSPSKFNQRVNAYLKEHP ETPIIGIDRGERNLIYITVIDSTGKILEQRSLNTIQQFDYQKKLDNREKERVAARQAWSV VGTIKDLKQGYLSQVIHEIVDLMIHYQAVVVLENLNFGFKSKRTGIAEKAVYQQFEKMLI DKLNCLVLKDYPAEKVGGVLNPYQLTDQFTSFAKMGTQSGFLFYVPAPYTSKIDPLTGFV DPFVWKTIKNHESRKHFLEGFDFLHYDVKTGDFILHFKMNRNLSFQRGLPGFMPAWDIVF EKNETQFDAKGTPFIAGKRIVPVIENHRFTGRYRDLYPANELIALLEEKGIVFRDGSNIL PKLLENDDSHAIDTMVALIRSVLQMRNSNAATGEDYINSPVRDLNGVCFDSRFQNPEWPM DADANGAYHIALKGQLLLNHLKESKDLKLQNGISNQDWLAYIQELRN |
| Streptococcus thermophilus Cas9 | G3ECR1 | 5 | MLFNKCIIISINLDFSNKEKCMTKPYSIGLDIGTNSVGWAVITDNYKVPSKKMKVLGNTS KKYIKKNLLGVLLFDSGITAEGRRLKRTARRRYTRRRNRILYLQEIFSTEMATLDDAFFQ RLDDSFLVPDDKRDSKYPIFGNLVEEKVYHDEFPTIYHLRKYLADSTKKADLRLVYLALA HMIKYRGHFLIEGEFNSKNDIQKNFQDFLDTYNAIFESDLSLENSKQLEEIVKDKISKL EKKDRILKLFPGEKNSGIFSEFLKLIVGNQADFRKCFNLDEKASLHFSKESYDEDLETLL GYIGDDYSDVFLKAKKLYDAILLSGFLTVTDNETEAPLSSAMIKRYNEHKEDLALLKEYI RNISLKTYNEVFKDDTKNGYAGYIDGKTNQEDFYVYLKNLLAEFEGADYFLEKIDREDFL RKQRTFDNGSIPYQIHLQEMRAILDKQAKFYPFLAKNKERIEKILTFRIPYYVGPLARGN SDFAWSIRKRNEKITPWNFEDVIDKESSAEAFINRMTSFDLYLPEEKVLPKHSLLYETFN VYNELTKVRFIAESMRDYQFLDSKQKKDIVRLYFKDKRKVTDKDIIEYLHAIYGYDGIEL KGIEKQFNSSLSTYHDLLNIINDKEFLDDSSNEAIIEEIIHTLTIFEDREMIKQRLSKFE NIFDKSVLKKLSRRHYTGWGKLSAKLINGIRDEKSGNTILDYLIDDGISNRNFMQLIHDD ALSFKKKIQKAQIIGDEDKGNIKEVVKSLPGSPAIKKGILQSIKIVDELVKVMGGRKPES IVVEMARENQYTNQGKSNSQQRLKRLEKSLKELGSKILKENIPAKLSKIDNNALQNDRLY LYYLQNGKDMYTGDDLDIDRLSNYDIDHIIPQAFLKDNSIDNKVLVSSASNRGKSDDFPS LEVVKKRKTFWYQLLKSKLISQRKFDNLTKAERGGLLPEDKAGFIQRQLVETRQITKHVA RLLDEKFNNKKDENNRAVRTVKIITLKSTLVSQFRKDFELYKVREINDFHHAHDAYLNAV IASALLKKYPKLEPEFVYGDYPKYNSFRERKSATEKVYFYSNIMNIFKKSISLADGRVIE RPLIEVNEETGESVWNKESDLATVRRVLSYPQVNVVKKVEEQNHGLDRGKPKGLFNANLS |

TABLE 2-continued

Cas proteins of different organisms

| Name | UniProt Entry number | SEQ ID NO | Amino acid sequence |
|------|---------------------|-----------|---------------------|
| | | | SKPKPNSNENLVGAKEYLDPKKYGGYAGISNSFAVLVKGTIEKGAKKKITNVLEFQGISI LDRINYRKDKLNFLLEKGYKDIELIIELPKYSLFELSDGSRRMLASILSTNNKRGEIHKG NQIFLSQKFVKLLYHAKRISNTINENHRKYVENHKKEFEELFYYILEFNENYVGAKKNGK LLNSAFQSWQNHSIDELCSSFIGPTGSERKGLFELTSRGSAADFEFLGVKIPRYRDYTPS SLLKDATLIHQSVTGLYETRIDLAKLGEG |
| *Sutterella wadsworthensis* Cas9 | E7H313 | 6 | MTQSERRFSCSIGIDMGAKYTGVFYALFDREELPTNLNSKAMTLVMPETGPRYVQAQRTA VRHRLRGQKRYTLARKLAFLVVDDMIKKQEKRLTDEEWKRGREALSGLLKRRGYSRPNAD GEDLTPLENVRADVFAAHPAFSTYFSEVRSLAEQWEEFTANISNVEKFLGDPNIPADKEF IEFAVAEGLIDKTEKKAYQSALSTLRANANVLTGLRQMGHKPRSEYFKAIEADLKKDSRL AKINEAFGGAERLARLLGNLSNLQLRAERWYFNAPDIMKDRGWEPDRFKKTLVRAPKFFH PAKDQNKQHLELIKQIENSEDIIETLCTLDPNRTIPPYEDQNNRRPPLDQTLLLSPEKLT RQYGEIWKTWSARLTSAEPTLAPAAEILERSTDRKSRVAVNGHEPLPTLAYQLSYALQRA FDRSKALDPYALRALAAGSKSNKLTSARTALENCIGGQNVKTFLDCARRYYREADDAKVG LWFDNADGLLERSDLHPPMKKKILPLLVANILQTDETTGQKFLDEIWRKQIKGRETVASR CARIETVRKSFGGGFNIAYNTAQYREVNKLPRNAQDKELLTIRDRVAETADFIAANLGLS DEQKRKFANPFSLAQFYTLIETEVSGFSATTLAVHLENAWRMTIKDAVINGETVRAAQCS RLPAETARPFDGLVRRLVDRQAWEIAKRVSTDIQSKVDFSNGIVDVSIFVEENKFEFSAS VADLKKNKRVKDKMLSEAEKLETRWLIKNERIKKASRGTCPYTGDRLAEGGEIDHILPRS LIKDARGIVFNAEPNLIYASSRGNQLKKNQRYSLSDLKANYRNEIFKTSNIAAITAEIED VVTKLQQTHRLKFFDLLNEHEQDCVRHALFLDDDGSEARDAVLELLATQRRTRVNGTQIWM IKNLANKIREELQNWCKTTNNRLHFQAAATNVSDAKNLRLKLAQNQPDFEKPDIQPIASH SIDALCSFAVGSADAERDQNGFDYLDGKTVLGLYPQSCEVIHLQAKPQEEKSHFDSVAIF KEGIYAEQFLPIFTLNEKIWIGYETLNAKGERCGAIEVSGKQPKELLEMLAPFFNKPVGD LSAHATYRILKKPAYEFLAKAALQPLSAEEKRLAALLDALRYCTSRKSLMSLFMAANGKS LKKREDVLKPKLFQLKVELKGEKSFKLNGSLTLPVKQDWLRICDSPELADAFGKPCSADE LTSKLARIWKRPVMRDLAHAPVRREFSLPAIDNPSGGFRIRRTNLFGNELYQVHAINAKK YRGFASAGSNVDWSKGILFNELQHENLTECGGRFITSADVTPMSEWRKVVAEDNLSIWIA PGTEGRRYVRVETTFIQASHWFEQSVENWAITSPLSLPASFKVDKPAEFQKAVGTELSEL LGQPRSEIFIENVGNAKHIRFWYIVVSSNKKMNESYNNVSKS |
| *Filifactor alocis* Cas9 | D6GRK4 | 7 | MTKEYYLGLDVGTNSVGWAVTDSQYNLCKFKKKDMWGIRLFESANTAKDRRLQRGNRRRL ERKKQRIDLLQEIFSPEICKIDPTFFIRLNESRLHLEDKSNDFKYPLFIEKDYSDIEYYK EFPTIFHLRKHLIESEEKQDIRLIYLALHNIIKTRGHFLIDGDLQSAKQLRPILDTFLLS LQEEQNLSVSLSENQKDEYEEILKNRSIAKSEKVKKLKNLFEISDELEKEEKKAQSAVIE NFCKFIVGNKGDVCKFLRVSKEELEIDSFSFSEGKYEDDIVKNLEEKVPEKVYLFEQMKA MYDWNILVDILETEEYISFAKVKQYEKHKTNLRLLRDIILKYCTKDEYNRMFNDEKEAGS YTAYVGKLKKNNKKYWIEKKRNPEEFYKSLGKLLLDKIEPLKEDLEVLTMMIEECKNHTLL PIQKNKDNGVIPHQVHEVELKKILENAKKYYSFLTETDKDGYSVVQKIESIFRFRIPYYV GPLSTRHQEKGSNVWMVRKPGREDRIYPWNMEEIIDFEKSNENFITRMTNKCTYLIGEDV LPKHSLLYSKYMVLNELNNVKVRGKKLPTSLKQKVFEDLFENKSKVTGKNLLEYLQIQDK DIQIDDLSGFDKDFKTSLKSYLDFKKQIFGEEIEKESIQNMIEDIIKWITIYGNDKEMLK RVIRANYSNQLTEEQMKKITGFQYSGWGNFSKMFLKGISGSDVSTGETFDIITAMWETDN NLMQILSKKFTFMDNVEDFNSGKVGKIDKITYDSTVKEMFLSPENKRAVWQTIQVAEEIK KVMGCEPKKIFIEMARGGEKVKKRTKSRKAQLLELYAACEEDCRELIKEIEDRDERDFNS MKLFLYYTQFGKCMYSGDDIDINELIRGNSKWDRDHIYPQSKIKDDSIDNLVLVNKTYNA KKSNELLSEDIQKKMHSFWLSLLNKKLITKSKYDRLTRKGDFTDEELSGFIARQLVETRQ STKAIADIFKQIYSSEVVYVKSSLVSDFRKKPLNYLKSRRVNDYHHAKDAYLNIVVGNVY NKKFTSNPIQWMKKNRDTNYSLNKVFEHDVVINGEVIWEKCTYHEDTNTYDGGTLDRIRK IVERDNILYTEYAYCEKGELFNATIQNKNGNSTVSLKKGLDVKKYGGYFSANTSYFSLIE FEDKKGDRARHIIGVPIYIANMLEHSPSAFLEYCEQKGYQNVRILVEKIKKNSLLIINGY PLRIRGENEVDTSFKRAIQLKLDQKNYELVRNIEKFLEKYVEKKGNYPIDENRDHITHEK MNQLYEVLLSKMKKFNKKGMADPSDRIEKSKPKFIKLEDLIDKINVINKMLNLLRCDNDT KADLSLIELPKNAGSFVVKKNTIGKSKIILVNQSVTGLYENRREL |
| *Lactobacillus johnsonii* Cas9 | F4AF10 | 8 | MTKIKDDYIVGLDIGTDSCGWVAMNSNNDILKLQGKTAIGSRLFEGGKSAAERRLFRTTH RRIKRRRWRLKLLEEFFDPYMAEVDPYFFARLKESGLSPLDKRKTVSSIVFPTSAEDKKF YDDYPTIYHLRYKLMTEDEKFDLREVYLAIHHIIKYRGNFLYNTSVKDFKASKIDVKSSI EKLNELYENLGLDLNVEFNISNTAEIEKVLKDKQIFKRDKVKKIAELFAIKTDNKEQSKR IKDISKQVANAVLGYKTRFDTIALKEISKDELSDWNFKLSDIDADSKFEALMGNLDENEQ AILLTIKELFNEVTLNGIVEDGNTLSESMINKYNDHRDDLKLLKEVIENHIDRKKAKELA LAYDLYVNNRHGQLLQAKKKLGKIKPRSKEDFYKVVNKNLDDSRASKEIKKKIELDSFMP KQRTNANGVIPYQLQQLELDKIIENQSKYYPFLKEINPVSSHLKEAPYKLDELIRFPRVPY YVGPLISPNESTKDIQTKKNQNPFAWMIRKEEGRITPWNFDQKVDRIESANKFIKRMTTKD TYLFGEDVLPANSLLYQKFTVLNELNNIRINGKRISVDLKQEIYENLFKKHTTVTVKKLE NYLKENHNLVKVEIKGLADEKKFNSGLTTYNRFKNLNIFDNQIDDLKYRNDFEKIIEWST IFEDKSIYKEKLRSIDWLNEKQINALSNIRLQGWGRLSKKLLAQLHDHNGQTIIEQLWDS QNNFMQIVTQADFKDAIAKANQNLLVATSVEDILNNAYTSPANKKAIRQVIKVVDDIVKA ASGKVPKQIAIEFTRDADENPKRSQTRGSKLQKVVDLSTELASKTIAEELNEAIKDKKL VQDKYYLYFMQLGRDAYTGEPINIDEIQKYDIDHILPQSFIKDDALDNRVLVSRAVNNGK SDNVPVKLFGNEMAANLGMTIRKMWEEWKNIGLISKTKYNNLLTDPDHINKYKSAGFIRR QLVETSQIIKLVSTILQSRYPNTEIITVKAKYNHYLREKFDLYKSREVNDYHHAIDAYLS AICGNLLYQNYPNLRPPFFVYGQYKKFSSDPDKEKAIFNKTRKFSFISQLLKNKSENSKEI AKKLKRAYQFKYMLVSRETETRDQEMFKMTVYPRFSHDTVKAPRNLIPKKMGMSPDIYGG |

TABLE 2-continued

Cas proteins of different organisms

| Name | UniProt Entry number | SEQ ID NO | Amino acid sequence |
|---|---|---|---|
| | | | YTNNSDAYMVIVRIDKKKGTEYKILGIPTRELVNLKKAEKEDHYKSYLKEILTPRILYNK<br>NGKRDKKITSFEIVKSKIPYKQVIQDGDKKFMLGSSTYVYNAKQLTLSTESMKAITNNFD<br>KDSDENDALIKAYDEILDKVDKYLPLFDINKFREKLHSGREKFIKLSLEDKKDTILKVLE<br>GLHDNAVMTKIPTIGLSTPLGFMQFPNGVILSENAKLIYQSPTGLFKKSVKISDL |
| Campylo-<br>bacter<br>lari<br>Cas9 | F1UFN3 | 9 | MRILGFDIGINSIGWAFVENDELKDCGVRIFTKAENPKNKESLALPRRNARSSRRRLKRR<br>KARLIAIKRILAKELKLNYKDYVAADGELPKAYEGSLASVYELRYKALTQNLETKDLARV<br>ILHIAKHRGYMNKNEKKSNDAKKGKILSALKNNALKLENYQSVGEYFYKEFFQKYKKNTK<br>NFIKIRNTKDNYNNCVLSSDLEKELKLILEKQKEFGYNYSEDFINEILKVAFFQRPLKDF<br>SHLVGACTFFEEEKRACKNSYSAWEFVALTKIINEIKSLEKISGEIVPTQTINEVLNLIL<br>DKGSITYKKFRSCINLHESISFKSLKYDKENAENAKLIDFRKLVEFKKALGVHSLSRQEL<br>DQISTHITLIKDNVKLKTVLEKYNLSNEQINNLLEIEFNDYINLSFKALGMILPLMREGK<br>RYDEACEIANLKPKTVDEKKDFLPAFCDSIFAHELSNPVVNRAISEYRKVLNALLKKYCK<br>VHKIHLELARDVGLSKKAREKIEKEQKENQAVNAWALKECENIGLKASAKNILKLKLWKE<br>QKEICIYSGNKISIEHLKDEKALEVDHIYPYSRSFDDSFINKVLVFTKENQEKLNKTPFE<br>AFGKNIEKWSKIQTLAQNLPYKKKNKILDENFKDKQQEDFISRNLNDTRYIATLIAKYTK<br>EYLNFLLLSENENANLKSGEKGSKIHVQTISGMLTSVLRHTWGFDKKDRNNHLHHALDAI<br>IVAYSTNSIIKAFSDFRKNQELLKARFYAKELTSDNYKHQVKFFEPFKSFREKILSKIDE<br>IFVSKPPRKRARRALHKDTFHSENKIIDKCSYNSKEGLQIALSCGRVRKIGTKYVENDTI<br>VRVDIFKKQNKFYAIPIYAMDFALGILPNKIVITGKDKNNNPKQWQTIDESYEFCFSLYK<br>NDLILLQKKNMQEPEFAYYNDFSISTSSICVEKHDNKFENLTSNQKLLFSNAKEGSVKVE<br>SLGIQNLKVFEKYIITPLGDKIKADFQPRENISLKTSKKYGLR |
| Parvib-<br>aculum<br>lavamen-<br>tivorans<br>Cas9 | A7HP89 | 10 | MERIFGFDIGTTSIGFSVIDYSSTQSAGNIQRLGVRIFPEARDPDGTPLNQQRRQKRMMR<br>RQLRRRRIRRKALNETLHEAGFLPAYGSADWPVVMADEPYELRRRGLEEGLSAYEFGRAI<br>YHLAQHRHFKGRELEESDTPDPDVDDEKEAANERAATLKALKNEQTTLGAWLARRPPSDR<br>KRGIHAHRNVVAEEFERLWEVQSKFHPALKSEEMRARISDTIFAQRPVFWRKNTLGECRF<br>MPGEPLCPKGSWLSQQRRMLEKLNNLAIAGGNARPLDAEERDAILSKLQQQASMSWPGVR<br>SALKALYQRGEPGAEKSLKFNLELGGESKLLGNALEAKLADMFGPDWPAHPRKQEIRHA<br>VHERLWAADYGETPDKKRVIILSEKDRKAHREAAANSFVADFGITGEQAAQLQALKLPTG<br>WEPYSIPALNLFLAELEKGERFGALVNGPDWEGWRRTNFPHRNQPTGEILDKLPSPASKE<br>ERERISQLRNPTVVRTQNELRKVVNNLIGLYGKPDRIRIEVGRDVGKSKREREEIQSGIR<br>RNEKQRRKATEDLIKNGIANPSRDDVEKWILWKEGQERCPYTGDQIGFNALFREGRYEVE<br>HIWPRSRSFDNSPRNKTLCRKDVNIEKGNRMPFEAFGHDEDRWSAIQIRLQGMVSAKGGT<br>GMSPGKVKRFLAKTMPEDFAARQLNDTRYAAKQILAQLKRLWPDMGPEAPVKVEAVTGQV<br>TAQLRKLWTLNNILADDGEKTRADHRHHAIDALTVACTHPGMTNKLSRYWQLRDDPRAEK<br>PALTPPWDTIRADAEKAVSEIVVSHRVRKKVSGPLHKETTYGDTGTDIKTKSGTYRQFVT<br>RKKIESLSKGELDEIRDPRIKEIVAAHVAGRGGDPKKAFPPYPCVSPGGPEIRKVRLTSK<br>QQLNLMAQTGNGYADLGSNHHIAIYRLPDGKADFEIVSLFDASRRLAQRNPIVQRTRADG<br>ASFVMSLAAGEAIMIPEGSKKGIWIVQGVWASGQVVLERDTDADHSTTTRPMPNPILKDD<br>AKKVSIDPIGRVRPSND |
| Myco-<br>plasma<br>galli-<br>septicum<br>Cas9 | A0A0F6<br>CLF2 | 11 | MNNSIKSKPEVTIGLDLGVGSVGWAIVDNETNIIHHLGSRLFSQAKTAEDRRSFRGVRRL<br>IRRRKYKLKRFVNLIWKYNSYPGFKNKEDILNNYQEQQKLHNTVLNLKSEALNAKIDPKA<br>LSWILHDYLKNRGHFYEDNRDFNVYPTKELAKYFDKYGYYKGIIDSKEDNDNKLEEELTK<br>YKFSNKHWLEEVKKVLSNQTGLPEKFKEEYESLFSYVRNYSEGPGSINSVSPYGIYHLDE<br>KEGKVVQKYNNIWDKTIGKCNIFPDEYRAPKNSPIAMIFNEINELSTIRSYSIYLTGWFI<br>NQEFKKAYLNKLLDLLIKTNGEKPIDARQFKKLREETIAESIGKETLKDVENEEKLEKED<br>HKWKLKGLKLNTNGKIQYNDLSSLAKFVHKLKQHLKLDFLLEDQYATLDKINFLQSLFVY<br>LGKHLRYNNRVDSANLKEFSDSNRLFERVLQEQKDGLFKLFEQTDKDDEKILAQTHSLST<br>KAMLLAITRMTNLDNDEDNQKNNDKGWNFEAIKNFDQKFIDITKTNNNLSLKQDKRYLDD<br>RFINDAILSPGVKRILREATKVFNAILKQFSQEYDVTKVVIELARELSEEKELENNKNYK<br>KLIKKNSDKISEGLKALDIAEDKIEDILKSPTKSYKVLLWLQQDHIDPYSQKEIAFEDIL<br>TKTEKTEIDHIIPYSISFDDSSSNKLLVLAESNQAKSNQTPYEFITSGNAGIKWEDYEAY<br>CRKFKDGDTSLLDSTQRSKKFAKMMKTDTSSKYDIGFLARNLNDTRYATIVFRDALKDYA<br>NNHLVEDKPMFKVVCINGGVTSFLRKNFDKSWYAKKDRDKNIHHAVDASIISIFSNKTKT<br>LFDQLTQFADYKLFKNTDGSWKKIDPKTGVVTEVTDENWKQIRVRNQVSKIAEEIDKCIQ<br>DSNIERKARYSRKIENKTNISLFNDTVYSAKKVGYDDQIKRKNLKTLDIDESVEENKNSK<br>VKKQFVYRKLVNVSLLNNDKLADLFAEKEDILMYRANPWVINLAEQIFNEYTENRKIKSQ<br>NVFGKYMLDLTKEFPEKFSEAFVKSMLRNKTAIIYNVEKKVVHRIKRLKILSSELKENKL<br>SNVIIRSKNESGTKLSYQDTINSVALMIMRSIDPTAKKQYIRVPLNTLNLHLGDHDFDLH<br>NIDAYLKKPKFVKYLKANEIGDEYKPWRVLISGSLLIHKRDKKLMYISSFQNLNDLIEIK<br>NLIETEYKENVDSDPKKKKKASQILRLSTILNDYILLDAKDNFDILGLSKNRIDEILNS<br>KLDLDKIAK |
| Treponema<br>denticola<br>Cas9 | Q730W6 | 12 | MKKEIKDYFLGLDVGTGSVGWAVTDTDYKLLKANRKDLWGMRCFETAETAEVRRLHRGAR<br>RRIERRKKRIKLLQELFSQEIAKTDEGFFQRMKESPPYAEDKTILQENTLFNDKDFADKT<br>YHKAYPTINHLIKAWIENKVKPDPRLLYLACHNIIKKRGHFLFEGDFDSENQFDTSIQAL<br>FEYLREDMEVDIDADSQKVKEILKDSSLKNSEKQSRLNKILGLKPSDKQKKAITNLISGN<br>KINFADLYDNPDLKDAEKNSISFSKDDFDALSDDLASILGDSFELLLKAKAVYNCSVLSK<br>VIGDEQYLSFAKVKIYEKHKTDLTKLKNVIKKHFPKDYKKVFGYNKNEKNNNYSGYVGV<br>CKTKSKKLIINNSVNQEDFYKFLKTILSAKSEIKEVNDILTEIETGTFLPKQISKSNAEI<br>PYQLRKMELEKILSNAEKHFSFLKQKDEKGLSHSEKIIMLLTFKIPYYIGPINDNHKKFF<br>PDRCWVVKKEKSPSGKTTPWNFFDHIDKEKTAEAFITSRTNFCTYLVGESVLPKSSLLYS |

TABLE 2-continued

Cas proteins of different organisms

| Name | UniProt Entry number | SEQ ID NO | Amino acid sequence |
|---|---|---|---|
| | | | EYTVLNEINNLQIIIDGKNICDIKLKQKIYEDLFKKYKKITQKQISTFIKHEGICNKTDE<br>VIILGIDKECTSSLKSYIELKNIFGKQVDEISTKNMLEEIIRWATIYDEGEGKTILKTKI<br>KAEYGKYCSDEQIKKILNLKFSGWGRLSRKFLETVTSEMPGFSEPVNIITAMRETQNNLM<br>ELLSSEFTFTENIKKINSGFEDAEKQFSYDGLVKPLFLSPSVKKMLWQTLKLVKEISHIT<br>QAPPKKIFIEMAKGAELEPARTKTRLKILQDLYNNCKNDADAFSSEIKDLSGKIENEDNL<br>RLRSDKLYLYYTQLGKCMYCGKPIEIGHVFDTSNYDIDHIYPQSKIKDDSISNRVLVCSS<br>CNKNKEDKYPLKSEIQSKQRGFWNFLQRNNFISLEKLNRLTRATPISDDETAKFIARQLV<br>ETRQATKVAAKVLEKMFPETKIVYSKAETVSMFRNKFDIVKCREINDFHHAHDAYLNIVV<br>GNVYNTKFTNNPWNFIKEKRDNPKIADTYNYYKVFDYDVKRNNITAWEKGKTIITVKDML<br>KRNTPIYTRQAACKKGELFNQTIMKKGLGQHPLKKEGPFSNISKYGGYNKVSAAYYTLIE<br>YEEKGNKIRSLETIPLYLVKDIQKDQDVLKSYLTDLLGKKEFKILVPKIKINSLLKINGF<br>PCHITGKTNDSFLLRPAVQFCCSNNEVLYFKKIIRFSEIRSQREKIGKTISPYEDLSFRS<br>YIKENLWKKTKNDEIGEKEFYDLLQKKNLEIYDMLLTKHKDTIYKKRPNSATIDILVKGK<br>EKFKSLIIENQFEVILEILKLFSATRNVSDLQHIGGSKYSGVAKIGNKISSLDNCILIYQ<br>SITGIFEKRIDLLKV |
| Lachnospiraceae bacterium ND2006 Cpf1 | A0A182 DWE3 | 13 | AASKLEKFTNCYSLSKTLRFKAIPVGKTQENIDNKRLLVEDEKRAEDYKGVKKLLDRYYL<br>SFINDVLHSIKLKNLNNYISLFRKKTRTEKENKELENLEINLRKEIAKAFKGAAGYKSLF<br>KKDIIETILPEAADDKDEIALVNSFNGFTTAFTGFFDNRENMFSEEAKSTSIAFRCINEN<br>LTRYISNMDIFEKVDAIFDKHEVQEIKEKILNSDYDVEDFFEGEFFNFVLTQEGIDVYNA<br>IIGGFVTESGEKIKGLNEYINLYNAKTKQALPKFKPLYKQVLSDRESLSFYGEGYTSDEE<br>VLEVFRNTLNKNSEIFSSIKKLEKLFKNFDEYSSAGIFVKNGPAISTISKDIFGEWNLIR<br>DKWNAEYDDIHLKKKAVVTEKYEDDRRKSFKKIGSFSLEQLQEYADADLSVVEKLKEIII<br>QKVDEIYKVYGSSEKLFDADFVLEKSLKKNDAVVAIMKDLLDSVKSFENYIKAFFGEGKE<br>TNRDESFYGDFVLAYDILLKVDHIYDAIRNYVTQKPYSKDKFKLYFQNPQFMGGWDKDKE<br>TDYRATILRYGSKYYLAIMDKKYAKCLQKIDKDDVNGNYEKINYKLLPGPNKMLPKVFFS<br>KKWMAYYNPSEDIQKIYKNGTFKKGDMFNLNDCHKLIDFFKDSISRYPKWSNAYDFNFSE<br>TEKYKDIAGFYREVEEQGYKVSFESASKKEVDKLVEEGKLYMFQIYNKDFSDKSHGTPNL<br>HTMYFKLLFDENNHGQIRLSGGAELFMRRASLKKEELVVHPANSPIANKNPDNPKKTTTL<br>SYDVYKDKRFSEDQYELHIPIAINKCPKNIFKINTEVRVLLKHDDNPYVIGIDRGERNLL<br>YIVVVDGKGNIVEQYSLNEIINNFNGIRIKTDYHSLLDKKEKERFEARQNWTSIENIKEL<br>KAGYISQVVHKICELVEKYDAVIALEDLNSGFKNSRVKVEKQVYQKFEKMLIDKLNYMVD<br>KKSNPCATGGALKGYQITNKFESFKSMSTQNGFIFYIPAWLTSKIDPSTGFVNLLKTKYT<br>SIADSKKFISSFDRIMYVPEEDLFEFALDYKNFSRTDADYIKKWKLYSYGNRIRIFAAAK<br>KNNVFAWEEVCLTSAYKELFNKYGINYQQGDIRALLCEQSDKAFYSSFMALMSLMLQMRN<br>SITGRTDVDFLISPVKNSDGIFYDSRNYEAQENAILPKNADANGAYNIARKVLWAIGQFK<br>KAEDEKLDKVKIAISNKEWLEYAQTSVK |

It should be noted that all the amino acid modifications described herein were derived in the context of the amino acid sequence of Streptococcus pyogenes Cas9 (SEQ ID NO:1) through extensive experimentation. However, one skilled in the art would readily appreciate that these modifications are transferrable to other CRISPR-Cas nucleases, which share significant homology with the Streptococcus pyogenes Cas9.

To determine whether these modifications could be transferred to another nuclease, the equivalent or corresponding counterpart residues between the two amino acid sequences are determined, typically based on the sequence or structural homology between the sequences. To establish homology, the amino acid sequence of the Streptococcus pyogenes Cas9 is directly compared to the sequence of a second nuclease. After aligning the sequences, using one or more of the homology alignment programs well known in the art, such as CLUSTALW (for example using conserved residues between species), allowing for necessary insertions and deletions in order to maintain alignment (i. e. avoiding the elimination of conserved residues through arbitrary deletion and insertion), the residues equivalent or corresponding to particular amino acid residues in the primary sequence of the Streptococcus pyogenes Cas9 are defined. Alignment of conserved residues preferably should conserve at least 20%, preferably at least 30%, preferably at least 40%, preferably at least 50%, preferably at least 60%, preferably at least 70%, preferably at least 80%, preferably at least 90%, preferably at least 95%, more preferably at least 96%, even more preferably at least 98%, even more preferably at least 99% and most preferably 100% of residues. Equivalent or corresponding counterpart residues may also be defined by determining structural homology between the nucleases, that is at the level of tertiary structure for the nucleases or certain domains thereof whose structures have been determined. In this case, equivalent or corresponding residues are defined as those, for which the atomic coordinates of two or more of the mainchain atoms of a particular amino acid residue of the Streptococcus pyogenes Cas9 (N on N, CA on CA, Con C and O on O) are within 0.13 nm and preferably 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the Streptococcus pyogenes Cas9 in which the modifications are introduced, what is meant to be conveyed is that the polypeptides according to the present invention may be constructed into any other CRISPR-Cas nuclease which has a significant sequence or structural homology with the Streptococcus pyogenes Cas9.

In various embodiments, the polypeptide comprises at least one combination of deletions selected from the group consisting of ΔREC1-a ΔHNH (Δ510-655 Δ775-909), ΔREC1-c ΔHNH (Δ662-710 Δ775-909), ΔREC2 ΔHNH (Δ180-308 Δ775-909), ΔREC2-d ΔHNH (Δ199-283 Δ775-

909), ΔHNH ΔRuvCIII-b (Δ775-909 Δ1002-1074), ΔREC3 ΔHNH (Δ498-712 Δ775-909), ΔREC3 ΔHNH ΔRuvCIII-b (Δ498-712 Δ775-909 Δ1002-1074), ΔREC2 ΔREC3 ΔHNH ΔRuvCIII-b (Δ180-308 Δ498-712 Δ775-909 Δ1002-1074), and ΔREC2 ΔHNH ΔRuvCIII-b (Δ180-308 Δ775-909 Δ1002-1074).

In various embodiments, the polypeptide further comprises at least one missense mutation selected from the group consisting of G12R, T13K, T13R, N14K, N497K, T657K, T657R, N767K, T770K, T770R, Q920K, Q920R, S1109R, D1135K, D1135R, S1338R and combinations thereof, wherein the position numbering is in accordance with SEQ ID NO:1.

In various embodiments, the polypeptide comprises at least one combination of modifications selected from the group consisting of ΔREC1-c ΔHNH G12R, ΔREC1-c ΔHNH T13K, ΔREC1-c ΔHNH T13R, ΔREC1-c ΔHNH N14K, ΔREC1-c ΔHNH N497K, ΔREC1-c ΔHNH T657K, ΔREC1-c ΔHNH T657R, ΔREC1-c ΔHNH N767K, ΔREC1-c ΔHNH T770K, ΔREC1-c ΔHNH T770R, ΔREC1-c ΔHNH Q920K, ΔREC1-c ΔHNH Q920R, ΔREC1-c ΔHNH S1109R, ΔREC1-c ΔHNH D1135K, ΔREC1-c ΔHNH D1135R, ΔREC1-c ΔHNH S1338R, ΔREC1-c ΔHNH T657R T13K, ΔREC1-c ΔHNH T657R N497K, ΔREC1-c ΔHNH T657R T770K, ΔREC1-c ΔHNH T657R Q920K, ΔREC1-c ΔHNH T657R S1109R, ΔREC1-c ΔHNH T657R D1135K, ΔREC2 ΔHNH ΔRuvCIII-b T13K, ΔREC2 ΔHNH ΔRuvCIII-b T657K, ΔREC2 ΔHNH ΔRuvCIII-b T657R, ΔREC2 ΔHNH ΔRuvCIII-b 770K, ΔREC2 ΔHNH ΔRuvCIII-b Q920K, ΔREC2 ΔHNH ΔRuvCIII-b S1109R, and ΔREC2 ΔHNH ΔRuvCIII-b D1135K.

Without wishing to be bound to any theory, it is believed that the polypeptide according to the afore-mentioned aspects can be used as a site-directed modifying polypeptide, i.e. a CRISPR-Cas protein, and functions as an essential component of a CRISPR-Cas system in site-directed modification of a target DNA. Since smaller Cas proteins are easier to package in delivery vehicles, higher delivery efficiencies can be expected.

In general, "CRISPR-Cas system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR-Cas system), a guide sequence (also referred to as a "spacer" in the context of an endogenous CRISPR-Cas system), or other sequences and transcripts from a CRISPR locus. In some embodiments, one or more elements of a CRISPR-Cas system is derived from a type I, type II, or type III CRISPR-Cas system. In some embodiments, one or more elements of a CRISPR-Cas system are derived from an organism comprising an endogenous CRISPR-Cas system, such as *Streptococcus pyogenes*. In general, a CRISPR-Cas system is characterized by elements that promote the formation of a CRISPR complex at the site of a target sequence (also referred to as a protospacer in the context of an endogenous CRISPR-Cas system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell.

In preferred embodiments of the invention, the CRISPR-Cas system is a type II CRISPR-Cas system and the Cas enzyme is Cas9, which binds to a target genomic locus and catalyzes DNA cleavage. Enzymatic action by Cas9 derived from *Streptococcus pyogenes* or any closely related Cas9 generates double stranded breaks at target site sequences, which hybridize to guide sequences of length 17 to 24 nucleotides inclusive. The target locus contains a protospacer-adjacent motif (PAM), whose sequence varies according to the bacteria species where the Cas9 originates from. For the Cas9 from *Streptococcus pyogenes*, the PAM sequence is NGG/NRG, while for the Cas9 from *Staphylococcus aureus*, the PAM sequence is NNGRRT. The PAM of Cas9 follows the 17-24 nucleotides of the target sequence. CRISPR activity through Cas9 for site-specific DNA recognition or cleavage is defined in part by the guide sequence, the tracr sequence, and the PAM sequence. More aspects of the CRISPR-Cas system are described in Karginov and Hannon, The CRISPR-Cas system: small RNA-guided defense in bacteria and archae, Mole Cell 2010, January 15; 37(1): 7.

The term "site-directed modifying polypeptide" as used herein refers to a polypeptide that binds RNA and is targeted to a specific DNA sequence. A site-directed modifying polypeptide as described herein is targeted to a specific DNA sequence by the RNA molecule to which it is bound. The RNA molecule comprises a sequence that is complementary to a target sequence within the target DNA, thus targeting the bound polypeptide to a specific location within the target DNA (the target sequence).

The term "cleavage" as used herein refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a DNA-targeting RNA and a site-directed modifying polypeptide is used for targeted double-stranded DNA cleavage.

The term "nuclease" as used herein refers to an enzyme possessing catalytic activity for DNA cleavage.

The RNA molecule that binds to the site-directed modifying polypeptide and targets the polypeptide to a specific location within the target DNA is referred to herein as the "DNA-targeting RNA" or "DNA-targeting RNA polynucleotide" (also referred to herein as a "guide RNA" or "gRNA"). A subject DNA-targeting RNA comprises two segments, a "DNA-targeting segment" and a "protein-binding segment." By "segment" it is meant a segment/section/region of a molecule, e.g., a contiguous stretch of nucleotides in an RNA. A segment can also mean a region/section of a complex such that a segment may comprise regions of more than one molecule. For example, in some cases the protein-binding segment of a DNA-targeting RNA is one RNA molecule and the protein-binding segment therefore comprises a region of that RNA molecule. In other cases, the protein-binding segment of a DNA-targeting RNA comprises two separate molecules that are hybridized along a region of complementarity. As an illustrative, non-limiting example, a protein-binding segment of a DNA-targeting RNA that comprises two separate molecules can comprise (i) base pairs 40-75 of a first RNA molecule that is 100 base pairs in length; and (ii) base pairs 10-25 of a second RNA molecule that is 50 base pairs in length. The definition of "segment," unless otherwise specifically defined in a particular context, is not limited to a specific number of total base pairs, is not limited to any particular number of base pairs from a given RNA molecule, is not limited to a particular number of separate molecules within a complex, and may include regions of RNA molecules that are of any total length and may or may not include regions with complementarity to other molecules.

The DNA-targeting segment (or "DNA-targeting sequence") comprises a nucleotide sequence that is complementary to a specific sequence within a target DNA (the complementary strand of the target DNA). The protein-binding segment (or "protein-binding sequence") interacts with a site-directed modifying polypeptide. When the site-directed modifying polypeptide is a Cas9 or Cas9 related polypeptide, e.g. the polypeptide described herein, site-specific cleavage of or recruitment of an effector domain to the target DNA occurs at locations determined by both (i) base-pairing complementarity between the DNA-targeting RNA and the target DNA; and (ii) a short motif (referred to as the protospacer adjacent motif (PAM)) in the target DNA.

The protein-binding segment of a subject DNA-targeting RNA comprises two complementary stretches of nucleotides that hybridize to one another to form a double stranded RNA duplex (dsRNA duplex).

In some embodiments, a subject nucleic acid (e.g., a DNA-targeting RNA, a nucleic acid comprising a nucleotide sequence encoding a DNA-targeting RNA; a nucleic acid encoding a site-directed polypeptide; etc.) comprises a modification or sequence that provides for an additional desirable feature (e.g., modified or regulated stability; subcellular targeting; tracking, e.g., a fluorescent label; a binding site for a protein or protein complex; etc.). Non-limiting examples include: a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

In some embodiments, a DNA-targeting RNA comprises an additional segment at either the 5' or 3' end that provides for any of the features described above. For example, a suitable third segment can comprise a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and protein complexes); a stability control sequence; a sequence that forms a dsRNA duplex (i.e., a hairpin)); a sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

A subject DNA-targeting RNA and a subject site-directed modifying polypeptide (i.e., site-directed polypeptide) form a complex (i.e., bind via non-covalent interactions). The DNA-targeting RNA provides target specificity to the complex by comprising a nucleotide sequence that is complementary to a sequence of a target DNA. The site-directed modifying polypeptide of the complex provides the site-specific activity. In other words, the site-directed modifying polypeptide is guided to a target DNA sequence (e.g. a target sequence in a chromosomal nucleic acid; a target sequence in an extrachromosomal nucleic acid, e.g. an episomal nucleic acid, a minicircle, etc.; a target sequence in a mitochondrial nucleic acid; a target sequence in a chloroplast nucleic acid; a target sequence in a plasmid; etc.) by virtue of its association with the protein-binding segment of the DNA-targeting RNA.

In some embodiments, a subject DNA-targeting RNA comprises two separate RNA molecules (RNA polynucleotides: an "activator-RNA" and a "targeter-RNA", see below) and is referred to herein as a "double-molecule DNA-targeting RNA" or a "two-molecule DNA-targeting RNA." In other embodiments, the subject DNA-targeting RNA is a single RNA molecule (single RNA polynucleotide) and is referred to herein as a "single-molecule DNA-targeting RNA," a "single-guide RNA," or an "sgRNA." The term "DNA-targeting RNA" or "gRNA" is inclusive, referring both to double-molecule DNA-targeting RNAs and to single-molecule DNA-targeting RNAs (i.e., sg RNAs).

An exemplary two-molecule DNA-targeting RNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA-like molecule (targeter-RNA) comprises both the DNA-targeting segment (single stranded) of the DNA-targeting RNA and a stretch ("duplex-forming segment") of nucleotides that forms one-half of the dsRNA duplex of the protein-binding segment of the DNA-targeting RNA. A corresponding tracrRNA-like molecule (activator-RNA) comprises a stretch of nucleotides (duplex-forming segment) that forms the other half of the dsRNA duplex of the protein-binding segment of the DNA-targeting RNA. In other words, a stretch of nucleotides of a crRNA-like molecule are complementary to and hybridize with a stretch of nucleotides of a tracrRNA-like molecule to form the dsRNA duplex of the protein-binding domain of the DNA-targeting RNA. As such, each crRNA-like molecule can be said to have a corresponding tracrRNA-like molecule. The crRNA-like molecule additionally provides the single stranded DNA-targeting segment. Thus, a crRNA-like and a tracrRNA-like molecule (as a corresponding pair) hybridize to form a DNA-targeting RNA. The exact sequence of a given crRNA or tracrRNA molecule is characteristic of the species in which the RNA molecules are found. A subject double-molecule DNA-targeting RNA can comprise any corresponding crRNA and tracrRNA pair. A subject double-molecule DNA-targeting RNA can comprise any corresponding crRNA and tracrRNA pair.

The term "activator-RNA" is used herein to mean a tracrRNA-like molecule of a double-molecule DNA-targeting RNA. The term "targeter-RNA" is used herein to mean a crRNA-like molecule of a double-molecule DNA-targeting RNA. The term "duplex-forming segment" is used herein to mean the stretch of nucleotides of an activator-RNA or a targeter-RNA that contributes to the formation of the dsRNA duplex by hybridizing to a stretch of nucleotides of a corresponding activator-RNA or targeter-RNA molecule. In other words, an activator-RNA comprises a duplex-forming segment that is complementary to the duplex-forming segment of the corresponding targeter-RNA. As such, an activator-RNA comprises a duplex-forming segment while a targeter-RNA comprises both a duplex-forming segment and the DNA-targeting segment of the DNA-targeting RNA. Therefore, a subject double-molecule DNA-targeting RNA can be comprised of any corresponding activator-RNA and targeter-RNA pair.

The polypeptide of the invention may be prepared recombinantly or produced by in vitro transcription/translation. The polypeptide may also be prepared synthetically, preferably using a commercially available peptide synthesizer. Methods of synthetic peptide synthesis include, but are not limited to liquid-phase peptide synthesis and solid-phase peptide synthesis. Methods to produce peptides synthetically and according protocols are well-known in the art (Nilsson, B L et al. (2005) Annu Rev Biophys Biomol Struct, 34, 91).

The CRISPR-Cas nuclease activity of the polypeptide can be determined by a variety of assays known in the art, for example by Surveyor cleavage assay or by deep sequencing the targeted genomic loci.

The CRISPR-Cas DNA-binding activity of the polypeptide can be determined by a variety of assays known in the art, depending on what effector domain is fused to the polypeptide. If a transcriptional regulatory domain is fused to the polypeptide, a fluorescence reporter assay or a qRT-PCR experiment to measure the expression of endogenous genes can be performed, as described in the examples of the present application.

It should be noted that proteins comprising the polypeptide described herein are also encompassed in the present application.

In a third aspect, the invention relates to a nucleic acid molecule comprising or consisting of a nucleic acid encoding a polypeptide described herein.

In various embodiments, the nucleic acid molecule is a recombinant expression vector.

The term "nucleic acid molecule" or "nucleic acid" as used herein refers to a polymeric form of nucleotides of any length, either deoxyribonucleotides or ribonucleotides, or analogs thereof. Nucleic acid molecules may have any three-dimensional structure, and may perform any function, known or unknown. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A nucleic acid molecule may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors can direct the expression of genes to which they are operatively-linked. Such vectors are referred to herein as "expression vectors." Common expression vectors of utility in recombinant DNA techniques are often in the form of plasmids. Further discussion of vectors is provided herein.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

In various embodiments, the vector further comprises regulatory elements for controlling expression of the polypeptide.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein. With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc, Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., Gene Expression Technology: Methods in Enzymology 185, Academic Press, San Diego, Calif. (1990) 60-89).

In some embodiments, a vector is a yeast expression vector. Examples of vectors for expression in yeast *Saccharomyces cerevisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989.

In some embodiments, the recombinant mammalian expression vector can direct expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-

379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

In some embodiments, a regulatory element is operably linked to one or more elements of a CRISPR-Cas system so as to drive expression of the one or more elements of the CRISPR-Cas system. In general, CRISPRs constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena,* and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium,* Azarcus, *Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema,* and *Thermotoga.*

The polypeptides and nucleic acid molecules described above are preferably non-naturally occurring. The present invention provides the polypeptides and nucleic acid molecules preferably in recombinant, synthetic, isolated, and/or purified form.

In a fourth aspect, to a composition comprising the polypeptide and/or the nucleic acid molecule described above.

The composition preferably also comprises other essential components of a CRISPR-Cas system, e.g. a guide RNA.

In a fifth aspect, the invention relates to a method of site-specific engineering of a target DNA, the method comprising contacting the target DNA with a CRISPR-Cas system comprising the polypeptide, nucleic acid molecule or composition described herein, and recruiting an effector domain to the target site.

Without wishing to be bound to any theory, the polypeptide described herein comprises: (a) an RNA-binding portion that interacts with the DNA-targeting RNA of a CRISPR-Cas system; and (b) DNA-binding portion that interacts with the target DNA. It may also comprise an activity portion that exhibits nuclease activity that creates a single-stranded nick or double stranded break in the target DNA of the CRISPR-Cas system, wherein the site of the double stranded break is determined by the DNA-targeting RNA, wherein preferably the contacting occurs under conditions that are permissive for nonhomologous end joining (NHEJ) or homology-directed repair (HDR), preferably HDR, and the target DNA is cleaved and rejoined to produce a modified DNA sequence.

It is within the knowledge of the skilled person to utilize the polypeptide, the recombinant expression vector, or the composition of the invention effectively in the site-directed engineering of a target DNA, including genome editing or base editing, in the light of the afore-described aspects and the common general knowledge regarding CRISPR-Cas systems.

In various embodiments, the target DNA is extrachromosomal (e.g. an episomal sequence, a minicircle sequence, a mitochondrial sequence, a chloroplast sequence, etc.) or is part of a chromosome in vitro, in an isolated or cultured cell, or in a cell in an organism.

In various embodiments, the cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, an invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, and a human cell. In various embodiments, the organism is selected from the group consisting of: an archaea, a bacterium, a eukaryotic single-cell organism, an algae, a plant, an animal, an invertebrate, a fly, a worm, a cnidarian, a vertebrate, a fish, a frog, a bird, a mammal, an ungulate, a rodent, a rat, a mouse, and a non-human primate.

Also encompassed in the present application are cells and non-human organisms genetically engineered by the method described herein.

In a sixth aspect, the invention relates to use of the polypeptide, nucleic acid molecule or composition described herein in site-directed nucleic acid modification, preferably as a component in a CRISPR-Cas system.

The present invention is further illustrated by the following examples. However, it should be understood, that the invention is not limited to the exemplified embodiments.

EXAMPLES

Materials and Methods

Example 1: CRISPR-Cas Nucleases with Missense Mutations and Deletions

Overall, the inventors aimed to truncate different Cas enzymes, including Cas9 from *Streptococcus pyogenes,* rationally guided by the solved crystal structures of these proteins (Nishimasu, H. et al. *Cell* 156, 935-949 (2014); Nishimasu, H. et al. *Cell* 162, 1113-1126 (2015); Yamano, T.

et al. *Cell* 165, 949-962 (2016)). For example, disrupting protein secondary structures (α-helices and β-sheets) was avoided.

As a proof-of-concept, the inventors deleted different parts of a catalytically dead Cas9 gene from *Streptococcus pyogenes* (dSpCas9) fused to a tripartite activator, VP64-p65-Rta (VPR) (Chavez, A. et al. *Nat Methods* 12, 326-328, doi:10.1038/nmeth.3312 (2015)), and then tested the ability of each truncated dSpCas9-VPR fusion to activate the expression of a zsGreen reporter that was under the control of a minimal promoter with multiple binding sites for the enzyme. Using published crystal structures of SpCas9 as a guide, the inventors focused primarily on eliminating regions of the protein that appear to be globular and are not in contact with either the DNA or the gRNA. Furthermore, the start and end residues of each target region must be spatially close together so that the deleted portion of the protein could be replaced with a short linker. The regions of the dSpCas9 protein that were deleted are summarized in FIGS. 1-5.

Figure 6:
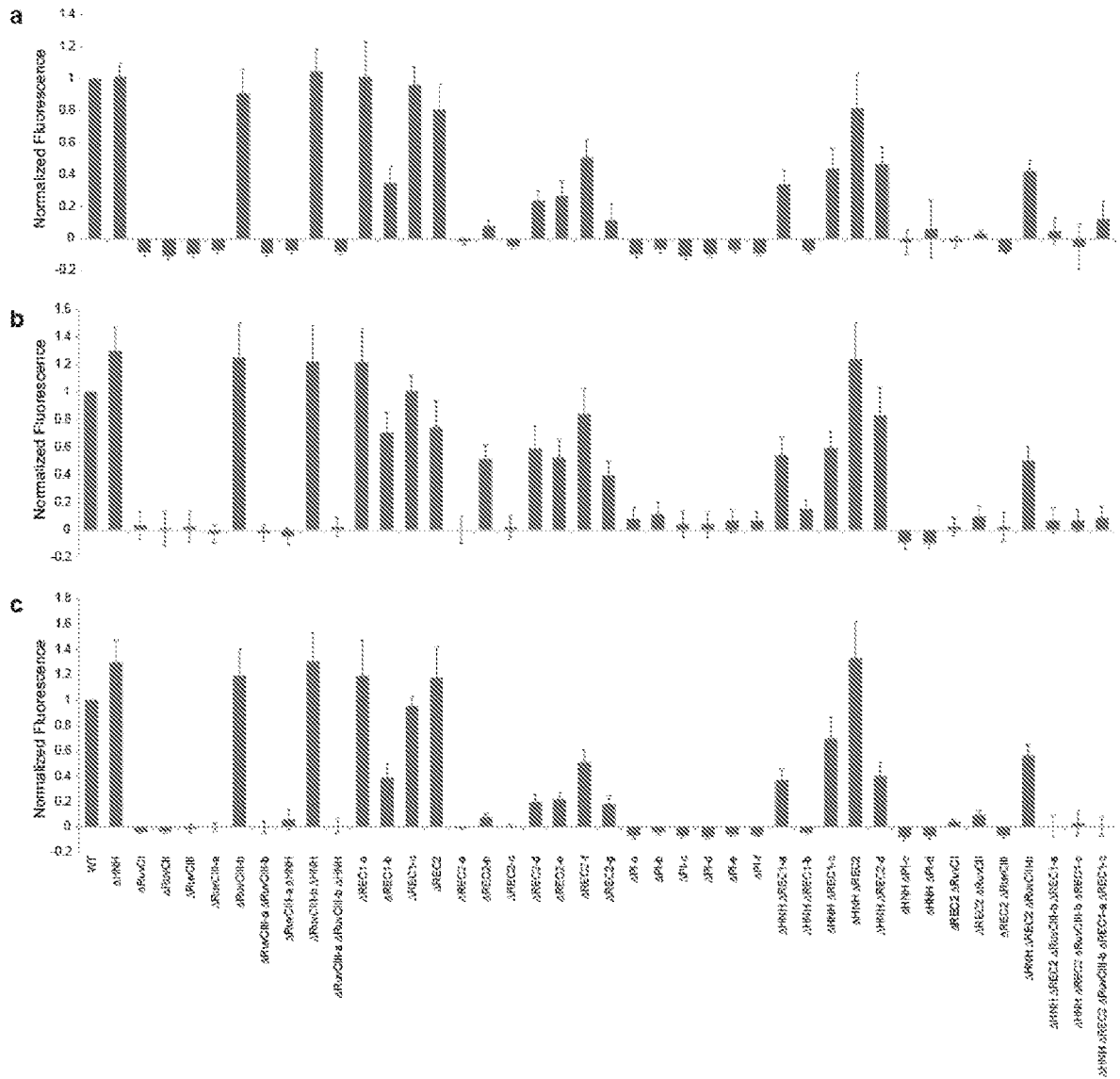
FIG. 6 shows the results of reporter assays of 41 different truncated constructs, with deletions in various parts of the REC or NUC lobe. (a) A minimal promoter containing two binding sites for a dSpCas9-VPR activator was used and the cells were analysed 24 hours after transfection. (b) A minimal promoter containing two binding sites was used and the cells were analysed 48 hours after transfection. (c) A minimal promoter containing three binding sites was used and the cells were analysed 24 hours after transfection.

The results of the reporter assays for all the truncated constructs (except those involving REC3) are shown in FIG. 6. Within the nuclease lobe (FIG. 6), it was found that removal of the entire HNH nuclease domain did not affect the ability of dSpCas9-VPR to activate gene expression significantly. However, removal of the RuvCI, RuvCII, or RuvCIII domain resulted in complete abolishment of reporter gene activation. Subsequently, smaller fragments of the RuvCIII domain were deleted and it was found that removal of one of the fragments, RuvCIII-b, did not hamper the regulatory activity of dSpCas9-VPR significantly.

For the REC lobe, it was examined whether any segments of the REC1, REC2, or PI domains, which are involved in DNA recognition, may be removed without causing the dSpCas9 scaffold to lose its function completely (FIG. 6). Previous mutational analysis of the REC1 domain found that Δ97-150 and Δ312-409, which are regions of Cas9 that interact with a repeat:anti-repeat duplex of the gRNA, abolished DNA cleavage of the enzyme. Hence, deletions that were located towards the back portion of the REC1 domain were tested instead and it was found that Δ510-655 (ΔREC1-a) and Δ662-710 (ΔREC1-c) did not affect the transcriptional activation function of dSpCas9-VPR significantly. Additionally, while a previous study showed that a Cas9 mutant lacking the REC2 domain retained only 50% of the DNA cleavage activity of the wildtype enzyme, it was found that removal of the REC2 domain from dSpCas9-VPR reduced reporter gene activation by only around 20%. Surprisingly, deletions of smaller fragments of the REC2 domain were more deleterious than removal of the entire domain. It was also found that removal of any segment of the PI domain abolished the activity of dSpCas9-VPR completely.

The inventors further asked whether different deletions could be combined to yield smaller but functional dSpCas9-VPR enzymes (FIG. 6). While pairing of ΔHNH with ΔREC2 gave the same extent of reporter gene activation as ΔREC2 alone, combining ΔHNH with either ΔREC1-a or ΔREC1-c significantly reduced the activity of dSpCas9-VPR, although each of the individual deletions did not have an obvious effect. Nevertheless, it was found that five of the combinatorial deletions tested still resulted in smaller dSpCas9-VPR constructs that gave at least 30% of the activity of the full-length enzyme. Of these, the smallest scaffold contains three separate deletions, namely ΔHNH, ΔREC2, and ΔRuvCIII-b.

Figure 7:
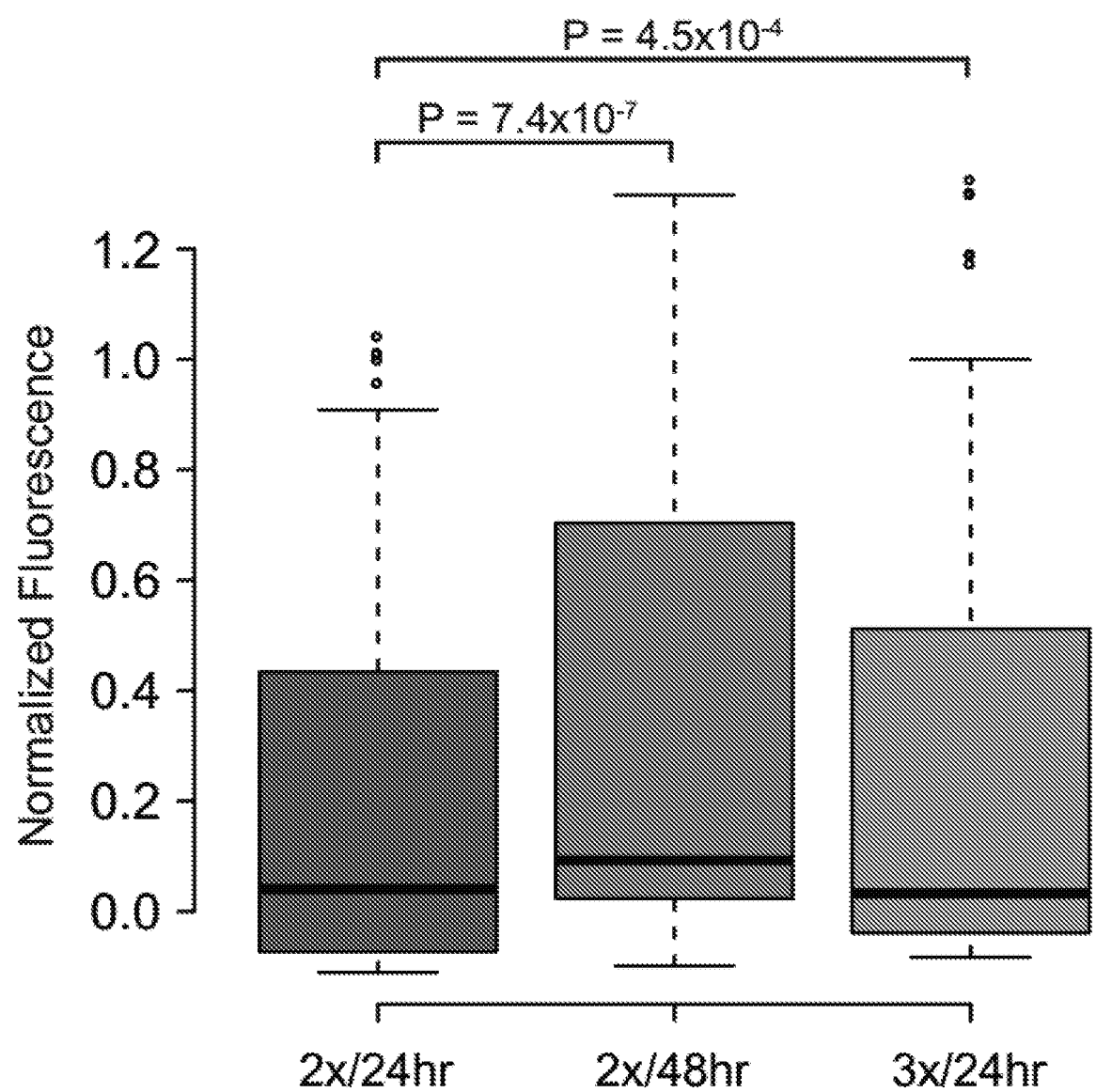
FIG. 7 shows a boxplot that summarizes the results of reporter assays of different truncated constructs. 2× indicates that a fluorescence reporter with two binding sites for the dCas9-VPR enzyme was used, while 3× indicates that a fluorescence reporter with three binding sites was used. 24 hr and 48 hr indicates the time after transfection when the assays were performed.

In the reporter experiments, the inventors tested two or three binding sites for the enzyme as well as different time durations post-transfection before performing the assays. Overall, it was observed that a longer time duration led to a more significant improvement in the extent of gene activation than an additional binding site (FIG. 7). Some of the truncated enzymes appeared to be non-functional when assayed at 24 hours post-transfection, but were still able to activate zsGreen expression at 48 hours after transfection (FIG. 6). The slower kinetics may be a result of poorer binding between the enzyme and the DNA when different parts of the dSpCas9 scaffold have been removed. Taken together, the data indicated the possibility to shrink the size of dSpCas9 and possibly other Cas9 proteins for DNA recognition.

Figure 8:
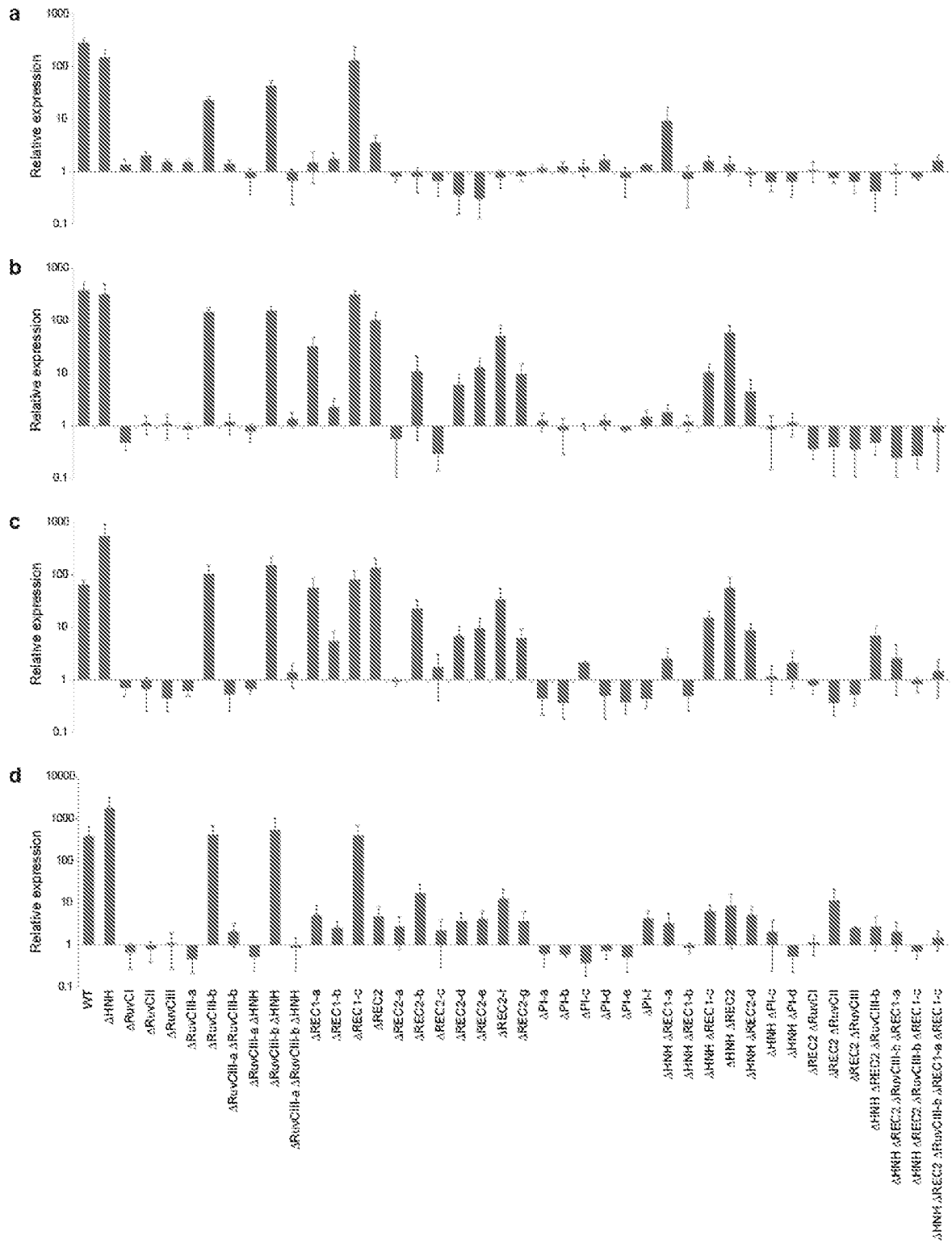
FIG. 8 shows the results of quantitative real-time PCR (qRT-PCR) experiments to measure the expression levels of (a) ACTC, (b) ASCL1, (c) MIAT, and (d) TTN in HEK293 cells, when the cells were transfected with different truncated constructs and a relevant guide RNA targeting the endogenous gene-of-interest. In these experiments, the cells were harvested 48 hours after transfection.

Next, the inventors evaluated the performance of all the truncated constructs (except those involving REC3) in a native cellular context. It was tested whether the various constructs can activate four different endogenous genes (ACTC, ASCL1, MIAT, and TTN) in HEK293T cells. From quantitative real-time PCR (qRT-PCR) experiments (FIG. 8), it was found that ΔHNH, ΔRuvCIII-b, ΔHNH ΔRuvCIII-b, and ΔREC1-c performed as well as the original full-length enzyme at all four endogenous genomic loci. Unexpectedly, it was also observed that several truncated constructs, despite being able to switch on the reporter gene robustly, did not perform well in the native cellular context, either failing to activate some of the genes completely or up-regulating gene expression at levels much lower than the full-length dCas9-VPR protein. This may be because there are multiple binding sites for the enzyme in the promoter driving the reporter gene and that the sequence for this artificial binding site is known to be able to recruit the CRISPR-Cas9 system very efficiently.

Figure 9:
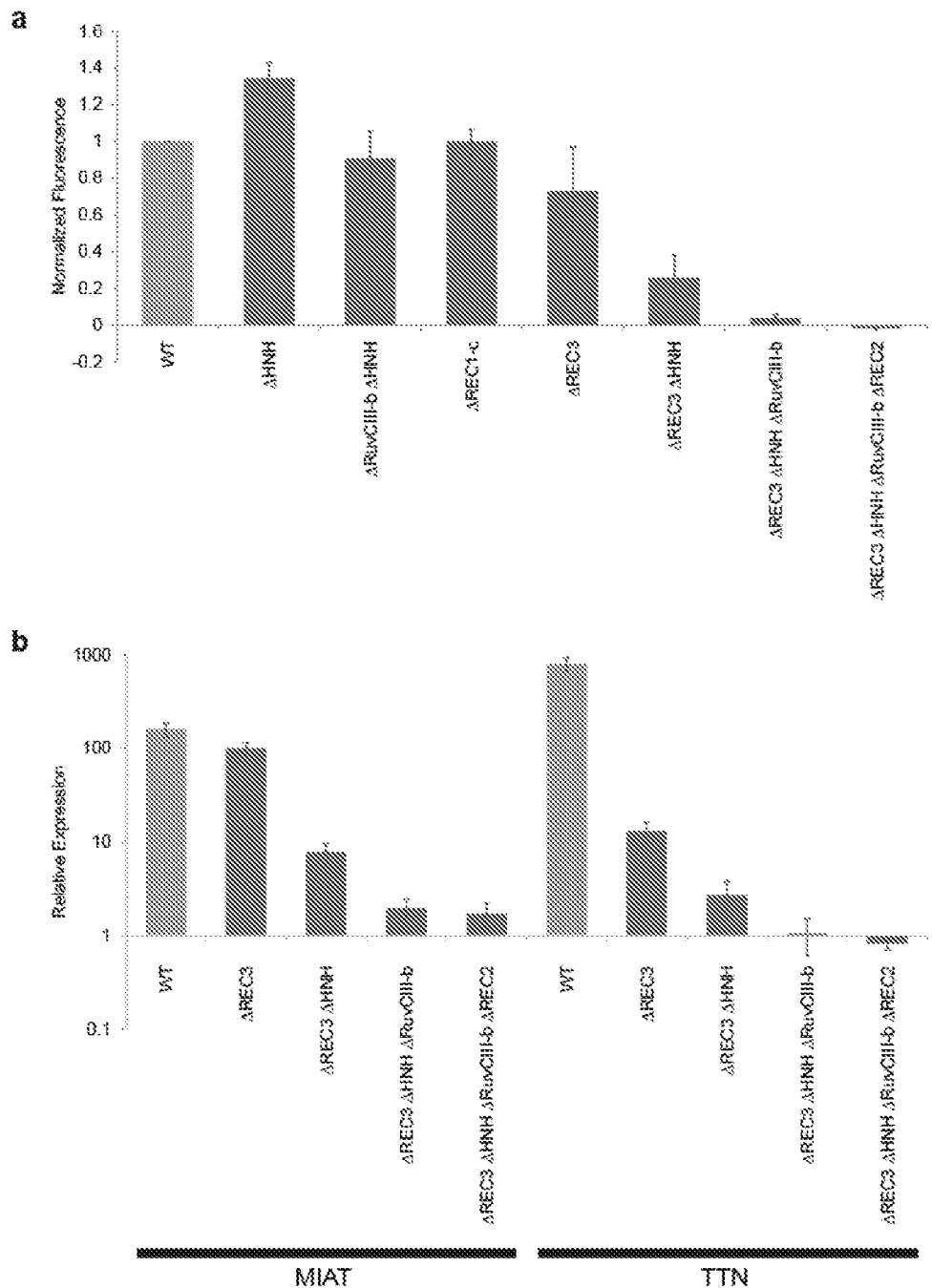
FIG. 9 shows the results of experiments evaluating the effect of deleting the REC3 domain, either by itself or in combination with other domains. (a) Reporter assays of various REC3 truncations in comparison with the original full-length protein (WT) and three other truncations (ΔHNH, ΔRuvCIII-b ΔHNH, and ΔREC1-c) that we had found to perform similarly to wildtype. (b) Expression levels of either MIAT or TTN in HEK293 cells measured by qRT-PCR, when the cells were transfected with different REC3 truncated constructs and a corresponding gRNA targeting the gene-of-interest.

Most recently, an important non-catalytic domain within the Cas9 REC lobe (termed REC3) was reported to recognize target complementarity and govern the cleavage specificity of the enzyme. Importantly, in the absence of REC3, it was found that the binding affinity of Cas9 for the target DNA was still close to wildtype, although cleavage rate decreased by 1000-fold. Hence, the inventors tested whether deletion of REC3, either by itself or in combination with other truncations, will affect the ability of the Cas9 protein to function as a robust scaffold. The inventors fused the VPR tripartite activator to different REC3 deletion constructs and performed reporter assays and qRT-PCR experiments (FIG. 9). Overall, it was found that removal of REC3 alone marginally affected the ability of dSpCas9-VPR to activate either the fluorescence reporter or two endogenous genes, MIAT and TTN. Removal of both REC3 and HNH further degraded the performance of the scaffold, but the dSpCas9-VPR enzyme was still able to activate the reporter and the two endogenous genes reasonably well. This indicates that the ΔREC3 ΔHNH construct is a suitable candidate for further engineering and optimization.

Figure 10:
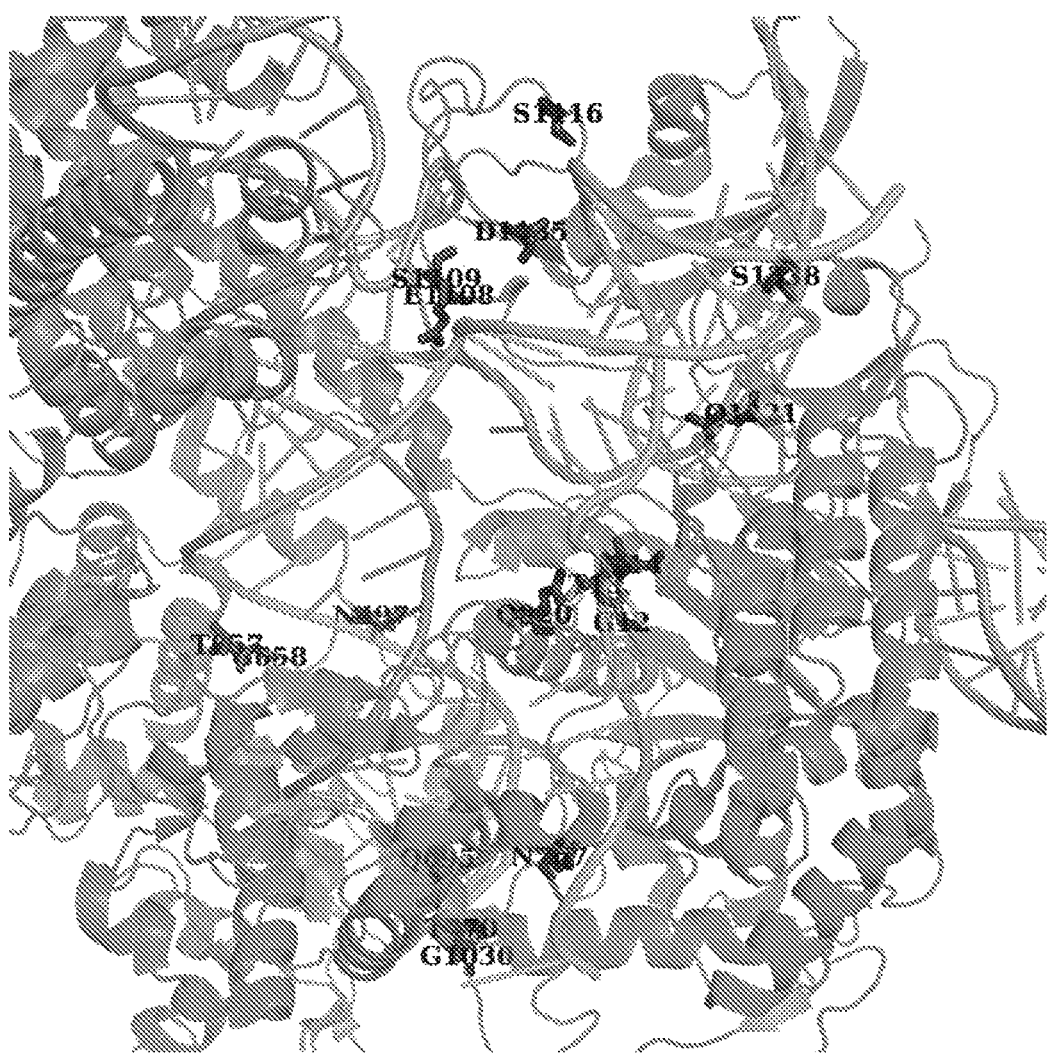
FIG. 10 shows a ribbon diagram of dSpCas9 bound to a gRNA and a target DNA. The residues that are within 5 Å of the DNA are represented as sticks.
Figure 11:
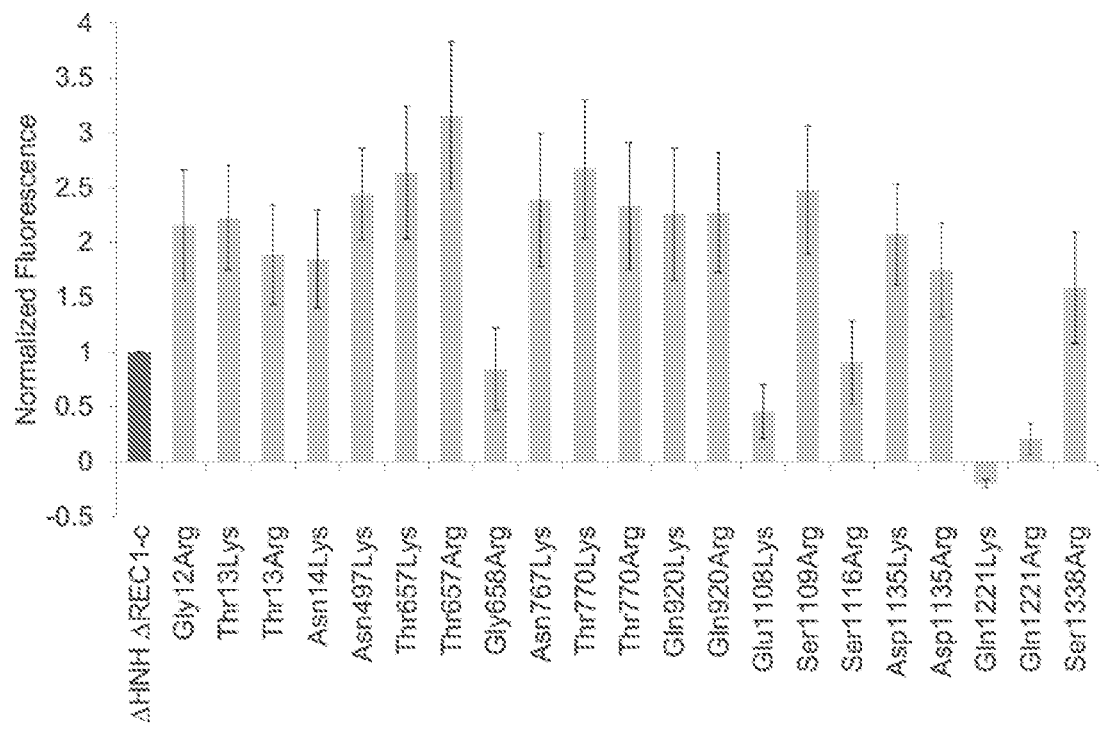
FIG. 11 shows the reporter assays of constructs, each of which has 1 mutation introduced into deletions of HNH and REC1-c ("2ple").
Figure 12:
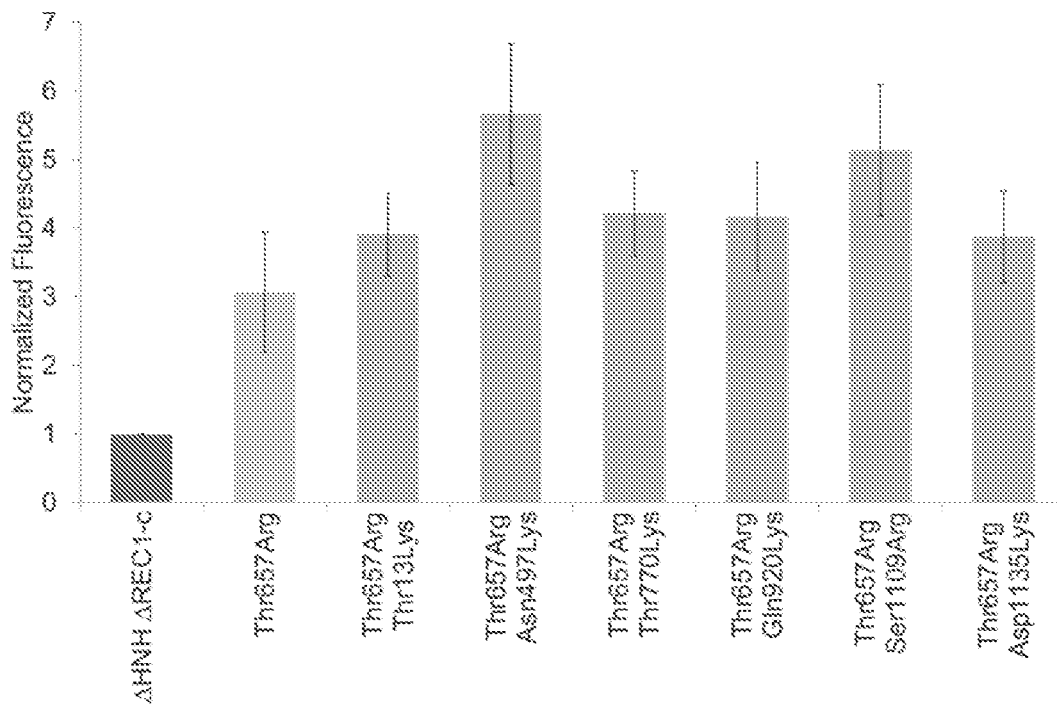
FIG. 12 shows the reporter assays of constructs, each of which has 2 different mutations introduced into deletions of HNH and REC1-c ("2ple").
Figure 13:
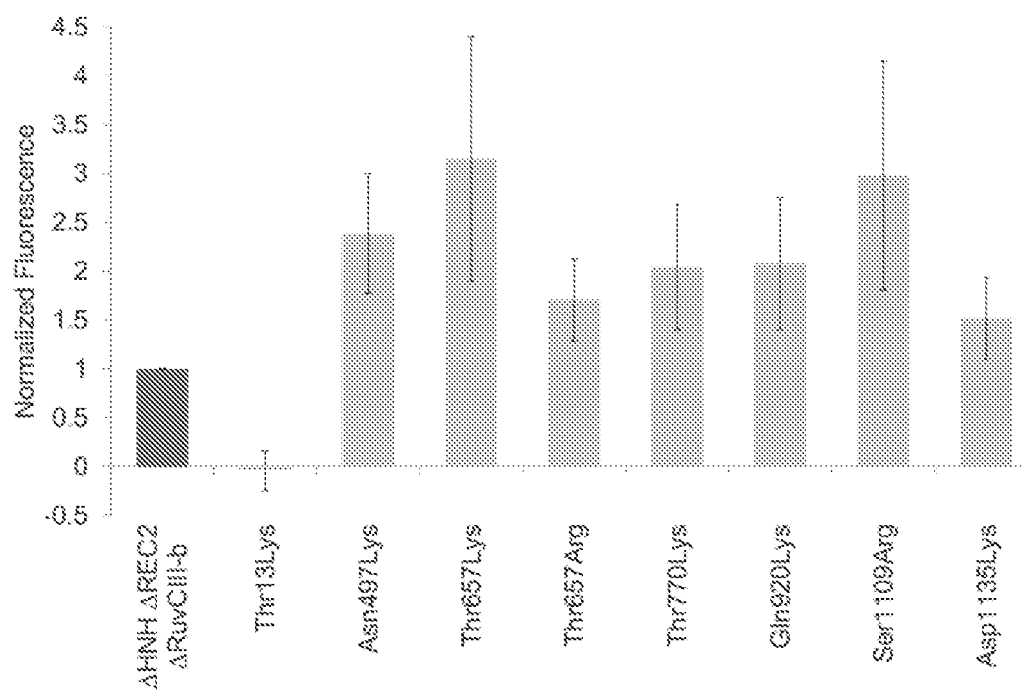
FIG. 13 shows the reporter assays of constructs, each of which has 1 mutation introduced into HNH, REC2, and RuvCIII-b ("3ple").

It was hypothesized that the performance of the dCas9 scaffolds may be improved by enhancing the binding between each scaffold and the underlying DNA. Since the DNA backbone is negatively charged, the inventors sought to introduce positively charged amino acids (lysine or arginine) into the dCas9 protein. From existing crystal structures of SpCas9, the inventors selected a handful of residues that are poorly conserved and thus may not be important in the CRISPR-Cas9 system, that can accommodate a mutation to either lysine or arginine based on computational simulations, and that are sufficiently close to the targeted DNA for further testing (FIG. 10). The inventors introduced the mutations individually into the ΔHNH ΔREC1-c construct and performed the reporter assay. Notably, it was observed that most of the selected mutations could enhance the performance of ΔHNH ΔREC1-c (FIG. 11). The inventors also introduced a subset of the mutations into the ΔHNH ΔREC2 ΔRuvCIII-b construct and performed the reporter assay. It was observed that most of the tested mutations could enhance the performance of ΔHNH ΔREC2 ΔRuvCIII-b (FIG. 13). The next steps are to comprehensively evaluate the mutations in combinations (FIG. 12) and to further test whether they could help to improve the ability of a truncated dCas9-VPR protein to activate gene expression in an endogenous cellular context.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

---

What is claimed is:

1. A polypeptide having at least 50% sequence identity to *Streptococcus pyogenes* Cas9 having the amino acid sequence set forth in SEQ ID NO:1 over its entire length; wherein said polypeptide comprises at least one combination of deletions selected from the group consisting of ΔHNH ΔRuvCIII-b (Δ775-909 Δ1002-1074), ΔREC3 ΔHNH ΔRuvCIII-b (Δ498-712 Δ775-909 Δ1002-1074), ΔREC2 ΔREC3 ΔHNH ΔRuvCIII-b (Δ180-308 Δ498-712 Δ775-909 Δ1002-1074), and ΔREC2 ΔHNH ΔRuvCIII-b (Δ180-308 Δ775-909 Δ1002-1074); wherein the polypeptide comprises a PI domain (1099-1368), wherein the position numbering is in accordance with SEQ ID NO:1; and wherein the polypeptide has CRISPR-Cas DNA-binding activity.

2. The polypeptide of claim 1, wherein the polypeptide further comprises at least one missense mutation selected from the group consisting of G12R, T13K, T13R, N14K, N497K, T657K, T657R, N767K, T770K, T770R, Q920K, Q920R, S1109R, D1135K, D1135R, S1338R, and combinations thereof.

3. The polypeptide of claim 1 wherein the polypeptide comprises at least one combination of modifications selected from the group consisting of ΔREC2 ΔHNH ΔRuvCIII-b T13K, ΔREC2 ΔHNH ΔRuvCIII-b T657K, ΔREC2 ΔHNH T657R, ΔREC2 ΔHNH ΔRuvCIII-b 770K, ΔREC2 ΔHNH Q920K, ΔREC2 ΔHNH ΔRuvCIII-b S1109R, ΔREC2 ΔHNH D1135K, and combinations thereof.

4. The polypeptide of claim 1, wherein the polypeptide has the amino acid sequence set forth in any one of SEQ ID Nos:16, 23, 24, 25, 26, 29, and 30.

5. A nucleic acid molecule comprising or consisting of a nucleic acid encoding the polypeptide of claim 1.

6. The nucleic acid molecule of claim 5, wherein the nucleic acid molecule is a recombinant expression vector.

7. The nucleic acid molecule of claim 6, wherein the recombinant expression vector further comprises at least one regulatory element for controlling expression of the polypeptide.

8. A composition comprising the polypeptide of claim 1 and a guide RNA.

9. A method of site-specific engineering of a target DNA, the method comprising:
   contacting the target DNA with a CRISPR-Cas system comprising the polypeptide of claim 1, wherein the CRISPR-Cas DNA-binding activity of the polypeptide recruits an effector domain to the target DNA.

10. The method of claim 9, wherein the target DNA is extrachromosomal or is part of a chromosome in vitro, in vivo, or in a cell.

* * * * *

SEQUENCE LISTING

```
<160> NUMBER OF SEQ ID NOS: 30

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
```

```
            145                 150                 155                 160
        Met Ile Lys Phe Arg Gly His Phe Leu Ile Glu Gly Asp Leu Asn Pro
                            165                 170                 175

Asp Asn Ser Asp Val Asp Lys Leu Phe Ile Gln Leu Val Gln Thr Tyr
                            180                 185                 190

Asn Gln Leu Phe Glu Glu Asn Pro Ile Asn Ala Ser Gly Val Asp Ala
                            195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
        225                 230                 235                 240

Leu Ile Ala Leu Ser Leu Gly Leu Thr Pro Asn Phe Lys Ser Asn Phe
                            245                 250                 255

Asp Leu Ala Glu Asp Ala Lys Leu Gln Leu Ser Lys Asp Thr Tyr Asp
                            260                 265                 270

Asp Asp Leu Asp Asn Leu Leu Ala Gln Ile Gly Asp Gln Tyr Ala Asp
                            275                 280                 285

Leu Phe Leu Ala Ala Lys Asn Leu Ser Asp Ala Ile Leu Leu Ser Asp
                            290                 295                 300

Ile Leu Arg Val Asn Thr Glu Ile Thr Lys Ala Pro Leu Ser Ala Ser
        305                 310                 315                 320

Met Ile Lys Arg Tyr Asp Glu His His Gln Asp Leu Thr Leu Leu Lys
                            325                 330                 335

Ala Leu Val Arg Gln Gln Leu Pro Glu Lys Tyr Lys Glu Ile Phe Phe
                            340                 345                 350

Asp Gln Ser Lys Asn Gly Tyr Ala Gly Tyr Ile Asp Gly Gly Ala Ser
                            355                 360                 365

Gln Glu Glu Phe Tyr Lys Phe Ile Lys Pro Ile Leu Glu Lys Met Asp
                            370                 375                 380

Gly Thr Glu Glu Leu Leu Val Lys Leu Asn Arg Glu Asp Leu Leu Arg
        385                 390                 395                 400

Lys Gln Arg Thr Phe Asp Asn Gly Ser Ile Pro His Gln Ile His Leu
                            405                 410                 415

Gly Glu Leu His Ala Ile Leu Arg Arg Gln Glu Asp Phe Tyr Pro Phe
                            420                 425                 430

Leu Lys Asp Asn Arg Glu Lys Ile Glu Lys Ile Leu Thr Phe Arg Ile
                            435                 440                 445

Pro Tyr Tyr Val Gly Pro Leu Ala Arg Gly Asn Ser Arg Phe Ala Trp
                            450                 455                 460

Met Thr Arg Lys Ser Glu Glu Thr Ile Thr Pro Trp Asn Phe Glu Glu
        465                 470                 475                 480

Val Val Asp Lys Gly Ala Ser Ala Gln Ser Phe Ile Glu Arg Met Thr
                            485                 490                 495

Asn Phe Asp Lys Asn Leu Pro Asn Glu Lys Val Leu Pro Lys His Ser
                            500                 505                 510

Leu Leu Tyr Glu Tyr Phe Thr Val Tyr Asn Glu Leu Thr Lys Val Lys
                            515                 520                 525

Tyr Val Thr Glu Gly Met Arg Lys Pro Ala Phe Leu Ser Gly Glu Gln
                            530                 535                 540

Lys Lys Ala Ile Val Asp Leu Leu Phe Lys Thr Asn Arg Lys Val Thr
        545                 550                 555                 560

Val Lys Gln Leu Lys Glu Asp Tyr Phe Lys Lys Ile Glu Cys Phe Asp
                            565                 570                 575
```

```
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990
```

```
Val Gly Thr Ala Leu Ile Lys Lys  Tyr Pro Lys Leu Glu  Ser Glu Phe
            995                 1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

<210> SEQ ID NO 2
<211> LENGTH: 1053
<212> TYPE: PRT
```

<213> ORGANISM: Staphylococcus aureus

<400> SEQUENCE: 2

```
Met Lys Arg Asn Tyr Ile Leu Gly Leu Asp Ile Gly Ile Thr Ser Val
 1               5                  10                  15
Gly Tyr Gly Ile Ile Asp Tyr Glu Thr Arg Asp Val Ile Asp Ala Gly
            20                  25                  30
Val Arg Leu Phe Lys Glu Ala Asn Val Glu Asn Asn Glu Gly Arg Arg
        35                  40                  45
Ser Lys Arg Gly Ala Arg Arg Leu Lys Arg Arg Arg His Arg Ile
    50                  55                  60
Gln Arg Val Lys Lys Leu Leu Phe Asp Tyr Asn Leu Leu Thr Asp His
65                  70                  75                  80
Ser Glu Leu Ser Gly Ile Asn Pro Tyr Glu Ala Arg Val Lys Gly Leu
                85                  90                  95
Ser Gln Lys Leu Ser Glu Glu Phe Ser Ala Ala Leu Leu His Leu
            100                 105                 110
Ala Lys Arg Arg Gly Val His Asn Val Asn Glu Val Glu Glu Asp Thr
        115                 120                 125
Gly Asn Glu Leu Ser Thr Lys Glu Gln Ile Ser Arg Asn Ser Lys Ala
    130                 135                 140
Leu Glu Glu Lys Tyr Val Ala Glu Leu Gln Leu Glu Arg Leu Lys Lys
145                 150                 155                 160
Asp Gly Glu Val Arg Gly Ser Ile Asn Arg Phe Lys Thr Ser Asp Tyr
                165                 170                 175
Val Lys Glu Ala Lys Gln Leu Leu Lys Val Gln Lys Ala Tyr His Gln
            180                 185                 190
Leu Asp Gln Ser Phe Ile Asp Thr Tyr Ile Asp Leu Leu Glu Thr Arg
        195                 200                 205
Arg Thr Tyr Tyr Glu Gly Pro Gly Glu Gly Ser Pro Phe Gly Trp Lys
    210                 215                 220
Asp Ile Lys Glu Trp Tyr Glu Met Leu Met Gly His Cys Thr Tyr Phe
225                 230                 235                 240
Pro Glu Glu Leu Arg Ser Val Lys Tyr Ala Tyr Asn Ala Asp Leu Tyr
                245                 250                 255
Asn Ala Leu Asn Asp Leu Asn Asn Leu Val Ile Thr Arg Asp Glu Asn
            260                 265                 270
Glu Lys Leu Glu Tyr Tyr Glu Lys Phe Gln Ile Ile Glu Asn Val Phe
        275                 280                 285
Lys Gln Lys Lys Lys Pro Thr Leu Lys Gln Ile Ala Lys Glu Ile Leu
    290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
            340                 345                 350
Lys Ile Leu Thr Ile Tyr Gln Ser Ser Glu Asp Ile Gln Glu Glu Leu
        355                 360                 365
Thr Asn Leu Asn Ser Glu Leu Thr Gln Glu Glu Ile Glu Gln Ile Ser
    370                 375                 380
Asn Leu Lys Gly Tyr Thr Gly Thr His Asn Leu Ser Leu Lys Ala Ile
385                 390                 395                 400
```

```
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
            420                 425                 430
Gln Lys Glu Ile Pro Thr Thr Leu Val Asp Asp Phe Ile Leu Ser Pro
        435                 440                 445
Val Val Lys Arg Ser Phe Ile Gln Ser Ile Lys Val Ile Asn Ala Ile
450                 455                 460
Ile Lys Lys Tyr Gly Leu Pro Asn Asp Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Arg Thr Thr
                500                 505                 510
Gly Lys Glu Asn Ala Lys Tyr Leu Ile Glu Lys Ile Lys Leu His Asp
        515                 520                 525
Met Gln Glu Gly Lys Cys Leu Tyr Ser Leu Glu Ala Ile Pro Leu Glu
        530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
                565                 570                 575
Gln Glu Glu Asn Ser Lys Lys Gly Asn Arg Thr Pro Phe Gln Tyr Leu
                580                 585                 590
Ser Ser Ser Asp Ser Lys Ile Ser Tyr Glu Thr Phe Lys Lys His Ile
        595                 600                 605
Leu Asn Leu Ala Lys Gly Lys Gly Arg Ile Ser Lys Thr Lys Lys Glu
        610                 615                 620
Tyr Leu Leu Glu Glu Arg Asp Ile Asn Arg Phe Ser Val Gln Lys Asp
625                 630                 635                 640
Phe Ile Asn Arg Asn Leu Val Asp Thr Arg Tyr Ala Thr Arg Gly Leu
                645                 650                 655
Met Asn Leu Leu Arg Ser Tyr Phe Arg Val Asn Asn Leu Asp Val Lys
                660                 665                 670
Val Lys Ser Ile Asn Gly Gly Phe Thr Ser Phe Leu Arg Arg Lys Trp
        675                 680                 685
Lys Phe Lys Lys Glu Arg Asn Lys Gly Tyr Lys His His Ala Glu Asp
        690                 695                 700
Ala Leu Ile Ile Ala Asn Ala Asp Phe Ile Phe Lys Glu Trp Lys Lys
705                 710                 715                 720
Leu Asp Lys Ala Lys Lys Val Met Glu Asn Gln Met Phe Glu Lys
                725                 730                 735
Gln Ala Glu Ser Met Pro Glu Ile Glu Thr Glu Gln Glu Tyr Lys Glu
                740                 745                 750
Ile Phe Ile Thr Pro His Gln Ile Lys His Ile Lys Asp Phe Lys Asp
        755                 760                 765
Tyr Lys Tyr Ser His Arg Val Asp Lys Lys Pro Asn Arg Glu Leu Ile
        770                 775                 780
Asn Asp Thr Leu Tyr Ser Thr Arg Lys Asp Lys Gly Asn Thr Leu
785                 790                 795                 800
Ile Val Asn Asn Leu Asn Gly Leu Tyr Asp Lys Asp Asn Asp Lys Leu
                805                 810                 815
Lys Lys Leu Ile Asn Lys Ser Pro Glu Lys Leu Leu Met Tyr His His
```

```
                  820                 825                 830
Asp Pro Gln Thr Tyr Gln Lys Leu Lys Leu Ile Met Glu Gln Tyr Gly
            835                 840                 845

Asp Glu Lys Asn Pro Leu Tyr Lys Tyr Glu Glu Thr Gly Asn Tyr
        850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
        930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
            995                1000                1005

Asn Asp Lys Arg Pro Pro Arg Ile Ile Lys Thr Ile Ala Ser Lys
        1010                1015                1020

Thr Gln Ser Ile Lys Lys Tyr Ser Thr Asp Ile Leu Gly Asn Leu
        1025                1030                1035

Tyr Glu Val Lys Ser Lys Lys His Pro Gln Ile Ile Lys Lys Gly
        1040                1045                1050

<210> SEQ ID NO 3
<211> LENGTH: 1082
<212> TYPE: PRT
<213> ORGANISM: Neiserria meningitides

<400> SEQUENCE: 3

Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Ala His Arg Leu Leu
65                  70                  75                  80

Arg Thr Arg Arg Leu Leu Lys Arg Glu Gly Val Leu Gln Ala Ala Asn
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140
```

-continued

```
Lys Asn Glu Gly Glu Thr Ala Asp Lys Glu Leu Gly Ala Leu Leu Lys
145                 150                 155                 160

Gly Val Ala Gly Asn Ala His Ala Leu Gln Thr Gly Asp Phe Arg Thr
            165                 170                 175

Pro Ala Glu Leu Ala Leu Asn Lys Phe Glu Lys Glu Ser Gly His Ile
        180                 185                 190

Arg Asn Gln Arg Ser Asp Tyr Ser His Thr Phe Ser Arg Lys Asp Leu
    195                 200                 205

Gln Ala Glu Leu Ile Leu Leu Phe Glu Lys Gln Lys Glu Phe Gly Asn
210                 215                 220

Pro His Val Ser Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
```

|     |     |     |     |     |     |     |     |     |     |     |     |     |
| --- | --- | --- | --- | --- | --- | --- | --- | --- | --- | --- | --- | --- |
|     |     |     | 565 |     |     |     | 570 |     |     |     | 575 |     |
| Arg | Leu | Asn | Glu | Lys | Gly | Tyr | Val | Glu | Ile | Asp | His | Ala | Leu | Pro | Phe |
|     |     |     | 580 |     |     |     | 585 |     |     |     | 590 |     |
| Ser | Arg | Thr | Trp | Asp | Asp | Ser | Phe | Asn | Asn | Lys | Val | Leu | Val | Leu | Gly |
|     |     | 595 |     |     |     | 600 |     |     |     | 605 |     |
| Ser | Glu | Asn | Gln | Asn | Lys | Gly | Asn | Gln | Thr | Pro | Tyr | Glu | Tyr | Phe | Asn |
|     | 610 |     |     |     | 615 |     |     |     | 620 |     |     |
| Gly | Lys | Asp | Asn | Ser | Arg | Glu | Trp | Gln | Glu | Phe | Lys | Ala | Arg | Val | Glu |
| 625 |     |     |     | 630 |     |     |     | 635 |     |     |     | 640 |
| Thr | Ser | Arg | Phe | Pro | Arg | Ser | Lys | Lys | Gln | Arg | Ile | Leu | Leu | Gln | Lys |
|     |     |     | 645 |     |     |     | 650 |     |     |     | 655 |
| Phe | Asp | Glu | Asp | Gly | Phe | Lys | Glu | Arg | Asn | Leu | Asn | Asp | Thr | Arg | Tyr |
|     |     |     | 660 |     |     |     | 665 |     |     |     | 670 |
| Val | Asn | Arg | Phe | Leu | Cys | Gln | Phe | Val | Ala | Asp | Arg | Met | Arg | Leu | Thr |
|     |     |     | 675 |     |     |     | 680 |     |     |     | 685 |
| Gly | Lys | Gly | Lys | Lys | Arg | Val | Phe | Ala | Ser | Asn | Gly | Gln | Ile | Thr | Asn |
|     |     | 690 |     |     |     | 695 |     |     |     | 700 |     |
| Leu | Leu | Arg | Gly | Phe | Trp | Gly | Leu | Arg | Lys | Val | Arg | Ala | Glu | Asn | Asp |
| 705 |     |     |     | 710 |     |     |     | 715 |     |     |     | 720 |
| Arg | His | His | Ala | Leu | Asp | Ala | Val | Val | Val | Ala | Cys | Ser | Thr | Val | Ala |
|     |     |     | 725 |     |     |     | 730 |     |     |     | 735 |
| Met | Gln | Gln | Lys | Ile | Thr | Arg | Phe | Val | Arg | Tyr | Lys | Glu | Met | Asn | Ala |
|     |     |     | 740 |     |     |     | 745 |     |     |     | 750 |
| Phe | Asp | Gly | Lys | Thr | Ile | Asp | Lys | Glu | Thr | Gly | Glu | Val | Leu | His | Gln |
|     |     |     | 755 |     |     |     | 760 |     |     |     | 765 |
| Lys | Thr | His | Phe | Pro | Gln | Pro | Trp | Glu | Phe | Phe | Ala | Gln | Glu | Val | Met |
|     | 770 |     |     |     | 775 |     |     |     | 780 |     |     |
| Ile | Arg | Val | Phe | Gly | Lys | Pro | Asp | Gly | Lys | Pro | Glu | Phe | Glu | Glu | Ala |
| 785 |     |     |     | 790 |     |     |     | 795 |     |     |     | 800 |
| Asp | Thr | Leu | Glu | Lys | Leu | Arg | Thr | Leu | Leu | Ala | Glu | Lys | Leu | Ser | Ser |
|     |     |     | 805 |     |     |     | 810 |     |     |     | 815 |
| Arg | Pro | Glu | Ala | Val | His | Glu | Tyr | Val | Thr | Pro | Leu | Phe | Val | Ser | Arg |
|     |     |     | 820 |     |     |     | 825 |     |     |     | 830 |
| Ala | Pro | Asn | Arg | Lys | Met | Ser | Gly | Gln | Gly | His | Met | Glu | Thr | Val | Lys |
|     |     |     | 835 |     |     |     | 840 |     |     |     | 845 |
| Ser | Ala | Lys | Arg | Leu | Asp | Glu | Gly | Val | Ser | Val | Leu | Arg | Val | Pro | Leu |
|     |     |     | 850 |     |     |     | 855 |     |     |     | 860 |
| Thr | Gln | Leu | Lys | Leu | Lys | Asp | Leu | Glu | Lys | Met | Val | Asn | Arg | Glu | Arg |
| 865 |     |     |     | 870 |     |     |     | 875 |     |     |     | 880 |
| Glu | Pro | Lys | Leu | Tyr | Glu | Ala | Leu | Lys | Ala | Arg | Leu | Glu | Ala | His | Lys |
|     |     |     | 885 |     |     |     | 890 |     |     |     | 895 |
| Asp | Asp | Pro | Ala | Lys | Ala | Phe | Ala | Glu | Pro | Phe | Tyr | Lys | Tyr | Asp | Lys |
|     |     |     | 900 |     |     |     | 905 |     |     |     | 910 |
| Ala | Gly | Asn | Arg | Thr | Gln | Gln | Val | Lys | Ala | Val | Arg | Val | Glu | Gln | Val |
|     |     | 915 |     |     |     | 920 |     |     |     | 925 |     |
| Gln | Lys | Thr | Gly | Val | Trp | Val | Arg | Asn | His | Asn | Gly | Ile | Ala | Asp | Asn |
|     | 930 |     |     |     | 935 |     |     |     | 940 |     |     |
| Ala | Thr | Met | Val | Arg | Val | Asp | Val | Phe | Glu | Lys | Gly | Asp | Lys | Tyr | Tyr |
| 945 |     |     |     | 950 |     |     |     | 955 |     |     |     | 960 |
| Leu | Val | Pro | Ile | Tyr | Ser | Trp | Gln | Val | Ala | Lys | Gly | Ile | Leu | Pro | Asp |
|     |     |     | 965 |     |     |     | 970 |     |     |     | 975 |
| Arg | Ala | Val | Val | Gln | Gly | Lys | Asp | Glu | Glu | Asp | Trp | Gln | Leu | Ile | Asp |
|     |     |     | 980 |     |     |     | 985 |     |     |     | 990 |

```
Asp Ser Phe Asn Phe Lys Phe Ser Leu His Pro Asn Asp Leu Val Glu
            995                 1000                1005

Val Ile Thr Lys Lys Ala Arg Met Phe Gly Tyr Phe Ala Ser Cys
        1010                1015                1020

His Arg Gly Thr Gly Asn Ile Asn Ile Arg Ile His Asp Leu Asp
        1025                1030                1035

His Lys Ile Gly Lys Asn Gly Ile Leu Glu Gly Ile Gly Val Lys
        1040                1045                1050

Thr Ala Leu Ser Phe Gln Lys Tyr Gln Ile Asp Glu Leu Gly Lys
        1055                1060                1065

Glu Ile Arg Pro Cys Arg Leu Lys Lys Arg Pro Pro Val Arg
        1070                1075                1080

<210> SEQ ID NO 4
<211> LENGTH: 1307
<212> TYPE: PRT
<213> ORGANISM: Acidaminococcus sp.

<400> SEQUENCE: 4

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
            85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
            115                 120                 125

Tyr Lys Gly Leu Phe Lys Ala Glu Leu Phe Asn Gly Lys Val Leu Lys
            130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
            165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
        210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
            245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
```

```
            275                 280                 285
Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
            370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
            690                 695                 700
```

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
            1010                1015                1020

Asn Cys Leu Val Leu Lys Asp Tyr Pro Ala Glu Lys Val Gly Gly
            1025                1030                1035

Val Leu Asn Pro Tyr Gln Leu Thr Asp Gln Phe Thr Ser Phe Ala
            1040                1045                1050

Lys Met Gly Thr Gln Ser Gly Phe Leu Phe Tyr Val Pro Ala Pro
            1055                1060                1065

Tyr Thr Ser Lys Ile Asp Pro Leu Thr Gly Phe Val Asp Pro Phe
            1070                1075                1080

Val Trp Lys Thr Ile Lys Asn His Glu Ser Arg Lys His Phe Leu
            1085                1090                1095

Glu Gly Phe Asp Phe Leu His Tyr Asp Val Lys Thr Gly Asp Phe
            1100                1105                1110

Ile Leu His Phe Lys Met Asn Arg Asn Leu Ser Phe Gln Arg Gly
1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 5
<211> LENGTH: 1409
<212> TYPE: PRT
<213> ORGANISM: Streptococcus thermophilus

<400> SEQUENCE: 5

Met Leu Phe Asn Lys Cys Ile Ile Ser Ile Asn Leu Asp Phe Ser
1               5                   10                  15

Asn Lys Glu Lys Cys Met Thr Lys Pro Tyr Ser Ile Gly Leu Asp Ile
                20                  25                  30

Gly Thr Asn Ser Val Gly Trp Ala Val Ile Thr Asp Asn Tyr Lys Val
                35                  40                  45

Pro Ser Lys Lys Met Lys Val Leu Gly Asn Thr Ser Lys Lys Tyr Ile
        50                  55                  60

Lys Lys Asn Leu Leu Gly Val Leu Leu Phe Asp Ser Gly Ile Thr Ala
65                  70                  75                  80

Glu Gly Arg Arg Leu Lys Arg Thr Ala Arg Arg Arg Tyr Thr Arg Arg
                85                  90                  95

Arg Asn Arg Ile Leu Tyr Leu Gln Glu Ile Phe Ser Thr Glu Met Ala
                100                 105                 110

Thr Leu Asp Asp Ala Phe Phe Gln Arg Leu Asp Asp Ser Phe Leu Val
            115                 120                 125

Pro Asp Asp Lys Arg Asp Ser Lys Tyr Pro Ile Phe Gly Asn Leu Val
        130                 135                 140

Glu Glu Lys Val Tyr His Asp Glu Phe Pro Thr Ile Tyr His Leu Arg
145                 150                 155                 160

Lys Tyr Leu Ala Asp Ser Thr Lys Lys Ala Asp Leu Arg Leu Val Tyr
                165                 170                 175

```
Leu Ala Leu Ala His Met Ile Lys Tyr Arg Gly His Phe Leu Ile Glu
                180                 185                 190

Gly Glu Phe Asn Ser Lys Asn Asn Asp Ile Gln Lys Asn Phe Gln Asp
            195                 200                 205

Phe Leu Asp Thr Tyr Asn Ala Ile Phe Glu Ser Asp Leu Ser Leu Glu
        210                 215                 220

Asn Ser Lys Gln Leu Glu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                245                 250                 255

Gly Ile Phe Ser Glu Phe Leu Lys Leu Ile Val Gly Asn Gln Ala Asp
            260                 265                 270

Phe Arg Lys Cys Phe Asn Leu Asp Glu Lys Ala Ser Leu His Phe Ser
        275                 280                 285

Lys Glu Ser Tyr Asp Glu Asp Leu Glu Thr Leu Leu Gly Tyr Ile Gly
    290                 295                 300

Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
                325                 330                 335

Pro Leu Ser Ser Ala Met Ile Lys Arg Tyr Asn Glu His Lys Glu Asp
            340                 345                 350

Leu Ala Leu Leu Lys Glu Tyr Ile Arg Asn Ile Ser Leu Lys Thr Tyr
        355                 360                 365

Asn Glu Val Phe Lys Asp Asp Thr Lys Asn Gly Tyr Ala Gly Tyr Ile
    370                 375                 380

Asp Gly Lys Thr Asn Gln Glu Asp Phe Tyr Val Tyr Leu Lys Asn Leu
385                 390                 395                 400

Leu Ala Glu Phe Glu Gly Ala Asp Tyr Phe Leu Glu Lys Ile Asp Arg
                405                 410                 415

Glu Asp Phe Leu Arg Lys Gln Arg Thr Phe Asp Asn Gly Ser Ile Pro
            420                 425                 430

Tyr Gln Ile His Leu Gln Glu Met Arg Ala Ile Leu Asp Lys Gln Ala
        435                 440                 445

Lys Phe Tyr Pro Phe Leu Ala Lys Asn Lys Glu Arg Ile Glu Lys Ile
    450                 455                 460

Leu Thr Phe Arg Ile Pro Tyr Tyr Val Gly Pro Leu Ala Arg Gly Asn
465                 470                 475                 480

Ser Asp Phe Ala Trp Ser Ile Arg Lys Arg Asn Glu Lys Ile Thr Pro
                485                 490                 495

Trp Asn Phe Glu Asp Val Ile Asp Lys Glu Ser Ser Ala Glu Ala Phe
            500                 505                 510

Ile Asn Arg Met Thr Ser Phe Asp Leu Tyr Leu Pro Glu Glu Lys Val
        515                 520                 525

Leu Pro Lys His Ser Leu Leu Tyr Glu Thr Phe Asn Val Tyr Asn Glu
    530                 535                 540

Leu Thr Lys Val Arg Phe Ile Ala Glu Ser Met Arg Asp Tyr Gln Phe
545                 550                 555                 560

Leu Asp Ser Lys Gln Lys Lys Asp Ile Val Arg Leu Tyr Phe Lys Asp
                565                 570                 575

Lys Arg Lys Val Thr Asp Lys Asp Ile Ile Glu Tyr Leu His Ala Ile
            580                 585                 590
```

-continued

```
Tyr Gly Tyr Asp Gly Ile Glu Leu Lys Gly Ile Glu Lys Gln Phe Asn
        595                 600                 605

Ser Ser Leu Ser Thr Tyr His Asp Leu Leu Asn Ile Ile Asn Asp Lys
        610                 615                 620

Glu Phe Leu Asp Asp Ser Ser Asn Glu Ala Ile Ile Glu Glu Ile Ile
625                 630                 635                 640

His Thr Leu Thr Ile Phe Glu Asp Arg Glu Met Ile Lys Gln Arg Leu
                645                 650                 655

Ser Lys Phe Glu Asn Ile Phe Asp Lys Ser Val Leu Lys Lys Leu Ser
        660                 665                 670

Arg Arg His Tyr Thr Gly Trp Gly Lys Leu Ser Ala Lys Leu Ile Asn
        675                 680                 685

Gly Ile Arg Asp Glu Lys Ser Gly Asn Thr Ile Leu Asp Tyr Leu Ile
        690                 695                 700

Asp Asp Gly Ile Ser Asn Arg Asn Phe Met Gln Leu Ile His Asp Asp
705                 710                 715                 720

Ala Leu Ser Phe Lys Lys Ile Gln Lys Ala Gln Ile Ile Gly Asp
                725                 730                 735

Glu Asp Lys Gly Asn Ile Lys Glu Val Val Lys Ser Leu Pro Gly Ser
                740                 745                 750

Pro Ala Ile Lys Lys Gly Ile Leu Gln Ser Ile Lys Ile Val Asp Glu
        755                 760                 765

Leu Val Lys Val Met Gly Gly Arg Lys Pro Glu Ser Ile Val Val Glu
        770                 775                 780

Met Ala Arg Glu Asn Gln Tyr Thr Asn Gln Gly Lys Ser Asn Ser Gln
785                 790                 795                 800

Gln Arg Leu Lys Arg Leu Glu Lys Ser Leu Lys Glu Leu Gly Ser Lys
                805                 810                 815

Ile Leu Lys Glu Asn Ile Pro Ala Lys Leu Ser Lys Ile Asp Asn Asn
                820                 825                 830

Ala Leu Gln Asn Asp Arg Leu Tyr Leu Tyr Tyr Leu Gln Asn Gly Lys
        835                 840                 845

Asp Met Tyr Thr Gly Asp Asp Leu Asp Ile Asp Arg Leu Ser Asn Tyr
850                 855                 860

Asp Ile Asp His Ile Ile Pro Gln Ala Phe Leu Lys Asp Asn Ser Ile
865                 870                 875                 880

Asp Asn Lys Val Leu Val Ser Ser Ala Ser Asn Arg Gly Lys Ser Asp
                885                 890                 895

Asp Phe Pro Ser Leu Glu Val Val Lys Lys Arg Lys Thr Phe Trp Tyr
                900                 905                 910

Gln Leu Leu Lys Ser Lys Leu Ile Ser Gln Arg Lys Phe Asp Asn Leu
        915                 920                 925

Thr Lys Ala Glu Arg Gly Gly Leu Leu Pro Glu Asp Lys Ala Gly Phe
930                 935                 940

Ile Gln Arg Gln Leu Val Glu Thr Arg Gln Ile Thr Lys His Val Ala
945                 950                 955                 960

Arg Leu Leu Asp Glu Lys Phe Asn Asn Lys Lys Asp Glu Asn Asn Arg
                965                 970                 975

Ala Val Arg Thr Val Lys Ile Ile Thr Leu Lys Ser Thr Leu Val Ser
                980                 985                 990

Gln Phe Arg Lys Asp Phe Glu Leu Tyr Lys Val Arg Glu Ile Asn Asp
        995                 1000                1005

Phe His  His Ala His Asp Ala  Tyr Leu Asn Ala Val  Ile Ala Ser
```

-continued

|  | 1010 |  |  | 1015 |  |  | 1020 |  |  |
| --- | --- | --- | --- | --- | --- | --- | --- | --- | --- |

Ala Leu Leu Lys Lys Tyr Pro Lys Leu Glu Pro Glu Phe Val Tyr
    1025                    1030                      1035

Gly Asp Tyr Pro Lys Tyr Asn Ser Phe Arg Glu Arg Lys Ser Ala
    1040                    1045                      1050

Thr Glu Lys Val Tyr Phe Tyr Ser Asn Ile Met Asn Ile Phe Lys
    1055                    1060                      1065

Lys Ser Ile Ser Leu Ala Asp Gly Arg Val Ile Glu Arg Pro Leu
    1070                    1075                      1080

Ile Glu Val Asn Glu Glu Thr Gly Glu Ser Val Trp Asn Lys Glu
    1085                    1090                      1095

Ser Asp Leu Ala Thr Val Arg Arg Val Leu Ser Tyr Pro Gln Val
    1100                    1105                      1110

Asn Val Val Lys Lys Val Glu Glu Gln Asn His Gly Leu Asp Arg
    1115                    1120                      1125

Gly Lys Pro Lys Gly Leu Phe Asn Ala Asn Leu Ser Ser Lys Pro
    1130                    1135                      1140

Lys Pro Asn Ser Asn Glu Asn Leu Val Gly Ala Lys Glu Tyr Leu
    1145                    1150                      1155

Asp Pro Lys Lys Tyr Gly Gly Tyr Ala Gly Ile Ser Asn Ser Phe
    1160                    1165                      1170

Ala Val Leu Val Lys Gly Thr Ile Glu Lys Gly Ala Lys Lys Lys
    1175                    1180                      1185

Ile Thr Asn Val Leu Glu Phe Gln Gly Ile Ser Ile Leu Asp Arg
    1190                    1195                      1200

Ile Asn Tyr Arg Lys Asp Lys Leu Asn Phe Leu Leu Glu Lys Gly
    1205                    1210                      1215

Tyr Lys Asp Ile Glu Leu Ile Ile Glu Leu Pro Lys Tyr Ser Leu
    1220                    1225                      1230

Phe Glu Leu Ser Asp Gly Ser Arg Arg Met Leu Ala Ser Ile Leu
    1235                    1240                      1245

Ser Thr Asn Asn Lys Arg Gly Glu Ile His Lys Gly Asn Gln Ile
    1250                    1255                      1260

Phe Leu Ser Gln Lys Phe Val Lys Leu Leu Tyr His Ala Lys Arg
    1265                    1270                      1275

Ile Ser Asn Thr Ile Asn Glu Asn His Arg Lys Tyr Val Glu Asn
    1280                    1285                      1290

His Lys Lys Glu Phe Glu Glu Leu Phe Tyr Tyr Ile Leu Glu Phe
    1295                    1300                      1305

Asn Glu Asn Tyr Val Gly Ala Lys Lys Asn Gly Lys Leu Leu Asn
    1310                    1315                      1320

Ser Ala Phe Gln Ser Trp Gln Asn His Ser Ile Asp Glu Leu Cys
    1325                    1330                      1335

Ser Ser Phe Ile Gly Pro Thr Gly Ser Glu Arg Lys Gly Leu Phe
    1340                    1345                      1350

Glu Leu Thr Ser Arg Gly Ser Ala Ala Asp Phe Glu Phe Leu Gly
    1355                    1360                      1365

Val Lys Ile Pro Arg Tyr Arg Asp Tyr Thr Pro Ser Ser Leu Leu
    1370                    1375                      1380

Lys Asp Ala Thr Leu Ile His Gln Ser Val Thr Gly Leu Tyr Glu
    1385                    1390                      1395

Thr Arg Ile Asp Leu Ala Lys Leu Gly Glu Gly
    1400                    1405

<210> SEQ ID NO 6
<211> LENGTH: 1422
<212> TYPE: PRT
<213> ORGANISM: Sutterella wadsworthensis

<400> SEQUENCE: 6

```
Met Thr Gln Ser Glu Arg Arg Phe Ser Cys Ser Ile Gly Ile Asp Met
1               5                   10                  15

Gly Ala Lys Tyr Thr Gly Val Phe Tyr Ala Leu Phe Asp Arg Glu Glu
            20                  25                  30

Leu Pro Thr Asn Leu Asn Ser Lys Ala Met Thr Leu Val Met Pro Glu
        35                  40                  45

Thr Gly Pro Arg Tyr Val Gln Ala Gln Arg Thr Ala Val Arg His Arg
    50                  55                  60

Leu Arg Gly Gln Lys Arg Tyr Thr Leu Ala Arg Lys Leu Ala Phe Leu
65                  70                  75                  80

Val Val Asp Asp Met Ile Lys Lys Gln Glu Lys Arg Leu Thr Asp Glu
                85                  90                  95

Glu Trp Lys Arg Gly Arg Glu Ala Leu Ser Gly Leu Leu Lys Arg Arg
            100                 105                 110

Gly Tyr Ser Arg Pro Asn Ala Asp Gly Glu Asp Leu Thr Pro Leu Glu
        115                 120                 125

Asn Val Arg Ala Asp Val Phe Ala Ala His Pro Ala Phe Ser Thr Tyr
    130                 135                 140

Phe Ser Glu Val Arg Ser Leu Ala Glu Gln Trp Glu Glu Phe Thr Ala
145                 150                 155                 160

Asn Ile Ser Asn Val Glu Lys Phe Leu Gly Asp Pro Asn Ile Pro Ala
                165                 170                 175

Asp Lys Glu Phe Ile Glu Phe Ala Val Ala Glu Gly Leu Ile Asp Lys
            180                 185                 190

Thr Glu Lys Lys Ala Tyr Gln Ser Ala Leu Ser Thr Leu Arg Ala Asn
        195                 200                 205

Ala Asn Val Leu Thr Gly Leu Arg Gln Met Gly His Lys Pro Arg Ser
    210                 215                 220

Glu Tyr Phe Lys Ala Ile Glu Ala Asp Leu Lys Lys Asp Ser Arg Leu
225                 230                 235                 240

Ala Lys Ile Asn Glu Ala Phe Gly Gly Ala Glu Arg Leu Ala Arg Leu
                245                 250                 255

Leu Gly Asn Leu Ser Asn Leu Gln Leu Arg Ala Glu Arg Trp Tyr Phe
            260                 265                 270

Asn Ala Pro Asp Ile Met Lys Asp Arg Gly Trp Glu Pro Asp Arg Phe
        275                 280                 285

Lys Lys Thr Leu Val Arg Ala Phe Lys Phe Phe His Pro Ala Lys Asp
    290                 295                 300

Gln Asn Lys Gln His Leu Glu Leu Ile Lys Gln Ile Glu Asn Ser Glu
305                 310                 315                 320

Asp Ile Ile Glu Thr Leu Cys Thr Leu Asp Pro Asn Arg Thr Ile Pro
                325                 330                 335

Pro Tyr Glu Asp Gln Asn Asn Arg Arg Pro Pro Leu Asp Gln Thr Leu
            340                 345                 350

Leu Leu Ser Pro Glu Lys Leu Thr Arg Gln Tyr Gly Glu Ile Trp Lys
        355                 360                 365

Thr Trp Ser Ala Arg Leu Thr Ser Ala Glu Pro Thr Leu Ala Pro Ala
```

```
                370              375              380
Ala Glu Ile Leu Glu Arg Ser Thr Asp Arg Lys Ser Arg Val Ala Val
385              390              395              400

Asn Gly His Glu Pro Leu Pro Thr Leu Ala Tyr Gln Leu Ser Tyr Ala
                405              410              415

Leu Gln Arg Ala Phe Asp Arg Ser Lys Ala Leu Asp Pro Tyr Ala Leu
            420              425              430

Arg Ala Leu Ala Ala Gly Ser Lys Ser Asn Lys Leu Thr Ser Ala Arg
            435              440              445

Thr Ala Leu Glu Asn Cys Ile Gly Gly Gln Asn Val Lys Thr Phe Leu
450              455              460

Asp Cys Ala Arg Arg Tyr Tyr Arg Glu Ala Asp Asp Ala Lys Val Gly
465              470              475              480

Leu Trp Phe Asp Asn Ala Asp Gly Leu Leu Glu Arg Ser Asp Leu His
                485              490              495

Pro Pro Met Lys Lys Lys Ile Leu Pro Leu Leu Val Ala Asn Ile Leu
            500              505              510

Gln Thr Asp Glu Thr Thr Gly Gln Lys Phe Leu Asp Glu Ile Trp Arg
            515              520              525

Lys Gln Ile Lys Gly Arg Glu Thr Val Ala Ser Arg Cys Ala Arg Ile
530              535              540

Glu Thr Val Arg Lys Ser Phe Gly Gly Phe Asn Ile Ala Tyr Asn
545              550              555              560

Thr Ala Gln Tyr Arg Glu Val Asn Lys Leu Pro Arg Asn Ala Gln Asp
                565              570              575

Lys Glu Leu Leu Thr Ile Arg Asp Arg Val Ala Glu Thr Ala Asp Phe
            580              585              590

Ile Ala Ala Asn Leu Gly Leu Ser Asp Glu Gln Lys Arg Lys Phe Ala
            595              600              605

Asn Pro Phe Ser Leu Ala Gln Phe Tyr Thr Leu Ile Glu Thr Glu Val
610              615              620

Ser Gly Phe Ser Ala Thr Thr Leu Ala Val His Leu Glu Asn Ala Trp
625              630              635              640

Arg Met Thr Ile Lys Asp Ala Val Ile Asn Gly Glu Thr Val Arg Ala
                645              650              655

Ala Gln Cys Ser Arg Leu Pro Ala Glu Thr Ala Arg Pro Phe Asp Gly
            660              665              670

Leu Val Arg Arg Leu Val Asp Arg Gln Ala Trp Glu Ile Ala Lys Arg
            675              680              685

Val Ser Thr Asp Ile Gln Ser Lys Val Asp Phe Ser Asn Gly Ile Val
690              695              700

Asp Val Ser Ile Phe Val Glu Glu Asn Lys Phe Glu Phe Ser Ala Ser
705              710              715              720

Val Ala Asp Leu Lys Lys Asn Lys Arg Val Lys Asp Lys Met Leu Ser
                725              730              735

Glu Ala Glu Lys Leu Glu Thr Arg Trp Leu Ile Lys Asn Glu Arg Ile
            740              745              750

Lys Lys Ala Ser Arg Gly Thr Cys Pro Tyr Thr Gly Asp Arg Leu Ala
            755              760              765

Glu Gly Gly Glu Ile Asp His Ile Leu Pro Arg Ser Leu Ile Lys Asp
770              775              780

Ala Arg Gly Ile Val Phe Asn Ala Glu Pro Asn Leu Ile Tyr Ala Ser
785              790              795              800
```

-continued

Ser Arg Gly Asn Gln Leu Lys Lys Asn Gln Arg Tyr Ser Leu Ser Asp
            805                 810                 815

Leu Lys Ala Asn Tyr Arg Asn Glu Ile Phe Lys Thr Ser Asn Ile Ala
            820                 825                 830

Ala Ile Thr Ala Glu Ile Glu Asp Val Val Thr Lys Leu Gln Gln Thr
            835                 840                 845

His Arg Leu Lys Phe Phe Asp Leu Leu Asn Glu His Glu Gln Asp Cys
            850                 855                 860

Val Arg His Ala Leu Phe Leu Asp Asp Gly Ser Glu Ala Arg Asp Ala
865                 870                 875                 880

Val Leu Glu Leu Leu Ala Thr Gln Arg Arg Thr Arg Val Asn Gly Thr
            885                 890                 895

Gln Ile Trp Met Ile Lys Asn Leu Ala Asn Lys Ile Arg Glu Glu Leu
            900                 905                 910

Gln Asn Trp Cys Lys Thr Thr Asn Asn Arg Leu His Phe Gln Ala Ala
            915                 920                 925

Ala Thr Asn Val Ser Asp Ala Lys Asn Leu Arg Leu Lys Leu Ala Gln
            930                 935                 940

Asn Gln Pro Asp Phe Glu Lys Pro Asp Ile Gln Pro Ile Ala Ser His
945                 950                 955                 960

Ser Ile Asp Ala Leu Cys Ser Phe Ala Val Gly Ser Ala Asp Ala Glu
            965                 970                 975

Arg Asp Gln Asn Gly Phe Asp Tyr Leu Asp Gly Lys Thr Val Leu Gly
            980                 985                 990

Leu Tyr Pro Gln Ser Cys Glu Val Ile His Leu Gln Ala Lys Pro Gln
            995                 1000                1005

Glu Glu Lys Ser His Phe Asp Ser Val Ala Ile Phe Lys Glu Gly
1010                1015                1020

Ile Tyr Ala Glu Gln Phe Leu Pro Ile Phe Thr Leu Asn Glu Lys
1025                1030                1035

Ile Trp Ile Gly Tyr Glu Thr Leu Asn Ala Lys Gly Glu Arg Cys
1040                1045                1050

Gly Ala Ile Glu Val Ser Gly Lys Gln Pro Lys Glu Leu Leu Glu
1055                1060                1065

Met Leu Ala Pro Phe Phe Asn Lys Pro Val Gly Asp Leu Ser Ala
1070                1075                1080

His Ala Thr Tyr Arg Ile Leu Lys Lys Pro Ala Tyr Glu Phe Leu
1085                1090                1095

Ala Lys Ala Ala Leu Gln Pro Leu Ser Ala Glu Glu Lys Arg Leu
1100                1105                1110

Ala Ala Leu Leu Asp Ala Leu Arg Tyr Cys Thr Ser Arg Lys Ser
1115                1120                1125

Leu Met Ser Leu Phe Met Ala Ala Asn Gly Lys Ser Leu Lys Lys
1130                1135                1140

Arg Glu Asp Val Leu Lys Pro Lys Leu Phe Gln Leu Lys Val Glu
1145                1150                1155

Leu Lys Gly Glu Lys Ser Phe Lys Leu Asn Gly Ser Leu Thr Leu
1160                1165                1170

Pro Val Lys Gln Asp Trp Leu Arg Ile Cys Asp Ser Pro Glu Leu
1175                1180                1185

Ala Asp Ala Phe Gly Lys Pro Cys Ser Ala Asp Glu Leu Thr Ser
1190                1195                1200

-continued

Lys Leu Ala Arg Ile Trp Lys Arg Pro Val Met Arg Asp Leu Ala
1205                1210                1215

His Ala Pro Val Arg Arg Glu Phe Ser Leu Pro Ala Ile Asp Asn
1220                1225                1230

Pro Ser Gly Gly Phe Arg Ile Arg Arg Thr Asn Leu Phe Gly Asn
1235                1240                1245

Glu Leu Tyr Gln Val His Ala Ile Asn Ala Lys Lys Tyr Arg Gly
1250                1255                1260

Phe Ala Ser Ala Gly Ser Asn Val Asp Trp Ser Lys Gly Ile Leu
1265                1270                1275

Phe Asn Glu Leu Gln His Glu Asn Leu Thr Glu Cys Gly Gly Arg
1280                1285                1290

Phe Ile Thr Ser Ala Asp Val Thr Pro Met Ser Glu Trp Arg Lys
1295                1300                1305

Val Val Ala Glu Asp Asn Leu Ser Ile Trp Ile Ala Pro Gly Thr
1310                1315                1320

Glu Gly Arg Arg Tyr Val Arg Val Glu Thr Phe Ile Gln Ala
1325                1330                1335

Ser His Trp Phe Glu Gln Ser Val Glu Asn Trp Ala Ile Thr Ser
1340                1345                1350

Pro Leu Ser Leu Pro Ala Ser Phe Lys Val Asp Lys Pro Ala Glu
1355                1360                1365

Phe Gln Lys Ala Val Gly Thr Glu Leu Ser Glu Leu Leu Gly Gln
1370                1375                1380

Pro Arg Ser Glu Ile Phe Ile Glu Asn Val Gly Asn Ala Lys His
1385                1390                1395

Ile Arg Phe Trp Tyr Ile Val Ser Ser Asn Lys Lys Met Asn
1400                1405                1410

Glu Ser Tyr Asn Asn Val Ser Lys Ser
1415                1420

<210> SEQ ID NO 7
<211> LENGTH: 1365
<212> TYPE: PRT
<213> ORGANISM: Filifactor alocis

<400> SEQUENCE: 7

Met Thr Lys Glu Tyr Tyr Leu Gly Leu Asp Val Gly Thr Asn Ser Val
1               5                   10                  15

Gly Trp Ala Val Thr Asp Ser Gln Tyr Asn Leu Cys Lys Phe Lys Lys
                20                  25                  30

Lys Asp Met Trp Gly Ile Arg Leu Phe Glu Ser Ala Asn Thr Ala Lys
        35                  40                  45

Asp Arg Arg Leu Gln Arg Gly Asn Arg Arg Leu Glu Arg Lys Lys
    50                  55                  60

Gln Arg Ile Asp Leu Leu Gln Glu Ile Phe Ser Pro Glu Ile Cys Lys
65                  70                  75                  80

Ile Asp Pro Thr Phe Phe Ile Arg Leu Asn Glu Ser Arg Leu His Leu
                85                  90                  95

Glu Asp Lys Ser Asn Asp Phe Lys Tyr Pro Leu Phe Ile Glu Lys Asp
            100                 105                 110

Tyr Ser Asp Ile Glu Tyr Tyr Lys Glu Phe Pro Thr Ile Phe His Leu
        115                 120                 125

Arg Lys His Leu Ile Glu Ser Glu Glu Lys Gln Asp Ile Arg Leu Ile
    130                 135                 140

```
Tyr Leu Ala Leu His Asn Ile Ile Lys Thr Arg Gly His Phe Leu Ile
145                 150                 155                 160

Asp Gly Asp Leu Gln Ser Ala Lys Gln Leu Arg Pro Ile Leu Asp Thr
                165                 170                 175

Phe Leu Leu Ser Leu Gln Glu Glu Gln Asn Leu Ser Val Ser Leu Ser
            180                 185                 190

Glu Asn Gln Lys Asp Glu Tyr Glu Glu Ile Leu Lys Asn Arg Ser Ile
        195                 200                 205

Ala Lys Ser Glu Lys Val Lys Lys Leu Lys Asn Leu Phe Glu Ile Ser
    210                 215                 220

Asp Glu Leu Glu Lys Glu Lys Lys Ala Gln Ser Ala Val Ile Glu
225                 230                 235                 240

Asn Phe Cys Lys Phe Ile Val Gly Asn Lys Gly Asp Val Cys Lys Phe
                245                 250                 255

Leu Arg Val Ser Lys Glu Glu Leu Glu Ile Asp Ser Phe Ser Phe Ser
            260                 265                 270

Glu Gly Lys Tyr Glu Asp Asp Ile Val Lys Asn Leu Glu Glu Lys Val
        275                 280                 285

Pro Glu Lys Val Tyr Leu Phe Glu Gln Met Lys Ala Met Tyr Asp Trp
    290                 295                 300

Asn Ile Leu Val Asp Ile Leu Glu Thr Glu Glu Tyr Ile Ser Phe Ala
305                 310                 315                 320

Lys Val Lys Gln Tyr Glu Lys His Lys Thr Asn Leu Arg Leu Leu Arg
                325                 330                 335

Asp Ile Ile Leu Lys Tyr Cys Thr Lys Asp Glu Tyr Asn Arg Met Phe
            340                 345                 350

Asn Asp Glu Lys Glu Ala Gly Ser Tyr Thr Ala Tyr Val Gly Lys Leu
        355                 360                 365

Lys Lys Asn Asn Lys Lys Tyr Trp Ile Glu Lys Arg Asn Pro Glu
370                 375                 380

Glu Phe Tyr Lys Ser Leu Gly Lys Leu Leu Asp Lys Ile Glu Pro Leu
385                 390                 395                 400

Lys Glu Asp Leu Glu Val Leu Thr Met Met Ile Glu Glu Cys Lys Asn
                405                 410                 415

His Thr Leu Leu Pro Ile Gln Lys Asn Lys Asp Asn Gly Val Ile Pro
            420                 425                 430

His Gln Val His Glu Val Glu Leu Lys Lys Ile Leu Glu Asn Ala Lys
        435                 440                 445

Lys Tyr Tyr Ser Phe Leu Thr Glu Thr Asp Lys Asp Gly Tyr Ser Val
    450                 455                 460

Val Gln Lys Ile Glu Ser Ile Phe Arg Phe Arg Ile Pro Tyr Tyr Val
465                 470                 475                 480

Gly Pro Leu Ser Thr Arg His Gln Glu Lys Gly Ser Asn Val Trp Met
                485                 490                 495

Val Arg Lys Pro Gly Arg Glu Asp Arg Ile Tyr Pro Trp Asn Met Glu
            500                 505                 510

Glu Ile Ile Asp Phe Glu Lys Ser Asn Glu Asn Phe Ile Thr Arg Met
        515                 520                 525

Thr Asn Lys Cys Thr Tyr Leu Ile Gly Glu Asp Val Leu Pro Lys His
    530                 535                 540

Ser Leu Leu Tyr Ser Lys Tyr Met Val Leu Asn Glu Leu Asn Asn Val
545                 550                 555                 560
```

-continued

```
Lys Val Arg Gly Lys Lys Leu Pro Thr Ser Leu Lys Gln Lys Val Phe
            565                 570                 575
Glu Asp Leu Phe Glu Asn Lys Ser Lys Val Thr Gly Lys Asn Leu Leu
            580                 585                 590
Glu Tyr Leu Gln Ile Gln Asp Lys Asp Ile Gln Ile Asp Asp Leu Ser
            595                 600                 605
Gly Phe Asp Lys Asp Phe Lys Thr Ser Leu Lys Ser Tyr Leu Asp Phe
            610                 615                 620
Lys Lys Gln Ile Phe Gly Glu Glu Ile Glu Lys Ser Ile Gln Asn
625                 630                 635                 640
Met Ile Glu Asp Ile Ile Lys Trp Ile Thr Ile Tyr Gly Asn Asp Lys
                    645                 650                 655
Glu Met Leu Lys Arg Val Ile Arg Ala Asn Tyr Ser Asn Gln Leu Thr
            660                 665                 670
Glu Glu Gln Met Lys Lys Ile Thr Gly Phe Gln Tyr Ser Gly Trp Gly
            675                 680                 685
Asn Phe Ser Lys Met Phe Leu Lys Gly Ile Ser Gly Ser Asp Val Ser
            690                 695                 700
Thr Gly Glu Thr Phe Asp Ile Ile Thr Ala Met Trp Glu Thr Asp Asn
705                 710                 715                 720
Asn Leu Met Gln Ile Leu Ser Lys Lys Phe Thr Phe Met Asp Asn Val
                    725                 730                 735
Glu Asp Phe Asn Ser Gly Lys Val Gly Lys Ile Asp Lys Ile Thr Tyr
            740                 745                 750
Asp Ser Thr Val Lys Glu Met Phe Leu Ser Pro Glu Asn Lys Arg Ala
            755                 760                 765
Val Trp Gln Thr Ile Gln Val Ala Glu Glu Ile Lys Lys Val Met Gly
            770                 775                 780
Cys Glu Pro Lys Lys Ile Phe Ile Glu Met Ala Arg Gly Gly Glu Lys
785                 790                 795                 800
Val Lys Lys Arg Thr Lys Ser Arg Lys Ala Gln Leu Leu Glu Leu Tyr
                    805                 810                 815
Ala Ala Cys Glu Glu Asp Cys Arg Glu Leu Ile Lys Glu Ile Glu Asp
            820                 825                 830
Arg Asp Glu Arg Asp Phe Asn Ser Met Lys Leu Phe Leu Tyr Tyr Thr
            835                 840                 845
Gln Phe Gly Lys Cys Met Tyr Ser Gly Asp Asp Ile Asp Ile Asn Glu
            850                 855                 860
Leu Ile Arg Gly Asn Ser Lys Trp Asp Arg Asp His Ile Tyr Pro Gln
865                 870                 875                 880
Ser Lys Ile Lys Asp Asp Ser Ile Asp Asn Leu Val Leu Val Asn Lys
                    885                 890                 895
Thr Tyr Asn Ala Lys Lys Ser Asn Glu Leu Leu Ser Glu Asp Ile Gln
            900                 905                 910
Lys Lys Met His Ser Phe Trp Leu Ser Leu Asn Lys Lys Leu Ile
            915                 920                 925
Thr Lys Ser Lys Tyr Asp Arg Leu Thr Arg Lys Gly Asp Phe Thr Asp
            930                 935                 940
Glu Glu Leu Ser Gly Phe Ile Ala Arg Gln Leu Val Glu Thr Arg Gln
945                 950                 955                 960
Ser Thr Lys Ala Ile Ala Asp Ile Phe Lys Gln Ile Tyr Ser Ser Glu
                    965                 970                 975
Val Val Tyr Val Lys Ser Ser Leu Val Ser Asp Phe Arg Lys Lys Pro
```

```
                 980              985              990
Leu Asn Tyr Leu Lys Ser Arg Arg  Val Asn Asp Tyr His  His Ala Lys
                    995                 1000                1005

Asp Ala  Tyr Leu Asn Ile Val  Val Gly Asn Val Tyr  Asn Lys Lys
    1010                 1015                 1020

Phe Thr  Ser Asn Pro Ile Gln  Trp Met Lys Lys Asn  Arg Asp Thr
    1025                 1030                 1035

Asn Tyr  Ser Leu Asn Lys Val  Phe Glu His Asp Val  Val Ile Asn
    1040                 1045                 1050

Gly Glu  Val Ile Trp Glu Lys  Cys Thr Tyr His Glu  Asp Thr Asn
    1055                 1060                 1065

Thr Tyr  Asp Gly Gly Thr Leu  Asp Arg Ile Arg Lys  Ile Val Glu
    1070                 1075                 1080

Arg Asp  Asn Ile Leu Tyr Thr  Glu Tyr Ala Tyr Cys  Glu Lys Gly
    1085                 1090                 1095

Glu Leu  Phe Asn Ala Thr Ile  Gln Asn Lys Asn Gly  Asn Ser Thr
    1100                 1105                 1110

Val Ser  Leu Lys Lys Gly Leu  Asp Val Lys Lys Tyr  Gly Gly Tyr
    1115                 1120                 1125

Phe Ser  Ala Asn Thr Ser Tyr  Phe Ser Leu Ile Glu  Phe Glu Asp
    1130                 1135                 1140

Lys Lys  Gly Asp Arg Ala Arg  His Ile Ile Gly Val  Pro Ile Tyr
    1145                 1150                 1155

Ile Ala  Asn Met Leu Glu His  Ser Pro Ser Ala Phe  Leu Glu Tyr
    1160                 1165                 1170

Cys Glu  Gln Lys Gly Tyr Gln  Asn Val Arg Ile Leu  Val Glu Lys
    1175                 1180                 1185

Ile Lys  Lys Asn Ser Leu Leu  Ile Ile Asn Gly Tyr  Pro Leu Arg
    1190                 1195                 1200

Ile Arg  Gly Glu Asn Glu Val  Asp Thr Ser Phe Lys  Arg Ala Ile
    1205                 1210                 1215

Gln Leu  Lys Leu Asp Gln Lys  Asn Tyr Glu Leu Val  Arg Asn Ile
    1220                 1225                 1230

Glu Lys  Phe Leu Glu Lys Tyr  Val Glu Lys Lys Gly  Asn Tyr Pro
    1235                 1240                 1245

Ile Asp  Glu Asn Arg Asp His  Ile Thr His Glu Lys  Met Asn Gln
    1250                 1255                 1260

Leu Tyr  Glu Val Leu Leu Ser  Lys Met Lys Lys Phe  Asn Lys Lys
    1265                 1270                 1275

Gly Met  Ala Asp Pro Ser Asp  Arg Ile Glu Lys Ser  Lys Pro Lys
    1280                 1285                 1290

Phe Ile  Lys Leu Glu Asp Leu  Ile Asp Lys Ile Asn  Val Ile Asn
    1295                 1300                 1305

Lys Met  Leu Asn Leu Leu Arg  Cys Asp Asn Asp Thr  Lys Ala Asp
    1310                 1315                 1320

Leu Ser  Leu Ile Glu Leu Pro  Lys Asn Ala Gly Ser  Phe Val Val
    1325                 1330                 1335

Lys Lys  Asn Thr Ile Gly Lys  Ser Lys Ile Ile Leu  Val Asn Gln
    1340                 1345                 1350

Ser Val  Thr Gly Leu Tyr Glu  Asn Arg Arg Glu Leu
    1355                 1360                 1365

<210> SEQ ID NO 8
```

<211> LENGTH: 1375
<212> TYPE: PRT
<213> ORGANISM: Lactobacillus johnsonii

<400> SEQUENCE: 8

```
Met Thr Lys Ile Lys Asp Asp Tyr Ile Val Gly Leu Asp Ile Gly Thr
1               5                   10                  15

Asp Ser Cys Gly Trp Val Ala Met Asn Ser Asn Asn Asp Ile Leu Lys
            20                  25                  30

Leu Gln Gly Lys Thr Ala Ile Gly Ser Arg Leu Phe Glu Gly Gly Lys
        35                  40                  45

Ser Ala Ala Glu Arg Arg Leu Phe Arg Thr Thr His Arg Arg Ile Lys
    50                  55                  60

Arg Arg Arg Trp Arg Leu Lys Leu Leu Glu Glu Phe Phe Asp Pro Tyr
65                  70                  75                  80

Met Ala Glu Val Asp Pro Tyr Phe Phe Ala Arg Leu Lys Glu Ser Gly
                85                  90                  95

Leu Ser Pro Leu Asp Lys Arg Lys Thr Val Ser Ser Ile Val Phe Pro
            100                 105                 110

Thr Ser Ala Glu Asp Lys Lys Phe Tyr Asp Asp Tyr Pro Thr Ile Tyr
        115                 120                 125

His Leu Arg Tyr Lys Leu Met Thr Glu Asp Glu Lys Phe Asp Leu Arg
    130                 135                 140

Glu Val Tyr Leu Ala Ile His His Ile Ile Lys Tyr Arg Gly Asn Phe
145                 150                 155                 160

Leu Tyr Asn Thr Ser Val Lys Asp Phe Lys Ala Ser Lys Ile Asp Val
                165                 170                 175

Lys Ser Ser Ile Glu Lys Leu Asn Glu Leu Tyr Glu Asn Leu Gly Leu
            180                 185                 190

Asp Leu Asn Val Glu Phe Asn Ile Ser Asn Thr Ala Glu Ile Glu Lys
        195                 200                 205

Val Leu Lys Asp Lys Gln Ile Phe Lys Arg Asp Lys Val Lys Lys Ile
    210                 215                 220

Ala Glu Leu Phe Ala Ile Lys Thr Asp Asn Lys Glu Gln Ser Lys Arg
225                 230                 235                 240

Ile Lys Asp Ile Ser Lys Gln Val Ala Asn Ala Val Leu Gly Tyr Lys
                245                 250                 255

Thr Arg Phe Asp Thr Ile Ala Leu Lys Glu Ile Ser Lys Asp Glu Leu
            260                 265                 270

Ser Asp Trp Asn Phe Lys Leu Ser Asp Ile Asp Ala Asp Ser Lys Phe
        275                 280                 285

Glu Ala Leu Met Gly Asn Leu Asp Glu Asn Glu Gln Ala Ile Leu Leu
    290                 295                 300

Thr Ile Lys Glu Leu Phe Asn Glu Val Thr Leu Asn Gly Ile Val Glu
305                 310                 315                 320

Asp Gly Asn Thr Leu Ser Glu Ser Met Ile Asn Lys Tyr Asn Asp His
                325                 330                 335

Arg Asp Asp Leu Lys Leu Leu Lys Glu Val Ile Glu Asn His Ile Asp
            340                 345                 350

Arg Lys Lys Ala Lys Glu Leu Ala Leu Ala Tyr Asp Leu Tyr Val Asn
        355                 360                 365

Asn Arg His Gly Gln Leu Leu Gln Ala Lys Lys Leu Gly Lys Ile
    370                 375                 380

Lys Pro Arg Ser Lys Glu Asp Phe Tyr Lys Val Val Asn Lys Asn Leu
```

```
                385                 390                 395                 400
Asp Asp Ser Arg Ala Ser Lys Glu Ile Lys Lys Ile Glu Leu Asp
                    405                 410                 415

Ser Phe Met Pro Lys Gln Arg Thr Asn Ala Asn Gly Val Ile Pro Tyr
            420                 425                 430

Gln Leu Gln Gln Leu Glu Leu Asp Lys Ile Ile Glu Asn Gln Ser Lys
                435                 440                 445

Tyr Tyr Pro Phe Leu Lys Glu Ile Asn Pro Val Ser Ser His Leu Lys
        450                 455                 460

Glu Ala Pro Tyr Lys Leu Asp Glu Leu Ile Arg Phe Arg Val Pro Tyr
465                 470                 475                 480

Tyr Val Gly Pro Leu Ile Ser Pro Asn Glu Ser Thr Lys Asp Ile Gln
                    485                 490                 495

Thr Lys Lys Asn Gln Asn Phe Ala Trp Met Ile Arg Lys Glu Glu Gly
                500                 505                 510

Arg Ile Thr Pro Trp Asn Phe Asp Gln Lys Val Asp Arg Ile Glu Ser
            515                 520                 525

Ala Asn Lys Phe Ile Lys Arg Met Thr Thr Lys Asp Thr Tyr Leu Phe
        530                 535                 540

Gly Glu Asp Val Leu Pro Ala Asn Ser Leu Leu Tyr Gln Lys Phe Thr
545                 550                 555                 560

Val Leu Asn Glu Leu Asn Asn Ile Arg Ile Asn Gly Lys Arg Ile Ser
                    565                 570                 575

Val Asp Leu Lys Gln Glu Ile Tyr Glu Asn Leu Phe Lys Lys His Thr
                580                 585                 590

Thr Val Thr Val Lys Lys Leu Glu Asn Tyr Leu Lys Glu Asn His Asn
            595                 600                 605

Leu Val Lys Val Glu Ile Lys Gly Leu Ala Asp Glu Lys Lys Phe Asn
        610                 615                 620

Ser Gly Leu Thr Thr Tyr Asn Arg Phe Lys Asn Leu Asn Ile Phe Asp
625                 630                 635                 640

Asn Gln Ile Asp Asp Leu Lys Tyr Arg Asn Asp Phe Glu Lys Ile Ile
                    645                 650                 655

Glu Trp Ser Thr Ile Phe Glu Asp Lys Ser Ile Tyr Lys Glu Lys Leu
                660                 665                 670

Arg Ser Ile Asp Trp Leu Asn Glu Lys Gln Ile Asn Ala Leu Ser Asn
            675                 680                 685

Ile Arg Leu Gln Gly Trp Gly Arg Leu Ser Lys Lys Leu Leu Ala Gln
        690                 695                 700

Leu His Asp His Asn Gly Gln Thr Ile Ile Glu Gln Leu Trp Asp Ser
705                 710                 715                 720

Gln Asn Asn Phe Met Gln Ile Val Thr Gln Ala Asp Phe Lys Asp Ala
                    725                 730                 735

Ile Ala Lys Ala Asn Gln Asn Leu Leu Val Ala Thr Ser Val Glu Asp
                740                 745                 750

Ile Leu Asn Asn Ala Tyr Thr Ser Pro Ala Asn Lys Lys Ala Ile Arg
            755                 760                 765

Gln Val Ile Lys Val Val Asp Asp Ile Val Lys Ala Ala Ser Gly Lys
        770                 775                 780

Val Pro Lys Gln Ile Ala Ile Glu Phe Thr Arg Asp Ala Asp Glu Asn
785                 790                 795                 800

Pro Lys Arg Ser Gln Thr Arg Gly Ser Lys Leu Gln Lys Val Tyr Lys
                    805                 810                 815
```

-continued

Asp Leu Ser Thr Glu Leu Ala Ser Lys Thr Ile Ala Glu Glu Leu Asn
            820                 825                 830

Glu Ala Ile Lys Asp Lys Lys Leu Val Gln Asp Lys Tyr Tyr Leu Tyr
            835                 840                 845

Phe Met Gln Leu Gly Arg Asp Ala Tyr Thr Gly Glu Pro Ile Asn Ile
850                 855                 860

Asp Glu Ile Gln Lys Tyr Asp Ile Asp His Ile Leu Pro Gln Ser Phe
865                 870                 875                 880

Ile Lys Asp Asp Ala Leu Asp Asn Arg Val Leu Val Ser Arg Ala Val
                885                 890                 895

Asn Asn Gly Lys Ser Asp Asn Val Pro Val Lys Leu Phe Gly Asn Glu
            900                 905                 910

Met Ala Ala Asn Leu Gly Met Thr Ile Arg Lys Met Trp Glu Glu Trp
            915                 920                 925

Lys Asn Ile Gly Leu Ile Ser Lys Thr Lys Tyr Asn Asn Leu Leu Thr
            930                 935                 940

Asp Pro His Ile Asn Lys Tyr Lys Ser Ala Gly Phe Ile Arg Arg
945                 950                 955                 960

Gln Leu Val Glu Thr Ser Gln Ile Ile Lys Leu Val Ser Thr Ile Leu
            965                 970                 975

Gln Ser Arg Tyr Pro Asn Thr Glu Ile Ile Thr Val Lys Ala Lys Tyr
            980                 985                 990

Asn His Tyr Leu Arg Glu Lys Phe Asp Leu Tyr Lys Ser Arg Glu Val
        995                 1000                1005

Asn Asp Tyr His His Ala Ile Asp Ala Tyr Leu Ser Ala Ile Cys
        1010                1015                1020

Gly Asn Leu Leu Tyr Gln Asn Tyr Pro Asn Leu Arg Pro Phe Phe
        1025                1030                1035

Val Tyr Gly Gln Tyr Lys Lys Phe Ser Ser Asp Pro Asp Lys Glu
        1040                1045                1050

Lys Ala Ile Phe Asn Lys Thr Arg Lys Phe Ser Phe Ile Ser Gln
        1055                1060                1065

Leu Leu Lys Asn Lys Ser Glu Asn Ser Lys Glu Ile Ala Lys Lys
        1070                1075                1080

Leu Lys Arg Ala Tyr Gln Phe Lys Tyr Met Leu Val Ser Arg Glu
        1085                1090                1095

Thr Glu Thr Arg Asp Gln Glu Met Phe Lys Met Thr Val Tyr Pro
        1100                1105                1110

Arg Phe Ser His Asp Thr Val Lys Ala Pro Arg Asn Leu Ile Pro
        1115                1120                1125

Lys Lys Met Gly Met Ser Pro Asp Ile Tyr Gly Gly Tyr Thr Asn
        1130                1135                1140

Asn Ser Asp Ala Tyr Met Val Ile Val Arg Ile Asp Lys Lys Lys
        1145                1150                1155

Gly Thr Glu Tyr Lys Ile Leu Gly Ile Pro Thr Arg Glu Leu Val
        1160                1165                1170

Asn Leu Lys Lys Ala Glu Lys Glu Asp His Tyr Lys Ser Tyr Leu
        1175                1180                1185

Lys Glu Ile Leu Thr Pro Arg Ile Leu Tyr Asn Lys Asn Gly Lys
        1190                1195                1200

Arg Asp Lys Lys Ile Thr Ser Phe Glu Ile Val Lys Ser Lys Ile
        1205                1210                1215

```
Pro Tyr Lys Gln Val Ile Gln Asp Gly Asp Lys Lys Phe Met Leu
    1220            1225                1230

Gly Ser Ser Thr Tyr Val Tyr Asn Ala Lys Gln Leu Thr Leu Ser
        1235            1240                1245

Thr Glu Ser Met Lys Ala Ile Thr Asn Asn Phe Asp Lys Asp Ser
    1250            1255                1260

Asp Glu Asn Asp Ala Leu Ile Lys Ala Tyr Asp Glu Ile Leu Asp
    1265            1270                1275

Lys Val Asp Lys Tyr Leu Pro Leu Phe Asp Ile Asn Lys Phe Arg
    1280            1285                1290

Glu Lys Leu His Ser Gly Arg Glu Lys Phe Ile Lys Leu Ser Leu
    1295            1300                1305

Glu Asp Lys Lys Asp Thr Ile Leu Lys Val Leu Glu Gly Leu His
    1310            1315                1320

Asp Asn Ala Val Met Thr Lys Ile Pro Thr Ile Gly Leu Ser Thr
    1325            1330                1335

Pro Leu Gly Phe Met Gln Phe Pro Asn Gly Val Ile Leu Ser Glu
    1340            1345                1350

Asn Ala Lys Leu Ile Tyr Gln Ser Pro Thr Gly Leu Phe Lys Lys
    1355            1360                1365

Ser Val Lys Ile Ser Asp Leu
    1370            1375

<210> SEQ ID NO 9
<211> LENGTH: 1003
<212> TYPE: PRT
<213> ORGANISM: Campylobacter lari

<400> SEQUENCE: 9

Met Arg Ile Leu Gly Phe Asp Ile Gly Ile Asn Ser Ile Gly Trp Ala
1               5                   10                  15

Phe Val Glu Asn Asp Glu Leu Lys Asp Cys Gly Val Arg Ile Phe Thr
            20                  25                  30

Lys Ala Glu Asn Pro Lys Asn Lys Glu Ser Leu Ala Leu Pro Arg Arg
        35                  40                  45

Asn Ala Arg Ser Ser Arg Arg Leu Lys Arg Arg Lys Ala Arg Leu
    50                  55                  60

Ile Ala Ile Lys Arg Ile Leu Ala Lys Glu Leu Lys Leu Asn Tyr Lys
65                  70                  75                  80

Asp Tyr Val Ala Ala Asp Gly Glu Leu Pro Lys Ala Tyr Glu Gly Ser
                85                  90                  95

Leu Ala Ser Val Tyr Glu Leu Arg Tyr Lys Ala Leu Thr Gln Asn Leu
            100                 105                 110

Glu Thr Lys Asp Leu Ala Arg Val Ile Leu His Ile Ala Lys His Arg
        115                 120                 125

Gly Tyr Met Asn Lys Asn Glu Lys Ser Asn Asp Ala Lys Lys Gly
    130                 135                 140

Lys Ile Leu Ser Ala Leu Lys Asn Asn Ala Leu Lys Leu Glu Asn Tyr
145                 150                 155                 160

Gln Ser Val Gly Glu Tyr Phe Tyr Lys Glu Phe Phe Gln Lys Tyr Lys
                165                 170                 175

Lys Asn Thr Lys Asn Phe Ile Lys Ile Arg Asn Thr Lys Asp Asn Tyr
            180                 185                 190

Asn Asn Cys Val Leu Ser Ser Asp Leu Glu Lys Glu Leu Lys Leu Ile
        195                 200                 205
```

-continued

Leu Glu Lys Gln Lys Glu Phe Gly Tyr Asn Tyr Ser Glu Asp Phe Ile
    210                 215                 220

Asn Glu Ile Leu Lys Val Ala Phe Phe Gln Arg Pro Leu Lys Asp Phe
225                 230                 235                 240

Ser His Leu Val Gly Ala Cys Thr Phe Glu Glu Glu Lys Arg Ala
                245                 250                 255

Cys Lys Asn Ser Tyr Ser Ala Trp Glu Phe Val Ala Leu Thr Lys Ile
                260                 265                 270

Ile Asn Glu Ile Lys Ser Leu Glu Lys Ile Ser Gly Glu Ile Val Pro
        275                 280                 285

Thr Gln Thr Ile Asn Glu Val Leu Asn Leu Ile Leu Asp Lys Gly Ser
290                 295                 300

Ile Thr Tyr Lys Lys Phe Arg Ser Cys Ile Asn Leu His Glu Ser Ile
305                 310                 315                 320

Ser Phe Lys Ser Leu Lys Tyr Asp Lys Glu Asn Ala Glu Asn Ala Lys
                325                 330                 335

Leu Ile Asp Phe Arg Lys Leu Val Glu Phe Lys Lys Ala Leu Gly Val
                340                 345                 350

His Ser Leu Ser Arg Gln Glu Leu Asp Gln Ile Ser Thr His Ile Thr
        355                 360                 365

Leu Ile Lys Asp Asn Val Lys Leu Lys Thr Val Leu Glu Lys Tyr Asn
370                 375                 380

Leu Ser Asn Glu Gln Ile Asn Asn Leu Leu Glu Ile Glu Phe Asn Asp
385                 390                 395                 400

Tyr Ile Asn Leu Ser Phe Lys Ala Leu Gly Met Ile Leu Pro Leu Met
                405                 410                 415

Arg Glu Gly Lys Arg Tyr Asp Glu Ala Cys Glu Ile Ala Asn Leu Lys
                420                 425                 430

Pro Lys Thr Val Asp Glu Lys Lys Asp Phe Leu Pro Ala Phe Cys Asp
        435                 440                 445

Ser Ile Phe Ala His Glu Leu Ser Asn Pro Val Val Asn Arg Ala Ile
450                 455                 460

Ser Glu Tyr Arg Lys Val Leu Asn Ala Leu Leu Lys Lys Tyr Gly Lys
465                 470                 475                 480

Val His Lys Ile His Leu Glu Leu Ala Arg Asp Val Gly Leu Ser Lys
                485                 490                 495

Lys Ala Arg Glu Lys Ile Glu Lys Glu Gln Lys Glu Asn Gln Ala Val
                500                 505                 510

Asn Ala Trp Ala Leu Lys Glu Cys Glu Asn Ile Gly Leu Lys Ala Ser
        515                 520                 525

Ala Lys Asn Ile Leu Lys Leu Lys Leu Trp Lys Glu Gln Lys Glu Ile
530                 535                 540

Cys Ile Tyr Ser Gly Asn Lys Ile Ser Ile Glu His Leu Lys Asp Glu
545                 550                 555                 560

Lys Ala Leu Glu Val Asp His Ile Tyr Pro Tyr Ser Arg Ser Phe Asp
                565                 570                 575

Asp Ser Phe Ile Asn Lys Val Leu Val Phe Thr Lys Glu Asn Gln Glu
                580                 585                 590

Lys Leu Asn Lys Thr Pro Phe Glu Ala Phe Gly Lys Asn Ile Glu Lys
        595                 600                 605

Trp Ser Lys Ile Gln Thr Leu Ala Gln Asn Leu Pro Tyr Lys Lys Lys
610                 615                 620

-continued

Asn Lys Ile Leu Asp Glu Asn Phe Lys Asp Lys Gln Gln Glu Asp Phe
625                 630                 635                 640

Ile Ser Arg Asn Leu Asn Asp Thr Arg Tyr Ile Ala Thr Leu Ile Ala
            645                 650                 655

Lys Tyr Thr Lys Glu Tyr Leu Asn Phe Leu Leu Leu Ser Glu Asn Glu
            660                 665                 670

Asn Ala Asn Leu Lys Ser Gly Glu Lys Gly Ser Lys Ile His Val Gln
            675                 680                 685

Thr Ile Ser Gly Met Leu Thr Ser Val Leu Arg His Thr Trp Gly Phe
690                 695                 700

Asp Lys Lys Asp Arg Asn Asn His Leu His His Ala Leu Asp Ala Ile
705                 710                 715                 720

Ile Val Ala Tyr Ser Thr Asn Ser Ile Ile Lys Ala Phe Ser Asp Phe
            725                 730                 735

Arg Lys Asn Gln Glu Leu Leu Lys Ala Arg Phe Tyr Ala Lys Glu Leu
            740                 745                 750

Thr Ser Asp Asn Tyr Lys His Gln Val Lys Phe Glu Pro Phe Lys
            755                 760                 765

Ser Phe Arg Glu Lys Ile Leu Ser Lys Ile Asp Glu Ile Phe Val Ser
770                 775                 780

Lys Pro Pro Arg Lys Arg Ala Arg Arg Ala Leu His Lys Asp Thr Phe
785                 790                 795                 800

His Ser Glu Asn Lys Ile Ile Asp Lys Cys Ser Tyr Asn Ser Lys Glu
            805                 810                 815

Gly Leu Gln Ile Ala Leu Ser Cys Gly Arg Val Arg Lys Ile Gly Thr
            820                 825                 830

Lys Tyr Val Glu Asn Asp Thr Ile Val Arg Val Asp Ile Phe Lys Lys
            835                 840                 845

Gln Asn Lys Phe Tyr Ala Ile Pro Ile Tyr Ala Met Asp Phe Ala Leu
850                 855                 860

Gly Ile Leu Pro Asn Lys Ile Val Ile Thr Gly Lys Asp Lys Asn Asn
865                 870                 875                 880

Asn Pro Lys Gln Trp Gln Thr Ile Asp Glu Ser Tyr Glu Phe Cys Phe
            885                 890                 895

Ser Leu Tyr Lys Asn Asp Leu Ile Leu Leu Gln Lys Lys Asn Met Gln
            900                 905                 910

Glu Pro Glu Phe Ala Tyr Tyr Asn Asp Phe Ser Ile Ser Thr Ser Ser
            915                 920                 925

Ile Cys Val Glu Lys His Asp Asn Lys Phe Glu Asn Leu Thr Ser Asn
930                 935                 940

Gln Lys Leu Leu Phe Ser Asn Ala Lys Glu Gly Ser Val Lys Val Glu
945                 950                 955                 960

Ser Leu Gly Ile Gln Asn Leu Lys Val Phe Glu Lys Tyr Ile Ile Thr
            965                 970                 975

Pro Leu Gly Asp Lys Ile Lys Ala Asp Phe Gln Pro Arg Glu Asn Ile
            980                 985                 990

Ser Leu Lys Thr Ser Lys Lys Tyr Gly Leu Arg
            995                 1000

<210> SEQ ID NO 10
<211> LENGTH: 1037
<212> TYPE: PRT
<213> ORGANISM: Parvibaculum lavamentivorans

<400> SEQUENCE: 10

```
Met Glu Arg Ile Phe Gly Phe Asp Ile Gly Thr Thr Ser Ile Gly Phe
1               5                   10                  15

Ser Val Ile Asp Tyr Ser Ser Thr Gln Ser Ala Gly Asn Ile Gln Arg
            20                  25                  30

Leu Gly Val Arg Ile Phe Pro Glu Ala Arg Asp Pro Asp Gly Thr Pro
            35                  40                  45

Leu Asn Gln Gln Arg Arg Gln Lys Arg Met Met Arg Arg Gln Leu Arg
50                  55                  60

Arg Arg Arg Ile Arg Arg Lys Ala Leu Asn Glu Thr Leu His Glu Ala
65                  70                  75                  80

Gly Phe Leu Pro Ala Tyr Gly Ser Ala Asp Trp Pro Val Val Met Ala
                85                  90                  95

Asp Glu Pro Tyr Glu Leu Arg Arg Gly Leu Glu Glu Gly Leu Ser
                100                 105                 110

Ala Tyr Glu Phe Gly Arg Ala Ile Tyr His Leu Ala Gln His Arg His
        115                 120                 125

Phe Lys Gly Arg Glu Leu Glu Glu Ser Asp Thr Pro Asp Pro Asp Val
        130                 135                 140

Asp Asp Glu Lys Glu Ala Ala Asn Glu Arg Ala Ala Thr Leu Lys Ala
145                 150                 155                 160

Leu Lys Asn Glu Gln Thr Thr Leu Gly Ala Trp Leu Ala Arg Arg Pro
                165                 170                 175

Pro Ser Asp Arg Lys Arg Gly Ile His Ala His Arg Asn Val Val Ala
                180                 185                 190

Glu Glu Phe Glu Arg Leu Trp Glu Val Gln Ser Lys Phe His Pro Ala
            195                 200                 205

Leu Lys Ser Glu Glu Met Arg Ala Arg Ile Ser Asp Thr Ile Phe Ala
210                 215                 220

Gln Arg Pro Val Phe Trp Arg Lys Asn Thr Leu Gly Glu Cys Arg Phe
225                 230                 235                 240

Met Pro Gly Glu Pro Leu Cys Pro Lys Gly Ser Trp Leu Ser Gln Gln
                245                 250                 255

Arg Arg Met Leu Glu Lys Leu Asn Asn Leu Ala Ile Ala Gly Gly Asn
                260                 265                 270

Ala Arg Pro Leu Asp Ala Glu Glu Arg Asp Ala Ile Leu Ser Lys Leu
                275                 280                 285

Gln Gln Gln Ala Ser Met Ser Trp Pro Gly Val Arg Ser Ala Leu Lys
            290                 295                 300

Ala Leu Tyr Lys Gln Arg Gly Glu Pro Gly Ala Glu Lys Ser Leu Lys
305                 310                 315                 320

Phe Asn Leu Glu Leu Gly Gly Glu Ser Lys Leu Leu Gly Asn Ala Leu
                325                 330                 335

Glu Ala Lys Leu Ala Asp Met Phe Gly Pro Asp Trp Pro Ala His Pro
            340                 345                 350

Arg Lys Gln Glu Ile Arg His Ala Val His Glu Arg Leu Trp Ala Ala
            355                 360                 365

Asp Tyr Gly Glu Thr Pro Asp Lys Lys Arg Val Ile Ile Leu Ser Glu
370                 375                 380

Lys Asp Arg Lys Ala His Arg Glu Ala Ala Asn Ser Phe Val Ala
385                 390                 395                 400

Asp Phe Gly Ile Thr Gly Glu Gln Ala Ala Gln Leu Gln Ala Leu Lys
                405                 410                 415
```

```
Leu Pro Thr Gly Trp Glu Pro Tyr Ser Ile Pro Ala Leu Asn Leu Phe
            420                 425                 430

Leu Ala Glu Leu Glu Lys Gly Glu Arg Phe Gly Ala Leu Val Asn Gly
            435                 440                 445

Pro Asp Trp Glu Gly Trp Arg Arg Thr Asn Phe Pro His Arg Asn Gln
            450                 455                 460

Pro Thr Gly Glu Ile Leu Asp Lys Leu Pro Ser Pro Ala Ser Lys Glu
465                 470                 475                 480

Glu Arg Glu Arg Ile Ser Gln Leu Arg Asn Pro Thr Val Val Arg Thr
                    485                 490                 495

Gln Asn Glu Leu Arg Lys Val Val Asn Asn Leu Ile Gly Leu Tyr Gly
            500                 505                 510

Lys Pro Asp Arg Ile Arg Ile Glu Val Gly Arg Asp Val Gly Lys Ser
            515                 520                 525

Lys Arg Glu Arg Glu Glu Ile Gln Ser Gly Ile Arg Arg Asn Glu Lys
            530                 535                 540

Gln Arg Lys Lys Ala Thr Glu Asp Leu Ile Lys Asn Gly Ile Ala Asn
545                 550                 555                 560

Pro Ser Arg Asp Asp Val Glu Lys Trp Ile Leu Trp Lys Glu Gly Gln
                    565                 570                 575

Glu Arg Cys Pro Tyr Thr Gly Asp Gln Ile Gly Phe Asn Ala Leu Phe
            580                 585                 590

Arg Glu Gly Arg Tyr Glu Val Glu His Ile Trp Pro Arg Ser Arg Ser
            595                 600                 605

Phe Asp Asn Ser Pro Arg Asn Lys Thr Leu Cys Arg Lys Asp Val Asn
610                 615                 620

Ile Glu Lys Gly Asn Arg Met Pro Phe Glu Ala Phe Gly His Asp Glu
625                 630                 635                 640

Asp Arg Trp Ser Ala Ile Gln Ile Arg Leu Gln Gly Met Val Ser Ala
            645                 650                 655

Lys Gly Gly Thr Gly Met Ser Pro Gly Lys Val Lys Arg Phe Leu Ala
            660                 665                 670

Lys Thr Met Pro Glu Asp Phe Ala Ala Arg Gln Leu Asn Asp Thr Arg
            675                 680                 685

Tyr Ala Ala Lys Gln Ile Leu Ala Gln Leu Lys Arg Leu Trp Pro Asp
690                 695                 700

Met Gly Pro Glu Ala Pro Val Lys Val Glu Ala Val Thr Gly Gln Val
705                 710                 715                 720

Thr Ala Gln Leu Arg Lys Leu Trp Thr Leu Asn Asn Ile Leu Ala Asp
            725                 730                 735

Asp Gly Glu Lys Thr Arg Ala Asp His Arg His His Ala Ile Asp Ala
            740                 745                 750

Leu Thr Val Ala Cys Thr His Pro Gly Met Thr Asn Lys Leu Ser Arg
            755                 760                 765

Tyr Trp Gln Leu Arg Asp Asp Pro Arg Ala Glu Lys Pro Ala Leu Thr
            770                 775                 780

Pro Pro Trp Asp Thr Ile Arg Ala Asp Ala Glu Lys Ala Val Ser Glu
785                 790                 795                 800

Ile Val Val Ser His Arg Val Arg Lys Val Ser Gly Pro Leu His
                    805                 810                 815

Lys Glu Thr Thr Tyr Gly Asp Thr Gly Thr Asp Ile Lys Thr Lys Ser
            820                 825                 830

Gly Thr Tyr Arg Gln Phe Val Thr Arg Lys Lys Ile Glu Ser Leu Ser
```

```
        835                 840                 845

Lys Gly Glu Leu Asp Glu Ile Arg Asp Pro Arg Ile Lys Glu Ile Val
    850                 855                 860

Ala Ala His Val Ala Gly Arg Gly Gly Asp Pro Lys Lys Ala Phe Pro
865                 870                 875                 880

Pro Tyr Pro Cys Val Ser Pro Gly Gly Pro Glu Ile Arg Lys Val Arg
                885                 890                 895

Leu Thr Ser Lys Gln Gln Leu Asn Leu Met Ala Gln Thr Gly Asn Gly
            900                 905                 910

Tyr Ala Asp Leu Gly Ser Asn His His Ile Ala Ile Tyr Arg Leu Pro
        915                 920                 925

Asp Gly Lys Ala Asp Phe Glu Ile Val Ser Leu Phe Asp Ala Ser Arg
    930                 935                 940

Arg Leu Ala Gln Arg Asn Pro Ile Val Gln Arg Thr Arg Ala Asp Gly
945                 950                 955                 960

Ala Ser Phe Val Met Ser Leu Ala Ala Gly Glu Ala Ile Met Ile Pro
                965                 970                 975

Glu Gly Ser Lys Lys Gly Ile Trp Ile Val Gln Gly Val Trp Ala Ser
            980                 985                 990

Gly Gln Val Val Leu Glu Arg Asp  Thr Asp Ala Asp His  Ser Thr Thr
        995                 1000                1005

Thr Arg  Pro Met Pro Asn Pro  Ile Leu Lys Asp Asp  Ala Lys Lys
    1010                1015                1020

Val Ser  Ile Asp Pro Ile Gly  Arg Val Arg Pro Ser  Asn Asp
    1025                1030                1035

<210> SEQ ID NO 11
<211> LENGTH: 1269
<212> TYPE: PRT
<213> ORGANISM: Mycoplasma gallisepticum
<400> SEQUENCE: 11

Met Asn Asn Ser Ile Lys Ser Lys Pro Glu Val Thr Ile Gly Leu Asp
1               5                   10                  15

Leu Gly Val Gly Ser Val Gly Trp Ala Ile Val Asp Asn Glu Thr Asn
            20                  25                  30

Ile Ile His His Leu Gly Ser Arg Leu Phe Ser Gln Ala Lys Thr Ala
        35                  40                  45

Glu Asp Arg Arg Ser Phe Arg Gly Val Arg Arg Leu Ile Arg Arg Arg
    50                  55                  60

Lys Tyr Lys Leu Lys Arg Phe Val Asn Leu Ile Trp Lys Tyr Asn Ser
65                  70                  75                  80

Tyr Phe Gly Phe Lys Asn Lys Glu Asp Ile Leu Asn Asn Tyr Gln Glu
                85                  90                  95

Gln Gln Lys Leu His Asn Thr Val Leu Asn Leu Lys Ser Glu Ala Leu
            100                 105                 110

Asn Ala Lys Ile Asp Pro Lys Ala Leu Ser Trp Ile Leu His Asp Tyr
        115                 120                 125

Leu Lys Asn Arg Gly His Phe Tyr Glu Asp Asn Arg Asp Phe Asn Val
    130                 135                 140

Tyr Pro Thr Lys Glu Leu Ala Lys Tyr Phe Asp Lys Tyr Gly Tyr Tyr
145                 150                 155                 160

Lys Gly Ile Ile Asp Ser Lys Glu Asp Asn Asp Asn Lys Leu Glu Glu
                165                 170                 175
```

```
Glu Leu Thr Lys Tyr Lys Phe Ser Asn Lys His Trp Leu Glu Val
            180                 185                 190
Lys Lys Val Leu Ser Asn Gln Thr Gly Leu Pro Glu Lys Phe Lys Glu
            195                 200                 205
Glu Tyr Glu Ser Leu Phe Ser Tyr Val Arg Asn Tyr Ser Glu Gly Pro
            210                 215                 220
Gly Ser Ile Asn Ser Val Ser Pro Tyr Gly Ile Tyr His Leu Asp Glu
225                 230                 235                 240
Lys Glu Gly Lys Val Val Gln Lys Tyr Asn Asn Ile Trp Asp Lys Thr
                245                 250                 255
Ile Gly Lys Cys Asn Ile Phe Pro Asp Glu Tyr Arg Ala Pro Lys Asn
            260                 265                 270
Ser Pro Ile Ala Met Ile Phe Asn Glu Ile Asn Glu Leu Ser Thr Ile
            275                 280                 285
Arg Ser Tyr Ser Ile Tyr Leu Thr Gly Trp Phe Ile Asn Gln Glu Phe
            290                 295                 300
Lys Lys Ala Tyr Leu Asn Lys Leu Leu Asp Leu Leu Ile Lys Thr Asn
305                 310                 315                 320
Gly Glu Lys Pro Ile Asp Ala Arg Gln Phe Lys Lys Leu Arg Glu Glu
                325                 330                 335
Thr Ile Ala Glu Ser Ile Gly Lys Glu Thr Leu Lys Asp Val Glu Asn
            340                 345                 350
Glu Glu Lys Leu Glu Lys Glu Asp His Lys Trp Lys Leu Lys Gly Leu
            355                 360                 365
Lys Leu Asn Thr Asn Gly Lys Ile Gln Tyr Asn Asp Leu Ser Ser Leu
            370                 375                 380
Ala Lys Phe Val His Lys Leu Lys Gln His Leu Lys Leu Asp Phe Leu
385                 390                 395                 400
Leu Glu Asp Gln Tyr Ala Thr Leu Asp Lys Ile Asn Phe Leu Gln Ser
                405                 410                 415
Leu Phe Val Tyr Leu Gly Lys His Leu Arg Tyr Asn Asn Arg Val Asp
            420                 425                 430
Ser Ala Asn Leu Lys Glu Phe Ser Asp Ser Asn Arg Leu Phe Glu Arg
            435                 440                 445
Val Leu Gln Glu Gln Lys Asp Gly Leu Phe Lys Leu Phe Glu Gln Thr
450                 455                 460
Asp Lys Asp Asp Glu Lys Ile Leu Ala Gln Thr His Ser Leu Ser Thr
465                 470                 475                 480
Lys Ala Met Leu Leu Ala Ile Thr Arg Met Thr Asn Leu Asp Asn Asp
                485                 490                 495
Glu Asp Asn Gln Lys Asn Asn Asp Lys Gly Trp Asn Phe Glu Ala Ile
            500                 505                 510
Lys Asn Phe Asp Gln Lys Phe Ile Asp Ile Thr Lys Thr Asn Asn Asn
            515                 520                 525
Leu Ser Leu Lys Gln Asp Lys Arg Tyr Leu Asp Arg Phe Ile Asn
            530                 535                 540
Asp Ala Ile Leu Ser Pro Gly Val Lys Arg Ile Leu Arg Glu Ala Thr
545                 550                 555                 560
Lys Val Phe Asn Ala Ile Leu Lys Gln Phe Ser Gln Glu Tyr Asp Val
                565                 570                 575
Thr Lys Val Val Ile Glu Leu Ala Arg Glu Leu Ser Glu Glu Lys Glu
            580                 585                 590
Leu Glu Asn Asn Lys Asn Tyr Lys Lys Leu Ile Lys Lys Asn Ser Asp
```

-continued

Lys Ile Ser Glu Gly Leu Lys Ala Leu Asp Ile Ala Glu Asp Lys Ile
595                 600                 605
                610                 615                 620

Glu Asp Ile Leu Lys Ser Pro Thr Lys Ser Tyr Lys Val Leu Leu Trp
625                 630                 635                 640

Leu Gln Gln Asp His Ile Asp Pro Tyr Ser Gln Lys Glu Ile Ala Phe
                645                 650                 655

Glu Asp Ile Leu Thr Lys Thr Glu Lys Thr Glu Ile Asp His Ile Ile
                660                 665                 670

Pro Tyr Ser Ile Ser Phe Asp Asp Ser Ser Asn Lys Leu Leu Val
                675                 680                 685

Leu Ala Glu Ser Asn Gln Ala Lys Ser Asn Gln Thr Pro Tyr Glu Phe
690                 695                 700

Ile Thr Ser Gly Asn Ala Gly Ile Lys Trp Asp Tyr Glu Ala Tyr
705                 710                 715                 720

Cys Arg Lys Phe Lys Asp Gly Asp Thr Ser Leu Leu Asp Ser Thr Gln
                725                 730                 735

Arg Ser Lys Lys Phe Ala Lys Met Met Lys Thr Asp Thr Ser Ser Lys
                740                 745                 750

Tyr Asp Ile Gly Phe Leu Ala Arg Asn Leu Asn Asp Thr Arg Tyr Ala
                755                 760                 765

Thr Ile Val Phe Arg Asp Ala Leu Lys Asp Tyr Ala Asn Asn His Leu
770                 775                 780

Val Glu Asp Lys Pro Met Phe Lys Val Val Cys Ile Asn Gly Gly Val
785                 790                 795                 800

Thr Ser Phe Leu Arg Lys Asn Phe Asp Lys Ser Trp Tyr Ala Lys Lys
                805                 810                 815

Asp Arg Asp Lys Asn Ile His His Ala Val Asp Ala Ser Ile Ile Ser
                820                 825                 830

Ile Phe Ser Asn Lys Thr Lys Thr Leu Phe Asp Gln Leu Thr Gln Phe
                835                 840                 845

Ala Asp Tyr Lys Leu Phe Lys Asn Thr Asp Gly Ser Trp Lys Lys Ile
850                 855                 860

Asp Pro Lys Thr Gly Val Val Thr Glu Val Thr Asp Glu Asn Trp Lys
865                 870                 875                 880

Gln Ile Arg Val Arg Asn Gln Val Ser Lys Ile Ala Glu Glu Ile Asp
                885                 890                 895

Lys Cys Ile Gln Asp Ser Asn Ile Glu Arg Lys Ala Arg Tyr Ser Arg
                900                 905                 910

Lys Ile Glu Asn Lys Thr Asn Ile Ser Leu Phe Asn Asp Thr Val Tyr
                915                 920                 925

Ser Ala Lys Lys Val Gly Tyr Asp Asp Gln Ile Lys Arg Lys Asn Leu
                930                 935                 940

Lys Thr Leu Asp Ile Asp Glu Ser Val Glu Glu Asn Lys Asn Ser Lys
945                 950                 955                 960

Val Lys Lys Gln Phe Val Tyr Arg Lys Leu Val Asn Val Ser Leu Leu
                965                 970                 975

Asn Asn Asp Lys Leu Ala Asp Leu Phe Ala Glu Lys Glu Asp Ile Leu
                980                 985                 990

Met Tyr Arg Ala Asn Pro Trp Val Ile Asn Leu Ala Glu Gln Ile Phe
                995                 1000                1005

Asn Glu Tyr Thr Glu Asn Arg Lys Ile Lys Ser Gln Asn Val Phe
        1010                1015                1020

```
Gly Lys Tyr Met Leu Asp Leu Thr Lys Glu Phe Pro Glu Lys Phe
    1025                1030                1035

Ser Glu Ala Phe Val Lys Ser Met Leu Arg Asn Lys Thr Ala Ile
    1040                1045                1050

Ile Tyr Asn Val Glu Lys Lys Val Val His Arg Ile Lys Arg Leu
    1055                1060                1065

Lys Ile Leu Ser Ser Glu Leu Lys Glu Asn Lys Leu Ser Asn Val
    1070                1075                1080

Ile Ile Arg Ser Lys Asn Glu Ser Gly Thr Lys Leu Ser Tyr Gln
    1085                1090                1095

Asp Thr Ile Asn Ser Val Ala Leu Met Ile Met Arg Ser Ile Asp
    1100                1105                1110

Pro Thr Ala Lys Lys Gln Tyr Ile Arg Val Pro Leu Asn Thr Leu
    1115                1120                1125

Asn Leu His Leu Gly Asp His Asp Phe Asp Leu His Asn Ile Asp
    1130                1135                1140

Ala Tyr Leu Lys Lys Pro Lys Phe Val Lys Tyr Leu Lys Ala Asn
    1145                1150                1155

Glu Ile Gly Asp Glu Tyr Lys Pro Trp Arg Val Leu Ile Ser Gly
    1160                1165                1170

Ser Leu Leu Ile His Lys Arg Asp Lys Lys Leu Met Tyr Ile Ser
    1175                1180                1185

Ser Phe Gln Asn Leu Asn Asp Leu Ile Glu Ile Lys Asn Leu Ile
    1190                1195                1200

Glu Thr Glu Tyr Lys Glu Asn Val Asp Ser Asp Pro Lys Lys Lys
    1205                1210                1215

Lys Lys Ala Ser Gln Ile Leu Arg Ser Leu Ser Thr Ile Leu Asn
    1220                1225                1230

Asp Tyr Ile Leu Leu Asp Ala Lys Asp Asn Phe Asp Ile Leu Gly
    1235                1240                1245

Leu Ser Lys Asn Arg Ile Asp Glu Ile Leu Asn Ser Lys Leu Asp
    1250                1255                1260

Leu Asp Lys Ile Ala Lys
    1265

<210> SEQ ID NO 12
<211> LENGTH: 1395
<212> TYPE: PRT
<213> ORGANISM: Treponema denticola

<400> SEQUENCE: 12

Met Lys Lys Glu Ile Lys Asp Tyr Phe Leu Gly Leu Asp Val Gly
1               5                   10                  15

Gly Ser Val Gly Trp Ala Val Thr Asp Thr Asp Tyr Lys Leu Leu Lys
                20                  25                  30

Ala Asn Arg Lys Asp Leu Trp Gly Met Arg Cys Phe Glu Thr Ala Glu
            35                  40                  45

Thr Ala Glu Val Arg Arg Leu His Arg Gly Ala Arg Arg Ile Glu
    50                  55                  60

Arg Arg Lys Lys Arg Ile Lys Leu Leu Gln Glu Leu Phe Ser Gln Glu
65                  70                  75                  80

Ile Ala Lys Thr Asp Glu Gly Phe Phe Gln Arg Met Lys Glu Ser Pro
                85                  90                  95

Phe Tyr Ala Glu Asp Lys Thr Ile Leu Gln Glu Asn Thr Leu Phe Asn
```

-continued

```
                100                 105                 110
Asp Lys Asp Phe Ala Asp Lys Thr Tyr His Lys Ala Tyr Pro Thr Ile
            115                 120                 125

Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175

Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Ile Leu Gly Leu Lys
    210                 215                 220

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Asp Phe Asp Ala Leu Ser
            260                 265                 270

Asp Asp Leu Ala Ser Ile Leu Gly Asp Ser Phe Glu Leu Leu Leu Lys
        275                 280                 285

Ala Lys Ala Val Tyr Asn Cys Ser Val Leu Ser Lys Val Ile Gly Asp
    290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys His Phe Pro Lys
                325                 330                 335

Asp Tyr Lys Lys Val Phe Gly Tyr Asn Lys Asn Glu Lys Asn Asn Asn
            340                 345                 350

Asn Tyr Ser Gly Tyr Val Gly Val Cys Lys Thr Lys Ser Lys Lys Leu
        355                 360                 365

Ile Ile Asn Asn Ser Val Asn Gln Glu Asp Phe Tyr Lys Phe Leu Lys
    370                 375                 380

Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
                405                 410                 415

Asn Ala Glu Ile Pro Tyr Gln Leu Arg Lys Met Glu Leu Glu Lys Ile
            420                 425                 430

Leu Ser Asn Ala Glu Lys His Phe Ser Phe Leu Lys Gln Lys Asp Glu
        435                 440                 445

Lys Gly Leu Ser His Ser Glu Lys Ile Ile Met Leu Leu Thr Phe Lys
    450                 455                 460

Ile Pro Tyr Tyr Ile Gly Pro Ile Asn Asp Asn His Lys Lys Phe Phe
465                 470                 475                 480

Pro Asp Arg Cys Trp Val Val Lys Lys Glu Lys Ser Pro Ser Gly Lys
                485                 490                 495

Thr Thr Pro Trp Asn Phe Phe Asp His Ile Asp Lys Glu Lys Thr Ala
            500                 505                 510

Glu Ala Phe Ile Thr Ser Arg Thr Asn Phe Cys Thr Tyr Leu Val Gly
        515                 520                 525
```

-continued

```
Glu Ser Val Leu Pro Lys Ser Leu Leu Tyr Ser Glu Tyr Thr Val
    530                 535                 540
Leu Asn Glu Ile Asn Asn Leu Gln Ile Ile Ile Asp Gly Lys Asn Ile
545                 550                 555                 560
Cys Asp Ile Lys Leu Lys Gln Lys Ile Tyr Glu Asp Leu Phe Lys Lys
                    565                 570                 575
Tyr Lys Lys Ile Thr Gln Lys Gln Ile Ser Thr Phe Ile Lys His Glu
                580                 585                 590
Gly Ile Cys Asn Lys Thr Asp Glu Val Ile Ile Leu Gly Ile Asp Lys
            595                 600                 605
Glu Cys Thr Ser Ser Leu Lys Ser Tyr Ile Glu Leu Lys Asn Ile Phe
    610                 615                 620
Gly Lys Gln Val Asp Glu Ile Ser Thr Lys Asn Met Leu Glu Glu Ile
625                 630                 635                 640
Ile Arg Trp Ala Thr Ile Tyr Asp Glu Gly Glu Gly Lys Thr Ile Leu
                    645                 650                 655
Lys Thr Lys Ile Lys Ala Glu Tyr Gly Lys Tyr Cys Ser Asp Glu Gln
                660                 665                 670
Ile Lys Lys Ile Leu Asn Leu Lys Phe Ser Gly Trp Gly Arg Leu Ser
            675                 680                 685
Arg Lys Phe Leu Glu Thr Val Thr Ser Glu Met Pro Gly Phe Ser Glu
    690                 695                 700
Pro Val Asn Ile Ile Thr Ala Met Arg Glu Thr Gln Asn Asn Leu Met
705                 710                 715                 720
Glu Leu Leu Ser Ser Glu Phe Thr Phe Thr Glu Asn Ile Lys Lys Ile
                    725                 730                 735
Asn Ser Gly Phe Glu Asp Ala Glu Lys Gln Phe Ser Tyr Asp Gly Leu
                740                 745                 750
Val Lys Pro Leu Phe Leu Ser Pro Ser Val Lys Lys Met Leu Trp Gln
            755                 760                 765
Thr Leu Lys Leu Val Lys Glu Ile Ser His Ile Thr Gln Ala Pro Pro
    770                 775                 780
Lys Lys Ile Phe Ile Glu Met Ala Lys Gly Ala Glu Leu Glu Pro Ala
785                 790                 795                 800
Arg Thr Lys Thr Arg Leu Lys Ile Leu Gln Asp Leu Tyr Asn Asn Cys
                    805                 810                 815
Lys Asn Asp Ala Asp Ala Phe Ser Ser Glu Ile Lys Asp Leu Ser Gly
                820                 825                 830
Lys Ile Glu Asn Glu Asp Asn Leu Arg Leu Arg Ser Asp Lys Leu Tyr
            835                 840                 845
Leu Tyr Tyr Thr Gln Leu Gly Lys Cys Met Tyr Cys Gly Lys Pro Ile
    850                 855                 860
Glu Ile Gly His Val Phe Asp Thr Ser Asn Tyr Asp Ile Asp His Ile
865                 870                 875                 880
Tyr Pro Gln Ser Lys Ile Lys Asp Asp Ser Ile Ser Asn Arg Val Leu
                    885                 890                 895
Val Cys Ser Ser Cys Asn Lys Asn Lys Glu Asp Lys Tyr Pro Leu Lys
                900                 905                 910
Ser Glu Ile Gln Ser Lys Gln Arg Gly Phe Trp Asn Phe Leu Gln Arg
            915                 920                 925
Asn Asn Phe Ile Ser Leu Glu Lys Leu Asn Arg Leu Thr Arg Ala Thr
    930                 935                 940
```

```
Pro Ile Ser Asp Asp Glu Thr Ala Lys Phe Ile Ala Arg Gln Leu Val
945                 950                 955                 960

Glu Thr Arg Gln Ala Thr Lys Val Ala Ala Lys Val Leu Glu Lys Met
            965                 970                 975

Phe Pro Glu Thr Lys Ile Val Tyr Ser Lys Ala Glu Thr Val Ser Met
            980                 985                 990

Phe Arg Asn Lys Phe Asp Ile Val  Lys Cys Arg Glu Ile  Asn Asp Phe
        995              1000                 1005

His His  Ala His Asp Ala Tyr  Leu Asn Ile Val Val  Gly Asn Val
    1010                 1015                 1020

Tyr Asn  Thr Lys Phe Thr Asn  Asn Pro Trp Asn Phe  Ile Lys Glu
    1025                 1030                 1035

Lys Arg  Asp Asn Pro Lys Ile  Ala Asp Thr Tyr Asn  Tyr Tyr Lys
    1040                 1045                 1050

Val Phe  Asp Tyr Asp Val Lys  Arg Asn Asn Ile Thr  Ala Trp Glu
    1055                 1060                 1065

Lys Gly  Lys Thr Ile Ile Thr  Val Lys Asp Met Leu  Lys Arg Asn
    1070                 1075                 1080

Thr Pro  Ile Tyr Thr Arg Gln  Ala Ala Cys Lys Lys  Gly Glu Leu
    1085                 1090                 1095

Phe Asn  Gln Thr Ile Met Lys  Lys Gly Leu Gly Gln  His Pro Leu
    1100                 1105                 1110

Lys Lys  Glu Gly Pro Phe Ser  Asn Ile Ser Lys Tyr  Gly Gly Tyr
    1115                 1120                 1125

Asn Lys  Val Ser Ala Ala Tyr  Tyr Thr Leu Ile Glu  Tyr Glu Glu
    1130                 1135                 1140

Lys Gly  Asn Lys Ile Arg Ser  Leu Glu Thr Ile Pro  Leu Tyr Leu
    1145                 1150                 1155

Val Lys  Asp Ile Gln Lys Asp  Gln Asp Val Leu Lys  Ser Tyr Leu
    1160                 1165                 1170

Thr Asp  Leu Leu Gly Lys Lys  Glu Phe Lys Ile Leu  Val Pro Lys
    1175                 1180                 1185

Ile Lys  Ile Asn Ser Leu Leu  Lys Ile Asn Gly Phe  Pro Cys His
    1190                 1195                 1200

Ile Thr  Gly Lys Thr Asn Asp  Ser Phe Leu Leu Arg  Pro Ala Val
    1205                 1210                 1215

Gln Phe  Cys Cys Ser Asn Asn  Glu Val Leu Tyr Phe  Lys Lys Ile
    1220                 1225                 1230

Ile Arg  Phe Ser Glu Ile Arg  Ser Gln Arg Glu Lys  Ile Gly Lys
    1235                 1240                 1245

Thr Ile  Ser Pro Tyr Glu Asp  Leu Ser Phe Arg Ser  Tyr Ile Lys
    1250                 1255                 1260

Glu Asn  Leu Trp Lys Lys Thr  Lys Asn Asp Glu Ile  Gly Glu Lys
    1265                 1270                 1275

Glu Phe  Tyr Asp Leu Leu Gln  Lys Lys Asn Leu Glu  Ile Tyr Asp
    1280                 1285                 1290

Met Leu  Leu Thr Lys His Lys  Asp Thr Ile Tyr Lys  Lys Arg Pro
    1295                 1300                 1305

Asn Ser  Ala Thr Ile Asp Ile  Leu Val Lys Gly Lys  Glu Lys Phe
    1310                 1315                 1320

Lys Ser  Leu Ile Ile Glu Asn  Gln Phe Glu Val Ile  Leu Glu Ile
    1325                 1330                 1335

Leu Lys  Leu Phe Ser Ala Thr  Arg Asn Val Ser Asp  Leu Gln His
```

-continued

```
                1340                1345                1350

Ile Gly Gly Ser Lys Tyr Ser Gly Val Ala Lys Ile Gly Asn Lys
    1355                1360                1365

Ile Ser Ser Leu Asp Asn Cys Ile Leu Ile Tyr Gln Ser Ile Thr
    1370                1375                1380

Gly Ile Phe Glu Lys Arg Ile Asp Leu Leu Lys Val
    1385                1390                1395

<210> SEQ ID NO 13
<211> LENGTH: 1228
<212> TYPE: PRT
<213> ORGANISM: artificial sequence
<220> FEATURE:
<223> OTHER INFORMATION: engineered Lachnospiraceae bacterium ND2006
      Cas9

<400> SEQUENCE: 13

Ala Ala Ser Lys Leu Glu Lys Phe Thr Asn Cys Tyr Ser Leu Ser Lys
1               5                   10                  15

Thr Leu Arg Phe Lys Ala Ile Pro Val Gly Lys Thr Gln Glu Asn Ile
            20                  25                  30

Asp Asn Lys Arg Leu Leu Val Glu Asp Glu Lys Arg Ala Glu Asp Tyr
        35                  40                  45

Lys Gly Val Lys Lys Leu Leu Asp Arg Tyr Tyr Leu Ser Phe Ile Asn
    50                  55                  60

Asp Val Leu His Ser Ile Lys Leu Lys Asn Leu Asn Asn Tyr Ile Ser
65                  70                  75                  80

Leu Phe Arg Lys Lys Thr Arg Thr Glu Lys Glu Asn Lys Glu Leu Glu
                85                  90                  95

Asn Leu Glu Ile Asn Leu Arg Lys Glu Ile Ala Lys Ala Phe Lys Gly
            100                 105                 110

Ala Ala Gly Tyr Lys Ser Leu Phe Lys Lys Asp Ile Ile Glu Thr Ile
        115                 120                 125

Leu Pro Glu Ala Ala Asp Asp Lys Asp Glu Ile Ala Leu Val Asn Ser
    130                 135                 140

Phe Asn Gly Phe Thr Thr Ala Phe Thr Gly Phe Phe Asp Asn Arg Glu
145                 150                 155                 160

Asn Met Phe Ser Glu Glu Ala Lys Ser Thr Ser Ile Ala Phe Arg Cys
                165                 170                 175

Ile Asn Glu Asn Leu Thr Arg Tyr Ile Ser Asn Met Asp Ile Phe Glu
            180                 185                 190

Lys Val Asp Ala Ile Phe Asp Lys His Glu Val Gln Glu Ile Lys Glu
        195                 200                 205

Lys Ile Leu Asn Ser Asp Tyr Asp Val Glu Asp Phe Phe Glu Gly Glu
    210                 215                 220

Phe Phe Asn Phe Val Leu Thr Gln Glu Gly Ile Asp Val Tyr Asn Ala
225                 230                 235                 240

Ile Ile Gly Gly Phe Val Thr Glu Ser Gly Glu Lys Ile Lys Gly Leu
                245                 250                 255

Asn Glu Tyr Ile Asn Leu Tyr Asn Ala Lys Thr Lys Gln Ala Leu Pro
            260                 265                 270

Lys Phe Lys Pro Leu Tyr Lys Gln Val Leu Ser Asp Arg Glu Ser Leu
        275                 280                 285

Ser Phe Tyr Gly Glu Gly Tyr Thr Ser Asp Glu Glu Val Leu Glu Val
    290                 295                 300
```

```
Phe Arg Asn Thr Leu Asn Lys Asn Ser Glu Ile Phe Ser Ser Ile Lys
305                 310                 315                 320

Lys Leu Glu Lys Leu Phe Lys Asn Phe Asp Glu Tyr Ser Ser Ala Gly
                325                 330                 335

Ile Phe Val Lys Asn Gly Pro Ala Ile Ser Thr Ile Ser Lys Asp Ile
                340                 345                 350

Phe Gly Glu Trp Asn Leu Ile Arg Asp Lys Trp Asn Ala Glu Tyr Asp
            355                 360                 365

Asp Ile His Leu Lys Lys Ala Val Val Thr Glu Lys Tyr Glu Asp
        370                 375                 380

Asp Arg Arg Lys Ser Phe Lys Lys Ile Gly Ser Phe Ser Leu Glu Gln
385                 390                 395                 400

Leu Gln Glu Tyr Ala Asp Ala Asp Leu Ser Val Val Glu Lys Leu Lys
                405                 410                 415

Glu Ile Ile Ile Gln Lys Val Asp Glu Ile Tyr Lys Val Tyr Gly Ser
                420                 425                 430

Ser Glu Lys Leu Phe Asp Ala Asp Phe Val Leu Glu Lys Ser Leu Lys
                435                 440                 445

Lys Asn Asp Ala Val Val Ala Ile Met Lys Asp Leu Leu Asp Ser Val
450                 455                 460

Lys Ser Phe Glu Asn Tyr Ile Lys Ala Phe Phe Gly Glu Gly Lys Glu
465                 470                 475                 480

Thr Asn Arg Asp Glu Ser Phe Tyr Gly Asp Phe Val Leu Ala Tyr Asp
                485                 490                 495

Ile Leu Leu Lys Val Asp His Ile Tyr Asp Ala Ile Arg Asn Tyr Val
                500                 505                 510

Thr Gln Lys Pro Tyr Ser Lys Asp Lys Phe Lys Leu Tyr Phe Gln Asn
                515                 520                 525

Pro Gln Phe Met Gly Gly Trp Asp Lys Asp Lys Glu Thr Asp Tyr Arg
                530                 535                 540

Ala Thr Ile Leu Arg Tyr Gly Ser Lys Tyr Tyr Leu Ala Ile Met Asp
545                 550                 555                 560

Lys Lys Tyr Ala Lys Cys Leu Gln Lys Ile Asp Lys Asp Asp Val Asn
                565                 570                 575

Gly Asn Tyr Glu Lys Ile Asn Tyr Lys Leu Leu Pro Gly Pro Asn Lys
                580                 585                 590

Met Leu Pro Lys Val Phe Phe Ser Lys Lys Trp Met Ala Tyr Tyr Asn
                595                 600                 605

Pro Ser Glu Asp Ile Gln Lys Ile Tyr Lys Asn Gly Thr Phe Lys Lys
                610                 615                 620

Gly Asp Met Phe Asn Leu Asn Asp Cys His Lys Leu Ile Asp Phe Phe
625                 630                 635                 640

Lys Asp Ser Ile Ser Arg Tyr Pro Lys Trp Ser Asn Ala Tyr Asp Phe
                645                 650                 655

Asn Phe Ser Glu Thr Glu Lys Tyr Lys Asp Ile Ala Gly Phe Tyr Arg
                660                 665                 670

Glu Val Glu Glu Gln Gly Tyr Lys Val Ser Phe Glu Ser Ala Ser Lys
                675                 680                 685

Lys Glu Val Asp Lys Leu Val Glu Glu Gly Lys Leu Tyr Met Phe Gln
                690                 695                 700

Ile Tyr Asn Lys Asp Phe Ser Asp Lys Ser His Gly Thr Pro Asn Leu
705                 710                 715                 720

His Thr Met Tyr Phe Lys Leu Leu Phe Asp Glu Asn Asn His Gly Gln
```

```
                725              730              735
Ile Arg Leu Ser Gly Gly Ala Glu Leu Phe Met Arg Arg Ala Ser Leu
                740              745              750

Lys Lys Glu Glu Leu Val Val His Pro Ala Asn Ser Pro Ile Ala Asn
            755              760              765

Lys Asn Pro Asp Asn Pro Lys Thr Thr Thr Leu Ser Tyr Asp Val
        770              775              780

Tyr Lys Asp Lys Arg Phe Ser Glu Asp Gln Tyr Glu Leu His Ile Pro
785              790              795              800

Ile Ala Ile Asn Lys Cys Pro Lys Asn Ile Phe Lys Ile Asn Thr Glu
                805              810              815

Val Arg Val Leu Leu Lys His Asp Asp Asn Pro Tyr Val Ile Gly Ile
                820              825              830

Asp Arg Gly Glu Arg Asn Leu Leu Tyr Ile Val Val Val Asp Gly Lys
                835              840              845

Gly Asn Ile Val Glu Gln Tyr Ser Leu Asn Glu Ile Ile Asn Asn Phe
            850              855              860

Asn Gly Ile Arg Ile Lys Thr Asp Tyr His Ser Leu Leu Asp Lys Lys
865              870              875              880

Glu Lys Glu Arg Phe Glu Ala Arg Gln Asn Trp Thr Ser Ile Glu Asn
                885              890              895

Ile Lys Glu Leu Lys Ala Gly Tyr Ile Ser Gln Val Val His Lys Ile
            900              905              910

Cys Glu Leu Val Glu Lys Tyr Asp Ala Val Ile Ala Leu Glu Asp Leu
                915              920              925

Asn Ser Gly Phe Lys Asn Ser Arg Val Lys Val Glu Lys Gln Val Tyr
        930              935              940

Gln Lys Phe Glu Lys Met Leu Ile Asp Lys Leu Asn Tyr Met Val Asp
945              950              955              960

Lys Lys Ser Asn Pro Cys Ala Thr Gly Gly Ala Leu Lys Gly Tyr Gln
                965              970              975

Ile Thr Asn Lys Phe Glu Ser Phe Lys Ser Met Ser Thr Gln Asn Gly
            980              985              990

Phe Ile Phe Tyr Ile Pro Ala Trp Leu Thr Ser Lys Ile Asp Pro Ser
        995             1000             1005

Thr Gly Phe Val Asn Leu Leu Lys Thr Lys Tyr Thr Ser Ile Ala
    1010             1015             1020

Asp Ser Lys Lys Phe Ile Ser Ser Phe Asp Arg Ile Met Tyr Val
    1025             1030             1035

Pro Glu Glu Asp Leu Phe Glu Phe Ala Leu Asp Tyr Lys Asn Phe
    1040             1045             1050

Ser Arg Thr Asp Ala Asp Tyr Ile Lys Lys Trp Lys Leu Tyr Ser
    1055             1060             1065

Tyr Gly Asn Arg Ile Arg Ile Phe Ala Ala Ala Lys Lys Asn Asn
    1070             1075             1080

Val Phe Ala Trp Glu Glu Val Cys Leu Thr Ser Ala Tyr Lys Glu
    1085             1090             1095

Leu Phe Asn Lys Tyr Gly Ile Asn Tyr Gln Gln Gly Asp Ile Arg
    1100             1105             1110

Ala Leu Leu Cys Glu Gln Ser Asp Lys Ala Phe Tyr Ser Ser Phe
    1115             1120             1125

Met Ala Leu Met Ser Leu Met Leu Gln Met Arg Asn Ser Ile Thr
    1130             1135             1140
```

Gly Arg Thr Asp Val Asp Phe Leu Ile Ser Pro Val Lys Asn Ser
    1145                1150                1155

Asp Gly Ile Phe Tyr Asp Ser Arg Asn Tyr Glu Ala Gln Glu Asn
    1160                1165                1170

Ala Ile Leu Pro Lys Asn Ala Asp Ala Asn Gly Ala Tyr Asn Ile
    1175                1180                1185

Ala Arg Lys Val Leu Trp Ala Ile Gly Gln Phe Lys Lys Ala Glu
    1190                1195                1200

Asp Glu Lys Leu Asp Lys Val Lys Ile Ala Ile Ser Asn Lys Glu
    1205                1210                1215

Trp Leu Glu Tyr Ala Gln Thr Ser Val Lys
    1220                1225

<210> SEQ ID NO 14
<211> LENGTH: 1238
<212> TYPE: PRT
<213> ORGANISM: artificial sequence
<220> FEATURE:
<223> OTHER INFORMATION: engineered Streptococcus pyogenes Cas9

<400> SEQUENCE: 14

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

```
Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685
```

```
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
            725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
            755                 760                 765
Thr Thr Gln Lys Gly Gln Lys Gly Gly Ser Glu Leu Asp Lys Ala
770                 775                 780
Gly Phe Ile Lys Arg Gln Leu Val Glu Thr Arg Gln Ile Thr Lys His
785                 790                 795                 800
Val Ala Gln Ile Leu Asp Ser Arg Met Asn Thr Lys Tyr Asp Glu Asn
            805                 810                 815
Asp Lys Leu Ile Arg Glu Val Lys Val Ile Thr Leu Lys Ser Lys Leu
            820                 825                 830
Val Ser Asp Phe Arg Lys Asp Phe Gln Phe Tyr Lys Val Arg Glu Ile
            835                 840                 845
Asn Asn Tyr His His Ala His Asp Ala Tyr Leu Asn Ala Val Val Gly
850                 855                 860
Thr Ala Leu Ile Lys Lys Tyr Pro Lys Leu Glu Ser Glu Phe Val Tyr
865                 870                 875                 880
Gly Asp Tyr Lys Val Tyr Asp Val Arg Lys Met Ile Ala Lys Ser Glu
            885                 890                 895
Gln Glu Ile Gly Lys Ala Thr Ala Lys Tyr Phe Phe Tyr Ser Asn Ile
            900                 905                 910
Met Asn Phe Phe Lys Thr Glu Ile Thr Leu Ala Asn Gly Glu Ile Arg
            915                 920                 925
Lys Arg Pro Leu Ile Glu Thr Asn Gly Glu Thr Gly Glu Ile Val Trp
            930                 935                 940
Asp Lys Gly Arg Asp Phe Ala Thr Val Arg Lys Val Leu Ser Met Pro
945                 950                 955                 960
Gln Val Asn Ile Val Lys Lys Thr Glu Val Gln Thr Gly Gly Phe Ser
            965                 970                 975
Lys Glu Ser Ile Leu Pro Lys Arg Asn Ser Asp Lys Leu Ile Ala Arg
            980                 985                 990
Lys Lys Asp Trp Asp Pro Lys Lys Tyr Gly Gly Phe Asp Ser Pro Thr
            995                 1000                1005
Val Ala Tyr Ser Val Leu Val Val Ala Lys Val Glu Lys Gly Lys
    1010                1015                1020
Ser Lys Lys Leu Lys Ser Val Lys Glu Leu Leu Gly Ile Thr Ile
    1025                1030                1035
Met Glu Arg Ser Ser Phe Glu Lys Asn Pro Ile Asp Phe Leu Glu
    1040                1045                1050
Ala Lys Gly Tyr Lys Glu Val Lys Lys Asp Leu Ile Ile Lys Leu
    1055                1060                1065
Pro Lys Tyr Ser Leu Phe Glu Leu Glu Asn Gly Arg Lys Arg Met
    1070                1075                1080
Leu Ala Ser Ala Gly Glu Leu Gln Lys Gly Asn Glu Leu Ala Leu
    1085                1090                1095
Pro Ser Lys Tyr Val Asn Phe Leu Tyr Leu Ala Ser His Tyr Glu
```

```
              1100                1105                1110

Lys Leu Lys Gly Ser Pro Glu Asp Asn Glu Gln Lys Gln Leu Phe
        1115                1120                1125

Val Glu Gln His Lys His Tyr Leu Asp Glu Ile Ile Glu Gln Ile
1130                1135                1140

Ser Glu Phe Ser Lys Arg Val Ile Leu Ala Asp Ala Asn Leu Asp
        1145                1150                1155

Lys Val Leu Ser Ala Tyr Asn Lys His Arg Asp Lys Pro Ile Arg
    1160                1165                1170

Glu Gln Ala Glu Asn Ile Ile His Leu Phe Thr Leu Thr Asn Leu
1175                1180                1185

Gly Ala Pro Ala Ala Phe Lys Tyr Phe Asp Thr Thr Ile Asp Arg
        1190                1195                1200

Lys Arg Tyr Thr Ser Thr Lys Glu Val Leu Asp Ala Thr Leu Ile
1205                1210                1215

His Gln Ser Ile Thr Gly Leu Tyr Glu Thr Arg Ile Asp Leu Ser
    1220                1225                1230

Gln Leu Gly Gly Asp
    1235

<210> SEQ ID NO 15
<211> LENGTH: 1304
<212> TYPE: PRT
<213> ORGANISM: artificial sequence
<220> FEATURE:
<223> OTHER INFORMATION: engineered Streptococcus pyogenes Cas9

<400> SEQUENCE: 15

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
```

-continued

```
                210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
                450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
                530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
```

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Ala Ala Ile Val Pro Gln Ser Phe Leu Lys
            835                 840                 845

Asp Asp Ser Ile Asp Asn Lys Val Leu Thr Arg Ser Asp Lys Ala Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Gly Gly Gly Ser Gly Gly
            995                 1000                1005

Gly Ser Asp Lys Gly Arg Asp Phe Ala Thr Val Arg Lys Val Leu
    1010                1015                1020

Ser Met Pro Gln Val Asn Ile Val Lys Lys Thr Glu Val Gln Thr
    1025                1030                1035

Gly Gly Phe Ser Lys Glu Ser Ile Leu Pro Lys Arg Asn Ser Asp
    1040                1045                1050

Lys Leu Ile Ala Arg Lys Lys Asp Trp Asp Pro Lys Lys Tyr Gly
            1055                1060                1065

Gly Phe Asp Ser Pro Thr Val Ala Tyr Ser Val Leu Val Val Ala
        1070                1075                1080

Lys Val Glu Lys Gly Lys Ser Lys Lys Leu Lys Ser Val Lys Glu
        1085                1090                1095

Leu Leu Gly Ile Thr Ile Met Glu Arg Ser Ser Phe Glu Lys Asn
        1100                1105                1110

Pro Ile Asp Phe Leu Glu Ala Lys Gly Tyr Lys Glu Val Lys Lys
        1115                1120                1125

Asp Leu Ile Ile Lys Leu Pro Lys Tyr Ser Leu Phe Glu Leu Glu
        1130                1135                1140

Asn Gly Arg Lys Arg Met Leu Ala Ser Ala Gly Glu Leu Gln Lys
        1145                1150                1155

Gly Asn Glu Leu Ala Leu Pro Ser Lys Tyr Val Asn Phe Leu Tyr
        1160                1165                1170

Leu Ala Ser His Tyr Glu Lys Leu Lys Gly Ser Pro Glu Asp Asn
        1175                1180                1185

Glu Gln Lys Gln Leu Phe Val Glu Gln His Lys His Tyr Leu Asp
        1190                1195                1200

Glu Ile Ile Glu Gln Ile Ser Glu Phe Ser Lys Arg Val Ile Leu
        1205                1210                1215

Ala Asp Ala Asn Leu Asp Lys Val Leu Ser Ala Tyr Asn Lys His
        1220                1225                1230

Arg Asp Lys Pro Ile Arg Glu Gln Ala Glu Asn Ile Ile His Leu
        1235                1240                1245

Phe Thr Leu Thr Asn Leu Gly Ala Pro Ala Ala Phe Lys Tyr Phe
        1250                1255                1260

Asp Thr Thr Ile Asp Arg Lys Arg Tyr Thr Ser Thr Lys Glu Val
        1265                1270                1275

Leu Asp Ala Thr Leu Ile His Gln Ser Ile Thr Gly Leu Tyr Glu
        1280                1285                1290

Thr Arg Ile Asp Leu Ser Gln Leu Gly Gly Asp
        1295                1300

<210> SEQ ID NO 16
<211> LENGTH: 1174
<212> TYPE: PRT
<213> ORGANISM: artificial sequence
<220> FEATURE:
<223> OTHER INFORMATION: engineered Streptococcus pyogenes Cas9

<400> SEQUENCE: 16

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

-continued

```
Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
```

```
            515                 520                 525
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                    565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                    595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Gly Gly Gly Ser Glu Leu Asp Lys Ala
    770                 775                 780

Gly Phe Ile Lys Arg Gln Leu Val Glu Thr Arg Gln Ile Thr Lys His
785                 790                 795                 800

Val Ala Gln Ile Leu Asp Ser Arg Met Asn Thr Lys Tyr Asp Glu Asn
                    805                 810                 815

Asp Lys Leu Ile Arg Glu Val Lys Val Ile Thr Leu Lys Ser Lys Leu
                820                 825                 830

Val Ser Asp Phe Arg Lys Asp Phe Gln Phe Tyr Lys Val Arg Glu Ile
                835                 840                 845

Asn Asn Tyr His His Ala His Asp Ala Tyr Leu Asn Ala Val Val Gly
                850                 855                 860

Thr Ala Leu Ile Lys Lys Tyr Pro Gly Gly Ser Gly Gly Ser
865                 870                 875                 880

Asp Lys Gly Arg Asp Phe Ala Thr Val Arg Lys Val Leu Ser Met Pro
                    885                 890                 895

Gln Val Asn Ile Val Lys Lys Thr Glu Val Gln Thr Gly Gly Phe Ser
                900                 905                 910

Lys Glu Ser Ile Leu Pro Lys Arg Asn Ser Asp Lys Leu Ile Ala Arg
                915                 920                 925

Lys Lys Asp Trp Asp Pro Lys Lys Tyr Gly Gly Phe Asp Ser Pro Thr
                930                 935                 940
```

```
Val Ala Tyr Ser Val Leu Val Ala Lys Val Glu Lys Gly Lys Ser
945                 950                 955                 960

Lys Lys Leu Lys Ser Val Lys Glu Leu Leu Gly Ile Thr Ile Met Glu
                965                 970                 975

Arg Ser Ser Phe Glu Lys Asn Pro Ile Asp Phe Leu Glu Ala Lys Gly
            980                 985                 990

Tyr Lys Glu Val Lys Lys Asp Leu Ile Ile Lys Leu Pro Lys Tyr Ser
        995                 1000                1005

Leu Phe Glu Leu Glu Asn Gly Arg Lys Arg Met Leu Ala Ser Ala
    1010                1015                1020

Gly Glu Leu Gln Lys Gly Asn Glu Leu Ala Leu Pro Ser Lys Tyr
    1025                1030                1035

Val Asn Phe Leu Tyr Leu Ala Ser His Tyr Glu Lys Leu Lys Gly
    1040                1045                1050

Ser Pro Glu Asp Asn Glu Gln Lys Gln Leu Phe Val Glu Gln His
    1055                1060                1065

Lys His Tyr Leu Asp Glu Ile Ile Glu Gln Ile Ser Glu Phe Ser
    1070                1075                1080

Lys Arg Val Ile Leu Ala Asp Ala Asn Leu Asp Lys Val Leu Ser
    1085                1090                1095

Ala Tyr Asn Lys His Arg Asp Lys Pro Ile Arg Glu Gln Ala Glu
    1100                1105                1110

Asn Ile Ile His Leu Phe Thr Leu Thr Asn Leu Gly Ala Pro Ala
    1115                1120                1125

Ala Phe Lys Tyr Phe Asp Thr Thr Ile Asp Arg Lys Arg Tyr Thr
    1130                1135                1140

Ser Thr Lys Glu Val Leu Asp Ala Thr Leu Ile His Gln Ser Ile
    1145                1150                1155

Thr Gly Leu Tyr Glu Thr Arg Ile Asp Leu Ser Gln Leu Gly Gly
    1160                1165                1170

Asp

<210> SEQ ID NO 17
<211> LENGTH: 1227
<212> TYPE: PRT
<213> ORGANISM: artificial sequence
<220> FEATURE:
<223> OTHER INFORMATION: engineered Streptococcus pyogenes Cas9

<400> SEQUENCE: 17

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110
```

```
His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys Gly Gly
            500                 505                 510

Gly Ser Tyr Thr Gly Trp Gly Arg Leu Ser Arg Lys Leu Ile Asn Gly
        515                 520                 525

Ile Arg Asp Lys Gln Ser Gly Lys Thr Ile Leu Asp Phe Leu Lys Ser
```

```
               530                 535                 540
Asp Gly Phe Ala Asn Arg Asn Phe Met Gln Leu Ile His Asp Asp Ser
545                 550                 555                 560

Leu Thr Phe Lys Glu Asp Ile Gln Lys Ala Gln Val Ser Gly Gln Gly
                565                 570                 575

Asp Ser Leu His Glu His Ile Ala Asn Leu Ala Gly Ser Pro Ala Ile
                580                 585                 590

Lys Lys Gly Ile Leu Gln Thr Val Lys Val Asp Glu Leu Val Lys
                595                 600                 605

Val Met Gly Arg His Lys Pro Glu Asn Ile Val Ile Glu Met Ala Arg
610                 615                 620

Glu Asn Gln Thr Thr Gln Lys Gly Gln Lys Asn Ser Arg Glu Arg Met
625                 630                 635                 640

Lys Arg Ile Glu Glu Gly Ile Lys Glu Leu Gly Ser Gln Ile Leu Lys
                645                 650                 655

Glu His Pro Val Glu Asn Thr Gln Leu Gln Asn Glu Lys Leu Tyr Leu
                660                 665                 670

Tyr Tyr Leu Gln Asn Gly Arg Asp Met Tyr Val Asp Gln Glu Leu Asp
                675                 680                 685

Ile Asn Arg Leu Ser Asp Tyr Asp Val Ala Ala Ile Val Pro Gln Ser
                690                 695                 700

Phe Leu Lys Asp Asp Ser Ile Asp Asn Lys Val Leu Thr Arg Ser Asp
705                 710                 715                 720

Lys Ala Arg Gly Lys Ser Asp Asn Val Pro Ser Glu Glu Val Val Lys
                725                 730                 735

Lys Met Lys Asn Tyr Trp Arg Gln Leu Leu Asn Ala Lys Leu Ile Thr
                740                 745                 750

Gln Arg Lys Phe Asp Asn Leu Thr Lys Ala Glu Arg Gly Gly Leu Ser
                755                 760                 765

Glu Leu Asp Lys Ala Gly Phe Ile Lys Arg Gln Leu Val Glu Thr Arg
                770                 775                 780

Gln Ile Thr Lys His Val Ala Gln Ile Leu Asp Ser Arg Met Asn Thr
785                 790                 795                 800

Lys Tyr Asp Glu Asn Asp Lys Leu Ile Arg Glu Val Lys Val Ile Thr
                805                 810                 815

Leu Lys Ser Lys Leu Val Ser Asp Phe Arg Lys Asp Phe Gln Phe Tyr
                820                 825                 830

Lys Val Arg Glu Ile Asn Asn Tyr His His Ala His Asp Ala Tyr Leu
                835                 840                 845

Asn Ala Val Val Gly Thr Ala Leu Ile Lys Lys Tyr Pro Lys Leu Glu
850                 855                 860

Ser Glu Phe Val Tyr Gly Asp Tyr Lys Val Tyr Asp Val Arg Lys Met
865                 870                 875                 880

Ile Ala Lys Ser Glu Gln Glu Ile Gly Lys Ala Thr Ala Lys Tyr Phe
                885                 890                 895

Phe Tyr Ser Asn Ile Met Asn Phe Phe Lys Thr Glu Ile Thr Leu Ala
                900                 905                 910

Asn Gly Glu Ile Arg Lys Arg Pro Leu Ile Glu Thr Asn Gly Glu Thr
                915                 920                 925

Gly Glu Ile Val Trp Asp Lys Gly Arg Asp Phe Ala Thr Val Arg Lys
                930                 935                 940

Val Leu Ser Met Pro Gln Val Asn Ile Val Lys Lys Thr Glu Val Gln
945                 950                 955                 960
```

Thr Gly Gly Phe Ser Lys Glu Ser Ile Leu Pro Lys Arg Asn Ser Asp
            965                 970                 975

Lys Leu Ile Ala Arg Lys Lys Asp Trp Asp Pro Lys Lys Tyr Gly Gly
            980                 985                 990

Phe Asp Ser Pro Thr Val Ala Tyr Ser Val Leu Val Val Ala Lys Val
            995                 1000                1005

Glu Lys Gly Lys Ser Lys Lys Leu Lys Ser Val Lys Glu Leu Leu
        1010                1015                1020

Gly Ile Thr Ile Met Glu Arg Ser Ser Phe Glu Lys Asn Pro Ile
        1025                1030                1035

Asp Phe Leu Glu Ala Lys Gly Tyr Lys Glu Val Lys Lys Asp Leu
        1040                1045                1050

Ile Ile Lys Leu Pro Lys Tyr Ser Leu Phe Glu Leu Glu Asn Gly
        1055                1060                1065

Arg Lys Arg Met Leu Ala Ser Ala Gly Glu Leu Gln Lys Gly Asn
        1070                1075                1080

Glu Leu Ala Leu Pro Ser Lys Tyr Val Asn Phe Leu Tyr Leu Ala
        1085                1090                1095

Ser His Tyr Glu Lys Leu Lys Gly Ser Pro Glu Asp Asn Glu Gln
        1100                1105                1110

Lys Gln Leu Phe Val Glu Gln His Lys His Tyr Leu Asp Glu Ile
        1115                1120                1125

Ile Glu Gln Ile Ser Glu Phe Ser Lys Arg Val Ile Leu Ala Asp
        1130                1135                1140

Ala Asn Leu Asp Lys Val Leu Ser Ala Tyr Asn Lys His Arg Asp
        1145                1150                1155

Lys Pro Ile Arg Glu Gln Ala Glu Asn Ile Ile His Leu Phe Thr
        1160                1165                1170

Leu Thr Asn Leu Gly Ala Pro Ala Ala Phe Lys Tyr Phe Asp Thr
        1175                1180                1185

Thr Ile Asp Arg Lys Arg Tyr Thr Ser Thr Lys Glu Val Leu Asp
        1190                1195                1200

Ala Thr Leu Ile His Gln Ser Ile Thr Gly Leu Tyr Glu Thr Arg
        1205                1210                1215

Ile Asp Leu Ser Gln Leu Gly Gly Asp
        1220                1225

<210> SEQ ID NO 18
<211> LENGTH: 1324
<212> TYPE: PRT
<213> ORGANISM: artificial sequence
<220> FEATURE:
<223> OTHER INFORMATION: engineered Streptococcus pyogenes Cas9

<400> SEQUENCE: 18

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

```
Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Gly Gly Ser Ala Gln Val Ser Gly Gln
            660                 665                 670

Gly Asp Ser Leu His Glu His Ile Ala Asn Leu Ala Gly Ser Pro Ala
        675                 680                 685

Ile Lys Lys Gly Ile Leu Gln Thr Val Lys Val Val Asp Glu Leu Val
690                 695                 700

Lys Val Met Gly Arg His Lys Pro Glu Asn Ile Val Ile Glu Met Ala
705                 710                 715                 720

Arg Glu Asn Gln Thr Thr Gln Lys Gly Gln Lys Asn Ser Arg Glu Arg
                725                 730                 735

Met Lys Arg Ile Glu Glu Gly Ile Lys Glu Leu Gly Ser Gln Ile Leu
            740                 745                 750

Lys Glu His Pro Val Glu Asn Thr Gln Leu Gln Asn Glu Lys Leu Tyr
        755                 760                 765

Leu Tyr Tyr Leu Gln Asn Gly Arg Asp Met Tyr Val Asp Gln Glu Leu
770                 775                 780

Asp Ile Asn Arg Leu Ser Asp Tyr Asp Val Ala Ala Ile Val Pro Gln
785                 790                 795                 800

Ser Phe Leu Lys Asp Asp Ser Ile Asp Asn Lys Val Leu Thr Arg Ser
                805                 810                 815

Asp Lys Ala Arg Gly Lys Ser Asp Asn Val Pro Ser Glu Glu Val Val
            820                 825                 830

Lys Lys Met Lys Asn Tyr Trp Arg Gln Leu Leu Asn Ala Lys Leu Ile
        835                 840                 845

Thr Gln Arg Lys Phe Asp Asn Leu Thr Lys Ala Glu Arg Gly Gly Leu
850                 855                 860

Ser Glu Leu Asp Lys Ala Gly Phe Ile Lys Arg Gln Leu Val Glu Thr
865                 870                 875                 880

Arg Gln Ile Thr Lys His Val Ala Gln Ile Leu Asp Ser Arg Met Asn
                885                 890                 895

Thr Lys Tyr Asp Glu Asn Asp Lys Leu Ile Arg Glu Val Lys Val Ile
            900                 905                 910

Thr Leu Lys Ser Lys Leu Val Ser Asp Phe Arg Lys Asp Phe Gln Phe
```

-continued

```
              915                 920                 925
Tyr Lys Val Arg Glu Ile Asn Asn Tyr His His Ala His Asp Ala Tyr
        930                 935                 940
Leu Asn Ala Val Val Gly Thr Ala Leu Ile Lys Lys Tyr Pro Lys Leu
945                 950                 955                 960
Glu Ser Glu Phe Val Tyr Gly Asp Tyr Lys Val Tyr Asp Val Arg Lys
                965                 970                 975
Met Ile Ala Lys Ser Glu Gln Glu Ile Gly Lys Ala Thr Ala Lys Tyr
            980                 985                 990
Phe Phe Tyr Ser Asn Ile Met Asn Phe Phe Lys Thr Glu Ile Thr Leu
                995                1000                1005
Ala Asn Gly Glu Ile Arg Lys Arg Pro Leu Ile Glu Thr Asn Gly
       1010                1015                1020
Glu Thr Gly Glu Ile Val Trp Asp Lys Gly Arg Asp Phe Ala Thr
       1025                1030                1035
Val Arg Lys Val Leu Ser Met Pro Gln Val Asn Ile Val Lys Lys
       1040                1045                1050
Thr Glu Val Gln Thr Gly Gly Phe Ser Lys Glu Ser Ile Leu Pro
       1055                1060                1065
Lys Arg Asn Ser Asp Lys Leu Ile Ala Arg Lys Lys Asp Trp Asp
       1070                1075                1080
Pro Lys Lys Tyr Gly Gly Phe Asp Ser Pro Thr Val Ala Tyr Ser
       1085                1090                1095
Val Leu Val Val Ala Lys Val Glu Lys Gly Lys Ser Lys Lys Leu
       1100                1105                1110
Lys Ser Val Lys Glu Leu Leu Gly Ile Thr Ile Met Glu Arg Ser
       1115                1120                1125
Ser Phe Glu Lys Asn Pro Ile Asp Phe Leu Glu Ala Lys Gly Tyr
       1130                1135                1140
Lys Glu Val Lys Lys Asp Leu Ile Ile Lys Leu Pro Lys Tyr Ser
       1145                1150                1155
Leu Phe Glu Leu Glu Asn Gly Arg Lys Arg Met Leu Ala Ser Ala
       1160                1165                1170
Gly Glu Leu Gln Lys Gly Asn Glu Leu Ala Leu Pro Ser Lys Tyr
       1175                1180                1185
Val Asn Phe Leu Tyr Leu Ala Ser His Tyr Glu Lys Leu Lys Gly
       1190                1195                1200
Ser Pro Glu Asp Asn Glu Gln Lys Gln Leu Phe Val Glu Gln His
       1205                1210                1215
Lys His Tyr Leu Asp Glu Ile Ile Glu Gln Ile Ser Glu Phe Ser
       1220                1225                1230
Lys Arg Val Ile Leu Ala Asp Ala Asn Leu Asp Lys Val Leu Ser
       1235                1240                1245
Ala Tyr Asn Lys His Arg Asp Lys Pro Ile Arg Glu Gln Ala Glu
       1250                1255                1260
Asn Ile Ile His Leu Phe Thr Leu Thr Asn Leu Gly Ala Pro Ala
       1265                1270                1275
Ala Phe Lys Tyr Phe Asp Thr Thr Ile Asp Arg Lys Arg Tyr Thr
       1280                1285                1290
Ser Thr Lys Glu Val Leu Asp Ala Thr Leu Ile His Gln Ser Ile
       1295                1300                1305
Thr Gly Leu Tyr Glu Thr Arg Ile Asp Leu Ser Gln Leu Gly Gly
       1310                1315                1320
```

Asp

<210> SEQ ID NO 19
<211> LENGTH: 1240
<212> TYPE: PRT
<213> ORGANISM: artificial sequence
<220> FEATURE:
<223> OTHER INFORMATION: engineered Streptococcus pyogenes Cas9

<400> SEQUENCE: 19

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Asn Thr Glu Ile Thr Lys Ala Pro Leu Ser Ala Ser
            180                 185                 190

Met Ile Lys Arg Tyr Asp Glu His His Gln Asp Leu Thr Leu Leu Lys
        195                 200                 205

Ala Leu Val Arg Gln Gln Leu Pro Glu Lys Tyr Lys Glu Ile Phe Phe
    210                 215                 220

Asp Gln Ser Lys Asn Gly Tyr Ala Gly Tyr Ile Asp Gly Gly Ala Ser
225                 230                 235                 240

Gln Glu Glu Phe Tyr Lys Phe Ile Lys Pro Ile Leu Glu Lys Met Asp
                245                 250                 255

Gly Thr Glu Glu Leu Leu Val Lys Leu Asn Arg Glu Asp Leu Leu Arg
            260                 265                 270

Lys Gln Arg Thr Phe Asp Asn Gly Ser Ile Pro His Gln Ile His Leu
        275                 280                 285

Gly Glu Leu His Ala Ile Leu Arg Arg Gln Glu Asp Phe Tyr Pro Phe
    290                 295                 300

Leu Lys Asp Asn Arg Glu Lys Ile Glu Lys Ile Leu Thr Phe Arg Ile
305                 310                 315                 320

Pro Tyr Tyr Val Gly Pro Leu Ala Arg Gly Asn Ser Arg Phe Ala Trp
                325                 330                 335

Met Thr Arg Lys Ser Glu Glu Thr Ile Thr Pro Trp Asn Phe Glu Glu
            340                 345                 350
```

```
Val Val Asp Lys Gly Ala Ser Ala Gln Ser Phe Ile Glu Arg Met Thr
            355                 360                 365

Asn Phe Asp Lys Asn Leu Pro Asn Glu Lys Val Leu Pro Lys His Ser
370                 375                 380

Leu Leu Tyr Glu Tyr Phe Thr Val Tyr Asn Glu Leu Thr Lys Val Lys
385                 390                 395                 400

Tyr Val Thr Glu Gly Met Arg Lys Pro Ala Phe Leu Ser Gly Glu Gln
                405                 410                 415

Lys Lys Ala Ile Val Asp Leu Leu Phe Lys Thr Asn Arg Lys Val Thr
            420                 425                 430

Val Lys Gln Leu Lys Glu Asp Tyr Phe Lys Lys Ile Glu Cys Phe Asp
        435                 440                 445

Ser Val Glu Ile Ser Gly Val Glu Asp Arg Phe Asn Ala Ser Leu Gly
    450                 455                 460

Thr Tyr His Asp Leu Leu Lys Ile Ile Lys Asp Lys Asp Phe Leu Asp
465                 470                 475                 480

Asn Glu Glu Asn Glu Asp Ile Leu Glu Asp Ile Val Leu Thr Leu Thr
                485                 490                 495

Leu Phe Glu Asp Arg Glu Met Ile Glu Glu Arg Leu Lys Thr Tyr Ala
                500                 505                 510

His Leu Phe Asp Asp Lys Val Met Lys Gln Leu Lys Arg Arg Arg Tyr
            515                 520                 525

Thr Gly Trp Gly Arg Leu Ser Arg Lys Leu Ile Asn Gly Ile Arg Asp
    530                 535                 540

Lys Gln Ser Gly Lys Thr Ile Leu Asp Phe Leu Lys Ser Asp Gly Phe
545                 550                 555                 560

Ala Asn Arg Asn Phe Met Gln Leu Ile His Asp Asp Ser Leu Thr Phe
                565                 570                 575

Lys Glu Asp Ile Gln Lys Ala Gln Val Ser Gly Gln Gly Asp Ser Leu
                580                 585                 590

His Glu His Ile Ala Asn Leu Ala Gly Ser Pro Ala Ile Lys Lys Gly
            595                 600                 605

Ile Leu Gln Thr Val Lys Val Val Asp Glu Leu Val Lys Val Met Gly
        610                 615                 620

Arg His Lys Pro Glu Asn Ile Val Ile Glu Met Ala Arg Glu Asn Gln
625                 630                 635                 640

Thr Thr Gln Lys Gly Gln Lys Asn Ser Arg Glu Arg Met Lys Arg Ile
                645                 650                 655

Glu Glu Gly Ile Lys Glu Leu Gly Ser Gln Ile Leu Lys Glu His Pro
                660                 665                 670

Val Glu Asn Thr Gln Leu Gln Asn Glu Lys Leu Tyr Leu Tyr Tyr Leu
            675                 680                 685

Gln Asn Gly Arg Asp Met Tyr Val Asp Gln Glu Leu Asp Ile Asn Arg
        690                 695                 700

Leu Ser Asp Tyr Asp Val Ala Ala Ile Val Pro Gln Ser Phe Leu Lys
705                 710                 715                 720

Asp Asp Ser Ile Asp Asn Lys Val Leu Thr Arg Ser Asp Lys Ala Arg
                725                 730                 735

Gly Lys Ser Asp Asn Val Pro Ser Glu Glu Val Val Lys Lys Met Lys
                740                 745                 750

Asn Tyr Trp Arg Gln Leu Leu Asn Ala Lys Leu Ile Thr Gln Arg Lys
            755                 760                 765

Phe Asp Asn Leu Thr Lys Ala Glu Arg Gly Gly Leu Ser Glu Leu Asp
```

```
                    770               775               780
Lys Ala Gly Phe Ile Lys Arg Gln Leu Val Glu Thr Arg Gln Ile Thr
785               790               795               800

Lys His Val Ala Gln Ile Leu Asp Ser Arg Met Asn Thr Lys Tyr Asp
                805               810               815

Glu Asn Asp Lys Leu Ile Arg Glu Val Lys Val Ile Thr Leu Lys Ser
                820              825                830

Lys Leu Val Ser Asp Phe Arg Lys Asp Phe Gln Phe Tyr Lys Val Arg
                835              840                845

Glu Ile Asn Asn Tyr His His Ala His Asp Ala Tyr Leu Asn Ala Val
850               855               860

Val Gly Thr Ala Leu Ile Lys Lys Tyr Pro Lys Leu Glu Ser Glu Phe
865               870               875               880

Val Tyr Gly Asp Tyr Lys Val Tyr Asp Val Arg Lys Met Ile Ala Lys
                885              890                895

Ser Glu Gln Glu Ile Gly Lys Ala Thr Ala Lys Tyr Phe Phe Tyr Ser
                900              905                910

Asn Ile Met Asn Phe Phe Lys Thr Glu Ile Thr Leu Ala Asn Gly Glu
                915              920                925

Ile Arg Lys Arg Pro Leu Ile Glu Thr Asn Gly Glu Thr Gly Glu Ile
930               935               940

Val Trp Asp Lys Gly Arg Asp Phe Ala Thr Val Arg Lys Val Leu Ser
945               950               955               960

Met Pro Gln Val Asn Ile Val Lys Lys Thr Glu Val Gln Thr Gly Gly
                965              970                975

Phe Ser Lys Glu Ser Ile Leu Pro Lys Arg Asn Ser Asp Lys Leu Ile
                980              985                990

Ala Arg Lys Lys Asp Trp Asp Pro Lys Lys Tyr Gly Gly Phe Asp Ser
                995              1000               1005

Pro Thr Val Ala Tyr Ser Val Leu Val Val Ala Lys Val Glu Lys
1010              1015              1020

Gly Lys Ser Lys Lys Leu Lys Ser Val Lys Glu Leu Leu Gly Ile
1025              1030              1035

Thr Ile Met Glu Arg Ser Ser Phe Glu Lys Asn Pro Ile Asp Phe
1040              1045              1050

Leu Glu Ala Lys Gly Tyr Lys Glu Val Lys Lys Asp Leu Ile Ile
1055              1060              1065

Lys Leu Pro Lys Tyr Ser Leu Phe Glu Leu Glu Asn Gly Arg Lys
1070              1075              1080

Arg Met Leu Ala Ser Ala Gly Glu Leu Gln Lys Gly Asn Glu Leu
1085              1090              1095

Ala Leu Pro Ser Lys Tyr Val Asn Phe Leu Tyr Leu Ala Ser His
1100              1105              1110

Tyr Glu Lys Leu Lys Gly Ser Pro Glu Asp Asn Glu Gln Lys Gln
1115              1120              1125

Leu Phe Val Glu Gln His Lys His Tyr Leu Asp Glu Ile Ile Glu
1130              1135              1140

Gln Ile Ser Glu Phe Ser Lys Arg Val Ile Leu Ala Asp Ala Asn
1145              1150              1155

Leu Asp Lys Val Leu Ser Ala Tyr Asn Lys His Arg Asp Lys Pro
1160              1165              1170

Ile Arg Glu Gln Ala Glu Asn Ile Ile His Leu Phe Thr Leu Thr
1175              1180              1185
```

-continued

Asn Leu Gly Ala Pro Ala Ala Phe Lys Tyr Phe Asp Thr Thr Ile
    1190            1195                1200

Asp Arg Lys Arg Tyr Thr Ser Thr Lys Glu Val Leu Asp Ala Thr
    1205            1210                1215

Leu Ile His Gln Ser Ile Thr Gly Leu Tyr Glu Thr Arg Ile Asp
    1220            1225                1230

Leu Ser Gln Leu Gly Gly Asp
    1235            1240

<210> SEQ ID NO 20
<211> LENGTH: 1097
<212> TYPE: PRT
<213> ORGANISM: artificial sequence
<220> FEATURE:
<223> OTHER INFORMATION: engineered Streptococcus pyogenes Cas9

<400> SEQUENCE: 20

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys Gly Gly
            500                 505                 510

Gly Ser Tyr Thr Gly Trp Gly Arg Leu Ser Arg Lys Leu Ile Asn Gly
            515                 520                 525

Ile Arg Asp Lys Gln Ser Gly Lys Thr Ile Leu Asp Phe Leu Lys Ser
            530                 535                 540

Asp Gly Phe Ala Asn Arg Asn Phe Met Gln Leu Ile His Asp Asp Ser
545                 550                 555                 560

Leu Thr Phe Lys Glu Asp Ile Gln Lys Ala Gln Val Ser Gly Gln Gly
                565                 570                 575

Asp Ser Leu His Glu His Ile Ala Asn Leu Ala Gly Ser Pro Ala Ile
            580                 585                 590

Lys Lys Gly Ile Leu Gln Thr Val Lys Val Val Asp Glu Leu Val Lys
            595                 600                 605

Val Met Gly Arg His Lys Pro Glu Asn Ile Val Ile Glu Met Ala Arg
            610                 615                 620

Glu Asn Gln Thr Thr Gln Lys Gly Gln Lys Gly Gly Ser Glu Leu
625                 630                 635                 640

Asp Lys Ala Gly Phe Ile Lys Arg Gln Leu Val Glu Thr Arg Gln Ile
                645                 650                 655

Thr Lys His Val Ala Gln Ile Leu Asp Ser Arg Met Asn Thr Lys Tyr
            660                 665                 670

Asp Glu Asn Asp Lys Leu Ile Arg Glu Val Lys Val Ile Thr Leu Lys
            675                 680                 685

Ser Lys Leu Val Ser Asp Phe Arg Lys Asp Phe Gln Phe Tyr Lys Val
            690                 695                 700

Arg Glu Ile Asn Asn Tyr His His Ala His Asp Ala Tyr Leu Asn Ala
705                 710                 715                 720
```

Val Val Gly Thr Ala Leu Ile Lys Lys Tyr Pro Lys Leu Glu Ser Glu
        725                 730                 735

Phe Val Tyr Gly Asp Tyr Lys Val Tyr Asp Val Arg Lys Met Ile Ala
        740                 745                 750

Lys Ser Glu Gln Glu Ile Gly Lys Ala Thr Ala Lys Tyr Phe Phe Tyr
        755                 760                 765

Ser Asn Ile Met Asn Phe Phe Lys Thr Glu Ile Thr Leu Ala Asn Gly
        770                 775                 780

Glu Ile Arg Lys Arg Pro Leu Ile Glu Thr Asn Gly Glu Thr Gly Glu
785                 790                 795                 800

Ile Val Trp Asp Lys Gly Arg Asp Phe Ala Thr Val Arg Lys Val Leu
                805                 810                 815

Ser Met Pro Gln Val Asn Ile Val Lys Lys Thr Glu Val Gln Thr Gly
        820                 825                 830

Gly Phe Ser Lys Glu Ser Ile Leu Pro Lys Arg Asn Ser Asp Lys Leu
        835                 840                 845

Ile Ala Arg Lys Lys Asp Trp Asp Pro Lys Lys Tyr Gly Gly Phe Asp
        850                 855                 860

Ser Pro Thr Val Ala Tyr Ser Val Leu Val Val Ala Lys Val Glu Lys
865                 870                 875                 880

Gly Lys Ser Lys Lys Leu Lys Ser Val Lys Glu Leu Leu Gly Ile Thr
                885                 890                 895

Ile Met Glu Arg Ser Ser Phe Glu Lys Asn Pro Ile Asp Phe Leu Glu
        900                 905                 910

Ala Lys Gly Tyr Lys Glu Val Lys Lys Asp Leu Ile Ile Lys Leu Pro
        915                 920                 925

Lys Tyr Ser Leu Phe Glu Leu Glu Asn Gly Arg Lys Arg Met Leu Ala
        930                 935                 940

Ser Ala Gly Glu Leu Gln Lys Gly Asn Glu Leu Ala Leu Pro Ser Lys
945                 950                 955                 960

Tyr Val Asn Phe Leu Tyr Leu Ala Ser His Tyr Glu Lys Leu Lys Gly
                965                 970                 975

Ser Pro Glu Asp Asn Glu Gln Lys Gln Leu Phe Val Glu Gln His Lys
        980                 985                 990

His Tyr Leu Asp Glu Ile Ile Glu Gln Ile Ser Glu Phe Ser Lys Arg
        995                 1000                1005

Val Ile Leu Ala Asp Ala Asn Leu Asp Lys Val Leu Ser Ala Tyr
        1010                1015                1020

Asn Lys His Arg Asp Lys Pro Ile Arg Glu Gln Ala Glu Asn Ile
        1025                1030                1035

Ile His Leu Phe Thr Leu Thr Asn Leu Gly Ala Pro Ala Ala Phe
        1040                1045                1050

Lys Tyr Phe Asp Thr Thr Ile Asp Arg Lys Arg Tyr Thr Ser Thr
        1055                1060                1065

Lys Glu Val Leu Asp Ala Thr Leu Ile His Gln Ser Ile Thr Gly
        1070                1075                1080

Leu Tyr Glu Thr Arg Ile Asp Leu Ser Gln Leu Gly Gly Asp
        1085                1090                1095

<210> SEQ ID NO 21
<211> LENGTH: 1194
<212> TYPE: PRT
<213> ORGANISM: artificial sequence
<220> FEATURE:
<223> OTHER INFORMATION: engineered Streptococcus pyogenes Cas9

```
<400> SEQUENCE: 21

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
```

```
                    405                 410                 415
Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Gly Gly Ser Ala Gln Val Ser Gly Gln
            660                 665                 670

Gly Asp Ser Leu His Glu His Ile Ala Asn Leu Ala Gly Ser Pro Ala
            675                 680                 685

Ile Lys Lys Gly Ile Leu Gln Thr Val Lys Val Val Asp Glu Leu Val
            690                 695                 700

Lys Val Met Gly Arg His Lys Pro Glu Asn Ile Val Ile Glu Met Ala
705                 710                 715                 720

Arg Glu Asn Gln Thr Thr Gln Lys Gly Gln Lys Gly Gly Ser Glu
                725                 730                 735

Leu Asp Lys Ala Gly Phe Ile Lys Arg Gln Leu Val Glu Thr Arg Gln
            740                 745                 750

Ile Thr Lys His Val Ala Gln Ile Leu Asp Ser Arg Met Asn Thr Lys
            755                 760                 765

Tyr Asp Glu Asn Asp Lys Leu Ile Arg Glu Val Lys Val Ile Thr Leu
            770                 775                 780

Lys Ser Lys Leu Val Ser Asp Phe Arg Lys Asp Phe Gln Phe Tyr Lys
785                 790                 795                 800

Val Arg Glu Ile Asn Asn Tyr His His Ala His Asp Ala Tyr Leu Asn
                805                 810                 815

Ala Val Val Gly Thr Ala Leu Ile Lys Lys Tyr Pro Lys Leu Glu Ser
            820                 825                 830
```

Glu Phe Val Tyr Gly Asp Tyr Lys Val Tyr Asp Val Arg Lys Met Ile
            835                 840                 845

Ala Lys Ser Glu Gln Glu Ile Gly Lys Ala Thr Ala Lys Tyr Phe Phe
850                 855                 860

Tyr Ser Asn Ile Met Asn Phe Phe Lys Thr Glu Ile Thr Leu Ala Asn
865                 870                 875                 880

Gly Glu Ile Arg Lys Arg Pro Leu Ile Glu Thr Asn Gly Glu Thr Gly
                885                 890                 895

Glu Ile Val Trp Asp Lys Gly Arg Asp Phe Ala Thr Val Arg Lys Val
            900                 905                 910

Leu Ser Met Pro Gln Val Asn Ile Val Lys Lys Thr Glu Val Gln Thr
            915                 920                 925

Gly Gly Phe Ser Lys Glu Ser Ile Leu Pro Lys Arg Asn Ser Asp Lys
930                 935                 940

Leu Ile Ala Arg Lys Lys Asp Trp Asp Pro Lys Lys Tyr Gly Gly Phe
945                 950                 955                 960

Asp Ser Pro Thr Val Ala Tyr Ser Val Leu Val Val Ala Lys Val Glu
                965                 970                 975

Lys Gly Lys Ser Lys Lys Leu Lys Ser Val Lys Glu Leu Leu Gly Ile
            980                 985                 990

Thr Ile Met Glu Arg Ser Ser Phe Glu Lys Asn Pro Ile Asp Phe Leu
            995                 1000                1005

Glu Ala Lys Gly Tyr Lys Glu Val Lys Lys Asp Leu Ile Ile Lys
    1010                1015                1020

Leu Pro Lys Tyr Ser Leu Phe Glu Leu Glu Asn Gly Arg Lys Arg
    1025                1030                1035

Met Leu Ala Ser Ala Gly Glu Leu Gln Lys Gly Asn Glu Leu Ala
    1040                1045                1050

Leu Pro Ser Lys Tyr Val Asn Phe Leu Tyr Leu Ala Ser His Tyr
    1055                1060                1065

Glu Lys Leu Lys Gly Ser Pro Glu Asp Asn Glu Gln Lys Gln Leu
    1070                1075                1080

Phe Val Glu Gln His Lys His Tyr Leu Asp Glu Ile Ile Glu Gln
    1085                1090                1095

Ile Ser Glu Phe Ser Lys Arg Val Ile Leu Ala Asp Ala Asn Leu
    1100                1105                1110

Asp Lys Val Leu Ser Ala Tyr Asn Lys His Arg Asp Lys Pro Ile
    1115                1120                1125

Arg Glu Gln Ala Glu Asn Ile Ile His Leu Phe Thr Leu Thr Asn
    1130                1135                1140

Leu Gly Ala Pro Ala Ala Phe Lys Tyr Phe Asp Thr Thr Ile Asp
    1145                1150                1155

Arg Lys Arg Tyr Thr Ser Thr Lys Glu Val Leu Asp Ala Thr Leu
    1160                1165                1170

Ile His Gln Ser Ile Thr Gly Leu Tyr Glu Thr Arg Ile Asp Leu
    1175                1180                1185

Ser Gln Leu Gly Gly Asp
    1190

<210> SEQ ID NO 22
<211> LENGTH: 1110
<212> TYPE: PRT
<213> ORGANISM: artificial sequence
<220> FEATURE:

-continued

<223> OTHER INFORMATION: engineered Streptococcus pyogenes Cas9

<400> SEQUENCE: 22

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Asn Thr Glu Ile Thr Lys Ala Pro Leu Ser Ala Ser
            180                 185                 190

Met Ile Lys Arg Tyr Asp Glu His His Gln Asp Leu Thr Leu Leu Lys
        195                 200                 205

Ala Leu Val Arg Gln Gln Leu Pro Glu Lys Tyr Lys Glu Ile Phe Phe
    210                 215                 220

Asp Gln Ser Lys Asn Gly Tyr Ala Gly Tyr Ile Asp Gly Gly Ala Ser
225                 230                 235                 240

Gln Glu Glu Phe Tyr Lys Phe Ile Lys Pro Ile Leu Glu Lys Met Asp
                245                 250                 255

Gly Thr Glu Glu Leu Leu Val Lys Leu Asn Arg Glu Asp Leu Leu Arg
            260                 265                 270

Lys Gln Arg Thr Phe Asp Asn Gly Ser Ile Pro His Gln Ile His Leu
        275                 280                 285

Gly Glu Leu His Ala Ile Leu Arg Arg Gln Glu Asp Phe Tyr Pro Phe
    290                 295                 300

Leu Lys Asp Asn Arg Glu Lys Ile Glu Lys Ile Leu Thr Phe Arg Ile
305                 310                 315                 320

Pro Tyr Tyr Val Gly Pro Leu Ala Arg Gly Asn Ser Arg Phe Ala Trp
                325                 330                 335

Met Thr Arg Lys Ser Glu Glu Thr Ile Thr Pro Trp Asn Phe Glu Glu
            340                 345                 350

Val Val Asp Lys Gly Ala Ser Ala Gln Ser Phe Ile Glu Arg Met Thr
        355                 360                 365

Asn Phe Asp Lys Asn Leu Pro Asn Glu Lys Val Leu Pro Lys His Ser
    370                 375                 380

Leu Leu Tyr Glu Tyr Phe Thr Val Tyr Asn Glu Leu Thr Lys Val Lys
385                 390                 395                 400
```

```
Tyr Val Thr Glu Gly Met Arg Lys Pro Ala Phe Leu Ser Gly Glu Gln
                405                 410                 415
Lys Lys Ala Ile Val Asp Leu Leu Phe Lys Thr Asn Arg Lys Val Thr
            420                 425                 430
Val Lys Gln Leu Lys Glu Asp Tyr Phe Lys Lys Ile Glu Cys Phe Asp
        435                 440                 445
Ser Val Glu Ile Ser Gly Val Glu Asp Arg Phe Asn Ala Ser Leu Gly
    450                 455                 460
Thr Tyr His Asp Leu Leu Lys Ile Ile Lys Asp Lys Asp Phe Leu Asp
465                 470                 475                 480
Asn Glu Glu Asn Glu Asp Ile Leu Glu Asp Ile Val Leu Thr Leu Thr
                485                 490                 495
Leu Phe Glu Asp Arg Glu Met Ile Glu Glu Arg Leu Lys Thr Tyr Ala
            500                 505                 510
His Leu Phe Asp Asp Lys Val Met Lys Gln Leu Lys Arg Arg Arg Tyr
        515                 520                 525
Thr Gly Trp Gly Arg Leu Ser Arg Lys Leu Ile Asn Gly Ile Arg Asp
    530                 535                 540
Lys Gln Ser Gly Lys Thr Ile Leu Asp Phe Leu Lys Ser Asp Gly Phe
545                 550                 555                 560
Ala Asn Arg Asn Phe Met Gln Leu Ile His Asp Asp Ser Leu Thr Phe
                565                 570                 575
Lys Glu Asp Ile Gln Lys Ala Gln Val Ser Gly Gln Gly Asp Ser Leu
            580                 585                 590
His Glu His Ile Ala Asn Leu Ala Gly Ser Pro Ala Ile Lys Lys Gly
        595                 600                 605
Ile Leu Gln Thr Val Lys Val Val Asp Glu Leu Val Lys Val Met Gly
    610                 615                 620
Arg His Lys Pro Glu Asn Ile Val Ile Glu Met Ala Arg Glu Asn Gln
625                 630                 635                 640
Thr Thr Gln Lys Gly Gln Lys Gly Gly Gly Ser Glu Leu Asp Lys Ala
                645                 650                 655
Gly Phe Ile Lys Arg Gln Leu Val Glu Thr Arg Gln Ile Thr Lys His
            660                 665                 670
Val Ala Gln Ile Leu Asp Ser Arg Met Asn Thr Lys Tyr Asp Glu Asn
        675                 680                 685
Asp Lys Leu Ile Arg Glu Val Lys Val Ile Thr Leu Lys Ser Lys Leu
    690                 695                 700
Val Ser Asp Phe Arg Lys Asp Phe Gln Phe Tyr Lys Val Arg Glu Ile
705                 710                 715                 720
Asn Asn Tyr His His Ala His Asp Ala Tyr Leu Asn Ala Val Val Gly
                725                 730                 735
Thr Ala Leu Ile Lys Lys Tyr Pro Lys Leu Glu Ser Glu Phe Val Tyr
            740                 745                 750
Gly Asp Tyr Lys Val Tyr Asp Val Arg Lys Met Ile Ala Lys Ser Glu
        755                 760                 765
Gln Glu Ile Gly Lys Ala Thr Ala Lys Tyr Phe Phe Tyr Ser Asn Ile
    770                 775                 780
Met Asn Phe Phe Lys Thr Glu Ile Thr Leu Ala Asn Gly Glu Ile Arg
785                 790                 795                 800
Lys Arg Pro Leu Ile Glu Thr Asn Gly Glu Thr Gly Glu Ile Val Trp
                805                 810                 815
Asp Lys Gly Arg Asp Phe Ala Thr Val Arg Lys Val Leu Ser Met Pro
```

```
                820                 825                 830
Gln Val Asn Ile Val Lys Lys Thr Glu Val Gln Thr Gly Gly Phe Ser
            835                 840                 845
Lys Glu Ser Ile Leu Pro Lys Arg Asn Ser Asp Lys Leu Ile Ala Arg
850                 855                 860
Lys Lys Asp Trp Asp Pro Lys Lys Tyr Gly Gly Phe Asp Ser Pro Thr
865                 870                 875                 880
Val Ala Tyr Ser Val Leu Val Val Ala Lys Val Glu Lys Gly Lys Ser
            885                 890                 895
Lys Lys Leu Lys Ser Val Lys Glu Leu Leu Gly Ile Thr Ile Met Glu
            900                 905                 910
Arg Ser Ser Phe Glu Lys Asn Pro Ile Asp Phe Leu Glu Ala Lys Gly
            915                 920                 925
Tyr Lys Glu Val Lys Lys Asp Leu Ile Ile Lys Leu Pro Lys Tyr Ser
            930                 935                 940
Leu Phe Glu Leu Glu Asn Gly Arg Lys Arg Met Leu Ala Ser Ala Gly
945                 950                 955                 960
Glu Leu Gln Lys Gly Asn Glu Leu Ala Leu Pro Ser Lys Tyr Val Asn
            965                 970                 975
Phe Leu Tyr Leu Ala Ser His Tyr Glu Lys Leu Lys Gly Ser Pro Glu
            980                 985                 990
Asp Asn Glu Gln Lys Gln Leu Phe Val Glu Gln His Lys His Tyr Leu
            995                 1000                1005
Asp Glu Ile Ile Glu Gln Ile Ser Glu Phe Ser Lys Arg Val Ile
            1010                1015                1020
Leu Ala Asp Ala Asn Leu Asp Lys Val Leu Ser Ala Tyr Asn Lys
            1025                1030                1035
His Arg Asp Lys Pro Ile Arg Glu Gln Ala Glu Asn Ile Ile His
            1040                1045                1050
Leu Phe Thr Leu Thr Asn Leu Gly Ala Pro Ala Ala Phe Lys Tyr
            1055                1060                1065
Phe Asp Thr Thr Ile Asp Arg Lys Arg Tyr Thr Ser Thr Lys Glu
            1070                1075                1080
Val Leu Asp Ala Thr Leu Ile His Gln Ser Ile Thr Gly Leu Tyr
            1085                1090                1095
Glu Thr Arg Ile Asp Leu Ser Gln Leu Gly Gly Asp
            1100                1105                1110

<210> SEQ ID NO 23
<211> LENGTH: 1046
<212> TYPE: PRT
<213> ORGANISM: artificial sequence
<220> FEATURE:
<223> OTHER INFORMATION: engineered Streptococcus pyogenes Cas9

<400> SEQUENCE: 23

Met Asp Lys Lys Tyr Ser Ile Gly Leu Ala Ile Gly Thr Asn Ser Val
1               5                   10                  15
Gly Trp Ala Val Ile Thr Asp Glu Tyr Lys Val Pro Ser Lys Lys Phe
            20                  25                  30
Lys Val Leu Gly Asn Thr Asp Arg His Ser Ile Lys Lys Asn Leu Ile
        35                  40                  45
Gly Ala Leu Leu Phe Asp Ser Gly Glu Thr Ala Glu Ala Thr Arg Leu
    50                  55                  60
Lys Arg Thr Ala Arg Arg Arg Tyr Thr Arg Arg Lys Asn Arg Ile Cys
```

```
              65                   70                  75                   80
Tyr Leu Gln Glu Ile Phe Ser Asn Gly Met Ala Lys Val Asp Asp Ser
                    85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
            130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Asn Thr Glu Ile Thr Lys Ala Pro Leu Ser Ala Ser
                180                 185                 190
Met Ile Lys Arg Tyr Asp Glu His His Gln Asp Leu Thr Leu Leu Lys
                195                 200                 205
Ala Leu Val Arg Gln Gln Leu Pro Glu Lys Tyr Lys Glu Ile Phe Phe
210                 215                 220
Asp Gln Ser Lys Asn Gly Tyr Ala Gly Tyr Ile Asp Gly Gly Ala Ser
225                 230                 235                 240
Gln Glu Glu Phe Tyr Lys Phe Ile Lys Pro Ile Leu Glu Lys Met Asp
                245                 250                 255
Gly Thr Glu Glu Leu Leu Val Lys Leu Asn Arg Glu Asp Leu Leu Arg
                260                 265                 270
Lys Gln Arg Thr Phe Asp Asn Gly Ser Ile Pro His Gln Ile His Leu
            275                 280                 285
Gly Glu Leu His Ala Ile Leu Arg Arg Gln Glu Asp Phe Tyr Pro Phe
            290                 295                 300
Leu Lys Asp Asn Arg Glu Lys Ile Glu Lys Ile Leu Thr Phe Arg Ile
305                 310                 315                 320
Pro Tyr Tyr Val Gly Pro Leu Ala Arg Gly Asn Ser Arg Phe Ala Trp
                325                 330                 335
Met Thr Arg Lys Ser Glu Glu Thr Ile Thr Pro Trp Asn Phe Glu Glu
                340                 345                 350
Val Val Asp Lys Gly Ala Ser Ala Gln Ser Phe Ile Glu Arg Met Thr
            355                 360                 365
Asn Phe Asp Lys Asn Leu Pro Asn Glu Lys Val Leu Pro Lys His Ser
            370                 375                 380
Leu Leu Tyr Glu Tyr Phe Thr Val Tyr Asn Glu Leu Thr Lys Val Lys
385                 390                 395                 400
Tyr Val Thr Glu Gly Met Arg Lys Pro Ala Phe Leu Ser Gly Glu Gln
                405                 410                 415
Lys Lys Ala Ile Val Asp Leu Leu Phe Lys Thr Asn Arg Lys Val Thr
                420                 425                 430
Val Lys Gln Leu Lys Glu Asp Tyr Phe Lys Lys Ile Glu Cys Phe Asp
            435                 440                 445
Ser Val Glu Ile Ser Gly Val Glu Asp Arg Phe Asn Ala Ser Leu Gly
            450                 455                 460
Thr Tyr His Asp Leu Leu Lys Ile Ile Lys Asp Lys Asp Phe Leu Asp
465                 470                 475                 480
Asn Glu Glu Asn Glu Asp Ile Leu Glu Asp Ile Val Leu Thr Leu Thr
                485                 490                 495
```

```
Leu Phe Glu Asp Arg Glu Met Ile Glu Arg Leu Lys Thr Tyr Ala
            500                 505                 510

His Leu Phe Asp Asp Lys Val Met Lys Gln Leu Lys Arg Arg Tyr
            515                 520                 525

Thr Gly Trp Gly Arg Leu Ser Arg Lys Leu Ile Asn Gly Ile Arg Asp
            530                 535                 540

Lys Gln Ser Gly Lys Thr Ile Leu Asp Phe Leu Lys Ser Asp Gly Phe
545                 550                 555                 560

Ala Asn Arg Asn Phe Met Gln Leu Ile His Asp Ser Leu Thr Phe
            565                 570                 575

Lys Glu Asp Ile Gln Lys Ala Gln Val Ser Gly Gln Gly Asp Ser Leu
            580                 585                 590

His Glu His Ile Ala Asn Leu Ala Gly Ser Pro Ala Ile Lys Lys Gly
            595                 600                 605

Ile Leu Gln Thr Val Lys Val Val Asp Glu Leu Val Lys Val Met Gly
            610                 615                 620

Arg His Lys Pro Glu Asn Ile Val Ile Glu Met Ala Arg Glu Asn Gln
625                 630                 635                 640

Thr Thr Gln Lys Gly Gln Lys Gly Gly Ser Glu Leu Asp Lys Ala
            645                 650                 655

Gly Phe Ile Lys Arg Gln Leu Val Glu Thr Arg Gln Ile Thr Lys His
            660                 665                 670

Val Ala Gln Ile Leu Asp Ser Arg Met Asn Thr Lys Tyr Asp Glu Asn
            675                 680                 685

Asp Lys Leu Ile Arg Glu Val Lys Val Ile Thr Leu Lys Ser Lys Leu
            690                 695                 700

Val Ser Asp Phe Arg Lys Asp Phe Gln Phe Tyr Lys Val Arg Glu Ile
705                 710                 715                 720

Asn Asn Tyr His His Ala His Asp Ala Tyr Leu Asn Ala Val Val Gly
            725                 730                 735

Thr Ala Leu Ile Lys Lys Tyr Pro Gly Gly Ser Gly Gly Gly Ser
            740                 745                 750

Asp Lys Gly Arg Asp Phe Ala Thr Val Arg Lys Val Leu Ser Met Pro
            755                 760                 765

Gln Val Asn Ile Val Lys Lys Thr Glu Val Gln Thr Gly Gly Phe Ser
            770                 775                 780

Lys Glu Ser Ile Leu Pro Lys Arg Asn Ser Asp Lys Leu Ile Ala Arg
785                 790                 795                 800

Lys Lys Asp Trp Asp Pro Lys Lys Tyr Gly Gly Phe Asp Ser Pro Thr
            805                 810                 815

Val Ala Tyr Ser Val Leu Val Val Ala Lys Val Glu Lys Gly Lys Ser
            820                 825                 830

Lys Lys Leu Lys Ser Val Lys Glu Leu Leu Gly Ile Thr Ile Met Glu
            835                 840                 845

Arg Ser Ser Phe Glu Lys Asn Pro Ile Asp Phe Leu Glu Ala Lys Gly
            850                 855                 860

Tyr Lys Glu Val Lys Lys Asp Leu Ile Ile Lys Leu Pro Lys Tyr Ser
865                 870                 875                 880

Leu Phe Glu Leu Glu Asn Gly Arg Lys Arg Met Leu Ala Ser Ala Gly
            885                 890                 895

Glu Leu Gln Lys Gly Asn Glu Leu Ala Leu Pro Ser Lys Tyr Val Asn
            900                 905                 910
```

```
Phe Leu Tyr Leu Ala Ser His Tyr Glu Lys Leu Lys Gly Ser Pro Glu
            915                 920                 925

Asp Asn Glu Gln Lys Gln Leu Phe Val Glu Gln His Lys His Tyr Leu
        930                 935                 940

Asp Glu Ile Ile Glu Gln Ile Ser Glu Phe Ser Lys Arg Val Ile Leu
945                 950                 955                 960

Ala Asp Ala Asn Leu Asp Lys Val Leu Ser Ala Tyr Asn Lys His Arg
                965                 970                 975

Asp Lys Pro Ile Arg Glu Gln Ala Glu Asn Ile Ile His Leu Phe Thr
            980                 985                 990

Leu Thr Asn Leu Gly Ala Pro Ala  Ala Phe Lys Tyr Phe Asp Thr Thr
            995                 1000                1005

Ile Asp Arg Lys Arg Tyr Thr  Ser Thr Lys Glu Val  Leu Asp Ala
    1010                1015                1020

Thr Leu Ile His Gln Ser Ile  Thr Gly Leu Tyr Glu  Thr Arg Ile
    1025                1030                1035

Asp Leu Ser Gln Leu Gly Gly  Asp
    1040                1045

<210> SEQ ID NO 24
<211> LENGTH: 905
<212> TYPE: PRT
<213> ORGANISM: artificial sequence
<220> FEATURE:
<223> OTHER INFORMATION: engineered Streptococcus pyogenes Cas9

<400> SEQUENCE: 24

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Asn Thr Glu Ile Thr Lys Ala Pro Leu Ser Ala Ser
            180                 185                 190

Met Ile Lys Arg Tyr Asp Glu His His Gln Asp Leu Thr Leu Leu Lys
        195                 200                 205

Ala Leu Val Arg Gln Gln Leu Pro Glu Lys Tyr Lys Glu Ile Phe Phe
    210                 215                 220
```

```
Asp Gln Ser Lys Asn Gly Tyr Ala Gly Tyr Ile Asp Gly Gly Ala Ser
225                 230                 235                 240

Gln Glu Glu Phe Tyr Lys Phe Ile Lys Pro Ile Leu Glu Lys Met Asp
            245                 250                 255

Gly Thr Glu Glu Leu Leu Val Lys Leu Asn Arg Glu Asp Leu Leu Arg
        260                 265                 270

Lys Gln Arg Thr Phe Asp Asn Gly Ser Ile Pro His Gln Ile His Leu
    275                 280                 285

Gly Glu Leu His Ala Ile Leu Arg Arg Gln Glu Asp Phe Tyr Pro Phe
290                 295                 300

Leu Lys Asp Asn Arg Glu Lys Ile Glu Lys Ile Leu Thr Phe Arg Ile
305                 310                 315                 320

Pro Tyr Tyr Val Gly Pro Leu Ala Arg Gly Asn Ser Arg Phe Ala Trp
                325                 330                 335

Met Thr Arg Lys Ser Glu Glu Thr Ile Thr Pro Trp Asn Phe Glu Glu
            340                 345                 350

Val Val Asp Lys Gly Ala Ser Ala Gln Ser Phe Ile Glu Arg Met Thr
        355                 360                 365

Asn Phe Asp Lys Asn Leu Pro Asn Glu Lys Val Leu Pro Lys Gly Gly
    370                 375                 380

Gly Ser Tyr Thr Gly Trp Gly Arg Leu Ser Arg Lys Leu Ile Asn Gly
385                 390                 395                 400

Ile Arg Asp Lys Gln Ser Gly Lys Thr Ile Leu Asp Phe Leu Lys Ser
                405                 410                 415

Asp Gly Phe Ala Asn Arg Asn Phe Met Gln Leu Ile His Asp Asp Ser
            420                 425                 430

Leu Thr Phe Lys Glu Asp Ile Gln Lys Ala Gln Val Ser Gly Gln Gly
        435                 440                 445

Asp Ser Leu His Glu His Ile Ala Asn Leu Ala Gly Ser Pro Ala Ile
    450                 455                 460

Lys Lys Gly Ile Leu Gln Thr Val Lys Val Val Asp Glu Leu Val Lys
465                 470                 475                 480

Val Met Gly Arg His Lys Pro Glu Asn Ile Val Ile Glu Met Ala Arg
                485                 490                 495

Glu Asn Gln Thr Thr Gln Lys Gly Gln Lys Gly Gly Gly Ser Glu Leu
            500                 505                 510

Asp Lys Ala Gly Phe Ile Lys Arg Gln Leu Val Glu Thr Arg Gln Ile
        515                 520                 525

Thr Lys His Val Ala Gln Ile Leu Asp Ser Arg Met Asn Thr Lys Tyr
    530                 535                 540

Asp Glu Asn Asp Lys Leu Ile Arg Glu Val Lys Val Ile Thr Leu Lys
545                 550                 555                 560

Ser Lys Leu Val Ser Asp Phe Arg Lys Asp Phe Gln Phe Tyr Lys Val
                565                 570                 575

Arg Glu Ile Asn Asn Tyr His His Ala His Asp Ala Tyr Leu Asn Ala
            580                 585                 590

Val Val Gly Thr Ala Leu Ile Lys Lys Tyr Pro Gly Gly Gly Ser Gly
        595                 600                 605

Gly Gly Ser Asp Lys Gly Arg Asp Phe Ala Thr Val Arg Lys Val Leu
    610                 615                 620

Ser Met Pro Gln Val Asn Ile Val Lys Lys Thr Glu Val Gln Thr Gly
625                 630                 635                 640

Gly Phe Ser Lys Glu Ser Ile Leu Pro Lys Arg Asn Ser Asp Lys Leu
```

```
                    645                 650                 655
Ile Ala Arg Lys Lys Asp Trp Asp Pro Lys Lys Tyr Gly Gly Phe Asp
                660                 665                 670

Ser Pro Thr Val Ala Tyr Ser Val Leu Val Ala Lys Val Glu Lys
                675                 680                 685

Gly Lys Ser Lys Leu Lys Ser Val Lys Glu Leu Leu Gly Ile Thr
            690                 695                 700

Ile Met Glu Arg Ser Ser Phe Glu Lys Asn Pro Ile Asp Phe Leu Glu
705                 710                 715                 720

Ala Lys Gly Tyr Lys Glu Val Lys Lys Asp Leu Ile Ile Lys Leu Pro
                725                 730                 735

Lys Tyr Ser Leu Phe Glu Leu Glu Asn Gly Arg Lys Arg Met Leu Ala
                740                 745                 750

Ser Ala Gly Glu Leu Gln Lys Gly Asn Glu Leu Ala Leu Pro Ser Lys
                755                 760                 765

Tyr Val Asn Phe Leu Tyr Leu Ala Ser His Tyr Glu Lys Leu Lys Gly
            770                 775                 780

Ser Pro Glu Asp Asn Glu Gln Lys Gln Leu Phe Val Glu Gln His Lys
785                 790                 795                 800

His Tyr Leu Asp Glu Ile Ile Glu Gln Ile Ser Glu Phe Ser Lys Arg
                805                 810                 815

Val Ile Leu Ala Asp Ala Asn Leu Asp Lys Val Leu Ser Ala Tyr Asn
                820                 825                 830

Lys His Arg Asp Lys Pro Ile Arg Glu Gln Ala Glu Asn Ile Ile His
            835                 840                 845

Leu Phe Thr Leu Thr Asn Leu Gly Ala Pro Ala Ala Phe Lys Tyr Phe
        850                 855                 860

Asp Thr Thr Ile Asp Arg Lys Arg Tyr Thr Ser Thr Lys Glu Val Leu
865                 870                 875                 880

Asp Ala Thr Leu Ile His Gln Ser Ile Thr Gly Leu Tyr Glu Thr Arg
                885                 890                 895

Ile Asp Leu Ser Gln Leu Gly Gly Asp
            900                 905

<210> SEQ ID NO 25
<211> LENGTH: 1002
<212> TYPE: PRT
<213> ORGANISM: artificial sequence
<220> FEATURE:
<223> OTHER INFORMATION: engineered Streptococcus pyogenes Cas9

<400> SEQUENCE: 25

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
```

-continued

```
                100                 105                 110
His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Asn Thr Glu Ile Thr Lys Ala Pro Leu Ser Ala Ser
            180                 185                 190

Met Ile Lys Arg Tyr Asp Glu His His Gln Asp Leu Thr Leu Leu Lys
            195                 200                 205

Ala Leu Val Arg Gln Gln Leu Pro Glu Lys Tyr Lys Glu Ile Phe Phe
        210                 215                 220

Asp Gln Ser Lys Asn Gly Tyr Ala Gly Tyr Ile Asp Gly Gly Ala Ser
225                 230                 235                 240

Gln Glu Glu Phe Tyr Lys Phe Ile Lys Pro Ile Leu Glu Lys Met Asp
                245                 250                 255

Gly Thr Glu Glu Leu Leu Val Lys Leu Asn Arg Glu Asp Leu Leu Arg
            260                 265                 270

Lys Gln Arg Thr Phe Asp Asn Gly Ser Ile Pro His Gln Ile His Leu
        275                 280                 285

Gly Glu Leu His Ala Ile Leu Arg Arg Gln Glu Asp Phe Tyr Pro Phe
    290                 295                 300

Leu Lys Asp Asn Arg Glu Lys Ile Glu Lys Ile Leu Thr Phe Arg Ile
305                 310                 315                 320

Pro Tyr Tyr Val Gly Pro Leu Ala Arg Gly Asn Ser Arg Phe Ala Trp
                325                 330                 335

Met Thr Arg Lys Ser Glu Glu Thr Ile Thr Pro Trp Asn Phe Glu Glu
            340                 345                 350

Val Val Asp Lys Gly Ala Ser Ala Gln Ser Phe Ile Glu Arg Met Thr
        355                 360                 365

Asn Phe Asp Lys Asn Leu Pro Asn Glu Lys Val Leu Pro Lys His Ser
370                 375                 380

Leu Leu Tyr Glu Tyr Phe Thr Val Tyr Asn Glu Leu Thr Lys Val Lys
385                 390                 395                 400

Tyr Val Thr Glu Gly Met Arg Lys Pro Ala Phe Leu Ser Gly Glu Gln
                405                 410                 415

Lys Lys Ala Ile Val Asp Leu Leu Phe Lys Thr Asn Arg Lys Val Thr
            420                 425                 430

Val Lys Gln Leu Lys Glu Asp Tyr Phe Lys Lys Ile Glu Cys Phe Asp
        435                 440                 445

Ser Val Glu Ile Ser Gly Val Glu Asp Arg Phe Asn Ala Ser Leu Gly
    450                 455                 460

Thr Tyr His Asp Leu Leu Lys Ile Ile Lys Asp Lys Asp Phe Leu Asp
465                 470                 475                 480

Asn Glu Glu Asn Glu Asp Ile Leu Glu Asp Ile Val Leu Thr Leu Thr
                485                 490                 495

Leu Phe Glu Asp Arg Glu Met Ile Glu Glu Arg Leu Lys Thr Tyr Ala
            500                 505                 510

His Leu Phe Asp Asp Lys Val Met Lys Gln Leu Lys Arg Arg Arg Tyr
        515                 520                 525
```

```
Thr Gly Trp Gly Arg Leu Gly Gly Ser Ala Gln Val Ser Gly Gln
    530                 535                 540
Gly Asp Ser Leu His Glu His Ile Ala Asn Leu Ala Gly Ser Pro Ala
545                 550                 555                 560
Ile Lys Lys Gly Ile Leu Gln Thr Val Lys Val Val Asp Glu Leu Val
                565                 570                 575
Lys Val Met Gly Arg His Lys Pro Glu Asn Ile Val Ile Glu Met Ala
            580                 585                 590
Arg Glu Asn Gln Thr Thr Gln Lys Gly Gln Lys Gly Gly Ser Glu
        595                 600                 605
Leu Asp Lys Ala Gly Phe Ile Lys Arg Gln Leu Val Glu Thr Arg Gln
    610                 615                 620
Ile Thr Lys His Val Ala Gln Ile Leu Asp Ser Arg Met Asn Thr Lys
625                 630                 635                 640
Tyr Asp Glu Asn Asp Lys Leu Ile Arg Glu Val Lys Val Ile Thr Leu
                645                 650                 655
Lys Ser Lys Leu Val Ser Asp Phe Arg Lys Asp Phe Gln Phe Tyr Lys
            660                 665                 670
Val Arg Glu Ile Asn Asn Tyr His His Ala His Asp Ala Tyr Leu Asn
        675                 680                 685
Ala Val Val Gly Thr Ala Leu Ile Lys Lys Tyr Pro Gly Gly Gly Ser
    690                 695                 700
Gly Gly Gly Ser Asp Lys Gly Arg Asp Phe Ala Thr Val Arg Lys Val
705                 710                 715                 720
Leu Ser Met Pro Gln Val Asn Ile Val Lys Lys Thr Glu Val Gln Thr
                725                 730                 735
Gly Gly Phe Ser Lys Glu Ser Ile Leu Pro Lys Arg Asn Ser Asp Lys
            740                 745                 750
Leu Ile Ala Arg Lys Lys Asp Trp Asp Pro Lys Lys Tyr Gly Gly Phe
        755                 760                 765
Asp Ser Pro Thr Val Ala Tyr Ser Val Leu Val Val Ala Lys Val Glu
    770                 775                 780
Lys Gly Lys Ser Lys Lys Leu Lys Ser Val Lys Glu Leu Leu Gly Ile
785                 790                 795                 800
Thr Ile Met Glu Arg Ser Ser Phe Glu Lys Asn Pro Ile Asp Phe Leu
                805                 810                 815
Glu Ala Lys Gly Tyr Lys Glu Val Lys Lys Asp Leu Ile Ile Lys Leu
            820                 825                 830
Pro Lys Tyr Ser Leu Phe Glu Leu Glu Asn Gly Arg Lys Arg Met Leu
        835                 840                 845
Ala Ser Ala Gly Glu Leu Gln Lys Gly Asn Glu Leu Ala Leu Pro Ser
    850                 855                 860
Lys Tyr Val Asn Phe Leu Tyr Leu Ala Ser His Tyr Glu Lys Leu Lys
865                 870                 875                 880
Gly Ser Pro Glu Asp Asn Glu Gln Lys Gln Leu Phe Val Glu Gln His
                885                 890                 895
Lys His Tyr Leu Asp Glu Ile Ile Glu Gln Ile Ser Glu Phe Ser Lys
            900                 905                 910
Arg Val Ile Leu Ala Asp Ala Asn Leu Asp Lys Val Leu Ser Ala Tyr
        915                 920                 925
Asn Lys His Arg Asp Lys Pro Ile Arg Glu Gln Ala Glu Asn Ile Ile
    930                 935                 940
```

-continued

```
His Leu Phe Thr Leu Thr Asn Leu Gly Ala Pro Ala Ala Phe Lys Tyr
945                 950                 955                 960

Phe Asp Thr Thr Ile Asp Arg Lys Arg Tyr Thr Ser Thr Lys Glu Val
                965                 970                 975

Leu Asp Ala Thr Leu Ile His Gln Ser Ile Thr Gly Leu Tyr Glu Thr
            980                 985                 990

Arg Ile Asp Leu Ser Gln Leu Gly  Gly Asp
            995                 1000

<210> SEQ ID NO 26
<211> LENGTH: 861
<212> TYPE: PRT
<213> ORGANISM: artificial sequence
<220> FEATURE:
<223> OTHER INFORMATION: engineered Streptococcus pyogenes Cas9

<400> SEQUENCE: 26

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Asn Thr Glu Ile Thr Lys Ala Pro Leu Ser Ala Ser
            180                 185                 190

Met Ile Lys Arg Tyr Asp Glu His Gln Asp Leu Thr Leu Leu Lys
        195                 200                 205

Ala Leu Val Arg Gln Gln Leu Pro Glu Lys Tyr Lys Glu Ile Phe Phe
    210                 215                 220

Asp Gln Ser Lys Asn Gly Tyr Ala Gly Tyr Ile Asp Gly Gly Ala Ser
225                 230                 235                 240

Gln Glu Glu Phe Tyr Lys Phe Ile Lys Pro Ile Leu Glu Lys Met Asp
                245                 250                 255

Gly Thr Glu Glu Leu Leu Val Lys Leu Asn Arg Glu Asp Leu Leu Arg
            260                 265                 270

Lys Gln Arg Thr Phe Asp Asn Gly Ser Ile Pro His Gln Ile His Leu
        275                 280                 285

Gly Glu Leu His Ala Ile Leu Arg Arg Gln Glu Asp Phe Tyr Pro Phe
    290                 295                 300
```

```
Leu Lys Asp Asn Arg Glu Lys Ile Glu Lys Ile Leu Thr Phe Arg Ile
305                 310                 315                 320

Pro Tyr Tyr Val Gly Pro Leu Ala Arg Gly Asn Ser Arg Phe Ala Trp
            325                 330                 335

Met Thr Arg Lys Ser Glu Glu Thr Ile Thr Pro Trp Asn Phe Glu Glu
            340                 345                 350

Val Val Asp Lys Gly Ala Ser Ala Gln Ser Phe Ile Glu Arg Met Thr
            355                 360                 365

Asn Phe Asp Lys Asn Leu Pro Asn Glu Lys Val Leu Pro Lys Gly Gly
    370                 375                 380

Gly Ser Tyr Thr Gly Trp Gly Arg Leu Gly Gly Ser Ala Gln Val
385                 390                 395                 400

Ser Gly Gln Gly Asp Ser Leu His Glu His Ile Ala Asn Leu Ala Gly
                405                 410                 415

Ser Pro Ala Ile Lys Lys Gly Ile Leu Gln Thr Val Lys Val Val Asp
                420                 425                 430

Glu Leu Val Lys Val Met Gly Arg His Lys Pro Glu Asn Ile Val Ile
                435                 440                 445

Glu Met Ala Arg Glu Asn Gln Thr Thr Gln Lys Gly Gln Lys Gly Gly
450                 455                 460

Gly Ser Glu Leu Asp Lys Ala Gly Phe Ile Lys Arg Gln Leu Val Glu
465                 470                 475                 480

Thr Arg Gln Ile Thr Lys His Val Ala Gln Ile Leu Asp Ser Arg Met
                485                 490                 495

Asn Thr Lys Tyr Asp Glu Asn Asp Lys Leu Ile Arg Glu Val Lys Val
            500                 505                 510

Ile Thr Leu Lys Ser Lys Leu Val Ser Asp Phe Arg Lys Asp Phe Gln
            515                 520                 525

Phe Tyr Lys Val Arg Glu Ile Asn Asn Tyr His His Ala His Asp Ala
    530                 535                 540

Tyr Leu Asn Ala Val Val Gly Thr Ala Leu Ile Lys Lys Tyr Pro Gly
545                 550                 555                 560

Gly Gly Ser Gly Gly Gly Ser Asp Lys Gly Arg Asp Phe Ala Thr Val
                565                 570                 575

Arg Lys Val Leu Ser Met Pro Gln Val Asn Ile Val Lys Lys Thr Glu
            580                 585                 590

Val Gln Thr Gly Gly Phe Ser Lys Glu Ser Ile Leu Pro Lys Arg Asn
            595                 600                 605

Ser Asp Lys Leu Ile Ala Arg Lys Lys Asp Trp Asp Pro Lys Lys Tyr
    610                 615                 620

Gly Gly Phe Asp Ser Pro Thr Val Ala Tyr Ser Val Leu Val Val Ala
625                 630                 635                 640

Lys Val Glu Lys Gly Lys Ser Lys Lys Leu Lys Ser Val Lys Glu Leu
                645                 650                 655

Leu Gly Ile Thr Ile Met Glu Arg Ser Ser Phe Glu Lys Asn Pro Ile
                660                 665                 670

Asp Phe Leu Glu Ala Lys Gly Tyr Lys Glu Val Lys Lys Asp Leu Ile
            675                 680                 685

Ile Lys Leu Pro Lys Tyr Ser Leu Phe Glu Leu Glu Asn Gly Arg Lys
            690                 695                 700

Arg Met Leu Ala Ser Ala Gly Glu Leu Gln Lys Gly Asn Glu Leu Ala
705                 710                 715                 720

Leu Pro Ser Lys Tyr Val Asn Phe Leu Tyr Leu Ala Ser His Tyr Glu
```

```
                725                 730                 735
Lys Leu Lys Gly Ser Pro Glu Asp Asn Glu Gln Lys Gln Leu Phe Val
            740                 745                 750

Glu Gln His Lys His Tyr Leu Asp Glu Ile Ile Glu Gln Ile Ser Glu
            755                 760                 765

Phe Ser Lys Arg Val Ile Leu Ala Asp Ala Asn Leu Asp Lys Val Leu
            770                 775                 780

Ser Ala Tyr Asn Lys His Arg Asp Lys Pro Ile Arg Glu Gln Ala Glu
785                 790                 795                 800

Asn Ile Ile His Leu Phe Thr Leu Thr Asn Leu Gly Ala Pro Ala Ala
            805                 810                 815

Phe Lys Tyr Phe Asp Thr Thr Ile Asp Arg Lys Arg Tyr Thr Ser Thr
            820                 825                 830

Lys Glu Val Leu Asp Ala Thr Leu Ile His Gln Ser Ile Thr Gly Leu
            835                 840                 845

Tyr Glu Thr Arg Ile Asp Leu Ser Gln Leu Gly Gly Asp
            850                 855                 860

<210> SEQ ID NO 27
<211> LENGTH: 1156
<212> TYPE: PRT
<213> ORGANISM: artificial sequence
<220> FEATURE:
<223> OTHER INFORMATION: engineered Streptococcus pyogenes Cas9

<400> SEQUENCE: 27

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
```

-continued

```
                225                 230                 235                 240
Leu Ile Ala Leu Ser Leu Gly Leu Thr Pro Asn Phe Lys Ser Asn Phe
                    245                 250                 255
Asp Leu Ala Glu Asp Ala Lys Leu Gln Leu Ser Lys Asp Thr Tyr Asp
                    260                 265                 270
Asp Asp Leu Asp Asn Leu Leu Ala Gln Ile Gly Asp Gln Tyr Ala Asp
                    275                 280                 285
Leu Phe Leu Ala Ala Lys Asn Leu Ser Asp Ala Ile Leu Leu Ser Asp
                    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                    325                 330                 335
Ala Leu Val Arg Gln Gln Leu Pro Glu Lys Tyr Lys Glu Ile Phe Phe
                    340                 345                 350
Asp Gln Ser Lys Asn Gly Tyr Ala Gly Tyr Ile Asp Gly Gly Ala Ser
                    355                 360                 365
Gln Glu Glu Phe Tyr Lys Phe Ile Lys Pro Ile Leu Glu Lys Met Asp
                    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                    405                 410                 415
Gly Glu Leu His Ala Ile Leu Arg Arg Gln Glu Asp Phe Tyr Pro Phe
                    420                 425                 430
Leu Lys Asp Asn Arg Glu Lys Ile Glu Lys Ile Leu Thr Phe Arg Ile
                    435                 440                 445
Pro Tyr Tyr Val Gly Pro Leu Ala Arg Gly Asn Ser Arg Phe Ala Trp
                    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                    485                 490                 495
Asn Gly Gly Ser Val Ser Gly Gln Gly Asp Ser Leu His Glu His Ile
                    500                 505                 510
Ala Asn Leu Ala Gly Ser Pro Ala Ile Lys Lys Gly Ile Leu Gln Thr
                    515                 520                 525
Val Lys Val Val Asp Glu Leu Val Lys Val Met Gly Arg His Lys Pro
                    530                 535                 540
Glu Asn Ile Val Ile Glu Met Ala Arg Glu Asn Gln Thr Thr Gln Lys
545                 550                 555                 560
Gly Gln Lys Asn Ser Arg Glu Arg Met Lys Arg Ile Glu Glu Gly Ile
                    565                 570                 575
Lys Glu Leu Gly Ser Gln Ile Leu Lys Glu His Pro Val Glu Asn Thr
                    580                 585                 590
Gln Leu Gln Asn Glu Lys Leu Tyr Leu Tyr Tyr Leu Gln Asn Gly Arg
                    595                 600                 605
Asp Met Tyr Val Asp Gln Glu Leu Asp Ile Asn Arg Leu Ser Asp Tyr
                    610                 615                 620
Asp Val Ala Ala Ile Val Pro Gln Ser Phe Leu Lys Asp Asp Ser Ile
625                 630                 635                 640
Asp Asn Lys Val Leu Thr Arg Ser Asp Lys Ala Arg Gly Lys Ser Asp
                    645                 650                 655
```

```
Asn Val Pro Ser Glu Glu Val Lys Lys Met Lys Asn Tyr Trp Arg
            660                 665                 670

Gln Leu Leu Asn Ala Lys Leu Ile Thr Gln Arg Lys Phe Asp Asn Leu
        675                 680                 685

Thr Lys Ala Glu Arg Gly Gly Leu Ser Glu Leu Asp Lys Ala Gly Phe
    690                 695                 700

Ile Lys Arg Gln Leu Val Glu Thr Arg Gln Ile Thr Lys His Val Ala
705                 710                 715                 720

Gln Ile Leu Asp Ser Arg Met Asn Thr Lys Tyr Asp Glu Asn Asp Lys
                725                 730                 735

Leu Ile Arg Glu Val Lys Val Ile Thr Leu Lys Ser Lys Leu Val Ser
            740                 745                 750

Asp Phe Arg Lys Asp Phe Gln Phe Tyr Lys Val Arg Glu Ile Asn Asn
        755                 760                 765

Tyr His His Ala His Asp Ala Tyr Leu Asn Ala Val Val Gly Thr Ala
    770                 775                 780

Leu Ile Lys Lys Tyr Pro Lys Leu Glu Ser Glu Phe Val Tyr Gly Asp
785                 790                 795                 800

Tyr Lys Val Tyr Asp Val Arg Lys Met Ile Ala Lys Ser Glu Gln Glu
                805                 810                 815

Ile Gly Lys Ala Thr Ala Lys Tyr Phe Phe Tyr Ser Asn Ile Met Asn
            820                 825                 830

Phe Phe Lys Thr Glu Ile Thr Leu Ala Asn Gly Glu Ile Arg Lys Arg
        835                 840                 845

Pro Leu Ile Glu Thr Asn Gly Glu Thr Gly Glu Ile Val Trp Asp Lys
    850                 855                 860

Gly Arg Asp Phe Ala Thr Val Arg Lys Val Leu Ser Met Pro Gln Val
865                 870                 875                 880

Asn Ile Val Lys Lys Thr Glu Val Gln Thr Gly Gly Phe Ser Lys Glu
                885                 890                 895

Ser Ile Leu Pro Lys Arg Asn Ser Asp Lys Leu Ile Ala Arg Lys Lys
            900                 905                 910

Asp Trp Asp Pro Lys Lys Tyr Gly Gly Phe Asp Ser Pro Thr Val Ala
        915                 920                 925

Tyr Ser Val Leu Val Val Ala Lys Val Glu Lys Gly Lys Ser Lys Lys
    930                 935                 940

Leu Lys Ser Val Lys Glu Leu Leu Gly Ile Thr Ile Met Glu Arg Ser
945                 950                 955                 960

Ser Phe Glu Lys Asn Pro Ile Asp Phe Leu Glu Ala Lys Gly Tyr Lys
                965                 970                 975

Glu Val Lys Lys Asp Leu Ile Ile Lys Leu Pro Lys Tyr Ser Leu Phe
            980                 985                 990

Glu Leu Glu Asn Gly Arg Lys Arg Met Leu Ala Ser Ala Gly Glu Leu
        995                 1000                1005

Gln Lys Gly Asn Glu Leu Ala Leu Pro Ser Lys Tyr Val Asn Phe
    1010                1015                1020

Leu Tyr Leu Ala Ser His Tyr Glu Lys Leu Lys Gly Ser Pro Glu
    1025                1030                1035

Asp Asn Glu Gln Lys Gln Leu Phe Val Glu Gln His Lys His Tyr
    1040                1045                1050

Leu Asp Glu Ile Ile Glu Gln Ile Ser Glu Phe Ser Lys Arg Val
    1055                1060                1065
```

```
Ile Leu Ala Asp Ala Asn Leu Asp Lys Val Leu Ser Ala Tyr Asn
    1070                1075                1080

Lys His Arg Asp Lys Pro Ile Arg Glu Gln Ala Glu Asn Ile Ile
    1085                1090                1095

His Leu Phe Thr Leu Thr Asn Leu Gly Ala Pro Ala Ala Phe Lys
    1100                1105                1110

Tyr Phe Asp Thr Thr Ile Asp Arg Lys Arg Tyr Thr Ser Thr Lys
    1115                1120                1125

Glu Val Leu Asp Ala Thr Leu Ile His Gln Ser Ile Thr Gly Leu
    1130                1135                1140

Tyr Glu Thr Arg Ile Asp Leu Ser Gln Leu Gly Gly Asp
    1145                1150                1155

<210> SEQ ID NO 28
<211> LENGTH: 1026
<212> TYPE: PRT
<213> ORGANISM: artificial sequence
<220> FEATURE:
<223> OTHER INFORMATION: engineered Streptococcus pyogenes Cas9

<400> SEQUENCE: 28

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270
```

```
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
        370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Gly Gly Ser Val Ser Gly Gln Gly Asp Ser Leu His Glu His Ile
                500                 505                 510
Ala Asn Leu Ala Gly Ser Pro Ala Ile Lys Lys Gly Ile Leu Gln Thr
            515                 520                 525
Val Lys Val Val Asp Glu Leu Val Lys Val Met Gly Arg His Lys Pro
        530                 535                 540
Glu Asn Ile Val Ile Glu Met Ala Arg Glu Asn Gln Thr Thr Gln Lys
545                 550                 555                 560
Gly Gln Lys Gly Gly Ser Glu Leu Asp Lys Ala Gly Phe Ile Lys
                565                 570                 575
Arg Gln Leu Val Glu Thr Arg Gln Ile Thr Lys His Val Ala Gln Ile
            580                 585                 590
Leu Asp Ser Arg Met Asn Thr Lys Tyr Asp Glu Asn Asp Lys Leu Ile
        595                 600                 605
Arg Glu Val Lys Val Ile Thr Leu Lys Ser Lys Leu Val Ser Asp Phe
610                 615                 620
Arg Lys Asp Phe Gln Phe Tyr Lys Val Arg Glu Ile Asn Asn Tyr His
                630                 635                 640
His Ala His Asp Ala Tyr Leu Asn Ala Val Val Gly Thr Ala Leu Ile
            645                 650                 655
Lys Lys Tyr Pro Lys Leu Glu Ser Glu Phe Val Tyr Gly Asp Tyr Lys
            660                 665                 670
Val Tyr Asp Val Arg Lys Met Ile Ala Lys Ser Glu Gln Glu Ile Gly
            675                 680                 685
Lys Ala Thr Ala Lys Tyr Phe Phe Tyr Ser Asn Ile Met Asn Phe Phe
```

```
                690                 695                 700
Lys Thr Glu Ile Thr Leu Ala Asn Gly Glu Ile Arg Lys Arg Pro Leu
705                 710                 715                 720

Ile Glu Thr Asn Gly Glu Thr Gly Glu Ile Val Trp Asp Lys Gly Arg
                725                 730                 735

Asp Phe Ala Thr Val Arg Lys Val Leu Ser Met Pro Gln Val Asn Ile
                740                 745                 750

Val Lys Lys Thr Glu Val Gln Thr Gly Gly Phe Ser Lys Glu Ser Ile
            755                 760                 765

Leu Pro Lys Arg Asn Ser Asp Lys Leu Ile Ala Arg Lys Lys Asp Trp
        770                 775                 780

Asp Pro Lys Lys Tyr Gly Gly Phe Asp Ser Pro Thr Val Ala Tyr Ser
785                 790                 795                 800

Val Leu Val Val Ala Lys Val Glu Lys Gly Lys Ser Lys Lys Leu Lys
                805                 810                 815

Ser Val Lys Glu Leu Leu Gly Ile Thr Ile Met Glu Arg Ser Ser Phe
                820                 825                 830

Glu Lys Asn Pro Ile Asp Phe Leu Glu Ala Lys Gly Tyr Lys Glu Val
            835                 840                 845

Lys Lys Asp Leu Ile Ile Lys Leu Pro Lys Tyr Ser Leu Phe Glu Leu
        850                 855                 860

Glu Asn Gly Arg Lys Arg Met Leu Ala Ser Ala Gly Glu Leu Gln Lys
865                 870                 875                 880

Gly Asn Glu Leu Ala Leu Pro Ser Lys Tyr Val Asn Phe Leu Tyr Leu
                885                 890                 895

Ala Ser His Tyr Glu Lys Leu Lys Gly Ser Pro Glu Asp Asn Glu Gln
                900                 905                 910

Lys Gln Leu Phe Val Glu Gln His Lys His Tyr Leu Asp Glu Ile Ile
            915                 920                 925

Glu Gln Ile Ser Glu Phe Ser Lys Arg Val Ile Leu Ala Asp Ala Asn
        930                 935                 940

Leu Asp Lys Val Leu Ser Ala Tyr Asn Lys His Arg Asp Lys Pro Ile
945                 950                 955                 960

Arg Glu Gln Ala Glu Asn Ile Ile His Leu Phe Thr Leu Thr Asn Leu
                965                 970                 975

Gly Ala Pro Ala Ala Phe Lys Tyr Phe Asp Thr Thr Ile Asp Arg Lys
                980                 985                 990

Arg Tyr Thr Ser Thr Lys Glu Val  Leu Asp Ala Thr Leu Ile His Gln
            995                 1000                1005

Ser Ile  Thr Gly Leu Tyr Glu  Thr Arg Ile Asp Leu  Ser Gln Leu
    1010                1015                1020

Gly Gly Asp
    1025

<210> SEQ ID NO 29
<211> LENGTH: 962
<212> TYPE: PRT
<213> ORGANISM: artificial sequence
<220> FEATURE:
<223> OTHER INFORMATION: engineered Streptococcus pyogenes Cas9

<400> SEQUENCE: 29

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
```

```
                20                  25                  30
Lys Val Leu Gly Asn Thr Asp Arg His Ser Ile Lys Lys Asn Leu Ile
             35                  40                  45
Gly Ala Leu Leu Phe Asp Ser Gly Glu Thr Ala Glu Ala Thr Arg Leu
             50                  55                  60
Lys Arg Thr Ala Arg Arg Tyr Thr Arg Arg Lys Asn Arg Ile Cys
 65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
                130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
                195                 200                 205
Lys Ala Ile Leu Ser Ala Arg Leu Ser Lys Ser Arg Arg Leu Glu Asn
                210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
```

```
Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Gly Gly Ser Val Ser Gly Gln Gly Asp Ser Leu His Glu His Ile
                500                 505                 510

Ala Asn Leu Ala Gly Ser Pro Ala Ile Lys Lys Gly Ile Leu Gln Thr
            515                 520                 525

Val Lys Val Val Asp Glu Leu Val Lys Val Met Gly Arg His Lys Pro
        530                 535                 540

Glu Asn Ile Val Ile Glu Met Ala Arg Glu Asn Gln Thr Thr Gln Lys
545                 550                 555                 560

Gly Gln Lys Gly Gly Ser Glu Leu Asp Lys Ala Gly Phe Ile Lys
                565                 570                 575

Arg Gln Leu Val Glu Thr Arg Gln Ile Thr Lys His Val Ala Gln Ile
                580                 585                 590

Leu Asp Ser Arg Met Asn Thr Lys Tyr Asp Glu Asn Asp Lys Leu Ile
            595                 600                 605

Arg Glu Val Lys Val Ile Thr Leu Lys Ser Lys Leu Val Ser Asp Phe
        610                 615                 620

Arg Lys Asp Phe Gln Phe Tyr Lys Val Arg Glu Ile Asn Asn Tyr His
625                 630                 635                 640

His Ala His Asp Ala Tyr Leu Asn Ala Val Val Gly Thr Ala Leu Ile
                645                 650                 655

Lys Lys Tyr Pro Gly Gly Gly Ser Gly Gly Ser Asp Lys Gly Arg
                660                 665                 670

Asp Phe Ala Thr Val Arg Lys Val Leu Ser Met Pro Gln Val Asn Ile
            675                 680                 685

Val Lys Lys Thr Glu Val Gln Thr Gly Gly Phe Ser Lys Glu Ser Ile
        690                 695                 700

Leu Pro Lys Arg Asn Ser Asp Lys Leu Ile Ala Arg Lys Lys Asp Trp
705                 710                 715                 720

Asp Pro Lys Lys Tyr Gly Gly Phe Asp Ser Pro Thr Val Ala Tyr Ser
                725                 730                 735

Val Leu Val Val Ala Lys Val Glu Lys Gly Lys Ser Lys Lys Leu Lys
                740                 745                 750

Ser Val Lys Glu Leu Leu Gly Ile Thr Ile Met Glu Arg Ser Ser Phe
        755                 760                 765

Glu Lys Asn Pro Ile Asp Phe Leu Glu Ala Lys Gly Tyr Lys Glu Val
        770                 775                 780

Lys Lys Asp Leu Ile Ile Lys Leu Pro Lys Tyr Ser Leu Phe Glu Leu
785                 790                 795                 800

Glu Asn Gly Arg Lys Arg Met Leu Ala Ser Ala Gly Glu Leu Gln Lys
                805                 810                 815

Gly Asn Glu Leu Ala Leu Pro Ser Lys Tyr Val Asn Phe Leu Tyr Leu
            820                 825                 830

Ala Ser His Tyr Glu Lys Leu Lys Gly Ser Pro Glu Asp Asn Glu Gln
            835                 840                 845

Lys Gln Leu Phe Val Glu Gln His Lys His Tyr Leu Asp Glu Ile Ile
850                 855                 860
```

```
Glu Gln Ile Ser Glu Phe Ser Lys Arg Val Ile Leu Ala Asp Ala Asn
865                 870                 875                 880

Leu Asp Lys Val Leu Ser Ala Tyr Asn Lys His Arg Asp Lys Pro Ile
            885                 890                 895

Arg Glu Gln Ala Glu Asn Ile Ile His Leu Phe Thr Leu Thr Asn Leu
        900                 905                 910

Gly Ala Pro Ala Ala Phe Lys Tyr Phe Asp Thr Thr Ile Asp Arg Lys
        915                 920                 925

Arg Tyr Thr Ser Thr Lys Glu Val Leu Asp Ala Thr Leu Ile His Gln
        930                 935                 940

Ser Ile Thr Gly Leu Tyr Glu Thr Arg Ile Asp Leu Ser Gln Leu Gly
945                 950                 955                 960

Gly Asp

<210> SEQ ID NO 30
<211> LENGTH: 834
<212> TYPE: PRT
<213> ORGANISM: artificial sequence
<220> FEATURE:
<223> OTHER INFORMATION: engineered Streptococcus pyogenes Cas9

<400> SEQUENCE: 30

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Asn Thr Glu Ile Thr Lys Ala Pro Leu Ser Ala Ser
            180                 185                 190

Met Ile Lys Arg Tyr Asp Glu His His Gln Asp Leu Thr Leu Leu Lys
        195                 200                 205

Ala Leu Val Arg Gln Gln Leu Pro Glu Lys Tyr Lys Glu Ile Phe Phe
    210                 215                 220

Asp Gln Ser Lys Asn Gly Tyr Ala Gly Tyr Ile Asp Gly Gly Ala Ser
225                 230                 235                 240

Gln Glu Glu Phe Tyr Lys Phe Ile Lys Pro Ile Leu Glu Lys Met Asp
                245                 250                 255

Gly Thr Glu Glu Leu Leu Val Lys Leu Asn Arg Glu Asp Leu Leu Arg
```

```
            260                 265                 270
Lys Gln Arg Thr Phe Asp Asn Gly Ser Ile Pro His Gln Ile His Leu
        275                 280                 285
Gly Glu Leu His Ala Ile Leu Arg Arg Gln Glu Asp Phe Tyr Pro Phe
        290                 295                 300
Leu Lys Asp Asn Arg Glu Lys Ile Glu Lys Ile Leu Thr Phe Arg Ile
305                 310                 315                 320
Pro Tyr Tyr Val Gly Pro Leu Ala Arg Gly Asn Ser Arg Phe Ala Trp
                325                 330                 335
Met Thr Arg Lys Ser Glu Glu Thr Ile Thr Pro Trp Asn Phe Glu Glu
                340                 345                 350
Val Val Asp Lys Gly Ala Ser Ala Gln Ser Phe Ile Glu Arg Met Thr
                355                 360                 365
Asn Gly Gly Ser Val Ser Gly Gln Gly Asp Ser Leu His Glu His Ile
            370                 375                 380
Ala Asn Leu Ala Gly Ser Pro Ala Ile Lys Lys Gly Ile Leu Gln Thr
385                 390                 395                 400
Val Lys Val Val Asp Glu Leu Val Lys Val Met Gly Arg His Lys Pro
                405                 410                 415
Glu Asn Ile Val Ile Glu Met Ala Arg Glu Asn Gln Thr Thr Gln Lys
                420                 425                 430
Gly Gln Lys Gly Gly Ser Glu Leu Asp Lys Ala Gly Phe Ile Lys
            435                 440                 445
Arg Gln Leu Val Glu Thr Arg Gln Ile Thr Lys His Val Ala Gln Ile
        450                 455                 460
Leu Asp Ser Arg Met Asn Thr Lys Tyr Asp Glu Asn Asp Lys Leu Ile
465                 470                 475                 480
Arg Glu Val Lys Val Ile Thr Leu Lys Ser Lys Leu Val Ser Asp Phe
                485                 490                 495
Arg Lys Asp Phe Gln Phe Tyr Lys Val Arg Glu Ile Asn Asn Tyr His
            500                 505                 510
His Ala His Asp Ala Tyr Leu Asn Ala Val Val Gly Thr Ala Leu Ile
        515                 520                 525
Lys Lys Tyr Pro Gly Gly Ser Gly Gly Ser Asp Lys Gly Arg
        530                 535                 540
Asp Phe Ala Thr Val Arg Lys Val Leu Ser Met Pro Gln Val Asn Ile
545                 550                 555                 560
Val Lys Lys Thr Glu Val Gln Thr Gly Gly Phe Ser Lys Glu Ser Ile
                565                 570                 575
Leu Pro Lys Arg Asn Ser Asp Lys Leu Ile Ala Arg Lys Lys Asp Trp
                580                 585                 590
Asp Pro Lys Lys Tyr Gly Gly Phe Asp Ser Pro Thr Val Ala Tyr Ser
                595                 600                 605
Val Leu Val Val Ala Lys Val Glu Lys Gly Lys Ser Lys Lys Leu Lys
                610                 615                 620
Ser Val Lys Glu Leu Leu Gly Ile Thr Ile Met Glu Arg Ser Ser Phe
625                 630                 635                 640
Glu Lys Asn Pro Ile Asp Phe Leu Glu Ala Lys Gly Tyr Lys Glu Val
                645                 650                 655
Lys Lys Asp Leu Ile Ile Lys Leu Pro Lys Tyr Ser Leu Phe Glu Leu
                660                 665                 670
Glu Asn Gly Arg Lys Arg Met Leu Ala Ser Ala Gly Glu Leu Gln Lys
                675                 680                 685
```

```
Gly Asn Glu Leu Ala Leu Pro Ser Lys Tyr Val Asn Phe Leu Tyr Leu
    690             695             700

Ala Ser His Tyr Glu Lys Leu Lys Gly Ser Pro Glu Asp Asn Glu Gln
705             710             715                         720

Lys Gln Leu Phe Val Glu Gln His Lys His Tyr Leu Asp Glu Ile Ile
                725             730                 735

Glu Gln Ile Ser Glu Phe Ser Lys Arg Val Ile Leu Ala Asp Ala Asn
            740             745             750

Leu Asp Lys Val Leu Ser Ala Tyr Asn Lys His Arg Asp Lys Pro Ile
        755             760             765

Arg Glu Gln Ala Glu Asn Ile Ile His Leu Phe Thr Leu Thr Asn Leu
    770             775             780

Gly Ala Pro Ala Ala Phe Lys Tyr Phe Asp Thr Thr Ile Asp Arg Lys
785             790             795                         800

Arg Tyr Thr Ser Thr Lys Glu Val Leu Asp Ala Thr Leu Ile His Gln
            805             810             815

Ser Ile Thr Gly Leu Tyr Glu Thr Arg Ile Asp Leu Ser Gln Leu Gly
            820             825             830

Gly Asp
```

UNITED STATES PATENT AND TRADEMARK OFFICE
CERTIFICATE OF CORRECTION

PATENT NO. : 11,840,694 B2
APPLICATION NO. : 16/342319
DATED : December 12, 2023
INVENTOR(S) : Meng How Tan et al.

Page 1 of 1

It is certified that error appears in the above-identified patent and that said Letters Patent is hereby corrected as shown below:

In the Claims

Column 217, Claim 3, Line 52:
"ΔREC2 ΔHNH T657R" should read: --ΔREC2 ΔHNH ΔRuvCIII-b T657R,--.

Column 217, Claim 3, Line 53:
"ΔREC2 ΔHNH Q920K," should read: --ΔREC2 ΔHNH ΔRuvCIII-b Q920K,--.

Column 218, Claim 3, Lines 29-30:
"ΔREC2 ΔHNH D1135K," should read: --ΔREC2 ΔHNH ΔRuvCIII-b D1135K,--.

Signed and Sealed this
Twenty-eighth Day of January, 2025

Coke Morgan Stewart
*Acting Director of the United States Patent and Trademark Office*